US011525136B2

(12) United States Patent
Freier

(10) Patent No.: US 11,525,136 B2
(45) **Date of Patent: *Dec. 13, 2022**

(54) MODULATORS OF APOL1 EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/025,239

(22) Filed: Sep. 18, 2020

(65) Prior Publication Data

US 2021/0079395 A1 Mar. 18, 2021

Related U.S. Application Data

(63) Continuation of application No. 16/418,060, filed on May 21, 2019, now Pat. No. 10,927,377.

(60) Provisional application No. 62/674,865, filed on May 22, 2018.

(51) Int. Cl.

*C07H 21/04* (2006.01)
*C12N 15/113* (2010.01)
*A61P 13/02* (2006.01)

(52) U.S. Cl.

CPC ............ *C12N 15/113* (2013.01); *A61P 13/02* (2018.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/346* (2013.01); *C12N 2320/32* (2013.01); *C12N 2320/35* (2013.01)

(58) Field of Classification Search

None

See application file for complete search history.

(56) References Cited

U.S. PATENT DOCUMENTS

2003/0028013 A1* 2/2003 Wang .................... C07H 19/04 544/254
2016/0003808 A1 1/2016 Janssen et al.

FOREIGN PATENT DOCUMENTS

| | | | |
|---|---|---|---|
| WO | 2008050329 | A2 | 5/2008 |
| WO | 2015010135 | A2 | 1/2015 |
| WO | 2019226611 | A1 | 11/2019 |

OTHER PUBLICATIONS

Aghajan Mariam et al: "Antisense oligonucleotide treatment ameliorates IFN-[gamma]-induced proteinuria in APOLI-transgenic mice", JCI Insight, vol. 4, No. 12, Jun. 20, 2019 (Jun. 20, 2019).
Brauweiler Anne M. et al: "Interferon-[gamma] Protects from Staphylococcal Alpha Toxin-Induced Keratinocyte Death through Apolipoprotein LI", Journal of Investigative Dermatology, vol. 136, No. 3, Mar. 1, 2016 (Mar. 1, 2016), pp. 658-664.
International Search Report and Written Opinion for PCT/US2019/033244, dated Oct. 16, 2019.
Genovese, Giulio, et al. "Association of trypanolytic Apol 1 variants with kidney disease in African Americans." Science 329.5993 (2010): 841-845.

* cited by examiner

*Primary Examiner* — Kimberly Chong

(57) ABSTRACT

The present embodiments provide methods, compounds, and compositions useful for inhibiting APOL1 expression, which may be useful for treating, preventing, or ameliorating a disease associated with APOL1.

15 Claims, No Drawings

Specification includes a Sequence Listing.

SEQUENCE LISTING

```
<160> NUMBER OF SEQ ID NOS: 1949

<210> SEQ ID NO 1
<211> LENGTH: 2885
<212> TYPE: DNA
<213> ORGANISM: Homo sapien

<400> SEQUENCE: 1

gactttcact ttccctttcg aattcctcgg tatatcttgg ggactggagg acctgtctgg     60

ttattataca gacgcataac tggaggtggg atccacacag ctcagaacag ctggatcttg    120

ctcagtctct gccaggggaa gattccttgg aggaggccct gcagcgacat ggagggagct    180

gctttgctga gagtctctgt cctctgcatc tggatgagtg cacttttcct tggtgtggga    240

gtgagggcag aggaagctgg agcgagggtg caacaaaacg ttccaagtgg gacagatact    300

ggagatcctc aaagtaagcc cctcggtgac tgggctgctg gcaccatgga cccagagagc    360

agtatcttta ttgaggatgc cattaagtat ttcaaggaaa aagtgagcac acagaatctg    420

ctactcctgc tgactgataa tgaggcctgg aacggattcg tggctgctgc tgaactgccc    480

aggaatgagg cagatgagct ccgtaaagct ctggacaacc ttgcaagaca aatgatcatg    540

aaagacaaaa actggcacga taaaggccag cagtacagaa actggtttct gaaagagttt    600

cctcggttga aaagtgagct tgaggataac ataagaaggc tccgtgccct tgcagatggg    660

gttcagaagg tccacaaagg caccaccatc gccaatgtgg tgtctggctc tctcagcatt    720

tcctctggca tcctgaccct cgtcggcatg ggtctggcac ccttcacaga gggaggcagc    780

cttgtactct tggaacctgg gatggagttg ggaatcacag ccgctttgac cgggattacc    840

agcagtacca tggactacgg aaagaagtgg tggacacaag cccaagccca cgacctggtc    900

atcaaaagcc ttgacaaatt gaaggaggtg agggagtttt tgggtgagaa catatccaac    960

tttctttcct tagctggcaa tacttaccaa ctcacacgag gcattgggaa ggacatccgt   1020

gccctcagac gagccagagc caatcttcag tcagtaccgc atgcctcagc ctcacgcccc   1080

cgggtcactg agccaatctc agctgaaagc ggtgaacagg tggagagggt taatgaaccc   1140

agcatcctgg aaatgagcag aggagtcaag ctcacggatg tggcccctgt aagcttcttt   1200

cttgtgctgg atgtagtcta cctcgtgtac gaatcaaagc acttacatga gggggcaaag   1260

tcagagacag ctgaggagct gaagaaggtg gctcaggagc tggaggagaa gctaaacatt   1320

ctcaacaata attataagat tctgcaggcg gaccaagaac tgtgaccaca gggcagggca   1380
```

```
gccaccagga gagatatgcc tggcaggggc caggacaaaa tgcaaacttt tttttttttc   1440

tgagacagag tcttgctctg tcgccaagtt ggagtgcaat ggtgcgatct cagctcactg   1500

caagctctgc ctcccgtgtt caagcgattc tcctgccttg gcctcccaag tagctgggac   1560

tacaggcgcc taccaccatg cccagctaat tttgtatttt ttaatagaga tggggtttca   1620

ccatgttggc caggatggtc tcgatctcct gacctcttga tctgcccacc ttggcctccc   1680

aaagtgctgg gattacaggc gtgagccatc gcttttgacc caaatgcaaa cattttatta   1740

gggggataaa gagggtgagg taaagtttat ggaactgagt gttagggact ttggcatttc   1800

catagctgag cacagcaggg gaggggttaa tgcagatggc agtgcagcaa ggagaaggca   1860

ggaacattgg agcctgcaat aagggaaaaa tgggaactgg agagtgtggg gaatgggaag   1920

aagcagttta ctttagacta aagaatatat tggggggccg ggtgtagtgg ctcatgcctg   1980

taatccgagc actttgggag gccaaggcgg gcggatcacg aggtcaggag atcgagacca   2040

tcctggctaa cacagtgaaa ccccgtctct actaaaaata caaaaaaatta gccgggcatg   2100

gtggcgggcg cctgtagttc cagctaactg ggcggctgag gcaggagaat ggcgtgaacc   2160

tgggaggtgg agcttgcagt gagccgagat atcgccactg cactccagcc tgggtgacag   2220

agcgagactc catctcaaaa aaaaaaaaaa aaagaatata ttgacggaag aatagagagg   2280

aggcttgaag gaaccagcaa tgagaaggcc aggaaaagaa agagctgaaa atggagaaag   2340

cccaagagtt agaacagttg gatacaggag aagaaacagc ggctccacta cagacccagc   2400

cccaggttca atgtcctccg aagaatgaag tctttccctg gtgatggtcc cctgccctgt   2460

ctttccagca tccactctcc cttgtcctcc tgggggcata tctcagtcag gcagcggctt   2520

cctgatgatg gtcattgggg tggttgtcat gtgatgggtc ccctccaggt tactaaaggg   2580

tgcatgtccc ctgcttgaac actgaagggc aggtggtggg ccatggccat ggtccccagc   2640

tgaggagcag gtgtccctga gaacccaaac ttcccagaga gtatgtgaga accaaccaat   2700

gaaaacagtc ccatcgctct tacccggtaa gtaaacagtc agaaaattag catgaaagca   2760

gtttagcatt gggaggaagc tcagatctct agagctgtct tgtcgccgcc caggattgac   2820

ctgtgtgtaa gtcccaataa actcacctac tcatcaagct ggaaaaaaaa aaaaaaaaaa   2880

aaaaa                                                               2885
```

<210> SEQ ID NO 2
<211> LENGTH: 15454
<212> TYPE: DNA
<213> ORGANISM: Homo sapien

<400> SEQUENCE: 2

```
agaaccagct actcaggagg ctgaggtggg gggatggctt aagcccaggg gtttgaagct     60

gctgtgcgcg atgactgtgg cactgcaatt cagtcttggt gacagactga gaccctgtct    120

caaaaacata accaaaataa ccccaacggc attacaataa atatacaata agcatccaca    180

aggcatgtgt gggagactgt gcttatgccg atggcacggg caggagtaag gcaggcatca    240

ggggaatgtg gatgcacggg aggatgggga gtaatctgca gggtcccata gtatgtcagt    300

ggcaggtctt tctccttgag accacagcag acccccagcc ctgaggatgc gaggcaggtg    360

ggttggatga gagggatctg gatgtctggt ctcaggctgc tcctctaagg gcagcagcaa    420

ggagggtggg gctggactga aggtggaggg gagcgtgttt gctgtgcttg gtcatgagct    480

gctgggaagt tgtgactttc actttccctt tcgaattcct cggtatatct tggggactgg    540
```

-continued

```
aggacctgtc tggttattat acagacgcat aactggaggt gggatccaca cagctcagaa    600
cagctggatc ttgctcagtc tctgccaggg gaagattcct tggtaagttg gggacagttg    660
acctgcctcc atcttattct cacagctttt gtagataagc tgggagaggt taggtgactg    720
gttcagatag acaggaaagt agcggcaaag cctggatttg cacccaggct tgagtctgat    780
tgcttcccct ctcctgctgg gctcttaaac tatagagggt tggggaaaca gctcagatgg    840
gttcacaaag ctccctgggc tcagccctgg ttttgactgc tgagacacga ctgagtgaac    900
ccagaaggaa ggtttgtgtt gggggtgccc atctctttgg gaaatttgaa ggaaccaaag    960
aaggtggagg agaggaggtg acccagatcc cagcctgttc ttatggccag gccacaccaa   1020
ggctggcccc agggtgctgc tgctgaggcc caatgggggc aacagaattt tttttcaggt   1080
acaaggagtt cagaggtcat ctcacccacc ctgagtctga gcaccaactt gtgccaggcc   1140
ctgtggggaa actgaggccc tgggagcgga atgacttgcc cagggtcccg tgtcaggagg   1200
ctgagcaggt agatcatagg actccacgtc tctggccctc acctctgtcc ctctgttcag   1260
acttctgggg tgatggagaa gaaacaggct gtgctgtgtc cctaatggga aacgtggctg   1320
agacagggga gtgagaaggg tgcgttgcag aatggtgcct gtggcatgat gccagctttg   1380
caatcatgag attcaaaagc cacactgtgg aattgtgagt ataactacag gagtgagagc   1440
ttagatctct gtgttcatag aaggagaatc aaacctggaa acttttggat tattaaaatc   1500
aaacattttt gcttcaatat tagagtcaca agggcagatg ttggcctccc ctctgccctc   1560
caagagctgt gtgactctgg gaaattcacc tcccctccca gcctgagtat tttcccctgt   1620
aaaaaacctg atagagctgc caaaagtcca tgaaatcagg ggggtaattt ctgtgaaatc   1680
tgagtcatgg tcttatttgt tcttcaccaa aaagagatga tgaagcctgt aaccccagtg   1740
ctgtgggagg cagaggcggg aggatgactt gaggccagga gttcaagaca gcctgggaaa   1800
cacaggagat gctgtctcta tgaaatcaaa aattaacaaa ttagcccagc atggtagtgt   1860
gtacctgtag tcccagctac tcagaaggtt gaaggaggcg gatcacttga gcccaacaga   1920
tctaggctgc aatgagctag gatggtgtca aagccctgca gcctgggtga cagagcaaaa   1980
ctgtttatta aaaactaaac gaaaggccgg gcgcggtggc tcacgcctgt aatcccagca   2040
ctttgggagg ccaagacagg tggtcacgag gtcaggatat cgagaccatc ctggctaaca   2100
tggtgaaacc ctgtctctac taaaaataca aaaaaattag ccgggtgtcg tggcgggcac   2160
ctgtagtccc agctactcgg gaggctgagg caggagaatg gcgtgaaccc gggaggcaga   2220
gcttgtagcg agcctagatc gccccactgc actccagcct gggtgataga gcgagactcc   2280
atttcaaaaa aaaaatgaaa tgaaaatggt gatttctcag gaggagcaca ctgtctcaac   2340
ccctcttttc ctgctcaagg aggaggccct gcagcgacat ggagggagct gctttgctga   2400
gagtctctgt cctctgcatc tggtgagctt ggctcagagc cctgaggcgg gagggagggc   2460
tccctgtctg ggctgcacaa ttggactggg cttgggctgg gccagggcca tctgggcttc   2520
ttctaggaac caaagtcact tcccggaatt gaccaaccgg cagactcgcc cagggaggac   2580
ccgctgtatc ctagttgagg ctaacggtca atatccggcc tcaatattca gcagaggctc   2640
caggtcaggg tctgagccag gccaacaatg accaaggagg atgggatcca gggtgcagct   2700
cctcacaagt gtcgggggaa tccgaggcac cagctctctc taccctcctg ctcctctgct   2760
ctctcctggt cctcctgtgt cctcatggct catgagatgg tgttgagatg gctcccctgg   2820
cctaggggat cacacagtga acaaagcagg aagaaggcga agggatgccc ctctcctgtc   2880
acccttgtcc cttacagcaa gaagggccca gacgcccctc tgcatactcc cctggtgaac   2940
```

```
tgctgcccag gactgggtcc cccttttacc cttgctgcat ggagtcccca gaagacaaac   3000
atctgtgtgt ctgaaccctg agacaaaggc aggaaaggga aagagggagg cgagtggctt   3060
ttgaggaggg ggctttagta tgagagctgg aggatggaac cccatcaggg ggcccgggaa   3120
ccactgagct gttaaaataa agtctgcaaa caaagaccag ctgctggaag tgggtgtgcc   3180
agggagtgcg cagagacaca cggtgagaaa agaacaatgg taatgcttgg agccgcccct   3240
aactgggatg ggcctgaaat ggtattgtta ttatttatag tatcattatt agtcattttc   3300
atcttatttg taccctccct ctatctctcc tctccacctt ttcctaacat tctatcacca   3360
gttttatgtc ttccattagc aactttgtag ctgtaaataa tttacttaca actttcatat   3420
accctcagtt gtacccagta tttcttaact tccctcttta aaaaaatgat aatattaatc   3480
ctccttctcc ttcgttcagt gcttcacatc ccaactgcta cctttgtgct ttaaattttg   3540
tactaattgg tgttgataac aagtatattt agttctcata tttatatgtt gtgtatatgt   3600
tttggttttt ttttgtctta aacaagagac tactgagagc cagtaagact gaaagaaagg   3660
gcatcttcat atactgctag tttgagtgtg aattggtaca atttgcctgc agtgtggctc   3720
taggtataaa gccttttgag ttgttgatag cctctgacct gctcattcta ctcctacaaa   3780
tatcttaagg aaataatctc aaatgtgggc aaagttttat gcgaagaagg atgttctttg   3840
tagcataatt tatatgagga attagaaaca ccctgaggtc catcagctag ggaaagacag   3900
cagaggggac agggcagcac caggagggct tggcagccac agcaggggct gggctggcat   3960
ctggcaagat ccaggtcttt gtgggacaaa gaatcttaga gaagcaacgg ggacacaggc   4020
tgtccagtgc agcaccagtg aattcaccaa gatgaagagt tgagcacaga gtgtgagaca   4080
aggatttgca atgaggagtc atttaccatg agcgtgtata catgactcaa tattgtatat   4140
ttaagggagt agagcacagt cattgaaaac atggggttga agcagaagtc ctggctctag   4200
cactattgta aaaacactgg caagttccct aacttttgtg gattcctctg tgtttgaatg   4260
ggaaagtggt acccatctcc tggcctgtgt gtgatcatcg aatgagacac atgtaagagg   4320
ctctgcacat cgcagacatg caatacacac tggctatcac cagctagtta tcacacatgc   4380
tcccaggccc tggtcattgt cagaaccttc ctccccatct ctatttctgt gtatagactc   4440
tgtagtttct gtaatgatca gatggctgcc cgtcctctga ttatcttctc ctcatacccc   4500
aacaggatga gtgcactttt ccttggtgtg ggagtgaggg cagaggaagc tggagcgagg   4560
tgagtgtctg caaatagcag atgatggggg ctcagtgata gacaaacaat ctggtttagg   4620
ttggtcttgg tgtttgcttc caccccagag agatttgcag agccccggct gctcaagcaa   4680
gcctccctct gtccactggt ggctcacatt tgatcccaca atttgttttc tcctcctcaa   4740
gggtgcaaca aaacgttcca agtgggacag atactggaga tcctcaaagt aagcccctcg   4800
gtgactgggc tgctggcacc atggacccag gtaggctcac ctcctcttcc ctgctggttc   4860
ctactcgcac ttagaatgga gggtggcacc tccacagctg agtgagcccc agaagaaccc   4920
ggatggacta ggaggccaat gagtctgccc aaagcagcag aagaggtcac gtggagtccc   4980
ccgacccagg ggtctggggg tcatctgcat cctgacctct ccttagggtg acacggccca   5040
ggtgcccact tcctccctac cctggcacct agcaaatgac tcaagtgggg caggacatcc   5100
ttggggaagt ggaatcagcg gggggggggg ggagtgtggg gagagcaggg tccaggagga   5160
gaggagggct gggagaggag gttgaccagc agccccgacc tgtcacctcc cgctctgctc   5220
caagctgacc ctggggtgtt tccacctgag gctggtcccc tccctccagc tcttgccctg   5280
```

-continued

```
ccctagcccc tttgctctga gtggccctgt gggaatgtat cgggcctgat tcagcttcca   5340
gcttaactgg accccggtct gtcctttgcc acatcccctc tgtgtgacct ggcgctcctt   5400
acctcccttc tcctgtacca tgagaataat atttccccat gttgtcttga ggatcaaata   5460
taacacggct acctggcctg gccagtgcct gccacacaat agggcctccc taagggctgg   5520
ttcccatccc ctctactggt cccctgttga ttccaggtgg aagccacccc gtcccccccc   5580
agctgtgtta gggcacccgc cctgccctgc ccatcacaag cacctgctta ccagggatga   5640
ctgcctcagg caggggctga gttcagtcat ctaaaatacc cccggtcaaa gaaaaatctg   5700
aggcccaata gaattttaaa gagttaattg agtaagaaag gattgctgaa ttgggaaaca   5760
gcaaactgga ggaggcttcg tgctatggtg aaaaagtgtc ggagacaagg tttatcgggt   5820
gaatatgaaa ctgcagtaag gacattattt gattggttgc acttacaaaa ctgcctgttt   5880
gggtttacct tgttggaaaa tccctggtca cgttggtgcc agtgtgagtt tagggaggtc   5940
tccgaataca ggtgagaccg gaacttagcc ttgcccaggt tttgatgct gaagagagaa   6000
aaaagtcaaa gcaaaagcaa atcagctttt agtgcaaaac agaagtgcag gctcaggggt   6060
gggagtgcag gcggactcag aagagccagt cgggcccagt ggagtttggg gttcttgtct   6120
ttgctggttt attaaattaa ggtgtggagt aagcataagg atttctggga agaggtgggg   6180
atttcttgga attgggaggg caatgcagtt ttgtaccaaa catgggcata catggaacgg   6240
ctgtggtgcg ggtgggtgtg gggtttagtg agacaaggag ggtatgattg agtgtgaggc   6300
aaaacgtggg tcagacccag cgccgagttg gatctcactg gtcttagctg aattggccac   6360
ttcctgtttg tcaggatcct gtgggcccat cccctccccc tgtccctaca ggtggtttca   6420
gcaactcctt ctgtgtctgt catgtgaacc tgctgcctgg agttcttgtt tcttctgtga   6480
cctcccagta tccacatctc agcatggccc tctgtcagct ggctttaagt tttgtttgta   6540
tctaacagaa gtacccatct gatatgaccc cagttgagtt tcccatagct tgcagtttca   6600
gggggttaca gctgttctaa aggcctcgta ggtattgcct gtccaggaat gtttcagggc   6660
tggtttttgt tttaattttg cttttatatc caccagcccc accacatcaa gaaatacaca   6720
gatttagtgc cagaggttcc ttccatccaa acctgggttt ccttcctcct tttggtgaag   6780
aaggaaaaag aaaaaacaag acaatcgctc gcccagccaa gtcagcattg cgttcatttc   6840
cctaagcccc atttcctcag gagggcttcc tccccttaca gagttgccac ggcaaccaag   6900
tcagctctgc tcaggagccg ccctggacag caaactgggc tgtgctgagt cctgtccaag   6960
acgaggggag ggcagggaag attagaagcc gagagcactc agccgacccc ggaatcctta   7020
cgaagggctg ggctggggga ctgaggaaaa actctccccc caaaacaaga tgatctgtgg   7080
tttaataaca ggcccagctg ggtccagagg tgacagtgga gagccgtgta ccctgagacc   7140
agcctgcaga ggacagaggc aacatggagg tgcctcaagg atcagtgctg agggtcccgc   7200
ccccatgccc cgtcgaagaa ccccctccac tgcccatctg agagtgccca agaccagcag   7260
gaggaatctc ctttgcatgg tagttgtact caatgctgtg gagtttgaga cattattttt   7320
aaactttaaa tagccccaca ggtaagctat aagggagaat gcagagacca caggcatttt   7380
caaaacataa ggagttttaa tgttaaggag tttaaggaga atgtcaaaga aacattggcc   7440
ttggagtcaa atcctgagct tcctgcttga tggttttggg cggtgactct cgctgtctgg   7500
attttacttt cttcatctgt gaattaagaa tgaggtggcc gggcactgtg gctcacgcct   7560
gtaatcccaa catttgggag gccgaggcgg gcagatcaca aggtcaggag atcgagacga   7620
tcctgtctaa cacgatgaaa ccctgtctct actaaaaata caaaaaaaat taccaggcct   7680
```

```
ggtggcaggc gcctgtagtc ccagctactc aggaggctga ggcaggagaa tggcatgaac   7740
ccaggaggca gagcttgcag tgagccaaga tcgcaccact gcactccagc ctgggtgaga   7800
gagcaagact ccatcccccc aaaaaaaaga atgaggtctc ttgtgtgtgc acggcaagaa   7860
acaattttac atcatgcctc agtgcacaca caaatacata ctggtcccca gttccttatc   7920
tgcaattcca taattcccag atccctgcaa accacacgtt ttggtggcag ctgacttcag   7980
gagtaatcct gctctgtact gacttgagtt ctttgtagac ctaccattat tttttacatt   8040
taatgtgaat atttgcttgt ttcactgttg aaacatgtgt gggtgtgatt acagggagca   8100
gtccagcctc tgctgggaat ggtcaggaat ataccatatg caccccgtgt cctttctaaa   8160
atagtggaaa ttctgaatgc ctaaacacat ctggattcca ggaatttaca ttaagggata   8220
tatatttgaa ataacccaca aaaacaatac tcacccctgc tacgcttggt acactctgat   8280
attttcaaat tgattttctt tttaaaatgc tgcttttgaa ccaataattt cataacccaa   8340
tgatgtgttg atattcacat tttgaagaca ctggtataaa gtgtttgacc caacaggcat   8400
gtggcagatg gaagtgatca ctgggatgtt tccacttcct tggcctggaa ggctcacttc   8460
atgttggtgc tgagctgaaa aggattcatt cctctccaaa gcaccatggc actcccctgg   8520
tgtttcaatg ttctcaggct gccatagtaa aatatcacag gctgggtgac ttcaacatct   8580
ggcttttatt ttctcacaga tccagaggca agaagtccaa ggtgaaggtg ccaaaagggt   8640
tggagtctgg ggaggactct cttgctggct tatggaagct gcctttgcac tgtgtgctca   8700
cacagtcttc ttgtgtccct ttctgttctt acaataggac actagccctc taatagaatt   8760
agagccctac ccttgtgatc tcattcagtc ttaattgctt ccttaaaggc cagatctcca   8820
aatgtagtca cctgagttta aagcttcagc atatgaattt tgggggcaca caattccctc   8880
tatagcacta atgactccat aaaacaagtc ccacatcaca gctgtccagg aaaattaaca   8940
tgtagtcatc tcttatgcaa tggctgttat gcactcccac actttcctcc aaccttatcc   9000
tttcttcttt ccaactagag agcagtatct ttattgagga tgccattaag tatttcaagg   9060
aaaaagtgag cacacagaat ctgctactcc tgctgactga taatgaggcc tggaacggat   9120
tcgtggctgc tgctgaactg cccaggtaag ctccatgggg ttacctccat tgggcactcc   9180
ggcgatgcca cccagctctc ccctgggcta gttttccctg acaggcacac ctcctccagg   9240
cagcccccctc tgctgggctt gaggatgacc ttcttggcac tccaggaaga atatttcctc   9300
catgtccttc gctggcagtg agtagcctca ggctgagggg ataggaagcc cacaggaaca   9360
gggtcatttc tgccatctgc tggtgatggg aactttgcca gttactttct cactttcagc   9420
ctttcttcat caatggagtt ttattgtgag aaaaatgaga tcgtgcatgt aaagtgctta   9480
gcataatgac tgacacacag taggtgcaca gttaacgtta acatcttaca agcttggtgg   9540
aaacagaacc agggttaagg atcttcttct tgaagatggg agcccagcag gacttgacct   9600
ttgggacaag tcagaaaaat cctgacctaa ccaatgtgtg ttcctgggga tgctggctgg   9660
agcccttttt ctcatctgag gaattccata aacacggcag gacccttctg ctggtccagg   9720
atgccgagag gctggagtgg agttgcacag cgctgggtct ctttccagct ctgtctgtgt   9780
ccagtccctg ggctctgggc ttatgtcaga gactggaaac tgtcatcagt ctaataggaa   9840
tagcaactca atgtgatagg agtgtggtga aggccttaga ggcaactcca ggtcaaaggt   9900
ggggaaccaa caccaagatc ctgcccaaag gcccagagag accgggatca gcgtcagagc   9960
ctggagtcag gatggagcaa gagtcagcct tggttgtagg acaagcagga aggctggggc  10020
```

-continued accagggctg ggactagggt gtggaaagag aggcaccaag ggcttgaaac ttaaggaggt 10080
catgaacttg cagaggacat gtgagtggga gagggatatt tcttccctgt ctggatgatc 10140
ccaacactca tgggcatata gggtcatggt tgcctgtgtc tctcacacca cgccttggaa 10200
ctggcaagtt ctgggctacc ctttgagacc ttcttctctt ctacacagag aaacccctga 10260
cattgacaag cagtatgtct tagtgaccat tttcatagta gaattagttg ctgccaattt 10320
gtgtaatttc agggatactg agcagactca caacttccca accaaggagg aaaacacttc 10380
ctctaccatc ttgtccaaat tcaggtcttt tcagcattag caatttatat aggtggttct 10440
gaaagtgttt tgaatcttct agaggttcca taaaattgca aatggccttg gtgtgcacac 10500
aggtgaagct gtcactacta aggcatcagt taggctggtg acacctgcga gtgagacctg 10560
gaaggttggg ggtgcaggtg gtaggtcagg aggcagtaag gtggctggag cgtccatgtg 10620
gagccagaat gaatagccag atctcccact ccagtcagct ggggcagtgg ccagaaccag 10680
tagccttcag ccaggtgaaa gggcatgagg cattggaagg gagcagatgc caggcaaagt 10740
gaactcctgt ctctccgggg ttttgttttt gtttgaattc aaagtactca gagatagcca 10800
gactgcaatg tctgagggca cccttacctt tgacaccacc tgcaaattta aggggatttc 10860
taaatccatc ctttgatttt gtaattcact ggaaggactc acataactca ctgaaaactg 10920
ctatttcaca attgtggttg atcacacgga aagaacacag attaaaatca gcctaagaaa 10980
gagacacacg gggcagagtt tgggagggtt ttaagtgtga agcttcattg tcctcaggac 11040
gctgtgttct cctgtgtgaa tgtgggacaa aacacatgcg gtgttgccaa ccagggaagc 11100
tcacccagtt aaggaaaaat tcctgtgaat cacattaaac cagaaatgaa gcctttttc 11160 aggattgttg ttacagggga gggagactga gcccagctcc aaatatagta aagacagagg 11220
gggagtcaca gccaacacca gggtgggggc gggagatgga acaggactga taggagacac 11280
cagagtgggg ggttcctgct aaattggcct aacaggattc tcactaaagg caggtcagac 11340
actcacccat caatggtggg ggtgaagagc ataatcagat agcaaagcgt aatcagacag 11400
caagggggga agaccctccc taaactgact tggggagatt cttgctgagc tgggtggtgc 11460
aggtccagca agcagtgggt ggctgtggaa ggccaaggtc ggcgcctagt ggagaagagg 11520
ctcagaagag cccagctgga gttggtcaag gagaaagtcc ttctttctca acccatgcct 11580
tagtgtccag agtatctgct ggggctggat cacaagctgc cctcatggct gacctggagt 11640
ctccagcccc tccctgaggt ctaacccctt tagtccccgg gtcctctggg atcaggaaag 11700
acaccaaata gccccaaacc ccatcatcca tcagattcct atacggtccc gtggccaaat 11760
caccaggcaa agacagatgt tcctaccagg caggacattc caggggcctg gagatcactt 11820
cccaggagct gaggacaaag ggaaggcctc tctttgggta aagttcatgc ttcactttcc 11880
tgccatcctg ggaataaggt ctctttgtct cactctcact gctctttgtt catctgcaga 11940
gttttccctc tccaaacact ttggcagtca cggtgttgac ctgcccttga atgaggaggc 12000
atctttatca aacacctacc atgaaagagc atctgagatg cctttaagat atttatttcc 12060
atatggaata aatattgagg agtatctatg atgaacaaaa tgtgtttgag tttgaaagat 12120
aattaattcc atttgtaaaa tttgtttcta tttgatcgat agtgaaagct ctgcaattta 12180
cacaggatag agatcacatg gagctcattt cacagacagg gaaactgcat ttcttttttt 12240 ttttttttt tttgagttgg agtcttgctc tgtcgcccaa gctggagtgc agtggcgcga 12300
tctcggctca ctgcaagctc tgcctcccgg ttcaagcaat tctcctgcct cagcctcctg 12360
agtagctggg actacaggcg cccaccacca cgcccggcta attttttgaa tttttggtag 12420
agacagggtt tcaccgtatt agtcaggatg gtctcaatct cctgaccttg tgatccaccc 12480
gccttggcct cccaaagtgc tgggattaca ggtgtgagcc accacaccga gccaaaactg 12540
catttcttaa tcctttaacc tttccttgtg caggaatgag gcagatgagc tccgtaaagc 12600
tctggacaac cttgcaagac aaatgatcat gaaagacaaa aactggcacg ataaaggcca 12660
gcagtacaga aactggtttc tgaaagagtt tcctcggttg aaaagtgagc ttgaggataa 12720
cataagaagg ctccgtgccc ttgcagatgg ggttcagaag gtccacaaag gcaccaccat 12780
cgccaatgtg gtgtctggct ctctcagcat ttcctctggc atcctgaccc tcgtcggcat 12840
gggtctggca cccttcacag agggaggcag ccttgtactc ttggaacctg ggatggagtt 12900
gggaatcaca gccgctttga ccgggattac cagcagtacc atggactacg gaaagaagtg 12960
gtggacacaa gcccaagccc acgacctggt catcaaaagc cttgacaaat tgaaggaggt 13020
gagggagttt ttgggtgaga acatatccaa ctttctttcc ttagctggca atacttacca 13080
actcacacga ggcattggga aggacatccg tgccctcaga cgagccagag ccaatcttca 13140
gtcagtaccg catgcctcag cctcacgccc ccgggtcact gagccaatct cagctgaaag 13200
cggtgaacag gtggagaggg ttaatgaacc cagcatcctg gaaatgagca gaggagtcaa 13260
gctcacggat gtggcccctg taagcttctt tcttgtgctg gatgtagtct acctcgtgta 13320
cgaatcaaag cacttacatg agggggcaaa gtcagagaca gctgaggagc tgaagaaggt 13380
ggctcaggag ctggaggaga agctaaacat tctcaacaat aattataaga ttctgcaggc 13440
ggaccaagaa ctgtgaccac agggcagggc agccaccagg agagatatgc ctggcagggg 13500
ccaggacaaa atgcaaactt tttttttttt ctgagacaga gtcttgctct gtcgccaagt 13560
tggagtgcaa tggtgcgatc tcagctcact gcaagctctg cctcccgtgt tcaagcgatt 13620
ctcctgcctt ggcctcccaa gtagctggga ctacaggcgc ctaccaccat gcccagctaa 13680
tttttgtatt tttaatagag atggggtttc accatgttgg ccaggatggt ctcgatctcc 13740
tgacctcttg atctgcccac cttggcctcc caaagtgctg ggattacagg cgtgagccat 13800
cgcttttgac ccaaatgcaa acattttatt agggggataa agagggtgag gtaaagttta 13860
tggaactgag tgttagggac tttggcattt ccatagctga gcacagcagg ggaggggtta 13920
atgcagatgg cagtgcagca aggagaaggc aggaacattg gagcctgcaa taagggaaaa 13980
atgggaactg gagagtgtgg ggaatgggaa gaagcagttt actttagact aaagaatata 14040
ttggggggcc gggtgtagtg gctcatgcct gtaatccgag cactttggga ggccaaggcg 14100
ggcggatcac gaggtcagga gatcgagacc atcctggcta acacagtgaa accccgtctc 14160
tactaaaaat acaaaaaatt agccgggcat ggtggcgggc gcctgtagtt ccagctaact 14220
gggcggctga ggcaggagaa tggcgtgaac ctgggaggtg gagcttgcag tgagccgaga 14280
tatcgccact gcactccagc ctgggtgaca gagcgagact ccatctcaaa aaaaaaaaaa 14340
aaaagaatat attgacggaa gaatagagag gaggcttgaa ggaaccagca atgagaaggc 14400
caggaaaaga aagagctgaa aatggagaaa gcccaagagt tagaacagtt ggatacagga 14460
gaagaaacag cggctccact acagacccag ccccaggttc aatgtcctcc gaagaatgaa 14520
gtctttccct ggtgatggtc ccctgccctg tctttccagc atccactctc ccttgtcctc 14580
ctgggggcat atctcagtca ggcagcggct tcctgatgat ggtcattggg gtggttgtca 14640
tgtgatgggt cccctccagg ttactaaagg gtgcatgtcc cctgcttgaa cactgaaggg 14700
caggtggtgg gccatggcca tggtccccag ctgaggagca ggtgtccctg agaacccaaa 14760

```
cttcccagag agtatgtgag aaccaaccaa tgaaaacagt cccatcgctc ttacccggta  14820
agtaaacagt cagaaaatta gcatgaaagc agtttagcat tgggaggaag ctcagatctc  14880
tagagctgtc ttgtcgccgc ccaggattga cctgtgtgta agtcccaata aactcaccta  14940
ctcatcaagc tggacttgtt cgagtcattc tttggtctct cagctctttc caagctttgg  15000
gggccatcag tctcaagttt ttctcgtaat ggtggtgatg gtggttgtga tggcagcaga  15060
gtggtggggg ccttggcaag tggtcggtgc tcttccagac caggggacac cgatggaccg  15120
atgaagttcc aggggaactt gaagtgctgt gttggaaaga ggttaatttg ggaagaaagg  15180
aaaaatgaaa ggagatgcca ggaacaggtc aaggaacctt gaggtgtgtc caggagttca  15240
accccgcttg tggtcacgag acctcgcctc tctgagcctc agtttcctca tcagctgtag  15300
aagggtacct ggacaaggtg atgtctcagg tccacccagc tctccccatc ttgtgtcctg  15360
gagacttggg tccaatcagc actgactgat ggctgtgcct ttgtggtgcc gatggaggct  15420
cccctgggct ctgggtgcct gacttccctt cctc                              15454
```

<210> SEQ ID NO 3
<211> LENGTH: 2831
<212> TYPE: DNA
<213> ORGANISM: Homo sapien

<400> SEQUENCE: 3

```
gactttcact ttccctttcg aattcctcgg tatatcttgg ggactggagg acctgtctgg     60
ttattataca gacgcataac tggaggtggg atccacacag ctcagaacag ctggatcttg    120
ctcagtctct gccaggggaa gattccttgg aggaggccct gcagcgacat ggagggagct    180
gctttgctga gagtctctgt cctctgcatc tgggtgcaac aaaacgttcc aagtgggaca    240
gatactggag atcctcaaag taagcccctc ggtgactggg ctgctggcac catggaccca    300
gagagcagta tctttattga ggatgccatt aagtatttca aggaaaaagt gagcacacag    360
aatctgctac tcctgctgac tgataatgag gcctggaacg gattcgtggc tgctgctgaa    420
ctgcccagga atgaggcaga tgagctccgt aaagctctgg acaaccttgc aagacaaatg    480
atcatgaaag acaaaaactg gcacgataaa ggccagcagt acagaaactg gtttctgaaa    540
gagtttcctc ggttgaaaag tgagcttgag gataacataa gaaggctccg tgcccttgca    600
gatggggttc agaaggtcca caaaggcacc accatcgcca atgtggtgtc tggctctctc    660
agcatttcct ctggcatcct gaccctcgtc ggcatgggtc tggcaccctt cacagaggga    720
ggcagccttg tactcttgga acctgggatg gagttgggaa tcacagccgc tttgaccggg    780
attaccagca gtaccatgga ctacggaaag aagtggtgga cacaagccca agcccacgac    840
ctggtcatca aaagccttga caaattgaag gaggtgaggg agtttttggg tgagaacata    900
tccaactttc tttccttagc tggcaatact taccaactca cacgaggcat tgggaaggac    960
atccgtgccc tcagacgagc cagagccaat cttcagtcag taccgcatgc ctcagcctca   1020
cgcccccggg tcactgagcc aatctcagct gaaagcggtg aacaggtgga gagggttaat   1080
gaacccagca tcctggaaat gagcagagga gtcaagctca cggatgtggc ccctgtaagc   1140
ttctttcttg tgctggatgt agtctacctc gtgtacgaat caaagcactt acatgagggg   1200
gcaaagtcag agacagctga ggagctgaag aaggtggctc aggagctgga ggagaagcta   1260
aacattctca acaataatta taagattctg caggcggacc aagaactgtg accacagggc   1320
agggcagcca ccaggagaga tatgcctggc aggggccagg acaaaatgca aactttttttt   1380
tttttctgag acagagtctt gctctgtcgc caagttggag tgcaatggtg cgatctcagc   1440
```

tcactgcaag ctctgcctcc cgtgttcaag cgattctcct gccttggcct cccaagtagc 1500
tgggactaca ggcgcctacc accatgccca gctaattttt gtatttttaa tagagatggg 1560
gtttcaccat gttggccagg atggtctcga tctcctgacc tcttgatctg cccaccttgg 1620
cctcccaaag tgctgggatt acaggcgtga gccatcgctt ttgacccaaa tgcaaacatt 1680
ttattagggg gataaagagg gtgaggtaaa gtttatggaa ctgagtgtta gggactttgg 1740
catttccata gctgagcaca gcaggggagg ggttaatgca gatggcagtg cagcaaggag 1800
aaggcaggaa cattggagcc tgcaataagg gaaaaatggg aactggagag tgtggggaat 1860
gggaagaagc agtttacttt agactaaaga atatattggg gggccgggtg tagtggctca 1920
tgcctgtaat ccgagcactt tgggaggcca aggcgggcgg atcacgaggt caggagatcg 1980
agaccatcct ggctaacaca gtgaaacccc gtctctacta aaaatacaaa aaattagccg 2040
ggcatggtgg cgggcgcctg tagttccagc taactgggcg gctgaggcag gagaatggcg 2100
tgaacctggg aggtggagct tgcagtgagc cgagatatcg ccactgcact ccagcctggg 2160
tgacagagcg agactccatc tcaaaaaaaa aaaaaaaaag aatatattga cggaagaata 2220
gagaggaggc ttgaaggaac cagcaatgag aaggccagga aaagaaagag ctgaaaatgg 2280
agaaagccca agagttagaa cagttggata caggagaaga aacagcggct ccactacaga 2340
cccagcccca ggttcaatgt cctccgaaga atgaagtctt tccctggtga tggtcccctg 2400
ccctgtcttt ccagcatcca ctctcccttg tcctcctggg ggcatatctc agtcaggcag 2460
cggcttcctg atgatggtca ttggggtggt tgtcatgtga tgggtcccct ccaggttact 2520
aaagggtgca tgtcccctgc ttgaacactg aagggcaggt ggtgggccat ggccatggtc 2580
cccagctgag gagcaggtgt ccctgagaac ccaaacttcc cagagagtat gtgagaacca 2640
accaatgaaa acagtcccat cgctcttacc cggtaagtaa acagtcagaa aattagcatg 2700
aaagcagttt agcattggga ggaagctcag atctctagag ctgtcttgtc gccgcccagg 2760
attgacctgt gtgtaagtcc caataaactc acctactcat caagctggaa aaaaaaaaaa 2820
aaaaaaaaaa a 2831

<210> SEQ ID NO 4
<211> LENGTH: 2924
<212> TYPE: DNA
<213> ORGANISM: Homo sapien

<400> SEQUENCE: 4
gactttcact ttccctttcg aattcctcgg tatatcttgg ggactggagg acctgtctgg 60
ttattataca gacgcataac tggaggtggg atccacacag ctcagaacag ctggatcttg 120
ctcagtctct gccaggggaa gattccttgg aggagcacac tgtctcaacc cctcttttcc 180
tgctcaagga ggaggccctg cagcgacatg gagggagctg ctttgctgag agtctctgtc 240
ctctgcatct ggatgagtgc acttttcctt ggtgtgggag tgagggcaga ggaagctgga 300
gcgagggtgc aacaaaacgt tccaagtggg acagatactg gagatcctca aagtaagccc 360
ctcggtgact gggctgctgg caccatggac ccagagagca gtatctttat tgaggatgcc 420
attaagtatt tcaaggaaaa agtgagcaca cagaatctgc tactcctgct gactgataat 480
gaggcctgga acggattcgt ggctgctgct gaactgccca ggaatgaggc agatgagctc 540
cgtaaagctc tggacaacct tgcaagacaa atgatcatga aagacaaaaa ctggcacgat 600
aaaggccagc agtacagaaa ctggtttctg aaagagtttc ctcggttgaa aagtgagctt 660

-continued

```
gaggataaca taagaaggct ccgtgccctt gcagatgggg ttcagaaggt ccacaaaggc    720
accaccatcg ccaatgtggt gtctggctct ctcagcattt cctctggcat cctgaccctc    780
gtcggcatgg gtctggcacc cttcacagag ggaggcagcc ttgtactctt ggaacctggg    840
atggagttgg gaatcacagc cgctttgacc gggattacca gcagtaccat ggactacgga    900
aagaagtggt ggacacaagc ccaagcccac gacctggtca tcaaaagcct tgacaaattg    960
aaggaggtga gggagttttt gggtgagaac atatccaact ttctttcctt agctggcaat   1020
acttaccaac tcacacgagg cattgggaag gacatccgtg ccctcagacg agccagagcc   1080
aatcttcagt cagtaccgca tgcctcagcc tcacgccccc gggtcactga gccaatctca   1140
gctgaaagcg gtgaacaggt ggagagggtt aatgaaccca gcatcctgga aatgagcaga   1200
ggagtcaagc tcacggatgt ggcccctgta agcttctttc ttgtgctgga tgtagtctac   1260
ctcgtgtacg aatcaaagca cttacatgag gggggcaaagt cagagacagc tgaggagctg   1320
aagaaggtgg ctcaggagct ggaggagaag ctaaacattc tcaacaataa ttataagatt   1380
ctgcaggcgg accaagaact gtgaccacag ggcagggcag ccaccaggag agatatgcct   1440
ggcaggggcc aggacaaaat gcaaactttt tttttttct gagacagagt cttgctctgt    1500
cgccaagttg gagtgcaatg gtgcgatctc agctcactgc aagctctgcc tcccgtgttc   1560
aagcgattct cctgccttgg cctcccaagt agctgggact acaggcgcct accaccatgc   1620
ccagctaatt tttgtatttt taatagagat ggggtttcac catgttggcc aggatggtct   1680
cgatctcctg acctcttgat ctgcccacct tggcctccca aagtgctggg attacaggcg   1740
tgagccatcg cttttgaccc aaatgcaaac attttattag ggggataaag agggtgaggt   1800
aaagtttatg gaactgagtg ttagggactt tggcatttcc atagctgagc acagcagggg   1860
aggggttaat gcagatggca gtgcagcaag gagaaggcag gaacattgga gcctgcaata   1920
agggaaaaat gggaactgga gagtgtgggg aatgggaaga agcagtttac tttagactaa   1980
agaatatatt ggggggccgg gtgtagtggc tcatgcctgt aatccgagca ctttgggagg   2040
ccaaggcggg cggatcacga ggtcaggaga tcgagaccat cctggctaac acagtgaaac   2100
cccgtctcta ctaaaaatac aaaaaattag ccgggcatgg tggcgggcgc ctgtagttcc   2160
agctaactgg gcggctgagg caggagaatg gcgtgaacct gggaggtgga gcttgcagtg   2220
agccgagata tcgccactgc actccagcct gggtgacaga gcgagactcc atctcaaaaa   2280
aaaaaaaaaa aagaatatat tgacggaaga atagagagga ggcttgaagg aaccagcaat   2340
gagaaggcca ggaaaagaaa gagctgaaaa tggagaaagc ccaagagtta gaacagttgg   2400
atacaggaga agaaacagcg gctccactac agacccagcc ccaggttcaa tgtcctccga   2460
agaatgaagt ctttccctgg tgatggtccc ctgccctgtc tttccagcat ccactctccc   2520
ttgtcctcct gggggcatat ctcagtcagg cagcggcttc ctgatgatgg tcattggggt   2580
ggttgtcatg tgatgggtcc cctccaggtt actaaagggt gcatgtcccc tgcttgaaca   2640
ctgaagggca ggtggtgggc catggccatg gtccccagct gaggagcagg tgtccctgag   2700
aacccaaact tcccagagag tatgtgagaa ccaaccaatg aaaacagtcc catcgctctt   2760
acccggtaag taaacagtca gaaaattagc atgaaagcag tttagcattg ggaggaagct   2820
cagatctcta gagctgtctt gtcgccgccc aggattgacc tgtgtgtaag tcccaataaa   2880
ctcacctact catcaagctg gaaaaaaaaa aaaaaaaaaa aaaa                    2924

<210> SEQ ID NO 5
<211> LENGTH: 3039
```

<212> TYPE: DNA
<213> ORGANISM: Homo sapien

<400> SEQUENCE: 5

```
gactttcact ttccctttcg aattcctcgg tatatcttgg ggactggagg acctgtctgg     60
ttattataca gacgcataac tggaggtggg atccacacag ctcagaacag ctggatcttg    120
ctcagtctct gccaggggaa gattccttga cttctggggt gatggagaag aaacaggctg    180
tgctgtgtcc ctaatgggaa acgtggctga gacaggggag tgagaagggt gcgttgcaga    240
atggtgcctg tggcatgatg ccagctttgc aatcatgaga ttcaaaagcc acactgtgga    300
attgaggagg ccctgcagcg acatggaggg agctgctttg ctgagagtct ctgtcctctg    360
catctggatg agtgcacttt tccttggtgt gggagtgagg gcagaggaag ctggagcgag    420
ggtgcaacaa aacgttccaa gtgggacaga tactggagat cctcaaagta agcccctcgg    480
tgactgggct gctggcacca tggacccaga gagcagtatc tttattgagg atgccattaa    540
gtatttcaag gaaaaagtga gcacacagaa tctgctactc ctgctgactg ataatgaggc    600
ctggaacgga ttcgtggctg ctgctgaact gcccaggaat gaggcagatg agctccgtaa    660
agctctggac aaccttgcaa gacaaatgat catgaaagac aaaaactggc acgataaagg    720
ccagcagtac agaaactggt ttctgaaaga gtttcctcgg ttgaaaagtg agcttgagga    780
taacataaga aggctccgtg cccttgcaga tggggttcag aaggtccaca aaggcaccac    840
catcgccaat gtggtgtctg gctctctcag catttcctct ggcatcctga ccctcgtcgg    900
catgggtctg gcacccttca cagagggagg cagccttgta ctcttggaac ctgggatgga    960
gttgggaatc acagccgctt tgaccgggat taccagcagt accatggact acggaaagaa   1020
gtggtggaca caagcccaag cccacgacct ggtcatcaaa agccttgaca aattgaagga   1080
ggtgagggag tttttgggtg agaacatatc caactttctt tccttagctg gcaatactta   1140
ccaactcaca cgaggcattg ggaaggacat ccgtgccctc agacgagcca gagccaatct   1200
tcagtcagta ccgcatgcct cagcctcacg cccccgggtc actgagccaa tctcagctga   1260
aagcggtgaa caggtggaga gggttaatga acccagcatc ctggaaatga gcagaggagt   1320
caagctcacg gatgtggccc ctgtaagctt ctttcttgtg ctggatgtag tctacctcgt   1380
gtacgaatca aagcacttac atgagggggc aaagtcagag acagctgagg agctgaagaa   1440
ggtggctcag gagctggagg agaagctaaa cattctcaac aataattata agattctgca   1500
ggcggaccaa gaactgtgac cacagggcag ggcagccacc aggagagata tgcctggcag   1560
gggccaggac aaaatgcaaa cttttttttt tttctgagac agagtcttgc tctgtcgcca   1620
agttggagtg caatggtgcg atctcagctc actgcaagct ctgcctcccg tgttcaagcg   1680
attctcctgc cttggcctcc caagtagctg ggactacagg cgcctaccac catgcccagc   1740
taatttttgt atttttaata gagatggggt ttcaccatgt tggccaggat ggtctcgatc   1800
tcctgacctc ttgatctgcc caccttggcc tcccaaagtg ctgggattac aggcgtgagc   1860
catcgctttt gacccaaatg caaacatttt attaggggga taaagagggt gaggtaaagt   1920
ttatggaact gagtgttagg gactttggca tttccatagc tgagcacagc aggggagggg   1980
ttaatgcaga tggcagtgca gcaaggagaa ggcaggaaca ttggagcctg caataaggga   2040
aaaatgggaa ctggagagtg tggggaatgg gaagaagcag tttactttag actaaagaat   2100
atattggggg gccgggtgta gtggctcatg cctgtaatcc gagcactttg ggaggccaag   2160
gcgggcggat cacgaggtca ggagatcgag accatcctgg ctaacacagt gaaaccccgt   2220
```

ctctactaaa aatacaaaaa attagccggg catggtggcg ggcgcctgta gttccagcta 2280
actgggcggc tgaggcagga gaatggcgtg aacctgggag gtggagcttg cagtgagccg 2340
agatatcgcc actgcactcc agcctgggtg acagagcgag actccatctc aaaaaaaaaa 2400
aaaaaaagaa tatattgacg gaagaataga gaggaggctt gaaggaacca gcaatgagaa 2460
ggccaggaaa agaaagagct gaaaatggag aaagcccaag agttagaaca gttggataca 2520
ggagaagaaa cagcggctcc actacagacc cagccccagg ttcaatgtcc tccgaagaat 2580
gaagtctttc cctggtgatg gtcccctgcc ctgtctttcc agcatccact ctcccttgtc 2640
ctcctggggg catatctcag tcaggcagcg gcttcctgat gatggtcatt ggggtggttg 2700
tcatgtgatg ggtcccctcc aggttactaa agggtgcatg tcccctgctt gaacactgaa 2760
gggcaggtgg tgggccatgg ccatggtccc cagctgagga gcaggtgtcc ctgagaaccc 2820
aaacttccca gagagtatgt gagaaccaac caatgaaaac agtcccatcg ctcttacccg 2880
gtaagtaaac agtcagaaaa ttagcatgaa agcagtttag cattgggagg aagctcagat 2940
ctctagagct gtcttgtcgc cgcccaggat tgacctgtgt gtaagtccca ataaactcac 3000
ctactcatca agctggaaaa aaaaaaaaaa aaaaaaaaa 3039

<210> SEQ ID NO 6
<211> LENGTH: 541
<212> TYPE: DNA
<213> ORGANISM: Homo sapien

<400> SEQUENCE: 6
tggactgaag gtggagggga gcgtgtttgc tgtgcttggt catgagctgc tgggaagttg 60
tactttcact ttccctttcg aattcctcgg tatatcttgg ggactggagg acctgtctgg 120
ttattataca gacgcataac tggaggtggg atccacacag ctcagaacag ctggatcttg 180
ctcagtctct gccaggggaa gattccttgg aggaggccct gcagcgacat ggagggagct 240
gctttgctga gagtctctgt cctctgcatc tggatgagtg cacttttcct tggtgtggga 300
gtgagggcag aggaagctgg agcgagggtg caacaaaacg ttccaagtgg gacagatact 360
ggagatcctc aaagtaagcc cctcggtgac tgggctgctg gcaccatgga cccagagagc 420
agtatcttta ttgaggatgc cattaagtat ttcaaggaaa aagtgagcac acagaatctg 480
ctactcctgc tgactgataa tgaggcctgg aacggattcg tggctgctgc tgaactgccc 540
a 541

<210> SEQ ID NO 7
<211> LENGTH: 1784
<212> TYPE: DNA
<213> ORGANISM: Homo sapien

<400> SEQUENCE: 7
aaaaattttc cctttcgaat tcctcggtat atcttgggga ctggaggacc tgtctggtta 60
ttatacagac gcataactgg aggtgggatc cacacagctc agaacagctg gatcttgctc 120
agtctctgcc aggggaagat tccttggagg aggccctgca gcgacatgga gggagctgct 180
ttgctgagag tctctgtcct ctgcatctgg atgagtgcac ttttccttgg tgtgggagtg 240
agggcagagg aagctggagc gagggtgcaa caaaacgttc caagtgggac agatactgga 300
gatcctcaaa gtaagcccct cggtgactgg gctgctggca ccatggaccc aggcccagct 360
gggtccagag gtgacagtgg agagccgtgt accctgagac cagcctgcag aggacagagg 420
caacatggag gtgcctcaag gatcagtgct gagggtcccg cccccatgcc ccgtcgaaga 480

```
acccccctcca ctgcccatct gagagtgccc aagaccagca ggaggaatct cctttgcatg    540
agagcagtat ctttattgag gatgccatta agtatttcaa ggaaaaagtg agcacacaga    600
atctgctact cctgctgact gataatgagg cctggaacgg attcgtggct gctgctgaac    660
tgcccaggaa tgaggcagat gagctccgta aagctctgga caaccttgca agacaaatga    720
tcatgaaaga caaaaactgg cacgataaag gccagcagta cagaaactgg tttctgaaag    780
agtttcctcg gttgaaaagt aagcttgagg ataacataag aaggctccgt gcccttgcag    840
atggggttca gaaggtccac aaaggcacca ccatcgccaa tgtggtgtct ggctctctca    900
gcatttcctc tggcatcctg accctcgtcg gcatgggtct ggcacccttc acagagggag    960
gcagccttgt actcttggaa cctgggatgg agttgggaat cacagcagct ttgaccggga   1020
ttaccagcag taccatagac tacggaaaga agtggtggac acaagcccaa gcccacgacc   1080
tggtcatcaa aagccttgac aaattgaagg aggtgaagga gtttttgggt gagaacatat   1140
ccaactttct ttccttagct ggcaatactt accaactcac acgaggcatt gggaaggaca   1200
tccgtgccct cagacgagcc agagccaatc ttcagtcagt accgcatgcc tcagcctcac   1260
gcccccgggt cactgagcca atctcagctg aaagcggtga acaggtggag agagttaatg   1320
aacccagcat cctggaaatg agcagaggag tcaagctcac ggatgtggcc cctgtaagct   1380
tctttcttgt gctggatgta gtctacctcg tgtacgaatc aaagcactta catgaggggg   1440
caaagtcaga gacagctgag gagctgaaga aggtggctca ggagctggag gagaagctaa   1500
acattctcaa caataattat aattctgcag gcggaccaag aactgtgacc acagggcagg   1560
gcagccacca ggagagatat gcctggcagg ggccaggaca aaatgcaaac ttttttttt    1620
ttctgagaca gagtcttgct ctgtcgccaa gttggagtgc aatggtgcga tctcggctca   1680
ctgcaagctc tgcctcccgt gttcaagcga ttctcctgcc ttggcctccc aagtagctgg   1740
gactacaggc gcctaccacc atgcccagct aatttttgta tttt                  1784
```

<210> SEQ ID NO 8
<211> LENGTH: 210
<212> TYPE: DNA
<213> ORGANISM: Homo sapien

<400> SEQUENCE: 8

```
tggactgaag gtggagggga gcgtgtttgc tgtgcttggt catgagctgc tgggaagttg     60
tgactttcac tttccctttc gaattcctcg gtatatcttg gggactggag gacctgtctg    120
gttattatac agacgcataa ctggaggtgg gatccacaca gctcagaaca gctggatctt    180
gctcagtctc tgccagggga agattccttg                                     210
```

<210> SEQ ID NO 9
<211> LENGTH: 21000
<212> TYPE: DNA
<213> ORGANISM: Homo sapien

<400> SEQUENCE: 9

```
caaaagaaac tagagaatgc ctgttattgg attctagctt tctccattgt tttctagccg     60
tattgtttgt ccacagttta tctggactac atactgaatt ctttcctggc cacaagtctc    120
caaactaata ttttgctttt ctttttctct catttttctg acttggaatc accagaaatc    180
caaactgtgc ttttcttaaa gtcctgcaaa ctgaagcttg aaaactgtgt tatagtgaag    240
gaagagaaag accctctcat attattttta tattgttttg tactcagtac ctgttttaag    300
```

-continued

```
aaaaaacaac aaggaagtaa aaccaaagac aggcagcccg gcgccaggcc cgaaaccagg    360
cctgggcccg cctggcctaa acccattagt taaaaatcaa cttatgattc agaagccgat    420
gttattcata gattccttac attatgtaga agaacattgt gaaactccct gccctgttct    480
gttcccccct gacgacctgt gtatgcagcc cctgtcacgt accgcctgct tgctcaaatc    540
aatcatgacc ctttcgtgtg aaatctttag tgttgtgagc ccttaaaagg gacagaaatt    600
gtgcactcag ggagctcgga ttttaaggca gtagcttgcc gatgctccca gctgaataaa    660
gcccttcctt ctactactcg gtgtctgaga ggttttgtct gcagctcgtc ctgctacaat    720
agaattcaga ccaaactcgt gaccagagac tcatttgctt ctacagtgtt ttgtccaaaa    780
gatgttgaag aacggccagg cgcagtggct cacgcctgta atcccagcgc tttcggaggc    840
cgaggcaggc agatcacaac gccaagagat cgagaccatg ctggccaaga tggtgaaacg    900
ctgtctgtac taaaaataca aaaattagct gggcttggtg gtgcgtgcct gtagtcccag    960
ctacttggga ggctgaggca ggagaatcac ttgaacccgg gaggtggagg ttgcagtgag   1020
ccgagatcac aacactgcac tccagcctgg caacagagca agaatctgtc aaaaaaaaaa   1080
aaaaaaaaaa agttgttgaa gaacaaggag aaaacgtgaa aggaaaatca aatcttggga   1140
ccccaaaact cactggaaac agttaagctt agaaacggag tcactccaaa acctgccttt   1200
gtttttgctt ctaagcagat atttgcgaag acaaaaggca acatgttccc caggtagcct   1260
ccttcacaaa ttgctcacaa ggaaactcct tgtgggtccc agcagttttt accctgaggc   1320
agactttgtg taatttcatt gtgacaatgc aaattagcaa cttatcttta ctggtacatg   1380
ataaataaca agacttctgc ccaccctcag aaaaatgcac atatgcctgc ttcctctact   1440
ctatgttcat ttttatctta tataaaatgt agacgaactg tgcatgagac gaatgaataa   1500
ttgactgttc ctctaccccc tcctttcata gacaacctgt ggattcaagg agggctaatc   1560
aaagcttcac aagaatgtga ccactcacct cattacctat cctgtctttt ttcctttcct   1620
ccttccactc ctgcctgatt ttacacattt aaatactgga ggcctcaaaa ccctctgtga   1680
aaaacgagtg gaccccagaa cctcctgtga cttgtgtgac tttttcctgg gtgcatcctc   1740
aaccttggca gagtaaacat ctaaactgac tgagacgtgt cccagaccct ctttggttta   1800
caagtcttgc ctcctccctg agttgctgga tgaaagcaac gtcctctctt cttgcctcag   1860
tttcctcatc tgcaaaatca gatcataatc ctggcccatt gaggggatga ttataaaact   1920
caatcaaatg gagaagcatt tgcaaatgga atgtattgca aagtgtattg tgcagtccct   1980
gtgtaatcac cattctcttc ctgcctcata agctggtgtg tgtgtgtgta tgggtggggt   2040
gaggtggaca cgatgccccc agagatgttt gctcaggatg aaataggccc ccatggaagg   2100
gtcaggttgg cttctgtggt ttagctgcct ttgaggccct tctgcctggg gcaaagcaca   2160
aaagtccaat agcaatctgg ttgcatgact tcctagtcat ggaagtgtgg ctgagcagtg   2220
gtctctagtc cctccaccct gtgtgcctcg ggagtggaac acggggcagt ggcctctgct   2280
ggggaggatg ctgggggatc tctgaaagga ggcaatgcct gattttgtca ctgaacgatg   2340
agcatgattt ttccaggcgg tggaagcagg tgctcccggc agaagacccc atataagcaa   2400
atatctagaa gccacaaggc atggccttca acaagagcag gcctggtgcg gtggctcatg   2460
ccaaggtggg aggatcactt gaggcctgga gttcaagagt agcccagtca atatagtgag   2520
gcaccatctc taatataatt tttttaaaaa ttagctgggt ggttggctga tacctgtaga   2580
accagctact caggaggctg aggtgggggg atggcttaag cccaggggtt tgaagctgct   2640
gtgcgcgatg actgtggcac tgcaattcag tcttggtgac agactgagac cctgtctcaa   2700
```

-continued

```
aaacataacc aaaataaccc caacggcatt acaataaata tacaataagc atccacaagg   2760
catgtgtggg agactgtgct tatgccgatg gcacgggcag gagtaaggca ggcatcaggg   2820
gaatgtggat gcacgggagg atggggagta atctgcaggg tcccatagta tgtcagtggc   2880
aggtctttct ccttgagacc acagcagacc cccagccctg aggatgcgag gcaggtgggt   2940
tggatgagag ggatctggat gtctggtctc aggctgctcc tctaagggca gcagcaagga   3000
gggtggggct ggactgaagg tggaggggag cgtgtttgct gtgcttggtc atgagctgct   3060
gggaagttgt gactttcact ttccctttcg aattcctcgg tatatcttgg ggactggagg   3120
acctgtctgg ttattataca gacgcataac tggaggtggg atccacacag ctcagaacag   3180
ctggatcttg ctcagtctct gccaggggaa gattccttgg taagttgggg acagttgacc   3240
tgcctccatc ttattctcac agcttttgta gataagctgg gagaggttag gtgactggtt   3300
cagatagaca ggaaagtagc ggcaaagcct ggatttgcac ccaggcttga gtctgattgc   3360
ttcccctctc ctgctgggct cttaaactat agagggttgg ggaaacagct cagatgggtt   3420
cacaaagctc cctgggctca gccctggttt tgactgctga gacacgactg agtgaaccca   3480
gaaggaaggt ttgtgttggg ggtgcccatc tctttgggaa atttgaagga accaaagaag   3540
gtggaggaga ggaggtgacc cagatcccag cctgttctta tggccaggcc acaccaaggc   3600
tggccccagg gtgctgctgc tgaggcccaa tgggggcaac agaatttttt ttcaggtaca   3660
aggagttcag aggtcatctc acccaccctg agtctgagca ccaacttgtg ccaggccctg   3720
tggggaaact gaggccctgg gagcggaatg acttgcccag ggtcccgtgt caggaggctg   3780
agcaggtaga tcataggact ccacgtctct ggccctcacc tctgtccctc tgttcagact   3840
tctggggtga tggagaagaa acaggctgtg ctgtgtccct aatgggaaac gtggctgaga   3900
caggggagtg agaagggtgc gttgcagaat ggtgcctgtg gcatgatgcc agctttgcaa   3960
tcatgagatt caaaagccac actgtggaat tgtgagtata actacaggag tgagagctta   4020
gatctctgtg ttcatagaag gagaatcaaa cctggaaact tttggattat taaaatcaaa   4080
catttttgct tcaatattag agtcacaagg gcagatgttg gcctcccctc tgccctccaa   4140
gagctgtgtg actctgggaa attcacctcc cctcccagcc tgagtatttt cccctgtaaa   4200
aaacctgata gagctgccaa aagtccatga aatcaggggg gtaatttctg tgaaatctga   4260
gtcatggtct tatttgttct tcaccaaaaa gagatgatga agcctgtaac cccagtgctg   4320
tgggaggcag aggcgggagg atgacttgag gccaggagtt caagacagcc tgggaaacac   4380
aggagatgct gtctctatga aatcaaaaat taacaaatta gcccagcatg gtagtgtgta   4440
cctgtagtcc cagctactca gaaggttgaa ggaggcggat cacttgagcc caacagatct   4500
aggctgcaat gagctaggat ggtgtcaaag ccctgcagcc tgggtgacag agcaaaactg   4560
tttattaaaa actaaacgaa aggccgggcg cggtggctca cgcctgtaat cccagcactt   4620
tgggaggcca agacaggtgg tcacgaggtc aggatatcga gaccatcctg gctaacatgg   4680
tgaaaccctg tctctactaa aaatacaaaa aaattagccg ggtgtcgtgg cgggcacctg   4740
tagtcccagc tactcgggag gctgaggcag gagaatggcg tgaacccggg aggcagagct   4800
tgtagcgagc ctagatcgcc ccactgcact ccagcctggg tgatagagcg agactccatt   4860
tcaaaaaaaa aatgaaatga aaatggtgat ttctcaggag gagcacactg tctcaacccc   4920
tcttttcctg ctcaaggagg aggccctgca gcgacatgga gggagctgct ttgctgagag   4980
tctctgtcct ctgcatctgg tgagcttggc tcagagccct gaggcgggag ggagggctcc   5040
```

ctgtctgggc tgcacaattg gactgggctt gggctgggcc agggccatct gggcttcttc 5100
taggaaccaa agtcacttcc cggaattgac caaccggcag actcgcccag ggaggacccg 5160
ctgtatccta gttgaggcta acggtcaata tccggcctca atattcagca gaggctccag 5220
gtcagggtct gagccaggcc aacaatgacc aaggaggatg ggatccaggg tgcagctcct 5280
cacaagtgtc gggggaatcc gaggcaccag ctctctctac cctcctgctc ctctgctctc 5340
tcctggtcct cctgtgtcct catggctcat gagatggtgt tgagatggct cccctggcct 5400
aggggatcac acagtgaaca aagcaggaag aaggcgaagg gatgcccctc tcctgtcacc 5460
cttgtccctt acagcaagaa gggcccagac gcccctctgc atactcccct ggtgaactgc 5520
tgcccaggac tgggtccccc ttttaccctt gctgcatgga gtccccagaa gacaaacatc 5580
tgtgtgtctg aaccctgaga caaaggcagg aaagggaaag agggaggcga gtggcttttg 5640
aggaggggc tttagtatga gagctggagg atggaacccc atcagggggc ccgggaacca 5700
ctgagctgtt aaaataaagt ctgcaaacaa agaccagctg ctggaagtgg gtgtgccagg 5760
gagtgcgcag agacacacgg tgagaaaaga acaatggtaa tgcttggagc cgcccctaac 5820
tgggatgggc ctgaaatggt attgttatta tttatagtat cattattagt cattttcatc 5880
ttatttgtac cctccctcta tctctcctct ccaccttttc ctaacattct atcaccagtt 5940
ttatgtcttc cattagcaac tttgtagctg taaataattt acttacaact ttcatatacc 6000
ctcagttgta cccagtattt cttaacttcc ctctttaaaa aaatgataat attaatcctc 6060
cttctccttc gttcagtgct tcacatccca actgctacct ttgtgcttta aattttgtac 6120
taattggtgt tgataacaag tatatttagt tctcatattt atatgttgtg tatatgtttt 6180
ggtttttttt tgtcttaaac aagagactac tgagagccag taagactgaa agaaagggca 6240
tcttcatata ctgctagttt gagtgtgaat tggtacaatt tgcctgcagt gtggctctag 6300
gtataaagcc ttttgagttg ttgatagcct ctgacctgct cattctactc ctacaaatat 6360
cttaaggaaa taatctcaaa tgtgggcaaa gttttatgcg aagaaggatg ttctttgtag 6420
cataatttat atgaggaatt agaaacaccc tgaggtccat cagctaggga aagacagcag 6480
aggggacagg gcagcaccag gagggcttgg cagccacagc aggggctggg ctggcatctg 6540
gcaagatcca ggtctttgtg ggacaaagaa tcttagagaa gcaacgggga cacaggctgt 6600
ccagtgcagc accagtgaat tcaccaagat gaagagttga gcacagagtg tgagacaagg 6660
atttgcaatg aggagtcatt taccatgagc gtgtatacat gactcaatat tgtatattta 6720
agggagtaga gcacagtcat tgaaaacatg gggttgaagc agaagtcctg gctctagcac 6780
tattgtaaaa acactggcaa gttccctaac ttttgtggat tcctctgtgt ttgaatggga 6840
aagtggtacc catctcctgg cctgtgtgtg atcatcgaat gagacacatg taagaggctc 6900
tgcacatcgc agacatgcaa tacacactgg ctatcaccag ctagttatca cacatgctcc 6960
caggccctgg tcattgtcag aaccttcctc cccatctcta tttctgtgta tagactctgt 7020
agtttctgta atgatcagat ggctgcccgt cctctgatta tcttctcctc ataccccaac 7080
aggatgagtg cacttttcct tggtgtggga gtgagggcag aggaagctgg agcgaggtga 7140
gtgtctgcaa atagcagatg atgggggctc agtgatagac aaacaatctg gtttaggttg 7200
gtcttggtgt ttgcttccac cccagagaga tttgcagagc cccggctgct caagcaagcc 7260
tccctctgtc cactggtggc tcacatttga tcccacaatt tgttttctcc tcctcaaggg 7320
tgcaacaaaa cgttccaagt gggacagata ctggagatcc tcaaagtaag cccctcggtg 7380
actgggctgc tggcaccatg gacccaggta ggctcacctc ctcttccctg ctggttccta 7440
ctcgcactta gaatggaggg tggcacctcc acagctgagt gagccccaga agaacccgga 7500
tggactagga ggccaatgag tctgcccaaa gcagcagaag aggtcacgtg gagtccccg 7560
acccaggggt ctgggggtca tctgcatcct gacctctcct tagggtgaca cggcccaggt 7620
gcccacttcc tccctaccct ggcacctagc aaatgactca agtggggcag gacatccttg 7680
gggaagtgga atcagcgggg ggggggggga gtgtggggag agcagggtcc aggaggagag 7740
gagggctggg agaggaggtt gaccagcagc cccgacctgt cacctcccgc tctgctccaa 7800
gctgaccctg gggtgtttcc acctgaggct ggtcccctcc ctccagctct tgccctgccc 7860
tagccccttt gctctgagtg gccctgtggg aatgtatcgg gcctgattca gcttccagct 7920
taactggacc ccggtctgtc ctttgccaca tcccctctgt gtgacctggc gctccttacc 7980
tcccttctcc tgtaccatga gaataatatt tccccatgtt gtcttgagga tcaaatataa 8040
cacggctacc tggcctggcc agtgcctgcc acacaatagg gcctccctaa gggctggttc 8100
ccatcccctc tactggtccc ctgttgattc caggtggaag ccaccccgtc cccccccagc 8160
tgtgttaggg cacccgccct gccctgccca tcacaagcac ctgcttacca gggatgactg 8220
cctcaggcag gggctgagtt cagtcatcta aaataccccc ggtcaaagaa aaatctgagg 8280
cccaatagaa ttttaaagag ttaattgagt aagaaaggat tgctgaattg ggaaacagca 8340
aactggagga ggcttcgtgc tatggtgaaa aagtgtcgga gacaaggttt atcgggtgaa 8400
tatgaaactg cagtaaggac attatttgat tggttgcact tacaaaactg cctgtttggg 8460
tttaccttgt tggaaaatcc ctggtcacgt tggtgccagt gtgagtttag ggaggtctcc 8520
gaatacaggt gagaccggaa cttagccttg cccaggtttt tgatgctgaa gagagaaaaa 8580
agtcaaagca aaagcaaatc agcttttagt gcaaaacaga agtgcaggct caggggtggg 8640
agtgcaggcg gactcagaag agccagtcgg gcccagtgga gtttggggtt cttgtctttg 8700
ctggtttatt aaattaaggt gtggagtaag cataaggatt tctgggaaga ggtggggatt 8760
tcttggaatt gggagggcaa tgcagttttg taccaaacat gggcatacat ggaacggctg 8820
tggtgcgggt gggtgtgggg tttagtgaga caaggagggt atgattgagt gtgaggcaaa 8880
acgtgggtca gacccagcgc cgagttggat ctcactggtc ttagctgaat tggccacttc 8940
ctgtttgtca ggatcctgtg ggcccatccc ctccccctgt ccctacaggt ggtttcagca 9000
actccttctg tgtctgtcat gtgaacctgc tgcctggagt tcttgtttct tctgtgacct 9060
cccagtatcc acatctcagc atggccctct gtcagctggc tttaagtttt gtttgtatct 9120
aacagaagta cccatctgat atgaccccag ttgagtttcc catagcttgc agtttcaggg 9180
ggttacagct gttctaaagg cctcgtaggt attgcctgtc caggaatgtt tcagggctgg 9240
tttttgtttt aattttgctt ttatatccac cagccccacc acatcaagaa atacacagat 9300
ttagtgccag aggttccttc catccaaacc tgggtttcct tcctcctttt ggtgaagaag 9360
gaaaaagaaa aaacaagaca atcgctcgcc cagccaagtc agcattgcgt tcatttccct 9420
aagccccatt tcctcaggag ggcttcctcc ccttacagag ttgccacggc aaccaagtca 9480
gctctgctca ggagccgccc tggacagcaa actgggctgt gctgagtcct gtccaagacg 9540
aggggagggc agggaagatt agaagccgag agcactcagc cgaccccgga atccttacga 9600
agggctgggc tgggggactg aggaaaaact ctccccccaa aacaagatga tctgtggttt 9660
aataacaggc ccagctgggt ccagaggtga cagtggagag ccgtgtaccc tgagaccagc 9720
ctgcagagga cagaggcaac atggaggtgc ctcaaggatc agtgctgagg gtcccgcccc 9780

-continued

```
catgccccgt cgaagaaccc cctccactgc ccatctgaga gtgcccaaga ccagcaggag   9840
gaatctcctt tgcatggtag ttgtactcaa tgctgtggag tttgagacat tatttttaaa   9900
ctttaaatag ccccacaggt aagctataag ggagaatgca gagaccacag gcattttcaa   9960
aacataagga gttttaatgt taaggagttt aaggagaatg tcaaagaaac attggccttg  10020
gagtcaaatc ctgagcttcc tgcttgatgg ttttgggcgg tgactctcgc tgtctggatt  10080
ttactttctt catctgtgaa ttaagaatga ggtggccggg cactgtggct cacgcctgta  10140
atcccaacat ttgggaggcc gaggcgggca gatcacaagg tcaggagatc gagacgatcc  10200
tgtctaacac gatgaaaccc tgtctctact aaaaatacaa aaaaaattac caggcctggt  10260
ggcaggcgcc tgtagtccca gctactcagg aggctgaggc aggagaatgg catgaaccca  10320
ggaggcagag cttgcagtga gccaagatcg caccactgca ctccagcctg ggtgagagag  10380
caagactcca tccccccaaa aaaaagaatg aggtctcttg tgtgtgcacg gcaagaaaca  10440
atttacatc atgcctcagt gcacacacaa atacatactg gtccccagtt ccttatctgc  10500
aattccataa ttcccagatc cctgcaaacc acacgttttg gtggcagctg acttcaggag  10560
taatcctgct ctgtactgac ttgagttctt tgtagaccta ccattatttt ttacatttaa  10620
tgtgaatatt tgcttgtttc actgttgaaa catgtgtggg tgtgattaca gggagcagtc  10680
cagcctctgc tgggaatggt caggaatata ccatatgcac cccgtgtcct ttctaaaata  10740
gtggaaattc tgaatgccta aacacatctg gattccagga atttacatta agggatatat  10800
atttgaaata acccacaaaa acaatactca cccctgctac gcttggtaca ctctgatatt  10860
ttcaaattga ttttcttttt aaaatgctgc ttttgaacca ataatttcat aacccaatga  10920
tgtgttgata ttcacatttt gaagacactg gtataaagtg tttgacccaa caggcatgtg  10980
gcagatggaa gtgatcactg ggatgtttcc acttccttgg cctggaaggc tcacttcatg  11040
ttggtgctga gctgaaaagg attcattcct ctccaaagca ccatggcact cccctggtgt  11100
ttcaatgttc tcaggctgcc atagtaaaat atcacaggct gggtgacttc aacatctggc  11160
ttttatttc tcacagatcc agaggcaaga agtccaaggt gaaggtgcca aaagggttgg  11220
agtctgggga ggactctctt gctggcttat ggaagctgcc tttgcactgt gtgctcacac  11280
agtcttcttg tgtccctttc tgttcttaca ataggacact agccctctaa tagaattaga  11340
gccctaccct tgtgatctca ttcagtctta attgcttcct taaaggccag atctccaaat  11400
gtagtcacct gagtttaaag cttcagcata tgaattttgg gggcacacaa ttccctctat  11460
agcactaatg actccataaa acaagtccca catcacagct gtccaggaaa attaacatgt  11520
agtcatctct tatgcaatgg ctgttatgca ctcccacact ttcctccaac cttatccttt  11580
cttctttcca actagagagc agtatcttta ttgaggatgc cattaagtat ttcaaggaaa  11640
aagtgagcac acagaatctg ctactcctgc tgactgataa tgaggcctgg aacggattcg  11700
tggctgctgc tgaactgccc aggtaagctc catggggtta cctccattgg gcactccggc  11760
gatgccaccc agctctcccc tgggctagtt ttccctgaca ggcacacctc ctccaggcag  11820
ccccctctgc tgggcttgag gatgaccttc ttggcactcc aggaagaata tttcctccat  11880
gtccttcgct ggcagtgagt agcctcaggc tgaggggata ggaagcccac aggaacaggg  11940
tcatttctgc catctgctgg tgatgggaac tttgccagtt actttctcac tttcagcctt  12000
tcttcatcaa tggagtttta ttgtgagaaa aatgagatcg tgcatgtaaa gtgcttagca  12060
taatgactga cacacagtag gtgcacagtt aacgttaaca tcttacaagc ttggtggaaa  12120
cagaaccagg gttaaggatc ttcttcttga agatgggagc ccagcaggac ttgacctttg  12180
```

```
ggacaagtca gaaaaatcct gacctaacca atgtgtgttc ctggggatgc tggctggagc  12240
ccttttctc atctgaggaa ttccataaac acggcaggac ccttctgctg gtccaggatg  12300
ccgagaggct ggagtggagt tgcacagcgc tgggtctctt tccagctctg tctgtgtcca  12360
gtccctgggc tctgggctta tgtcagagac tggaaactgt catcagtcta ataggaatag  12420
caactcaatg tgataggagt gtggtgaagg ccttagaggc aactccaggt caaaggtggg  12480
gaaccaacac caagatcctg cccaaaggcc cagagagacc gggatcagcg tcagagcctg  12540
gagtcaggat ggagcaagag tcagccttgg ttgtaggaca agcaggaagg ctggggcacc  12600
agggctggga ctagggtgtg gaaagagagg caccaagggc ttgaaactta aggaggtcat  12660
gaacttgcag aggacatgtg agtgggagag ggatatttct tccctgtctg gatgatccca  12720
acactcatgg gcatataggg tcatggttgc ctgtgtctct cacaccacgc cttggaactg  12780
gcaagttctg ggctaccctt tgagaccttc ttctcttcta cacagagaaa cccctgacat  12840
tgacaagcag tatgtcttag tgaccatttt catagtagaa ttagttgctg ccaatttgtg  12900
taatttcagg gatactgagc agactcacaa cttcccaacc aaggaggaaa acacttcctc  12960
taccatcttg tccaaattca ggtcttttca gcattagcaa tttatatagg tggttctgaa  13020
agtgttttga atcttctaga ggttccataa aattgcaaat ggccttggtg tgcacacagg  13080
tgaagctgtc actactaagg catcagttag gctggtgaca cctgcgagtg agacctggaa  13140
ggttggggt gcaggtggta ggtcaggagg cagtaaggtg gctggagcgt ccatgtggag  13200
ccagaatgaa tagccagatc tcccactcca gtcagctggg gcagtggcca gaaccagtag  13260
ccttcagcca ggtgaaaggg catgaggcat tggaagggag cagatgccag gcaaagtgaa  13320
ctcctgtctc tccggggttt tgtttttgtt tgaattcaaa gtactcagag atagccagac  13380
tgcaatgtct gagggcaccc ttacctttga caccacctgc aaatttaagg ggatttctaa  13440
atccatcctt tgattttgta attcactgga aggactcaca taactcactg aaaactgcta  13500
tttcacaatt gtggttgatc acacggaaag aacacagatt aaaatcagcc taagaaagag  13560
acacacgggg cagagtttgg gagggtttta agtgtgaagc ttcattgtcc tcaggacgct  13620
gtgttctcct gtgtgaatgt gggacaaaac acatgcggtg ttgccaacca gggaagctca  13680
cccagttaag gaaaaattcc tgtgaatcac attaaaccag aaatgaagcc ttttttcagg  13740
attgttgtta caggggaggg agactgagcc cagctccaaa tatagtaaag acagaggggg  13800
agtcacagcc aacaccaggg tgggggcggg agatggaaca ggactgatag gagacaccag  13860
agtgggggt tcctgctaaa ttggcctaac aggattctca ctaaaggcag gtcagacact  13920
cacccatcaa tggtgggggt gaagagcata atcagatagc aaagcgtaat cagacagcaa  13980
ggggggaaga ccctccctaa actgacttgg ggagattctt gctgagctgg gtggtgcagg  14040
tccagcaagc agtgggtggc tgtggaaggc caaggtcggc gcctagtgga gaagaggctc  14100
agaagagccc agctggagtt ggtcaaggag aaagtccttc tttctcaacc catgccttag  14160
tgtccagagt atctgctggg gctggatcac aagctgccct catggctgac ctggagtctc  14220
cagcccctcc ctgaggtcta acccctttag tccccgggtc ctctgggatc aggaaagaca  14280
ccaaatagcc ccaaacccca tcatccatca gattcctata cggtcccgtg gccaaatcac  14340
caggcaaaga cagatgttcc taccaggcag gacattccag gggcctggag atcacttccc  14400
aggagctgag gacaaaggga aggcctctct ttgggtaaag ttcatgcttc actttcctgc  14460
catcctggga ataaggtctc tttgtctcac tctcactgct ctttgttcat ctgcagagtt  14520
```

-continued

```
ttccctctcc aaacactttg gcagtcacgg tgttgacctg cccttgaatg aggaggcatc  14580
tttatcaaac acctaccatg aaagagcatc tgagatgcct ttaagatatt tatttccata  14640
tggaataaat attgaggagt atctatgatg aacaaaatgt gtttgagttt gaaagataat  14700
taattccatt tgtaaaattt gtttctattt gatcgatagt gaaagctctg caatttacac  14760
aggatagaga tcacatggag ctcatttcac agacagggaa actgcatttc ttttttttt  14820
ttttttttt gagttggagt cttgctctgt cgcccaagct ggagtgcagt ggcgcgatct  14880
cggctcactg caagctctgc ctcccggttc aagcaattct cctgcctcag cctcctgagt  14940
agctgggact acaggcgccc accaccacgc ccggctaatt ttttgaattt ttggtagaga  15000
cagggtttca ccgtattagt caggatggtc tcaatctcct gaccttgtga tccacccgcc  15060
ttggcctccc aaagtgctgg gattacaggt gtgagccacc acaccgagcc aaaactgcat  15120
ttcttaatcc tttaaccttt ccttgtgcag gaatgaggca gatgagctcc gtaaagctct  15180
ggacaacctt gcaagacaaa tgatcatgaa agacaaaaac tggcacgata aaggccagca  15240
gtacagaaac tggtttctga aagagtttcc tcggttgaaa agtgagcttg aggataacat  15300
aagaaggctc cgtgcccttg cagatggggt tcagaaggtc cacaaaggca ccaccatcgc  15360
caatgtggtg tctggctctc tcagcatttc ctctggcatc ctgaccctcg tcggcatggg  15420
tctggcaccc ttcacagagg gaggcagcct tgtactcttg gaacctggga tggagttggg  15480
aatcacagcc gctttgaccg ggattaccag cagtaccatg gactacggaa agaagtggtg  15540
gacacaagcc caagcccacg acctggtcat caaaagcctt gacaaattga aggaggtgag  15600
ggagtttttg ggtgagaaca tatccaactt tctttcctta gctggcaata cttaccaact  15660
cacacgaggc attgggaagg acatccgtgc cctcagacga gccagagcca atcttcagtc  15720
agtaccgcat gcctcagcct cacgcccccg ggtcactgag ccaatctcag ctgaaagcgg  15780
tgaacaggtg gagagggtta atgaacccag catcctggaa atgagcagag gagtcaagct  15840
cacggatgtg gcccctgtaa gcttctttct tgtgctggat gtagtctacc tcgtgtacga  15900
atcaaagcac ttacatgagg gggcaaagtc agagacagct gaggagctga agaaggtggc  15960
tcaggagctg gaggagaagc taaacattct caacaataat tataagattc tgcaggcgga  16020
ccaagaactg tgaccacagg gcagggcagc caccaggaga gatatgcctg gcaggggcca  16080
ggacaaaatg caaacttttt tttttttctg agacagagtc ttgctctgtc gccaagttgg  16140
agtgcaatgg tgcgatctca gctcactgca agctctgcct cccgtgttca agcgattctc  16200
ctgccttggc ctcccaagta gctgggacta caggcgccta ccaccatgcc cagctaattt  16260
ttgtattttt aatagagatg gggtttcacc atgttggcca ggatggtctc gatctcctga  16320
cctcttgatc tgcccacctt ggcctcccaa agtgctggga ttacaggcgt gagccatcgc  16380
ttttgaccca aatgcaaaca ttttattagg gggataaaga gggtgaggta aagtttatgg  16440
aactgagtgt tagggacttt ggcatttcca tagctgagca cagcagggga ggggttaatg  16500
cagatggcag tgcagcaagg agaaggcagg aacattggag cctgcaataa gggaaaaatg  16560
ggaactggag agtgtgggga atgggaagaa gcagtttact ttagactaaa gaatatattg  16620
gggggccggg tgtagtggct catgcctgta atccgagcac tttgggaggc caaggcgggc  16680
ggatcacgag gtcaggagat cgagaccatc ctggctaaca cagtgaaacc ccgtctctac  16740
taaaaataca aaaaattagc cgggcatggt ggcgggcgcc tgtagttcca gctaactggg  16800
cggctgaggc aggagaatgg cgtgaacctg ggaggtggag cttgcagtga gccgagatat  16860
cgccactgca ctccagcctg ggtgacagag cgagactcca tctcaaaaaa aaaaaaaaaa  16920
```

agaatatatt gacggaagaa tagagaggag gcttgaagga accagcaatg agaaggccag 16980
gaaaagaaag agctgaaaat ggagaaagcc caagagttag aacagttgga tacaggagaa 17040
gaaacagcgg ctccactaca gacccagccc caggttcaat gtcctccgaa gaatgaagtc 17100
tttccctggt gatggtcccc tgccctgtct ttccagcatc cactctccct tgtcctcctg 17160
ggggcatatc tcagtcaggc agcggcttcc tgatgatggt cattggggtg gttgtcatgt 17220
gatgggtccc ctccaggtta ctaaagggtg catgtcccct gcttgaacac tgaagggcag 17280
gtggtgggcc atggccatgg tccccagctg aggagcaggt gtccctgaga acccaaactt 17340
cccagagagt atgtgagaac caaccaatga aaacagtccc atcgctctta cccggtaagt 17400
aaacagtcag aaaattagca tgaaagcagt ttagcattgg gaggaagctc agatctctag 17460
agctgtcttg tcgccgccca ggattgacct gtgtgtaagt cccaataaac tcacctactc 17520
atcaagctgg acttgttcga gtcattcttt ggtctctcag ctctttccaa gctttggggg 17580
ccatcagtct caagtttttc tcgtaatggt ggtgatggtg gttgtgatgg cagcagagtg 17640
gtgggggcct tggcaagtgg tcggtgctct tccagaccag gggacaccga tggaccgatg 17700
aagttccagg ggaacttgaa gtgctgtgtt ggaaagaggt taatttggga agaaaggaaa 17760
aatgaaagga gatgccagga acaggtcaag gaaccttgag gtgtgtccag gagttcaacc 17820
ccgcttgtgg tcacgagacc tcgcctctct gagcctcagt ttcctcatca gctgtagaag 17880
ggtacctgga caaggtgatg tctcaggtcc acccagctct ccccatcttg tgtcctggag 17940
acttgggtcc aatcagcact gactgatggc tgtgcctttg tggtgccgat ggaggctccc 18000
ctgggctctg ggtgcctgac ttcccttcct catgatcctt cttccagggt ctcgggaaac 18060
gaggcttcca tggcccctcc tgcttgctca ctggactctc actttcccag ctggtcattt 18120
ccctgagacc tcaaaacccc accaacccca ctggggcacc cacagaaagc ttgtacatgt 18180
ctggctctgg ctgagcacag gtgtggtttc catctgcgag tcagagcccg ggattgacat 18240
gggacgctcg aggctgacta gtgtcagagg ggcctgtgtg cagattggga gaagattatc 18300
gagtaataga ggggcaaaga gggacatcca gacagcaaac acccccatcc agtctgtcct 18360
cacgttttgc ccagactcct gcaagaactt ccagaatggt cttccatgtg caactgcccg 18420
tccctgccca tgtcctggat cattctccac actgcgccag gttgggcttt aacaagatca 18480
tgttttgggt ttttgggggt tttttgtttg tttgtttggt ctcactctgt tgtgaggctg 18540
gcgtcccgtg gcatgagcat ggctcactgc atcttggacc tcccggcctc aaactaccct 18600
tccaccttga ccccctgagt agctgggacc atccgtgtgt gccacattgc ccaggctggt 18660
ctcaaactcc tgagttcagg tgatctgttc gccttggcat tccaatgggc tgcaattaca 18720
gacacgagcc accgtgccca cctaagaaca tagatttgat cgagcaccca cttctgacca 18780
ttcaatggct tcccattact cttagcacaa agatgtaggc catgatgctg cctaaagtag 18840
cctgttgcgg cctggggtcc tgtgaaggaa gagccagagg caacgttctg gtgcagaggg 18900
tttctaggaa gtgattctag gagcagaact gaggatccag gagggaagga ggaaacgttg 18960
atacaagaag tttttgaatg ggccatccat atgggcaatg agaccttctg aggtgccttc 19020
aaggagcgtc ctcagaatct ttgtttccag ggaggagaca tggaggcctt tatccactgc 19080
tttagctgtg tcccaggggt tctggtacat tgtgtctttg ttctcattgg tttcaaagaa 19140
cttcttgatt tctgccttaa ttttgttatt tacccagtaa tcattcagga acacgttgtt 19200
caatttccat gtagttgtgc ggtttttagt gagtttctta atcctgagtt ctaatttgat 19260
tgcactgtgg tctgagacac tgtttgttat gatttccatt cttttgcatt tgctgaggaa 19320
tgttttactt ccaattatgt ggtcgacttt agaataagtg ttatacggtg ctgagaagaa 19380
agtatattct gttgatttgg gacggagagt tctgtagatg tctgttaggt ccactcagtc 19440
cagggctgag ttcaagtcct gaacatcctt gttaattttc tgtctcgttg acctgtctaa 19500
tattgacagt ggggtgttaa agtctcccac tgctattgtg tgggagtcta agtctctttg 19560
taggtctcta agaacttgtt ttatgaatct gcgtgctccc gtattgggtg catatatatt 19620
taggatagtt agctcttctt gttgcactga tgtttgttgg tttaaaagat cttttttgat 19680
ctttgttggt ttaaagtctg ttttatcaga gactaggatt gcaacccctg cttttttgtt 19740
tgtttgtttg tttgtttgtt ttgctttcca tttgcttggt aaatgttcct ccatcccttt 19800
attttcagcc tatgtgtgtt tttgcacatg agatgggtct cctgaataca gtacatcaac 19860
gggtcttgac tttatccaat ttgccagtct gtctgtttta attggggcat ttagcccatt 19920
tacatttaag gttcatattg ttatgtgtga atttgatcct gtcatcatga tgctagctga 19980
ttattttgca cattagttga tgcagtttct tcatggtatc attggtcttt atattttggt 20040
gtggttttgc agtgtctggt actggttttt cctttccata tttagtgctt ccttcaggag 20100
ctcatgtaag gccggcctgg tggtgacaaa atccctcagc atttgcttgt ctggaaagga 20160
ttttatttct cctttgctta tgaagcttag tttggctgga tatgaaattc tgggttgaaa 20220
attcttttct ttaagaatgt tgaatattgg tccccactct cttccagctt atatagggtt 20280
tctgcagaga gatccactgt tagtctgatg ggcttccctt cgtaggtaac gtgatctttc 20340
tctctggctg cccttaacat tttttccttc gtttcaacct tggagaatct gatgattatg 20400
tgtcttgggg ttgctcttct tgaagagtat cttagtggtg ttctctgtat ttcctgaatt 20460
tgaatgttgg cctggcttgc tggttgggga agttctcctg gataatatcc taaagtgtgt 20520
tttccagctt gtttccgttc tccccatcac tttcaggtac accaatcaat tgtaggttta 20580
atcttttcac atagtcccat atttcttgga ggctttattt gttccattgt cattcttttt 20640
tctctaattt tgtcttcaca cattgtttca gtaagttgat cttcaatctt tgatattccg 20700
cttgatcaat ttggctattg atagttgtgt atccttcacg aagttctcat gctgtgtttt 20760
tcagctccat caggtcattt acgttcttct ctaaactggt tattctagtt agcagctcct 20820
gtaacctttc atcaaggttc ttagcttcct tgcattgggt tacaacatgc tcctttagct 20880
cagaggagtt tctcattacc catcttctga agcctacttc tgtcaattcg tcaaattcat 20940
tctccatcca gttttgtgcc cttgctggag aggagttgca atcatttgga gaagagacat 21000

<210> SEQ ID NO 10
<211> LENGTH: 23
<212> TYPE: DNA
<213> ORGANISM: Artificial sequence
<220> FEATURE:
<223> OTHER INFORMATION: Primer

<400> SEQUENCE: 10
gctactcctg ctgactgata atg 23

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
aaggttgtcc agagctttac g 21

<210> SEQ ID NO 12
<211> LENGTH: 23
<212> TYPE: DNA
<213> ORGANISM: Artificial sequence
<220> FEATURE:
<223> OTHER INFORMATION: Probe

<400> SEQUENCE: 12
tgcccaggaa tgaggcagat gag 23

<210> SEQ ID NO 13
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
gttcaaaagc agcatt 16

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
aagatatacc gaggaa 16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
tcccctggca gagact 16

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
tcgctccagc ttcctc 16

<210> SEQ ID NO 17
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 17
ttactttgag gatctc 16

<210> SEQ ID NO 18
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 18

actgctggcc tttatc                                                   16


<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19

ggagccttct tatgtt                                                   16


<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20

ggtgcctttg tggacc                                                   16


<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 21

agacccatgc cgacga                                                   16


<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22

agcggctgtg attccc                                                   16


<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23

ctttccgtag tccatg                                                   16


<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24

acccaaaaac tccctc                                                   16
```

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 25
gcacggatgt ccttcc 16

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
gattggctca gtgacc 16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
tgggttcatt aaccct 16

<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
acgaggtaga ctacat 16

<210> SEQ ID NO 29
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 29
ttcttggtcc gcctgc 16

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 30
aatgtttgca tttggg 16

<210> SEQ ID NO 31
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 31
gtgctcagct atggaa 16

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
tagtctaaag taaact 16

<210> SEQ ID NO 33
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 33
gctggttcct tcaagc 16

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 34
cattcttcgg aggaca 16

<210> SEQ ID NO 35
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 35
tcaggaagcc gctgcc 16

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
acctgccctt cagtgt 16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 37
ctgtttactt accggg 16

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
tcaatcctgg gcggcg 16

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39
catgattgca aagctg 16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
gctttgtgaa cccatc 16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
caagcccagt ccaatt 16

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 42
gatgtttgtc ttctgg 16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
gccagtgtgt attgca 16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
acaaattgtg ggatca 16

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
ctaggtgcca gggtag 16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
cccccccccc gctgat 16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
gggccactca gagcaa 16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
gtggcaaagg acagac 16

<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
ccctattgtg tggcag 16

<210> SEQ ID NO 50
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 50
tttttctttg accggg 16

<210> SEQ ID NO 51
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 51
cgaagcctcc tccagt 16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
cacccgataa accttg 16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
aggcagtttt gtaagt 16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
attcggagac ctccct 16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 55
cctgggcaag gctaag 16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
ttactccaca ccttaa 16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57

-continued tttggtacaa aactgc 16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
tgtctcacta aacccc 16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
gaccagtgag atccaa 16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
accacctgta gggaca 16

<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
gggtacttct gttaga 16

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
cagctgtaac cccctg 16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 63
cagccctgaa acattc 16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
gcgattgtct tgtttt 16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
gccgtggcaa ctctgt 16

<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
gggtcggctg agtgct 16

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 67
acctccatgt tgcctc 16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
gctggtcttg ggcact 16

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
cttatagctt acctgt 16

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
gagtcaccgc ccaaaa 16

<210> SEQ ID NO 71
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 71
ttgccgtgca cacaca 16

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 72
gtttgcaggg atctgg 16

<210> SEQ ID NO 73
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 73
caaagaactc aagtca 16

<210> SEQ ID NO 74
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
actgctccct gtaatc 16

<210> SEQ ID NO 75
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 75
tgtgtttagg cattca 16

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76
gttatgaaat tattgg 16

<210> SEQ ID NO 77
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 77
atgcctgttg ggtcaa                                                    16

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
gcaccaacat gaagtg                                                    16

<210> SEQ ID NO 79
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 79
acccttttgg cacctt                                                    16

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
ttctattaga gggcta                                                    16

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
gctttaaact caggtg                                                    16

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
gttttatgga gtcatt                                                    16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
gtgcataaca gccatt                                                    16

<210> SEQ ID NO 84

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
agatataccg aggaat 16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
ggatcccacc tccagt 16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
actcccacac caagga 16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
tactttgagg atctcc 16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
ctgctggcct ttatcg 16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
gagccttctt atgtta 16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
gtgcctttgt ggacct 16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
gacccatgcc gacgag 16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
gcggctgtga ttccca 16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
tttccgtagt ccatgg 16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
acctccttca atttgt 16

<210> SEQ ID NO 95
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 95
cacggatgtc cttccc 16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
attggctcag tgaccc 16

<210> SEQ ID NO 97
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 97
gggttcatta accctc 16

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
cgaggtagac tacatc 16

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
tcttggtccg cctgca 16

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
tgtttgcatt tgggtc 16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 101
tgctcagcta tggaaa 16

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
agtctaaagt aaactg 16

<210> SEQ ID NO 103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
ctggttcctt caagcc 16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
attcttcgga ggacat 16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 105
aggaagccgc tgcctg 16

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
tgcccttcag tgttca 16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
tgtttactta ccgggt 16

<210> SEQ ID NO 108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
caatcctggg cggcga 16

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109
atgattgcaa agctgg 16

<210> SEQ ID NO 110
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 110
aacccatctg agctgt 16

<210> SEQ ID NO 111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 111
gcccagtcca attgtg 16

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
actccatgca gcaagg 16

<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
gtctgcgatg tgcaga 16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
tgtgggatca aatgtg 16

<210> SEQ ID NO 115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 115
taggtgccag ggtagg 16

<210> SEQ ID NO 116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 116
cccccccccg ctgatt 16

<210> SEQ ID NO 117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 117
ggccactcag agcaaa 16

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
ggcaaaggac agaccg 16

<210> SEQ ID NO 119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 119
ccaggccagg tagccg 16

<210> SEQ ID NO 120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 120
gggtatttta gatgac 16

<210> SEQ ID NO 121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 121
gaagcctcct ccagtt 16

<210> SEQ ID NO 122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 122
acccgataaa ccttgt 16

<210> SEQ ID NO 123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 123
ggcagttttg taagtg 16

<210> SEQ ID NO 124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 124
ttcggagacc tcccta 16

<210> SEQ ID NO 125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 125
ctgggcaagg ctaagt 16

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
tactccacac cttaat 16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
ttggtacaaa actgca 16

<210> SEQ ID NO 128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
gtctcactaa acccca 16

<210> SEQ ID NO 129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 129
accagtgaga tccaac 16

<210> SEQ ID NO 130
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 130
ggatgggccc acagga 16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 131
ggtacttctg ttagat 16

<210> SEQ ID NO 132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 132
agctgtaacc ccctga 16

<210> SEQ ID NO 133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 133
agccctgaaa cattcc 16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 134
cgattgtctt gttttt 16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 135
ccgtggcaac tctgta 16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 136
gtcggctgag tgctct 16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 137
ccatgttgcc tctgtc 16

<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 138
ctggtcttgg gcactc 16

<210> SEQ ID NO 139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 139
tatagcttac ctgtgg 16

<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 140
gtcaccgccc aaaacc 16

<210> SEQ ID NO 141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 141
gccgtgcaca cacaag 16

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
ggatctggga attatg 16

<210> SEQ ID NO 143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 143
aaagaactca agtcag 16

<210> SEQ ID NO 144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 144
tgctccctgt aatcac 16

<210> SEQ ID NO 145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 145
gtgtttaggc attcag 16

<210> SEQ ID NO 146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 146
atgaaattat tggttc 16

<210> SEQ ID NO 147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 147
tgcctgttgg gtcaaa 16

<210> SEQ ID NO 148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 148
caccaacatg aagtga 16

<210> SEQ ID NO 149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 149
cccttttggc accttc 16

<210> SEQ ID NO 150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 150
tctattagag ggctag 16

<210> SEQ ID NO 151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 151
ctttaaactc aggtga 16

<210> SEQ ID NO 152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 152
ttatggagtc attagt 16

<210> SEQ ID NO 153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 153
tgcataacag ccattg 16

<210> SEQ ID NO 154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 154
cccaagatat accgag 16

<210> SEQ ID NO 155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 155
gaatcttccc ctggca 16

<210> SEQ ID NO 156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 156
caccctcgct ccagct 16

<210> SEQ ID NO 157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 157
cagcccagtc accgag 16

<210> SEQ ID NO 158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 158
tgtactgctg gccttt 16

<210> SEQ ID NO 159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 159
cacggagcct tcttat 16

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 160
ggtggtgcct ttgtgg 16

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 161
gccagaccca tgccga 16

<210> SEQ ID NO 162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 162
caaagcggct gtgatt 16

<210> SEQ ID NO 163

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 163
cttctttccg tagtcc 16

<210> SEQ ID NO 164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 164
gttctcaccc aaaaac 16

<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 165
gagggcacgg atgtcc 16

<210> SEQ ID NO 166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 166
tgagattggc tcagtg 16

<210> SEQ ID NO 167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 167
tgctgggttc attaac 16

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 168
gtaagtgctt tgattc 16

<210> SEQ ID NO 169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 169
cagttcttgg tccgcc 16

<210> SEQ ID NO 170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 170
tcaccctctt tatccc 16

<210> SEQ ID NO 171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 171
gctgtgctca gctatg 16

<210> SEQ ID NO 172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 172
tctttagtct aaagta 16

<210> SEQ ID NO 173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 173
taactcttgg gctttc 16

<210> SEQ ID NO 174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 174
cttcattctt cggagg 16

<210> SEQ ID NO 175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 175
tcatcaggaa gccgct 16

<210> SEQ ID NO 176
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 176
ggccatggcc caccac 16

<210> SEQ ID NO 177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 177
agcttcctcc caatgc 16

<210> SEQ ID NO 178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 178
aggtcaatcc tgggcg 16

<210> SEQ ID NO 179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 179
tctcatgatt gcaaag 16

<210> SEQ ID NO 180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 180
gtctcagcag tcaaaa 16

<210> SEQ ID NO 181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 181
ttggttccta gaagaa 16

<210> SEQ ID NO 182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 182
actgagggta tatgaa 16

<210> SEQ ID NO 183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 183
gtgtgataac tagctg 16

<210> SEQ ID NO 184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 184
ttttgttgca cccttg 16

<210> SEQ ID NO 185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 185
gtcatttgct aggtgc 16

<210> SEQ ID NO 186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 186
tggtcaacct cctctc 16

<210> SEQ ID NO 187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 187
atacattccc acaggg 16

<210> SEQ ID NO 188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 188
agggaggtaa ggagcg 16

<210> SEQ ID NO 189
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 189
aggccctatt gtgtgg 16

<210> SEQ ID NO 190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 190
attgggcctc agattt 16

<210> SEQ ID NO 191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 191
gcacgaagcc tcctcc 16

<210> SEQ ID NO 192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 192
attcacccga taaacc 16

<210> SEQ ID NO 193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 193
aacccaaaca ggcagt 16

<210> SEQ ID NO 194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 194
tgtattcgga gacctc 16

<210> SEQ ID NO 195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 195
aaacctgggc aaggct 16

<210> SEQ ID NO 196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 196
atgcttactc cacacc 16

<210> SEQ ID NO 197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 197
cccatgtttg gtacaa 16

<210> SEQ ID NO 198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 198
ccttgtctca ctaaac 16

<210> SEQ ID NO 199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 199
ctaagaccag tgagat 16

<210> SEQ ID NO 200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 200
gaaaccacct gtaggg 16

<210> SEQ ID NO 201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 201
gatgggtact tctgtt 16

<210> SEQ ID NO 202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 202
ttagaacagc tgtaac 16

<210> SEQ ID NO 203
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 203
gggctggtgg atataa 16

<210> SEQ ID NO 204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 204
cgagcgattg tcttgt 16

<210> SEQ ID NO 205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 205
gttgccgtgg caactc 16

<210> SEQ ID NO 206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 206
gagtttttcc tcagtc 16

<210> SEQ ID NO 207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 207
gaggcacctc catgtt 16

<210> SEQ ID NO 208
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 208
caaaggagat tcctcc 16

<210> SEQ ID NO 209
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 209
ctcccttata gcttac 16

<210> SEQ ID NO 210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 210
cgagagtcac cgccca 16

<210> SEQ ID NO 211
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 211
ttcttgccgt gcacac 16

<210> SEQ ID NO 212
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 212
cgtgtggttt gcaggg 16

<210> SEQ ID NO 213
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 213
taggtctaca aagaac 16

<210> SEQ ID NO 214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 214
tggactgctc cctgta 16

<210> SEQ ID NO 215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 215
agatgtgttt aggcat 16

<210> SEQ ID NO 216
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 216
catcattggg ttatga 16

<210> SEQ ID NO 217
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 217
cacatgcctg ttgggt 16

<210> SEQ ID NO 218
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 218
ttttcagctc agcacc 16

<210> SEQ ID NO 219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 219
agactccaac cctttt 16

<210> SEQ ID NO 220
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 220
taattctatt agaggg 16

<210> SEQ ID NO 221
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 221
tgaagcttta aactca 16

<210> SEQ ID NO 222
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 222
gacttgtttt atggag 16

<210> SEQ ID NO 223
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 223
ggagtgcata acagcc 16

<210> SEQ ID NO 224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 224
ccccaagata taccga 16

<210> SEQ ID NO 225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 225
ggaatcttcc cctggc 16

<210> SEQ ID NO 226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 226
gcaccctcgc tccagc 16

<210> SEQ ID NO 227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 227
gcagcccagt caccga 16

<210> SEQ ID NO 228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 228
ctgtactgct ggcctt 16

<210> SEQ ID NO 229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 229
gcacggagcc ttctta 16

<210> SEQ ID NO 230
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 230
tggtggtgcc tttgtg 16

<210> SEQ ID NO 231
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 231
tgccagaccc atgccg 16

<210> SEQ ID NO 232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 232
cggtcaaagc ggctgt 16

<210> SEQ ID NO 233
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 233
acttctttcc gtagtc 16

<210> SEQ ID NO 234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 234
atatgttctc acccaa 16

<210> SEQ ID NO 235
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 235
tgagggcacg gatgtc 16

<210> SEQ ID NO 236
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 236
cagctgagat tggctc 16

<210> SEQ ID NO 237
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 237
atgctgggtt cattaa 16

<210> SEQ ID NO 238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 238
atgtaagtgc tttgat 16

<210> SEQ ID NO 239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 239
acagttcttg gtccgc 16

<210> SEQ ID NO 240
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 240
ctcaccctct ttatcc 16

<210> SEQ ID NO 241
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 241
ctgccatctg cattaa 16

<210> SEQ ID NO 242

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 242 cccccaata tattct 16

<210> SEQ ID NO 243
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 243
gttctaactc ttgggc 16

<210> SEQ ID NO 244
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 244
acttcattct tcggag 16

<210> SEQ ID NO 245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 245
atcatcagga agccgc 16

<210> SEQ ID NO 246
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 246
tggccatggc ccacca 16

<210> SEQ ID NO 247
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 247
gagcttcctc ccaatg 16

<210> SEQ ID NO 248
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 248
atgagtaggt gagttt 16

<210> SEQ ID NO 249
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 249
aatctcatga ttgcaa 16

<210> SEQ ID NO 250
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 250
tgtctcagca gtcaaa 16

<210> SEQ ID NO 251
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 251
tttggttcct agaaga 16

<210> SEQ ID NO 252
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 252
acaactgagg gtatat 16

<210> SEQ ID NO 253
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 253
agcatgtgtg ataact 16

<210> SEQ ID NO 254
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 254
tacctgggtc catggt 16

<210> SEQ ID NO 255
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 255
gagtcatttg ctaggt 16

<210> SEQ ID NO 256
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 256
gctggtcaac ctcctc 16

<210> SEQ ID NO 257
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 257
gatacattcc cacagg 16

<210> SEQ ID NO 258
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 258
aagggaggta aggagc 16

<210> SEQ ID NO 259
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 259
gaggccctat tgtgtg 16

<210> SEQ ID NO 260
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 260
tattgggcct cagatt 16

<210> SEQ ID NO 261
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 261
agcacgaagc ctcctc 16

-continued

<210> SEQ ID NO 262
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 262
tcatattcac ccgata 16

<210> SEQ ID NO 263
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 263
taaacccaaa caggca 16

<210> SEQ ID NO 264
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 264
ctgtattcgg agacct 16

<210> SEQ ID NO 265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 265
caaaaacctg ggcaag 16

<210> SEQ ID NO 266
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 266
tatgcttact ccacac 16

<210> SEQ ID NO 267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 267
tgcccatgtt tggtac 16

<210> SEQ ID NO 268
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 268
ctccttgtct cactaa 16

<210> SEQ ID NO 269
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 269
gctaagacca gtgaga 16

<210> SEQ ID NO 270
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 270
tgaaaccacc tgtagg 16

<210> SEQ ID NO 271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 271
agatgggtac ttctgt 16

<210> SEQ ID NO 272
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 272
ctttagaaca gctgta 16

<210> SEQ ID NO 273
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 273
ttcttgatgt ggtggg 16

<210> SEQ ID NO 274
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 274
gcgagcgatt gtcttg 16

<210> SEQ ID NO 275
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 275
ggttgccgtg gcaact 16

<210> SEQ ID NO 276
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 276
gggagagttt ttcctc 16

<210> SEQ ID NO 277
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 277
tgaggcacct ccatgt 16

<210> SEQ ID NO 278
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 278
gcaaaggaga ttcctc 16

<210> SEQ ID NO 279
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 279
tctcccttat agctta 16

<210> SEQ ID NO 280
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 280
gcgagagtca ccgccc 16

<210> SEQ ID NO 281
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 281
tttcttgccg tgcaca 16

<210> SEQ ID NO 282
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 282
agctgccacc aaaacg 16

<210> SEQ ID NO 283
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 283
gtaggtctac aaagaa 16

<210> SEQ ID NO 284
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 284
ctggactgct ccctgt 16

<210> SEQ ID NO 285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 285
cagatgtgtt taggca 16

<210> SEQ ID NO 286
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 286
acatcattgg gttatg 16

<210> SEQ ID NO 287
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 287
ccacatgcct gttggg 16

<210> SEQ ID NO 288
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 288
gaatcctttt cagctc 16

<210> SEQ ID NO 289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 289
cagactccaa cccttt 16

<210> SEQ ID NO 290
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 290
ctaattctat tagagg 16

<210> SEQ ID NO 291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 291
gctgaagctt taaact 16

<210> SEQ ID NO 292
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 292
gtgggacttg ttttat 16

<210> SEQ ID NO 293
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 293
gggagtgcat aacagc 16

<210> SEQ ID NO 294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 294

-continued

```
tccccaagat ataccg                                                   16


<210> SEQ ID NO 295
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 295

aggaatcttc ccctgg                                                   16


<210> SEQ ID NO 296
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 296

tgcaccctcg ctccag                                                   16


<210> SEQ ID NO 297
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 297

agcagcccag tcaccg                                                   16


<210> SEQ ID NO 298
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 298

tctgtactgc tggcct                                                   16


<210> SEQ ID NO 299
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 299

ggcacggagc cttctt                                                   16


<210> SEQ ID NO 300
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 300

atggtggtgc ctttgt                                                   16


<210> SEQ ID NO 301
<211> LENGTH: 16
<212> TYPE: DNA
<213> ORGANISM: Artificial sequence
```

<220> FEATURE:
<223> OTHER INFORMATION: Synthetic oligonucleotide

<400> SEQUENCE: 301
gtgccagacc catgcc 16

<210> SEQ ID NO 302
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 302
ccggtcaaag cggctg 16

<210> SEQ ID NO 303
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 303
cacttctttc cgtagt 16

<210> SEQ ID NO 304
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 304
gatatgttct caccca 16

<210> SEQ ID NO 305
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 305
ctgagggcac ggatgt 16

<210> SEQ ID NO 306
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 306
tcagctgaga ttggct 16

<210> SEQ ID NO 307
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 307
gatgctgggt tcatta 16

<210> SEQ ID NO 308
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 308
tcatgtaagt gctttg 16

<210> SEQ ID NO 309
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 309
cacagttctt ggtccg 16

<210> SEQ ID NO 310
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 310
tacctcaccc tcttta 16

<210> SEQ ID NO 311
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 311
actgccatct gcatta 16

<210> SEQ ID NO 312
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 312
gccccccaat atattc 16

<210> SEQ ID NO 313
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 313
tgttctaact cttggg 16

<210> SEQ ID NO 314
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 314
gacttcattc ttcgga 16

<210> SEQ ID NO 315
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 315
catcatcagg aagccg 16

<210> SEQ ID NO 316
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 316
atggccatgg cccacc 16

<210> SEQ ID NO 317
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 317
tgagcttcct cccaat 16

<210> SEQ ID NO 318
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 318
gatgagtagg tgagtt 16

<210> SEQ ID NO 319
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 319
gaatctcatg attgca 16

<210> SEQ ID NO 320
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 320
agatgggcac ccccaa 16

<210> SEQ ID NO 321

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 321
ttccgggaag tgactt 16

<210> SEQ ID NO 322
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 322
aacaccaatt agtaca 16

<210> SEQ ID NO 323
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 323
caatgaccag ggcctg 16

<210> SEQ ID NO 324
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 324
agcctacctg ggtcca 16

<210> SEQ ID NO 325
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 325
tgagtcattt gctagg 16

<210> SEQ ID NO 326
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 326
gaggtgacag gtcggg 16

<210> SEQ ID NO 327
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 327
cgatacattc ccacag 16

<210> SEQ ID NO 328
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 328
atggtacagg agaagg 16

<210> SEQ ID NO 329
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 329
ggaggcccta ttgtgt 16

<210> SEQ ID NO 330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 330
ctattgggcc tcagat 16

<210> SEQ ID NO 331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 331
atagcacgaa gcctcc 16

<210> SEQ ID NO 332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 332
ttcatattca cccgat 16

<210> SEQ ID NO 333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 333
gtaaacccaa acaggc 16

<210> SEQ ID NO 334
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 334
cctgtattcg gagacc 16

<210> SEQ ID NO 335
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 335
atcaaaaacc tgggca 16

<210> SEQ ID NO 336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 336
ttatgcttac tccaca 16

<210> SEQ ID NO 337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 337
atgcccatgt ttggta 16

<210> SEQ ID NO 338
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 338
cctccttgtc tcacta 16

<210> SEQ ID NO 339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 339
agctaagacc agtgag 16

<210> SEQ ID NO 340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 340
ctgaaaccac ctgtag 16

<210> SEQ ID NO 341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 341
cagatgggta cttctg 16

<210> SEQ ID NO 342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 342
gcctttagaa cagctg 16

<210> SEQ ID NO 343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 343
atttcttgat gtggtg 16

<210> SEQ ID NO 344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 344
ggcgagcgat tgtctt 16

<210> SEQ ID NO 345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 345
tggttgccgt ggcaac 16

<210> SEQ ID NO 346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 346
atcatcttgt tttggg 16

<210> SEQ ID NO 347
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 347
ttgaggcacc tccatg 16

<210> SEQ ID NO 348
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 348
atgcaaagga gattcc 16

<210> SEQ ID NO 349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 349
ttctccctta tagctt 16

<210> SEQ ID NO 350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 350
agcgagagtc accgcc 16

<210> SEQ ID NO 351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 351
gtttcttgcc gtgcac 16

<210> SEQ ID NO 352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 352
gtcagctgcc accaaa 16

<210> SEQ ID NO 353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 353
ggtaggtcta caaaga 16

<210> SEQ ID NO 354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 354
gaggctggac tgctcc 16

<210> SEQ ID NO 355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 355
ccagatgtgt ttaggc 16

<210> SEQ ID NO 356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 356
cacatcattg ggttat 16

<210> SEQ ID NO 357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 357
gccacatgcc tgttgg 16

<210> SEQ ID NO 358
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 358
gagaggaatg aatcct 16

<210> SEQ ID NO 359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 359
gagtcctccc cagact 16

<210> SEQ ID NO 360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 360
gctctaattc tattag 16

<210> SEQ ID NO 361
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 361
tgctgaagct ttaaac 16

<210> SEQ ID NO 362
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 362
tgtgggactt gtttta 16

<210> SEQ ID NO 363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 363
gtgggagtgc ataaca 16

<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 364
gtccccaaga tatacc 16

<210> SEQ ID NO 365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 365
ccaaggaatc ttcccc 16

<210> SEQ ID NO 366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 366
ttgcaccctc gctcca 16

<210> SEQ ID NO 367
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 367
gtgccagcag cccagt 16

<210> SEQ ID NO 368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 368
ttctgtactg ctggcc 16

<210> SEQ ID NO 369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 369
gggcacggag ccttct 16

<210> SEQ ID NO 370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 370
gatggtggtg cctttg 16

<210> SEQ ID NO 371
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 371
ggtgccagac ccatgc 16

<210> SEQ ID NO 372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 372
cccggtcaaa gcggct 16

<210> SEQ ID NO 373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 373
ccacttcttt ccgtag 16

<210> SEQ ID NO 374
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 374
agttggatat gttctc 16

<210> SEQ ID NO 375
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 375
tctgagggca cggatg 16

<210> SEQ ID NO 376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 376
ttcagctgag attggc 16

<210> SEQ ID NO 377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 377
ggatgctggg ttcatt 16

<210> SEQ ID NO 378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 378
ctcatgtaag tgcttt 16

<210> SEQ ID NO 379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 379
gtcacagttc ttggtc 16

<210> SEQ ID NO 380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 380
ttacctcacc ctcttt 16

<210> SEQ ID NO 381
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 381
cactgccatc tgcatt 16

<210> SEQ ID NO 382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 382
ggccccccaa tatatt 16

<210> SEQ ID NO 383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 383
ctgttctaac tcttgg 16

<210> SEQ ID NO 384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 384
agacttcatt cttcgg 16

<210> SEQ ID NO 385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 385
ccatcatcag gaagcc 16

<210> SEQ ID NO 386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 386
ggaccatggc catggc 16

<210> SEQ ID NO 387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 387
gatctgagct tcctcc 16

<210> SEQ ID NO 388
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 388
tgatgagtag gtgagt 16

<210> SEQ ID NO 389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 389
tgaatctcat gattgc 16

<210> SEQ ID NO 390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 390
gtgtggcctg gccata 16

<210> SEQ ID NO 391
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 391
cggttggtca attccg 16

<210> SEQ ID NO 392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 392
cagaggctat caacaa 16

<210> SEQ ID NO 393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 393
gttctgacaa tgacca 16

<210> SEQ ID NO 394
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 394
aggaggtgag cctacc 16

<210> SEQ ID NO 395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 395
ttgagtcatt tgctag 16

<210> SEQ ID NO 396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 396
gggaggtgac aggtcg 16

<210> SEQ ID NO 397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 397
cccgatacat tcccac 16

<210> SEQ ID NO 398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 398
catggtacag gagaag 16

<210> SEQ ID NO 399
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 399
gggaggccct attgtg 16

<210> SEQ ID NO 400

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 400
tctattgggc ctcaga 16

<210> SEQ ID NO 401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 401
catagcacga agcctc 16

<210> SEQ ID NO 402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 402
tttcatattc acccga 16

<210> SEQ ID NO 403
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 403
ggtaaaccca aacagg 16

<210> SEQ ID NO 404
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 404
acctgtattc ggagac 16

<210> SEQ ID NO 405
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 405
gcatcaaaaa cctggg 16

<210> SEQ ID NO 406
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 406
cttatgctta ctccac 16

<210> SEQ ID NO 407
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 407
tatgcccatg tttggt 16

<210> SEQ ID NO 408
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 408
accctccttg tctcac 16

<210> SEQ ID NO 409
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 409
cagctaagac cagtga 16

<210> SEQ ID NO 410
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 410
gctgaaacca cctgta 16

<210> SEQ ID NO 411
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 411
tcagatgggt acttct 16

<210> SEQ ID NO 412
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 412
ggcctttaga acagct 16

<210> SEQ ID NO 413
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 413
gtatttcttg atgtgg 16

<210> SEQ ID NO 414
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 414
gggcgagcga ttgtct 16

<210> SEQ ID NO 415
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 415
ttggttgccg tggcaa 16

<210> SEQ ID NO 416
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 416
gatcatcttg ttttgg 16

<210> SEQ ID NO 417
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 417
cttgaggcac ctccat 16

<210> SEQ ID NO 418
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 418
catgcaaagg agattc 16

<210> SEQ ID NO 419
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 419
attctccctt atagct 16

<210> SEQ ID NO 420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 420
cagcgagagt caccgc 16

<210> SEQ ID NO 421
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 421
tgtttcttgc cgtgca 16

<210> SEQ ID NO 422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 422
gaagtcagct gccacc 16

<210> SEQ ID NO 423
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 423
tggtaggtct acaaag 16

<210> SEQ ID NO 424
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 424
gaccattccc agcaga 16

<210> SEQ ID NO 425
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 425
tccagatgtg tttagg 16

<210> SEQ ID NO 426
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 426
acacatcatt gggtta 16

<210> SEQ ID NO 427
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 427
gatcacttcc atctgc 16

<210> SEQ ID NO 428
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 428
atggtgcttt ggagag 16

<210> SEQ ID NO 429
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 429
caagagagtc ctcccc 16

<210> SEQ ID NO 430
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 430
ggctctaatt ctatta 16

<210> SEQ ID NO 431
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 431
ggaattgtgt gccccc 16

<210> SEQ ID NO 432
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 432
gatgtgggac ttgttt 16

<210> SEQ ID NO 433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 433
tgtgggagtg cataac 16

<210> SEQ ID NO 434
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 434
agtccccaag atatac 16

<210> SEQ ID NO 435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 435
gcctcctcca aggaat 16

<210> SEQ ID NO 436
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 436
gttgcaccct cgctcc 16

<210> SEQ ID NO 437
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 437
tggtgccagc agccca 16

<210> SEQ ID NO 438
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 438
tttctgtact gctggc 16

<210> SEQ ID NO 439
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 439
agggcacgga gccttc 16

<210> SEQ ID NO 440
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 440
cgatggtggt gccttt 16

<210> SEQ ID NO 441
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 441
gggtgccaga cccatg 16

<210> SEQ ID NO 442
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 442
tcccggtcaa agcggc 16

<210> SEQ ID NO 443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 443
accacttctt tccgta 16

<210> SEQ ID NO 444
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 444
aagttggata tgttct 16

<210> SEQ ID NO 445
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 445
gtctgagggc acggat 16

<210> SEQ ID NO 446
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 446
tttcagctga gattgg 16

<210> SEQ ID NO 447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 447
aggatgctgg gttcat 16

<210> SEQ ID NO 448
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 448
cctcatgtaa gtgctt 16

<210> SEQ ID NO 449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 449
tggtcacagt tcttgg 16

<210> SEQ ID NO 450
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 450
actttacctc accctc 16

<210> SEQ ID NO 451
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 451
gcactgccat ctgcat 16

<210> SEQ ID NO 452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 452
cggcccccca atatat 16

<210> SEQ ID NO 453
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 453
actgttctaa ctcttg 16

<210> SEQ ID NO 454
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 454
aagacttcat tcttcg 16

<210> SEQ ID NO 455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 455
accatcatca ggaagc 16

<210> SEQ ID NO 456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 456
gggaccatgg ccatgg 16

<210> SEQ ID NO 457
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 457
agatctgagc ttcctc 16

<210> SEQ ID NO 458
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 458
ttgatgagta ggtgag 16

<210> SEQ ID NO 459
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 459
ttgaatctca tgattg 16

<210> SEQ ID NO 460
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 460
tgttgccccc attggg 16

<210> SEQ ID NO 461
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 461
tctgccggtt ggtcaa 16

<210> SEQ ID NO 462
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 462
gaatgagcag gtcaga 16

<210> SEQ ID NO 463
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 463
ggttctgaca atgacc 16

<210> SEQ ID NO 464
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 464
gaggaggtga gcctac 16

<210> SEQ ID NO 465
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 465
cttgagtcat ttgcta 16

<210> SEQ ID NO 466
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 466
cgggaggtga caggtc 16

<210> SEQ ID NO 467
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 467
gcccgataca ttccca 16

<210> SEQ ID NO 468
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 468
ctcatggtac aggaga 16

<210> SEQ ID NO 469
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 469
agggaggccc tattgt 16

<210> SEQ ID NO 470
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 470
ttctattggg cctcag 16

<210> SEQ ID NO 471
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 471
ccatagcacg aagcct 16

<210> SEQ ID NO 472
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 472
gtttcatatt cacccg 16

<210> SEQ ID NO 473
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 473
aggtaaaccc aaacag 16

<210> SEQ ID NO 474
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 474
cacctgtatt cggaga 16

<210> SEQ ID NO 475
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 475
agcatcaaaa acctgg 16

<210> SEQ ID NO 476
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 476
ccttatgctt actcca 16

<210> SEQ ID NO 477
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 477
gtatgcccat gtttgg 16

<210> SEQ ID NO 478
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 478
taccctcctt gtctca 16

<210> SEQ ID NO 479

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 479
tcagctaaga ccagtg 16

<210> SEQ ID NO 480
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 480
ttgctgaaac cacctg 16

<210> SEQ ID NO 481
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 481
atcagatggg tacttc 16

<210> SEQ ID NO 482
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 482
aggcctttag aacagc 16

<210> SEQ ID NO 483
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 483
cactaaatct gtgtat 16

<210> SEQ ID NO 484
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 484
tgggcgagcg attgtc 16

<210> SEQ ID NO 485
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 485
cttggttgcc gtggca 16

<210> SEQ ID NO 486
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 486
ctgttattaa accaca 16

<210> SEQ ID NO 487
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 487
ccttgaggca cctcca 16

<210> SEQ ID NO 488
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 488
ccatgcaaag gagatt 16

<210> SEQ ID NO 489
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 489
cattctccct tatagc 16

<210> SEQ ID NO 490
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 490
acagcgagag tcaccg 16

<210> SEQ ID NO 491
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 491
ttgtttcttg ccgtgc 16

<210> SEQ ID NO 492
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 492
tgaagtcagc tgccac 16

<210> SEQ ID NO 493
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 493
atggtaggtc tacaaa 16

<210> SEQ ID NO 494
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 494
attcctgacc attccc 16

<210> SEQ ID NO 495
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 495
atccagatgt gtttag 16

<210> SEQ ID NO 496
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 496
aacacatcat tgggtt 16

<210> SEQ ID NO 497
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 497
tgatcacttc catctg 16

<210> SEQ ID NO 498
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 498
catggtgctt tggaga 16

<210> SEQ ID NO 499
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 499
cataagccag caagag 16

<210> SEQ ID NO 500
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 500
gggctctaat tctatt 16

<210> SEQ ID NO 501
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 501
gggaattgtg tgcccc 16

<210> SEQ ID NO 502
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 502
tgatgtggga cttgtt 16

<210> SEQ ID NO 503
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 503
gtgtgggagt gcataa 16

<210> SEQ ID NO 504
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 504
cagtccccaa gatata 16

<210> SEQ ID NO 505
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 505
gggcctcctc caagga 16

<210> SEQ ID NO 506
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 506
tgttgcaccc tcgctc 16

<210> SEQ ID NO 507
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 507
atggtgccag cagccc 16

<210> SEQ ID NO 508
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 508
gtttctgtac tgctgg 16

<210> SEQ ID NO 509
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 509
aagggcacgg agcctt 16

<210> SEQ ID NO 510
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 510
gcgatggtgg tgcctt 16

<210> SEQ ID NO 511
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 511
agggtgccag acccat 16

<210> SEQ ID NO 512
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 512
atcccggtca aagcgg 16

<210> SEQ ID NO 513
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 513
caccacttct ttccgt 16

<210> SEQ ID NO 514
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 514
gaaagttgga tatgtt 16

<210> SEQ ID NO 515
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 515
cgtctgaggg cacgga 16

<210> SEQ ID NO 516
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 516
ctttcagctg agattg 16

<210> SEQ ID NO 517
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 517
caggatgctg ggttca 16

<210> SEQ ID NO 518
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 518
ccctcatgta agtgct 16

<210> SEQ ID NO 519
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 519
gtggtcacag ttcttg 16

<210> SEQ ID NO 520
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 520
aactttacct caccct 16

<210> SEQ ID NO 521
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 521
tccttgctgc actgcc 16

<210> SEQ ID NO 522
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 522
ccggcccccc aatata 16

<210> SEQ ID NO 523
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 523
caactgttct aactct 16

<210> SEQ ID NO 524
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 524
gcccccagga ggacaa 16

<210> SEQ ID NO 525
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 525
gaccatcatc aggaag 16

<210> SEQ ID NO 526
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 526
cacatactct ctggga 16

<210> SEQ ID NO 527
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 527
gagatctgag cttcct 16

<210> SEQ ID NO 528
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 528
cttgatgagt aggtga 16

<210> SEQ ID NO 529
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 529
ttctgttgcc cccatt 16

<210> SEQ ID NO 530
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 530
ctgggcgagt ctgccg 16

<210> SEQ ID NO 531
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 531
gtagaatgag caggtc 16

<210> SEQ ID NO 532
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 532
agagtctata cacaga 16

<210> SEQ ID NO 533
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 533
gagtaggaac cagcag 16

<210> SEQ ID NO 534
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 534
acttgagtca tttgct 16

<210> SEQ ID NO 535
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 535
gcgggaggtg acaggt 16

<210> SEQ ID NO 536
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 536
ggcccgatac attccc 16

<210> SEQ ID NO 537
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 537
tctcatggta caggag 16

<210> SEQ ID NO 538
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 538
tagggaggcc ctattg 16

<210> SEQ ID NO 539
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 539
attctattgg gcctca 16

<210> SEQ ID NO 540
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 540
caccatagca cgaagc 16

<210> SEQ ID NO 541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 541
agtttcatat tcaccc 16

<210> SEQ ID NO 542
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 542
caaggtaaac ccaaac 16

<210> SEQ ID NO 543
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 543
tcacctgtat tcggag 16

<210> SEQ ID NO 544
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 544
ctaaaagctg atttgc 16

<210> SEQ ID NO 545
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 545
tccttatgct tactcc 16

<210> SEQ ID NO 546
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 546
catgtatgcc catgtt 16

<210> SEQ ID NO 547
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 547
ataccctcct tgtctc 16

<210> SEQ ID NO 548
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 548
ttcagctaag accagt 16

<210> SEQ ID NO 549
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 549
gttgctgaaa ccacct 16

<210> SEQ ID NO 550
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 550
tatcagatgg gtactt 16

<210> SEQ ID NO 551
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 551
gaggccttta gaacag 16

<210> SEQ ID NO 552
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 552
gcactaaatc tgtgta 16

<210> SEQ ID NO 553
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 553
ctgggcgagc gattgt 16

<210> SEQ ID NO 554
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 554
acttggttgc cgtggc 16

<210> SEQ ID NO 555
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 555
cctgttatta aaccac 16

<210> SEQ ID NO 556
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 556
tccttgaggc acctcc 16

<210> SEQ ID NO 557
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 557
accatgcaaa ggagat 16

<210> SEQ ID NO 558

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 558
gcattctccc ttatag 16

<210> SEQ ID NO 559
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 559
gacagcgaga gtcacc 16

<210> SEQ ID NO 560
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 560
attgtttctt gccgtg 16

<210> SEQ ID NO 561
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 561
tcctgaagtc agctgc 16

<210> SEQ ID NO 562
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 562
aatggtaggt ctacaa 16

<210> SEQ ID NO 563
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 563
tattcctgac cattcc 16

<210> SEQ ID NO 564
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 564
aatccagatg tgttta 16

<210> SEQ ID NO 565
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 565
tcaacacatc attggg 16

<210> SEQ ID NO 566
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 566
gtgatcactt ccatct 16

<210> SEQ ID NO 567
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 567
ccatggtgct ttggag 16

<210> SEQ ID NO 568
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 568
ccataagcca gcaaga 16

<210> SEQ ID NO 569
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 569
agggctctaa ttctat 16

<210> SEQ ID NO 570
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 570
agggaattgt gtgccc 16

<210> SEQ ID NO 571
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 571
gtgatgtggg acttgt 16

<210> SEQ ID NO 572
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 572
agtgtgggag tgcata 16

<210> SEQ ID NO 573
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 573
ccagtcccca agatat 16

<210> SEQ ID NO 574
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 574
tcgctgcagg gcctcc 16

<210> SEQ ID NO 575
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 575
ttgttgcacc ctcgct 16

<210> SEQ ID NO 576
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 576
tctctgggtc catggt 16

<210> SEQ ID NO 577
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 577
agtttctgta ctgctg 16

<210> SEQ ID NO 578
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 578
caagggcacg gagcct 16

<210> SEQ ID NO 579
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 579
ggcgatggtg gtgcct 16

<210> SEQ ID NO 580
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 580
ctctgtgaag ggtgcc 16

<210> SEQ ID NO 581
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 581
aatcccggtc aaagcg 16

<210> SEQ ID NO 582
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 582
ccaccacttc tttccg 16

<210> SEQ ID NO 583
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 583
attgccagct aaggaa 16

<210> SEQ ID NO 584
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 584
gattggctct ggctcg 16

<210> SEQ ID NO 585
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 585
gctttcagct gagatt 16

<210> SEQ ID NO 586
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 586
gactcctctg ctcatt 16

<210> SEQ ID NO 587
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 587
cccctcatgt aagtgc 16

<210> SEQ ID NO 588
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 588
gccctgtggt cacagt 16

<210> SEQ ID NO 589
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 589
aaactttacc tcaccc 16

<210> SEQ ID NO 590
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 590
tctccttgct gcactg 16

<210> SEQ ID NO 591
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 591
cccggccccc caatat 16

<210> SEQ ID NO 592
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 592
ccaactgttc taactc 16

<210> SEQ ID NO 593
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 593
atgcccccag gaggac 16

<210> SEQ ID NO 594
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 594
caatgaccat catcag 16

<210> SEQ ID NO 595
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 595
tcacatactc tctggg 16

<210> SEQ ID NO 596
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 596
agagatctga gcttcc 16

<210> SEQ ID NO 597
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 597
gcttgatgag taggtg 16

<210> SEQ ID NO 598
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 598
tcctccttga gcagga 16

<210> SEQ ID NO 599
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 599
tgaactcctt gtacct 16

<210> SEQ ID NO 600
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 600
gtcctccctg ggcgag 16

<210> SEQ ID NO 601
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 601
ccacatttga gattat 16

<210> SEQ ID NO 602
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 602
cgggcagcca tctgat 16

<210> SEQ ID NO 603
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 603
caccctccat tctaag 16

<210> SEQ ID NO 604
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 604
cacttgagtc atttgc 16

<210> SEQ ID NO 605
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 605
agcgggaggt gacagg 16

<210> SEQ ID NO 606
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 606
aggcccgata cattcc 16

<210> SEQ ID NO 607
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 607
ttctcatggt acagga 16

<210> SEQ ID NO 608
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 608
ttagggaggc cctatt 16

<210> SEQ ID NO 609
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 609
aattctattg ggcctc 16

<210> SEQ ID NO 610
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 610
tcaccatagc acgaag 16

<210> SEQ ID NO 611
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 611
gcagtttcat attcac 16

<210> SEQ ID NO 612
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 612
gattttccaa caaggt 16

<210> SEQ ID NO 613
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 613
ctcacctgta ttcgga 16

<210> SEQ ID NO 614
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 614
gcactaaaag ctgatt 16

<210> SEQ ID NO 615
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 615
gaaatcctta tgctta 16

<210> SEQ ID NO 616
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 616
ccatgtatgc ccatgt 16

<210> SEQ ID NO 617
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 617

cataccctcc ttgtct                                                          16

<210> SEQ ID NO 618
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 618

aattcagcta agacca                                                          16

<210> SEQ ID NO 619
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 619

agttgctgaa accacc                                                          16

<210> SEQ ID NO 620
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 620

atatcagatg ggtact                                                          16

<210> SEQ ID NO 621
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 621

cgaggccttt agaaca                                                          16

<210> SEQ ID NO 622
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 622

ggcactaaat ctgtgt                                                          16

<210> SEQ ID NO 623
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 623

gctgggcgag cgattg                                                          16
```

<210> SEQ ID NO 624
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 624
gacttggttg ccgtgg 16

<210> SEQ ID NO 625
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 625
gcctgttatt aaacca 16

<210> SEQ ID NO 626
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 626
atccttgagg cacctc 16

<210> SEQ ID NO 627
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 627
ctaccatgca aaggag 16

<210> SEQ ID NO 628
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 628
tgcattctcc cttata 16

<210> SEQ ID NO 629
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 629
agacagcgag agtcac 16

<210> SEQ ID NO 630
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 630
aattgtttct tgccgt 16

<210> SEQ ID NO 631
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 631
gattactcct gaagtc 16

<210> SEQ ID NO 632
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 632
ataatggtag gtctac 16

<210> SEQ ID NO 633
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 633
atattcctga ccattc 16

<210> SEQ ID NO 634
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 634
gaatccagat gtgttt 16

<210> SEQ ID NO 635
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 635
atcaacacat cattgg 16

<210> SEQ ID NO 636
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 636
agtgatcact tccatc 16

<210> SEQ ID NO 637

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 637
gccatggtgc tttgga 16

<210> SEQ ID NO 638
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 638
cttccataag ccagca 16

<210> SEQ ID NO 639
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 639
tagggctcta attcta 16

<210> SEQ ID NO 640
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 640
gagggaattg tgtgcc 16

<210> SEQ ID NO 641
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 641
tgtgatgtgg gacttg 16

<210> SEQ ID NO 642
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 642
aagtgtggga gtgcat 16

<210> SEQ ID NO 643
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 643
aggtcctcca gtcccc 16

<210> SEQ ID NO 644
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 644
gtcgctgcag ggcctc 16

<210> SEQ ID NO 645
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 645
tttgttgcac cctcgc 16

<210> SEQ ID NO 646
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 646
gctctctggg tccatg 16

<210> SEQ ID NO 647
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 647
cagtttctgt actgct 16

<210> SEQ ID NO 648
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 648
gcaagggcac ggagcc 16

<210> SEQ ID NO 649
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 649
tggcgatggt ggtgcc 16

<210> SEQ ID NO 650
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 650
cctctgtgaa gggtgc 16

<210> SEQ ID NO 651
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 651
taatcccggt caaagc 16

<210> SEQ ID NO 652
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 652
tgtccaccac ttcttt 16

<210> SEQ ID NO 653
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 653
tattgccagc taagga 16

<210> SEQ ID NO 654
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 654
agattggctc tggctc 16

<210> SEQ ID NO 655
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 655
cgctttcagc tgagat 16

<210> SEQ ID NO 656
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 656
gcttgactcc tctgct 16

<210> SEQ ID NO 657
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 657
ccccctcatg taagtg 16

<210> SEQ ID NO 658
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 658
atctctcctg gtggct 16

<210> SEQ ID NO 659
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 659
taaactttac ctcacc 16

<210> SEQ ID NO 660
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 660
ttctccttgc tgcact 16

<210> SEQ ID NO 661
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 661
acccggcccc ccaata 16

<210> SEQ ID NO 662
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 662
tccaactgtt ctaact 16

<210> SEQ ID NO 663
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 663
tatgccccca ggagga                                              16

<210> SEQ ID NO 664
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 664
ccccaatgac catcat                                              16

<210> SEQ ID NO 665
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 665
ggttctcaca tactct                                              16

<210> SEQ ID NO 666
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 666
tagagatctg agcttc                                              16

<210> SEQ ID NO 667
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 667
agcttgatga gtaggt                                              16

<210> SEQ ID NO 668
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 668
gcctcctcct tgagca                                              16

<210> SEQ ID NO 669
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 669
gatgacctct gaactc                                              16

<210> SEQ ID NO 670
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 670
ggtcctccct gggcga 16

<210> SEQ ID NO 671
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 671
gcccacattt gagatt 16

<210> SEQ ID NO 672
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 672
aggacgggca gccatc 16

<210> SEQ ID NO 673
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 673
ccaccctcca ttctaa 16

<210> SEQ ID NO 674
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 674
ccacttgagt catttg 16

<210> SEQ ID NO 675
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 675
gagcgggagg tgacag 16

<210> SEQ ID NO 676
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 676
caggcccgat acattc 16

<210> SEQ ID NO 677
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 677
attctcatgg tacagg 16

<210> SEQ ID NO 678
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 678
cttagggagg ccctat 16

<210> SEQ ID NO 679
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 679
aaattctatt gggcct 16

<210> SEQ ID NO 680
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 680
ttcaccatag cacgaa 16

<210> SEQ ID NO 681
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 681
ccttactgca gtttca 16

<210> SEQ ID NO 682
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 682
gggattttcc aacaag 16

<210> SEQ ID NO 683
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 683
tctcacctgt attcgg 16

<210> SEQ ID NO 684
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 684
tgcactaaaa gctgat 16

<210> SEQ ID NO 685
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 685
cagaaatcct tatgct 16

<210> SEQ ID NO 686
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 686
tccatgtatg cccatg 16

<210> SEQ ID NO 687
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 687
cactcaatca taccct 16

<210> SEQ ID NO 688
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 688
caattcagct aagacc 16

<210> SEQ ID NO 689
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 689
ggagttgctg aaacca 16

<210> SEQ ID NO 690
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 690
catatcagat gggtac 16

<210> SEQ ID NO 691
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 691
acgaggcctt tagaac 16

<210> SEQ ID NO 692
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 692
ctctggcact aaatct 16

<210> SEQ ID NO 693
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 693
ggctgggcga gcgatt 16

<210> SEQ ID NO 694
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 694
tgacttggtt gccgtg 16

<210> SEQ ID NO 695
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 695
ggcctgttat taaacc 16

<210> SEQ ID NO 696
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 696
gatccttgag gcacct 16

<210> SEQ ID NO 697
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 697
actaccatgc aaagga 16

<210> SEQ ID NO 698
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 698
ctccttatgt tttgaa 16

<210> SEQ ID NO 699
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 699
cagacagcga gagtca 16

<210> SEQ ID NO 700
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 700
aaattgtttc ttgccg 16

<210> SEQ ID NO 701
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 701
ggattactcc tgaagt 16

<210> SEQ ID NO 702
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 702
aataatggta ggtcta 16

<210> SEQ ID NO 703
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 703
tatattcctg accatt 16

<210> SEQ ID NO 704
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 704
ggaatccaga tgtgtt 16

<210> SEQ ID NO 705
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 705
tatcaacaca tcattg 16

<210> SEQ ID NO 706
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 706
cagtgatcac ttccat 16

<210> SEQ ID NO 707
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 707
acattgaaac accagg 16

<210> SEQ ID NO 708
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 708
gcttccataa gccagc 16

<210> SEQ ID NO 709
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 709
gtagggctct aattct 16

<210> SEQ ID NO 710
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 710
agagggaatt gtgtgc 16

<210> SEQ ID NO 711
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 711
ctgtgatgtg ggactt 16

<210> SEQ ID NO 712
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 712
aaagtgtggg agtgca 16

<210> SEQ ID NO 713
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 713
aggaattcga aaggga 16

<210> SEQ ID NO 714
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 714
ataataacca gacagg 16

<210> SEQ ID NO 715
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 715
gcactcatcc agatgc 16

<210> SEQ ID NO 716

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 716
tccagtatct gtccca 16

<210> SEQ ID NO 717
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 717
gtgtgctcac tttttc 16

<210> SEQ ID NO 718
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 718
gttatcctca agctca 16

<210> SEQ ID NO 719
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 719
accttctgaa ccccat 16

<210> SEQ ID NO 720
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 720
gacgagggtc aggatg 16

<210> SEQ ID NO 721
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 721
catcccaggt tccaag 16

<210> SEQ ID NO 722
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 722
atggtactgc tggtaa 16

<210> SEQ ID NO 723
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 723
ggcttgggct tgtgtc 16

<210> SEQ ID NO 724
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 724
gtgtgagttg gtaagt 16

<210> SEQ ID NO 725
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 725
atgcggtact gactga 16

<210> SEQ ID NO 726
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 726
cacctgttca ccgctt 16

<210> SEQ ID NO 727
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 727
gccacatccg tgagct 16

<210> SEQ ID NO 728
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 728
cctgcagaat cttata 16

<210> SEQ ID NO 729
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 729
ccctgccagg catatc 16

<210> SEQ ID NO 730
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 730
ccaaagtccc taacac 16

<210> SEQ ID NO 731
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 731
tattgcaggc tccaat 16

<210> SEQ ID NO 732
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 732
tcttccgtca atatat 16

<210> SEQ ID NO 733
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 733
tgggtctgta gtggag 16

<210> SEQ ID NO 734
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 734
tgcctgactg agatat 16

<210> SEQ ID NO 735
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 735
ccatcacatg acaacc 16

<210> SEQ ID NO 736
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 736
ccgggtaaga gcgatg 16

<210> SEQ ID NO 737
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 737
cggcgacaag acagct 16

<210> SEQ ID NO 738
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 738
agcaaacacg ctcccc 16

<210> SEQ ID NO 739
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 739
gcaacgcacc cttctc 16

<210> SEQ ID NO 740
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 740
acaggcttca tcatct 16

<210> SEQ ID NO 741
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 741
agcctctgct gaatat 16

<210> SEQ ID NO 742
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 742
gatcttgcca gatgcc 16

<210> SEQ ID NO 743
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 743
atcactgagc ccccat 16

<210> SEQ ID NO 744
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 744
tcaccctaag gagagg 16

<210> SEQ ID NO 745
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 745
acttccccaa ggatgt 16

<210> SEQ ID NO 746
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 746
agggtcagct tggagc 16

<210> SEQ ID NO 747
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 747
gttaagctgg aagctg 16

<210> SEQ ID NO 748
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 748
agccgtgtta tatttg 16

<210> SEQ ID NO 749
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 749
tgccctaaca cagctg 16

<210> SEQ ID NO 750
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 750
ttcccaattc agcaat 16

<210> SEQ ID NO 751
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 751
ttgtctccga cacttt 16

<210> SEQ ID NO 752
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 752
aagtgcaacc aatcaa 16

<210> SEQ ID NO 753
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 753
ctaaactcac actggc 16

<210> SEQ ID NO 754
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 754
ctaagttccg gtctca 16

<210> SEQ ID NO 755
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 755
actccactgg gcccga 16

<210> SEQ ID NO 756
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 756
gcattgccct cccaat 16

<210> SEQ ID NO 757
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 757
caccacagcc gttcca 16

<210> SEQ ID NO 758
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 758
ctgggtctga cccacg 16

<210> SEQ ID NO 759
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 759
caggatcctg acaaac 16

<210> SEQ ID NO 760
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 760
caggttcaca tgacag 16

<210> SEQ ID NO 761
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 761
aactgcaagc tatggg 16

<210> SEQ ID NO 762
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 762
gacaggcaat acctac 16

<210> SEQ ID NO 763
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 763
ggatggaagg aacctc 16

<210> SEQ ID NO 764
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 764
tgaacgcaat gctgac 16

<210> SEQ ID NO 765
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 765
gctctcggct tctaat 16

<210> SEQ ID NO 766
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 766
cggctctcca ctgtca 16

<210> SEQ ID NO 767
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 767
gcactctcag atgggc 16

<210> SEQ ID NO 768
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 768
acagcattga gtacaa 16

<210> SEQ ID NO 769
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 769
atcaagcagg aagctc 16

<210> SEQ ID NO 770
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 770
ccggccacct cattct 16

<210> SEQ ID NO 771
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 771
ccagtatgta tttgtg 16

<210> SEQ ID NO 772
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 772
cagtacagag caggat 16

<210> SEQ ID NO 773
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 773
cacatgtttc aacagt 16

<210> SEQ ID NO 774
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 774
tttagaaagg acacgg 16

<210> SEQ ID NO 775
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 775
aatatcagag tgtacc 16

<210> SEQ ID NO 776
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 776
tcaaacactt tatacc 16

<210> SEQ ID NO 777
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 777
ggaagtggaa acatcc 16

<210> SEQ ID NO 778
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 778
gttgaagtca cccagc 16

<210> SEQ ID NO 779
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 779
gactgtgtga gcacac 16

<210> SEQ ID NO 780
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 780
catttggaga tctggc 16

<210> SEQ ID NO 781
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 781
attagtgcta tagagg 16

<210> SEQ ID NO 782
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 782
ttgcataaga gatgac 16

<210> SEQ ID NO 783
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 783
gaggaattcg aaaggg 16

<210> SEQ ID NO 784
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 784
gtataataac cagaca 16

<210> SEQ ID NO 785
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 785
tgcactcatc cagatg 16

<210> SEQ ID NO 786
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 786
ctccagtatc tgtccc 16

<210> SEQ ID NO 787
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 787
ggaccttctg aacccc 16

<210> SEQ ID NO 788
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 788
cgacgagggt caggat 16

<210> SEQ ID NO 789
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 789
ccatcccagg ttccaa 16

<210> SEQ ID NO 790
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 790
catggtactg ctggta 16

<210> SEQ ID NO 791
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 791
tttgatgacc aggtcg 16

<210> SEQ ID NO 792
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 792
cgtgtgagtt ggtaag 16

<210> SEQ ID NO 793
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 793
catgcggtac tgactg 16

<210> SEQ ID NO 794
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 794
ccacctgttc accgct 16

<210> SEQ ID NO 795

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 795
gggccacatc cgtgag 16

<210> SEQ ID NO 796
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 796
gccaaagtcc ctaaca 16

<210> SEQ ID NO 797
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 797
ttcttccgtc aatata 16

<210> SEQ ID NO 798
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 798
gctgggtctg tagtgg 16

<210> SEQ ID NO 799
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 799
ctgcctgact gagata 16

<210> SEQ ID NO 800
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 800
cccatcacat gacaac 16

<210> SEQ ID NO 801
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 801
accgggtaag agcgat 16

<210> SEQ ID NO 802
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 802
gcggcgacaa gacagc 16

<210> SEQ ID NO 803
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 803
tctgcaacgc accctt 16

<210> SEQ ID NO 804
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 804
ttaccaagga atcttc 16

<210> SEQ ID NO 805
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 805
cgcctccttc aacctt 16

<210> SEQ ID NO 806
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 806
gaccctgacc tggagc 16

<210> SEQ ID NO 807
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 807
gcactggaca gcctgt 16

<210> SEQ ID NO 808
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 808
ttgtctatca ctgagc 16

<210> SEQ ID NO 809
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 809
gtcaccctaa ggagag 16

<210> SEQ ID NO 810
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 810
gctgattcca cttccc 16

<210> SEQ ID NO 811
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 811
ccccagggtc agcttg 16

<210> SEQ ID NO 812
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 812
agttaagctg gaagct 16

<210> SEQ ID NO 813
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 813
tagccgtgtt atattt 16

<210> SEQ ID NO 814
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 814
tgaactcagc ccctgc 16

<210> SEQ ID NO 815
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 815
tttcccaatt cagcaa 16

<210> SEQ ID NO 816
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 816
cttgtctccg acactt 16

<210> SEQ ID NO 817
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 817
taagtgcaac caatca 16

<210> SEQ ID NO 818
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 818
cctaaactca cactgg 16

<210> SEQ ID NO 819
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 819
gctaagttcc ggtctc 16

<210> SEQ ID NO 820
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 820
aactccactg ggcccg 16

<210> SEQ ID NO 821
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 821
actgcattgc cctccc 16

<210> SEQ ID NO 822
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 822
gcaccacagc cgttcc 16

<210> SEQ ID NO 823
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 823
acaggatcct gacaaa 16

<210> SEQ ID NO 824
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 824
aaactgcaag ctatgg 16

<210> SEQ ID NO 825
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 825
tggacaggca atacct 16

<210> SEQ ID NO 826
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 826
atgaacgcaa tgctga 16

<210> SEQ ID NO 827
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 827
tgctctcggc ttctaa 16

<210> SEQ ID NO 828
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 828
acggctctcc actgtc 16

<210> SEQ ID NO 829
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 829
ggcactctca gatggg 16

<210> SEQ ID NO 830
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 830
cacagcattg agtaca 16

<210> SEQ ID NO 831
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 831
accatcaagc aggaag 16

<210> SEQ ID NO 832
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 832
cccggccacc tcattc 16

<210> SEQ ID NO 833
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 833
accagtatgt atttgt 16

<210> SEQ ID NO 834
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 834
tcagtacaga gcagga 16

<210> SEQ ID NO 835
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 835
acacatgttt caacag 16

<210> SEQ ID NO 836
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 836
ttttagaaag gacacg 16

<210> SEQ ID NO 837
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 837
aaatatcaga gtgtac 16

<210> SEQ ID NO 838
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 838
gtcaaacact ttatac 16

<210> SEQ ID NO 839
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 839
gtgagccttc caggcc 16

<210> SEQ ID NO 840
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 840
gatgttgaag tcaccc 16

<210> SEQ ID NO 841
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 841
aagactgtgt gagcac 16

<210> SEQ ID NO 842
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 842
tacatttgga gatctg 16

<210> SEQ ID NO 843
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 843
cattagtgct atagag 16

<210> SEQ ID NO 844
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 844
attgcataag agatga 16

<210> SEQ ID NO 845
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 845
cgaggaattc gaaagg 16

<210> SEQ ID NO 846
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 846
tgtataataa ccagac 16

<210> SEQ ID NO 847
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 847
gtgcactcat ccagat 16

<210> SEQ ID NO 848
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 848
atctccagta tctgtc 16

<210> SEQ ID NO 849
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 849
gattctgtgt gctcac 16

<210> SEQ ID NO 850
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 850
atgttatcct caagct 16

<210> SEQ ID NO 851
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 851
tggaccttct gaaccc 16

<210> SEQ ID NO 852
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 852
ccgacgaggg tcagga 16

<210> SEQ ID NO 853
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 853
actccatccc aggttc 16

<210> SEQ ID NO 854
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 854
ccatggtact gctggt 16

<210> SEQ ID NO 855
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 855
ttttgatgac caggtc 16

<210> SEQ ID NO 856
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 856
ccttcccaat gcctcg 16

<210> SEQ ID NO 857
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 857
gcatgcggta ctgact 16

<210> SEQ ID NO 858
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 858
tccacctgtt caccgc 16

<210> SEQ ID NO 859
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 859
tacatccagc acaaga 16

<210> SEQ ID NO 860
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 860
cgcctgcaga atctta 16

<210> SEQ ID NO 861
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 861
gcccctgcca ggcata 16

<210> SEQ ID NO 862
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 862
tgccaaagtc cctaac 16

<210> SEQ ID NO 863
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 863
ttcccttatt gcaggc 16

<210> SEQ ID NO 864
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 864
attcttccgt caatat 16

<210> SEQ ID NO 865
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 865
ggctgggtct gtagtg 16

<210> SEQ ID NO 866
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 866
gctgcctgac tgagat 16

<210> SEQ ID NO 867
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 867
acccatcaca tgacaa 16

<210> SEQ ID NO 868
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 868
taccgggtaa gagcga 16

<210> SEQ ID NO 869
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 869
ggcggcgaca agacag 16

<210> SEQ ID NO 870
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 870
acagcaaaca cgctcc 16

<210> SEQ ID NO 871
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 871
attctgcaac gcaccc 16

<210> SEQ ID NO 872
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 872
ctgtccccaa cttacc 16

<210> SEQ ID NO 873
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 873
tccgcctcct tcaacc 16

<210> SEQ ID NO 874

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 874
caccctggat cccatc 16

<210> SEQ ID NO 875
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 875
ctcttcatct tggtga 16

<210> SEQ ID NO 876
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 876
ccagattgtt tgtcta 16

<210> SEQ ID NO 877
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 877
tgtcacccta aggaga 16

<210> SEQ ID NO 878
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 878
cgctgattcc acttcc 16

<210> SEQ ID NO 879
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 879
accccagggt cagctt 16

<210> SEQ ID NO 880
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 880
cagttaagct ggaagc 16

<210> SEQ ID NO 881
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 881
gtagccgtgt tatatt 16

<210> SEQ ID NO 882
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 882
actgaactca gcccct 16

<210> SEQ ID NO 883
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 883
gtttcccaat tcagca 16

<210> SEQ ID NO 884
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 884
ccttgtctcc gacact 16

<210> SEQ ID NO 885
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 885
gtaagtgcaa ccaatc 16

<210> SEQ ID NO 886
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 886
ccctaaactc acactg 16

<210> SEQ ID NO 887
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 887
ggctaagttc cggtct 16

<210> SEQ ID NO 888
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 888
aaactccact gggccc 16

<210> SEQ ID NO 889
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 889
aactgcattg ccctcc 16

<210> SEQ ID NO 890
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 890
ccgcaccaca gccgtt 16

<210> SEQ ID NO 891
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 891
cgctgggtct gaccca 16

<210> SEQ ID NO 892
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 892
cacaggatcc tgacaa 16

<210> SEQ ID NO 893
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 893
agcaggttca catgac 16

<210> SEQ ID NO 894
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 894
cctgaaactg caagct 16

<210> SEQ ID NO 895
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 895
ctggacaggc aatacc 16

<210> SEQ ID NO 896
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 896
ttggatggaa ggaacc 16

<210> SEQ ID NO 897
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 897
aatgaacgca atgctg 16

<210> SEQ ID NO 898
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 898
gtgctctcgg cttcta 16

<210> SEQ ID NO 899
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 899
cacggctctc cactgt 16

<210> SEQ ID NO 900
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 900
gggcactctc agatgg 16

<210> SEQ ID NO 901
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 901
ccacagcatt gagtac 16

<210> SEQ ID NO 902
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 902
aaccatcaag caggaa 16

<210> SEQ ID NO 903
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 903
agtgcccggc cacctc 16

<210> SEQ ID NO 904
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 904
ggaccagtat gtattt 16

<210> SEQ ID NO 905
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 905
gtcagtacag agcagg 16

<210> SEQ ID NO 906
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 906
cacacatgtt tcaaca 16

<210> SEQ ID NO 907
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 907
atttccacta ttttag 16

<210> SEQ ID NO 908
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 908
gaaaatatca gagtgt 16

<210> SEQ ID NO 909
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 909
ggtcaaacac tttata 16

<210> SEQ ID NO 910
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 910
agtgagcctt ccaggc 16

<210> SEQ ID NO 911
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 911
agatgttgaa gtcacc 16

<210> SEQ ID NO 912
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 912
gggacacaag aagact 16

<210> SEQ ID NO 913
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 913
ctacatttgg agatct 16

<210> SEQ ID NO 914
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 914
tcattagtgc tataga 16

<210> SEQ ID NO 915
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 915
cattgcataa gagatg 16

<210> SEQ ID NO 916
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 916
ccgaggaatt cgaaag 16

<210> SEQ ID NO 917
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 917
ctgtataata accaga 16

<210> SEQ ID NO 918
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 918
agtgcactca tccaga 16

<210> SEQ ID NO 919
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 919
gatctccagt atctgt 16

<210> SEQ ID NO 920
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 920
tatgttatcc tcaagc 16

<210> SEQ ID NO 921
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 921
gtggaccttc tgaacc 16

<210> SEQ ID NO 922
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 922
gccgacgagg gtcagg 16

<210> SEQ ID NO 923
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 923
aactccatcc caggtt 16

<210> SEQ ID NO 924
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 924
tccatggtac tgctgg 16

<210> SEQ ID NO 925
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 925
cttttgatga ccaggt 16

<210> SEQ ID NO 926
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 926
gtccttccca atgcct 16

<210> SEQ ID NO 927
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 927
ggcatgcggt actgac 16

<210> SEQ ID NO 928
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 928
ctccacctgt tcaccg 16

<210> SEQ ID NO 929
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 929
ctacatccag cacaag 16

<210> SEQ ID NO 930
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 930
ccgcctgcag aatctt 16

<210> SEQ ID NO 931
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 931
ttttgtcctg gcccct 16

<210> SEQ ID NO 932
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 932
atgccaaagt ccctaa 16

<210> SEQ ID NO 933
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 933
tttcccttat tgcagg 16

<210> SEQ ID NO 934
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 934
tattcttccg tcaata 16

<210> SEQ ID NO 935
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 935
ggacattgaa cctggg 16

<210> SEQ ID NO 936
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 936
cgctgcctga ctgaga 16

<210> SEQ ID NO 937
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 937
gacccatcac atgaca 16

<210> SEQ ID NO 938
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 938
ttaccgggta agagcg 16

<210> SEQ ID NO 939
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 939
gggcggcgac aagaca 16

<210> SEQ ID NO 940
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 940
cacagcaaac acgctc 16

<210> SEQ ID NO 941
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 941
cattctgcaa cgcacc 16

<210> SEQ ID NO 942
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 942
gcaggtcaac tgtccc 16

<210> SEQ ID NO 943
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 943
atccgcctcc ttcaac 16

<210> SEQ ID NO 944
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 944
attcccccga cacttg 16

<210> SEQ ID NO 945
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 945
actcttcatc ttggtg 16

<210> SEQ ID NO 946
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 946
aacctaaacc agattg 16

<210> SEQ ID NO 947
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 947
gtgtcaccct aaggag 16

<210> SEQ ID NO 948
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 948
ccgctgattc cacttc 16

<210> SEQ ID NO 949
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 949
caggtggaaa cacccc 16

<210> SEQ ID NO 950
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 950
ccagttaagc tggaag 16

<210> SEQ ID NO 951
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 951
ggtagccgtg ttatat 16

<210> SEQ ID NO 952
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 952
gactgaactc agcccc 16

<210> SEQ ID NO 953

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 953
tgtttcccaa ttcagc 16

<210> SEQ ID NO 954
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 954
accttgtctc cgacac 16

<210> SEQ ID NO 955
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 955
tgtaagtgca accaat 16

<210> SEQ ID NO 956
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 956
tccctaaact cacact 16

<210> SEQ ID NO 957
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 957
aggctaagtt ccggtc 16

<210> SEQ ID NO 958
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 958
caaactccac tgggcc 16

<210> SEQ ID NO 959
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 959
aaactgcatt gccctc 16

<210> SEQ ID NO 960
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 960
cccgcaccac agccgt 16

<210> SEQ ID NO 961
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 961
gcgctgggtc tgaccc 16

<210> SEQ ID NO 962
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 962
ccacaggatc ctgaca 16

<210> SEQ ID NO 963
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 963
taaagccagc tgacag 16

<210> SEQ ID NO 964
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 964
ccctgaaact gcaagc 16

<210> SEQ ID NO 965
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 965
cctggacagg caatac 16

<210> SEQ ID NO 966
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 966
tttggatgga aggaac 16

<210> SEQ ID NO 967
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 967
aaatgaacgc aatgct 16

<210> SEQ ID NO 968
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 968
agtgctctcg gcttct 16

<210> SEQ ID NO 969
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 969
acacggctct ccactg 16

<210> SEQ ID NO 970
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 970
tgggcactct cagatg 16

<210> SEQ ID NO 971
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 971
actccacagc attgag 16

<210> SEQ ID NO 972
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 972
aaaccatcaa gcagga 16

<210> SEQ ID NO 973
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 973
acaagagacc tcattc 16

<210> SEQ ID NO 974
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 974
gggaccagta tgtatt 16

<210> SEQ ID NO 975
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 975
aagtcagtac agagca 16

<210> SEQ ID NO 976
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 976
ccacacatgt ttcaac 16

<210> SEQ ID NO 977
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 977
gaatttccac tatttt 16

<210> SEQ ID NO 978
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 978
ggttcaaaag cagcat 16

<210> SEQ ID NO 979
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 979
gggtcaaaca ctttat 16

<210> SEQ ID NO 980
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 980
aagtgagcct tccagg 16

<210> SEQ ID NO 981
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 981
cagatgttga agtcac 16

<210> SEQ ID NO 982
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 982
cctattgtaa gaacag 16

<210> SEQ ID NO 983
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 983
tcaggtgact acattt 16

<210> SEQ ID NO 984
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 984
gtcattagtg ctatag 16

<210> SEQ ID NO 985
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 985
ccattgcata agagat 16

<210> SEQ ID NO 986
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 986
accgaggaat tcgaaa 16

<210> SEQ ID NO 987
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 987
cgtctgtata ataacc 16

<210> SEQ ID NO 988
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 988
aagtgcactc atccag 16

<210> SEQ ID NO 989
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 989
ggatctccag tatctg 16

<210> SEQ ID NO 990
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 990
ttatgttatc ctcaag 16

<210> SEQ ID NO 991
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 991
tgtggacctt ctgaac 16

<210> SEQ ID NO 992
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 992
tgccgacgag ggtcag 16

<210> SEQ ID NO 993
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 993
caactccatc ccaggt 16

<210> SEQ ID NO 994
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 994
agtccatggt actgct 16

<210> SEQ ID NO 995
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 995
gcttttgatg accagg 16

<210> SEQ ID NO 996
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 996
tgtccttccc aatgcc 16

<210> SEQ ID NO 997
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 997
gaggcatgcg gtactg 16

<210> SEQ ID NO 998
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 998
tctccacctg ttcacc 16

<210> SEQ ID NO 999
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 999
agactacatc cagcac 16

<210> SEQ ID NO 1000
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1000
tccgcctgca gaatct 16

<210> SEQ ID NO 1001
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1001
attttgtcct ggcccc 16

<210> SEQ ID NO 1002
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1002
tggaaatgcc aaagtc 16

<210> SEQ ID NO 1003
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1003
cagttcccat ttttcc 16

<210> SEQ ID NO 1004
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1004
ctattcttcc gtcaat 16

<210> SEQ ID NO 1005
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1005
aggacattga acctgg 16

<210> SEQ ID NO 1006
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1006
ccgctgcctg actgag 16

<210> SEQ ID NO 1007
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1007
ggacccatca catgac 16

<210> SEQ ID NO 1008
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1008
cttaccgggt aagagc 16

<210> SEQ ID NO 1009
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1009
tgggcggcga caagac 16

<210> SEQ ID NO 1010
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1010
accaagcaca gcaaac 16

<210> SEQ ID NO 1011
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1011
accattctgc aacgca 16

<210> SEQ ID NO 1012
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1012
ggaggcaggt caactg 16

<210> SEQ ID NO 1013
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1013
tgaccacctg tcttgg 16

<210> SEQ ID NO 1014
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1014
ggtgcctcgg attccc 16

<210> SEQ ID NO 1015
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1015
gtgctcaact cttcat 16

<210> SEQ ID NO 1016
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1016
ccaagaccaa cctaaa 16

<210> SEQ ID NO 1017
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1017
cgtgtcaccc taagga 16

<210> SEQ ID NO 1018
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1018
cccgctgatt ccactt 16

<210> SEQ ID NO 1019
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1019
tcaggtggaa acaccc 16

<210> SEQ ID NO 1020
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1020
tccagttaag ctggaa 16

<210> SEQ ID NO 1021
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1021
caggtagccg tgttat 16

<210> SEQ ID NO 1022
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1022
tgactgaact cagccc 16

<210> SEQ ID NO 1023
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1023
gctgtttccc aattca 16

<210> SEQ ID NO 1024
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1024
aaccttgtct ccgaca 16

<210> SEQ ID NO 1025
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1025
ttgtaagtgc aaccaa 16

<210> SEQ ID NO 1026
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1026
gacctcccta aactca 16

<210> SEQ ID NO 1027
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1027
aaggctaagt tccggt 16

<210> SEQ ID NO 1028
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1028
gacaagaacc ccaaac 16

<210> SEQ ID NO 1029
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1029
aaaactgcat tgccct 16

<210> SEQ ID NO 1030
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1030
acccgcacca cagccg 16

<210> SEQ ID NO 1031
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1031
agatccaact cggcgc 16

<210> SEQ ID NO 1032

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1032
cccacaggat cctgac 16

<210> SEQ ID NO 1033
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1033
cttaaagcca gctgac 16

<210> SEQ ID NO 1034
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1034
ccccctgaaa ctgcaa 16

<210> SEQ ID NO 1035
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1035
tcctggacag gcaata 16

<210> SEQ ID NO 1036
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1036
aggtttggat ggaagg 16

<210> SEQ ID NO 1037
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1037
gaaatgaacg caatgc 16

<210> SEQ ID NO 1038
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1038
gagtgctctc ggcttc 16

<210> SEQ ID NO 1039
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1039
tacacggctc tccact 16

<210> SEQ ID NO 1040
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1040
ttgggcactc tcagat 16

<210> SEQ ID NO 1041
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1041
aactccacag cattga 16

<210> SEQ ID NO 1042
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1042
gcccaaaacc atcaag 16

<210> SEQ ID NO 1043
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1043
cacaagagac ctcatt 16

<210> SEQ ID NO 1044
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1044
tatggaattg cagata 16

<210> SEQ ID NO 1045
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1045
caagtcagta cagagc 16

<210> SEQ ID NO 1046
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1046
cccacacatg tttcaa 16

<210> SEQ ID NO 1047
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1047
agaatttcca ctattt 16

<210> SEQ ID NO 1048
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1048
tggttcaaaa gcagca 16

<210> SEQ ID NO 1049
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1049
tgggtcaaac acttta 16

<210> SEQ ID NO 1050
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1050
gaagtgagcc ttccag 16

<210> SEQ ID NO 1051
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1051
ccagatgttg aagtca 16

<210> SEQ ID NO 1052
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1052
tcctattgta agaaca 16

<210> SEQ ID NO 1053
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1053
ctcaggtgac tacatt 16

<210> SEQ ID NO 1054
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1054
agtcattagt gctata 16

<210> SEQ ID NO 1055
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1055
gccattgcat aagaga 16

<210> SEQ ID NO 1056
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1056
taccgaggaa ttcgaa 16

<210> SEQ ID NO 1057
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1057
cacctccagt tatgcg 16

<210> SEQ ID NO 1058
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1058
aaagtgcact catcca 16

<210> SEQ ID NO 1059
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1059
aggatctcca gtatct 16

<210> SEQ ID NO 1060
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1060
cttatgttat cctcaa 16

<210> SEQ ID NO 1061
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1061
ttgtggacct tctgaa 16

<210> SEQ ID NO 1062
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1062
atgccgacga gggtca 16

<210> SEQ ID NO 1063
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1063
gattcccaac tccatc 16

<210> SEQ ID NO 1064
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1064
tagtccatgg tactgc 16

<210> SEQ ID NO 1065
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1065
aggcttttga tgacca 16

<210> SEQ ID NO 1066
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1066
atgtccttcc caatgc 16

<210> SEQ ID NO 1067
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1067
tgaggcatgc ggtact 16

<210> SEQ ID NO 1068
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1068
accctctcca cctgtt 16

<210> SEQ ID NO 1069
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1069
tagactacat ccagca 16

<210> SEQ ID NO 1070
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1070
gtccgcctgc agaatc 16

<210> SEQ ID NO 1071
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1071
aaaagcgatg gctcac 16

<210> SEQ ID NO 1072
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1072
gctatggaaa tgccaa 16

<210> SEQ ID NO 1073
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1073
tccagttccc attttt 16

<210> SEQ ID NO 1074
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1074
ctctctattc ttccgt 16

<210> SEQ ID NO 1075
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1075
ggaggacatt gaacct 16

<210> SEQ ID NO 1076
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1076
gccgctgcct gactga 16

<210> SEQ ID NO 1077
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1077
cagtgttcaa gcaggg 16

<210> SEQ ID NO 1078
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 1078
acttaccggg taagag 16

<210> SEQ ID NO 1079
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1079
ctgggcggcg acaaga 16

<210> SEQ ID NO 1080
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1080
gaccaagcac agcaaa 16

<210> SEQ ID NO 1081
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1081
caccattctg caacgc 16

<210> SEQ ID NO 1082
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1082
caatcagact caagcc 16

<210> SEQ ID NO 1083
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1083
cgtgaccacc tgtctt 16

<210> SEQ ID NO 1084
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1084
gagctggtgc ctcgga 16

<210> SEQ ID NO 1085
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1085
cctcattgca aatcct 16

<210> SEQ ID NO 1086
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1086
gctctgcaaa tctctc 16

<210> SEQ ID NO 1087
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1087
ccgtgtcacc ctaagg 16

<210> SEQ ID NO 1088
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1088
ccccgctgat tccact 16

<210> SEQ ID NO 1089
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1089
ctcaggtgga aacacc 16

<210> SEQ ID NO 1090
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1090
gtccagttaa gctgga 16

<210> SEQ ID NO 1091
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1091
ccaggtagcc gtgtta 16

<210> SEQ ID NO 1092
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1092
atgactgaac tcagcc 16

<210> SEQ ID NO 1093
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1093
cctccagttt gctgtt 16

<210> SEQ ID NO 1094
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1094
aaaccttgtc tccgac 16

<210> SEQ ID NO 1095
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1095
tttgtaagtg caacca 16

<210> SEQ ID NO 1096
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1096
agacctccct aaactc 16

<210> SEQ ID NO 1097
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1097
caaggctaag ttccgg 16

<210> SEQ ID NO 1098
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1098
aagacaagaa ccccaa 16

<210> SEQ ID NO 1099
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1099
caaaactgca ttgccc 16

<210> SEQ ID NO 1100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1100
acccacccgc accaca 16

<210> SEQ ID NO 1101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1101
gagatccaac tcggcg 16

<210> SEQ ID NO 1102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1102
gcccacagga tcctga 16

<210> SEQ ID NO 1103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1103
aaccccctga aactgc 16

<210> SEQ ID NO 1104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1104
ttcctggaca ggcaat 16

<210> SEQ ID NO 1105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1105
caggtttgga tggaag 16

<210> SEQ ID NO 1106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1106
ggaaatgaac gcaatg 16

<210> SEQ ID NO 1107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1107
tgagtgctct cggctt 16

<210> SEQ ID NO 1108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1108
gtacacggct ctccac 16

<210> SEQ ID NO 1109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1109
cttgggcact ctcaga 16

<210> SEQ ID NO 1110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1110
aaactccaca gcattg 16

<210> SEQ ID NO 1111

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1111
cgcccaaaac catcaa 16

<210> SEQ ID NO 1112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1112
acacacaaga gacctc 16

<210> SEQ ID NO 1113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1113
ttatggaatt gcagat 16

<210> SEQ ID NO 1114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1114
tcaagtcagt acagag 16

<210> SEQ ID NO 1115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1115
cacccacaca tgtttc 16

<210> SEQ ID NO 1116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1116
cagaatttcc actatt 16

<210> SEQ ID NO 1117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1117
ttggttcaaa agcagc 16

<210> SEQ ID NO 1118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1118
ttgggtcaaa cacttt 16

<210> SEQ ID NO 1119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1119
catgaagtga gccttc 16

<210> SEQ ID NO 1120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1120
gccagatgtt gaagtc 16

<210> SEQ ID NO 1121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1121
gtcctattgt aagaac 16

<210> SEQ ID NO 1122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1122
actcaggtga ctacat 16

<210> SEQ ID NO 1123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1123
gagtcattag tgctat 16

<210> SEQ ID NO 1124
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1124
cagccattgc ataaga 16

<210> SEQ ID NO 1125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1125
ataccgagga attcga 16

<210> SEQ ID NO 1126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1126
ccacctccag ttatgc 16

<210> SEQ ID NO 1127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1127
aaaagtgcac tcatcc 16

<210> SEQ ID NO 1128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1128
gaggatctcc agtatc 16

<210> SEQ ID NO 1129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1129
cttcttatgt tatcct 16

<210> SEQ ID NO 1130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1130
tttgtggacc ttctga 16

<210> SEQ ID NO 1131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1131
catgccgacg agggtc 16

<210> SEQ ID NO 1132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1132
ctgtgattcc caactc 16

<210> SEQ ID NO 1133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1133
gtagtccatg gtactg 16

<210> SEQ ID NO 1134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1134
aaggcttttg atgacc 16

<210> SEQ ID NO 1135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1135
gatgtccttc ccaatg 16

<210> SEQ ID NO 1136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1136
ctgaggcatg cggtac 16

<210> SEQ ID NO 1137
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1137
aaccctctcc acctgt 16

<210> SEQ ID NO 1138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1138
gtagactaca tccagc 16

<210> SEQ ID NO 1139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1139
ggtccgcctg cagaat 16

<210> SEQ ID NO 1140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1140
gggtcaaaag cgatgg 16

<210> SEQ ID NO 1141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1141
agctatggaa atgcca 16

<210> SEQ ID NO 1142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1142
tctccagttc ccattt 16

<210> SEQ ID NO 1143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1143
agcctcctct ctattc 16

<210> SEQ ID NO 1144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1144
cggaggacat tgaacc 16

<210> SEQ ID NO 1145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1145
agccgctgcc tgactg 16

<210> SEQ ID NO 1146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1146
tcagtgttca agcagg 16

<210> SEQ ID NO 1147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1147
tacttaccgg gtaaga 16

<210> SEQ ID NO 1148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1148
cctgggcggc gacaag 16

<210> SEQ ID NO 1149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1149
tgaccaagca cagcaa 16

<210> SEQ ID NO 1150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1150
gcaccattct gcaacg 16

<210> SEQ ID NO 1151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1151
tctatagttt aagagc 16

<210> SEQ ID NO 1152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1152
tcccgcctca gggctc 16

<210> SEQ ID NO 1153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1153
acaccatctc atgagc 16

<210> SEQ ID NO 1154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1154
gtttttacaa tagtgc 16

<210> SEQ ID NO 1155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1155
gcttgcttga gcagcc 16

<210> SEQ ID NO 1156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1156
gccgtgtcac cctaag 16

<210> SEQ ID NO 1157
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 1157
cccccgctga ttccac 16

<210> SEQ ID NO 1158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1158
cctcaggtgg aaacac 16

<210> SEQ ID NO 1159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1159
ggtccagtta agctgg 16

<210> SEQ ID NO 1160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1160
gccaggtagc cgtgtt 16

<210> SEQ ID NO 1161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1161
gatgactgaa ctcagc 16

<210> SEQ ID NO 1162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1162
cctcctccag tttgct 16

<210> SEQ ID NO 1163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1163
taaaccttgt ctccga 16

<210> SEQ ID NO 1164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1164
ttttgtaagt gcaacc 16

<210> SEQ ID NO 1165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1165
gagacctccc taaact 16

<210> SEQ ID NO 1166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1166
gcaaggctaa gttccg 16

<210> SEQ ID NO 1167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1167
caaagacaag aacccc 16

<210> SEQ ID NO 1168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1168
acaaaactgc attgcc 16

<210> SEQ ID NO 1169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1169
actaaacccc acaccc 16

<210> SEQ ID NO 1170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1170
tgagatccaa ctcggc 16

<210> SEQ ID NO 1171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1171
ggcccacagg atcctg 16

<210> SEQ ID NO 1172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1172
cttctgttag atacaa 16

<210> SEQ ID NO 1173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1173
taaccccctg aaactg 16

<210> SEQ ID NO 1174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1174
attcctggac aggcaa 16

<210> SEQ ID NO 1175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1175
ccaggtttgg atggaa 16

<210> SEQ ID NO 1176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1176
gggaaatgaa cgcaat 16

<210> SEQ ID NO 1177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1177
ctgagtgctc tcggct 16

<210> SEQ ID NO 1178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1178
ggtacacggc tctcca 16

<210> SEQ ID NO 1179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1179
tcttgggcac tctcag 16

<210> SEQ ID NO 1180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1180
atgtctcaaa ctccac 16

<210> SEQ ID NO 1181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1181
ccgcccaaaa ccatca 16

<210> SEQ ID NO 1182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1182
gcacacacaa gagacc 16

<210> SEQ ID NO 1183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1183
gaattatgga attgca 16

<210> SEQ ID NO 1184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1184
actcaagtca gtacag 16

<210> SEQ ID NO 1185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1185
gtaatcacac ccacac 16

<210> SEQ ID NO 1186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1186
ttcagaattt ccacta 16

<210> SEQ ID NO 1187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1187
attggttcaa aagcag 16

<210> SEQ ID NO 1188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1188
gttgggtcaa acactt 16

<210> SEQ ID NO 1189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1189
acatgaagtg agcctt 16

<210> SEQ ID NO 1190

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1190
tttggcacct tcacct 16

<210> SEQ ID NO 1191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1191
ttagagggct agtgtc 16

<210> SEQ ID NO 1192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1192
aactcaggtg actaca 16

<210> SEQ ID NO 1193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1193
ggagtcatta gtgcta 16

<210> SEQ ID NO 1194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1194
acagccattg cataag 16

<210> SEQ ID NO 1195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1195
tataccgagg aattcg 16

<210> SEQ ID NO 1196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1196
cccacctcca gttatg 16

<210> SEQ ID NO 1197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1197
caaggaaaag tgcact 16

<210> SEQ ID NO 1198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1198
tgaggatctc cagtat 16

<210> SEQ ID NO 1199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1199
ttcatgatca tttgtc 16

<210> SEQ ID NO 1200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1200
ccttcttatg ttatcc 16

<210> SEQ ID NO 1201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1201
ctttgtggac cttctg 16

<210> SEQ ID NO 1202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1202
ccatgccgac gagggt 16

<210> SEQ ID NO 1203
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1203
gctgtgattc ccaact 16

<210> SEQ ID NO 1204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1204
cgtagtccat ggtact 16

<210> SEQ ID NO 1205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1205
caaggctttt gatgac 16

<210> SEQ ID NO 1206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1206
ggatgtcctt cccaat 16

<210> SEQ ID NO 1207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1207
ggctcagtga cccggg 16

<210> SEQ ID NO 1208
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1208
attaaccctc tccacc 16

<210> SEQ ID NO 1209
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1209
ggtagactac atccag 16

<210> SEQ ID NO 1210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1210
tggtccgcct gcagaa 16

<210> SEQ ID NO 1211
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1211
cagctatgga aatgcc 16

<210> SEQ ID NO 1212
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1212
actctccagt tcccat 16

<210> SEQ ID NO 1213
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1213
caagcctcct ctctat 16

<210> SEQ ID NO 1214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1214
ttcggaggac attgaa 16

<210> SEQ ID NO 1215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1215
aagccgctgc ctgact 16

<210> SEQ ID NO 1216
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1216
ttcagtgttc aagcag 16

<210> SEQ ID NO 1217
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1217
tcctgggcgg cgacaa 16

<210> SEQ ID NO 1218
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1218
ggcaccattc tgcaac 16

<210> SEQ ID NO 1219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1219
caaccctcta tagttt 16

<210> SEQ ID NO 1220
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1220
ggagccctcc ctcccg 16

<210> SEQ ID NO 1221
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1221
tgtgtgatcc cctagg 16

<210> SEQ ID NO 1222
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1222
gccagtgttt ttacaa 16

<210> SEQ ID NO 1223
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1223
tgagccacca gtggac 16

<210> SEQ ID NO 1224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1224
ccccccgctg attcca 16

<210> SEQ ID NO 1225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1225
agcctcaggt ggaaac 16

<210> SEQ ID NO 1226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1226
gggtccagtt aagctg 16

<210> SEQ ID NO 1227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1227
tagatgactg aactca 16

<210> SEQ ID NO 1228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1228
gcctcctcca gtttgc 16

<210> SEQ ID NO 1229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1229
gataaacctt gtctcc 16

<210> SEQ ID NO 1230
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1230
gttttgtaag tgcaac 16

<210> SEQ ID NO 1231
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1231
ggagacctcc ctaaac 16

<210> SEQ ID NO 1232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1232
ggcaaggcta agttcc 16

<210> SEQ ID NO 1233
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1233
cagcaaagac aagaac 16

<210> SEQ ID NO 1234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1234
gtacaaaact gcattg 16

<210> SEQ ID NO 1235
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1235
cactaaaccc cacacc 16

<210> SEQ ID NO 1236
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1236

gtgagatcca actcgg                                                    16

<210> SEQ ID NO 1237
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1237

tgggcccaca ggatcc                                                    16

<210> SEQ ID NO 1238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1238

acttctgtta gataca                                                    16

<210> SEQ ID NO 1239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1239

gtaaccccct gaaact                                                    16

<210> SEQ ID NO 1240
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1240

aacattcctg gacagg                                                    16

<210> SEQ ID NO 1241
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1241

cccaggtttg gatgga                                                    16

<210> SEQ ID NO 1242
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1242
```

-continued agggaaatga acgcaa 16

<210> SEQ ID NO 1243
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1243
gctgagtgct ctcggc 16

<210> SEQ ID NO 1244
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1244
gggtacacgg ctctcc 16

<210> SEQ ID NO 1245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1245
gtcttgggca ctctca 16

<210> SEQ ID NO 1246
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1246
taatgtctca aactcc 16

<210> SEQ ID NO 1247
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1247
accgcccaaa accatc 16

<210> SEQ ID NO 1248
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1248
tgcacacaca agagac 16

<210> SEQ ID NO 1249
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1249
ggaattatgg aattgc 16

<210> SEQ ID NO 1250
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1250
aactcaagtc agtaca 16

<210> SEQ ID NO 1251
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1251
ccctgtaatc acaccc 16

<210> SEQ ID NO 1252
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1252
tattggttca aaagca 16

<210> SEQ ID NO 1253
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1253
ctgttgggtc aaacac 16

<210> SEQ ID NO 1254
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1254
aacatgaagt gagcct 16

<210> SEQ ID NO 1255
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1255
ttttggcacc ttcacc 16

<210> SEQ ID NO 1256
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1256
attagagggc tagtgt 16

<210> SEQ ID NO 1257
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1257
aaactcaggt gactac 16

<210> SEQ ID NO 1258
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1258
tggagtcatt agtgct 16

<210> SEQ ID NO 1259
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1259
aacagccatt gcataa 16

<210> SEQ ID NO 1260
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1260
caagatatac cgagga 16

<210> SEQ ID NO 1261
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1261
ttcccctggc agagac 16

<210> SEQ ID NO 1262
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1262
ccctcgctcc agcttc 16

<210> SEQ ID NO 1263
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1263
cttactttga ggatct 16

<210> SEQ ID NO 1264
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1264
tactgctggc ctttat 16

<210> SEQ ID NO 1265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1265
cggagccttc ttatgt 16

<210> SEQ ID NO 1266
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1266
tggtgccttt gtggac 16

<210> SEQ ID NO 1267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1267
cagacccatg ccgacg 16

<210> SEQ ID NO 1268
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1268
aagcggctgt gattcc 16

<210> SEQ ID NO 1269

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1269
tctttccgta gtccat 16

<210> SEQ ID NO 1270
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1270
cacccaaaaa ctccct 16

<210> SEQ ID NO 1271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1271
ggcacggatg tccttc 16

<210> SEQ ID NO 1272
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1272
agattggctc agtgac 16

<210> SEQ ID NO 1273
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1273
ctgggttcat taaccc 16

<210> SEQ ID NO 1274
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1274
cacgaggtag actaca 16

<210> SEQ ID NO 1275
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1275
gttcttggtc cgcctg 16

<210> SEQ ID NO 1276
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1276
accctcttta tccccc 16

<210> SEQ ID NO 1277
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1277
tgtgctcagc tatgga 16

<210> SEQ ID NO 1278
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1278
ttagtctaaa gtaaac 16

<210> SEQ ID NO 1279
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1279
tgctggttcc ttcaag 16

<210> SEQ ID NO 1280
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1280
tcattcttcg gaggac 16

<210> SEQ ID NO 1281
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1281
atcaggaagc cgctgc 16

<210> SEQ ID NO 1282
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1282
atggcccacc acctgc 16

<210> SEQ ID NO 1283
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1283
gctaattttc tgactg 16

<210> SEQ ID NO 1284
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1284
gtcaatcctg ggcggc 16

<210> SEQ ID NO 1285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1285
tcatgattgc aaagct 16

<210> SEQ ID NO 1286
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1286
agctttgtga acccat 16

<210> SEQ ID NO 1287
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1287
gcccaagccc agtcca 16

<210> SEQ ID NO 1288
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1288
agggtatatg aaagtt 16

<210> SEQ ID NO 1289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1289
agccagtgtg tattgc 16

<210> SEQ ID NO 1290
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1290
ttgcaccctt gaggag 16

<210> SEQ ID NO 1291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1291
gctaggtgcc agggta 16

<210> SEQ ID NO 1292
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1292
cccccccccc cgctga 16

<210> SEQ ID NO 1293
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1293
acattcccac agggcc 16

<210> SEQ ID NO 1294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1294
ggatgtggca aaggac 16

<210> SEQ ID NO 1295
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1295
gccctattgt gtggca 16

<210> SEQ ID NO 1296
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1296
atttttcttt gaccgg 16

<210> SEQ ID NO 1297
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1297
acgaagcctc ctccag 16

<210> SEQ ID NO 1298
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1298
tcacccgata aacctt 16

<210> SEQ ID NO 1299
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1299
cccaaacagg cagttt 16

<210> SEQ ID NO 1300
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1300
tattcggaga cctccc 16

<210> SEQ ID NO 1301
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1301
acctgggcaa ggctaa 16

<210> SEQ ID NO 1302
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1302
cttactccac acctta 16

<210> SEQ ID NO 1303
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1303
gtttggtaca aaactg 16

<210> SEQ ID NO 1304
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1304
ttgtctcact aaaccc 16

<210> SEQ ID NO 1305
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1305
aagaccagtg agatcc 16

<210> SEQ ID NO 1306
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1306
aaccacctgt agggac 16

<210> SEQ ID NO 1307
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1307
tgggtacttc tgttag 16

<210> SEQ ID NO 1308
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1308
acagctgtaa ccccct 16

<210> SEQ ID NO 1309
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1309
tggtggatat aaaagc 16

<210> SEQ ID NO 1310
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1310
agcgattgtc ttgttt 16

<210> SEQ ID NO 1311
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1311
tgccgtggca actctg 16

<210> SEQ ID NO 1312
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1312
gtttttcctc agtccc 16

<210> SEQ ID NO 1313
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1313
ggcacctcca tgttgc 16

<210> SEQ ID NO 1314
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1314
tgctggtctt gggcac 16

<210> SEQ ID NO 1315
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 1315
ccttatagct tacctg 16

<210> SEQ ID NO 1316
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1316
agagtcaccg cccaaa 16

<210> SEQ ID NO 1317
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1317
cttgccgtgc acacac 16

<210> SEQ ID NO 1318
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1318
tggtttgcag ggatct 16

<210> SEQ ID NO 1319
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1319
acaaagaact caagtc 16

<210> SEQ ID NO 1320
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1320
gactgctccc tgtaat 16

<210> SEQ ID NO 1321
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1321
atgtgtttag gcattc 16

<210> SEQ ID NO 1322
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1322
cattgggtta tgaaat 16

<210> SEQ ID NO 1323
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1323
catgcctgtt gggtca 16

<210> SEQ ID NO 1324
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1324
gctcagcacc aacatg 16

<210> SEQ ID NO 1325
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1325
actccaaccc ttttgg 16

<210> SEQ ID NO 1326
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1326
attctattag agggct 16

<210> SEQ ID NO 1327
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1327
aagctttaaa ctcagg 16

<210> SEQ ID NO 1328
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1328
cttgttttat ggagtc 16

<210> SEQ ID NO 1329
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1329
agtgcataac agccat 16

<210> SEQ ID NO 1330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1330
ccaagatata ccgagg 16

<210> SEQ ID NO 1331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1331
aatcttcccc tggcag 16

<210> SEQ ID NO 1332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1332
accctcgctc cagctt 16

<210> SEQ ID NO 1333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1333
gggcttactt tgagga 16

<210> SEQ ID NO 1334
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1334
gtactgctgg ccttta 16

<210> SEQ ID NO 1335
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1335
acggagcctt cttatg 16

<210> SEQ ID NO 1336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1336
gtggtgcctt tgtgga 16

<210> SEQ ID NO 1337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1337
ccagacccat gccgac 16

<210> SEQ ID NO 1338
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1338
aaagcggctg tgattc 16

<210> SEQ ID NO 1339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1339
ttctttccgt agtcca 16

<210> SEQ ID NO 1340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1340
tcacccaaaa actccc 16

<210> SEQ ID NO 1341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1341
agggcacgga tgtcct 16

<210> SEQ ID NO 1342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1342
gagattggct cagtga 16

<210> SEQ ID NO 1343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1343
gctgggttca ttaacc 16

<210> SEQ ID NO 1344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1344
taagtgcttt gattcg 16

<210> SEQ ID NO 1345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1345
agttcttggt ccgcct 16

<210> SEQ ID NO 1346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1346
caccctcttt atcccc 16

<210> SEQ ID NO 1347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1347
ctgtgctcag ctatgg 16

<210> SEQ ID NO 1348

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1348
ctttagtcta aagtaa 16

<210> SEQ ID NO 1349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1349
actcttgggc tttctc 16

<210> SEQ ID NO 1350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1350
ttcattcttc ggagga 16

<210> SEQ ID NO 1351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1351
catcaggaag ccgctg 16

<210> SEQ ID NO 1352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1352
gccatggccc accacc 16

<210> SEQ ID NO 1353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1353
gctttcatgc taattt 16

<210> SEQ ID NO 1354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1354
ggtcaatcct gggcgg 16

<210> SEQ ID NO 1355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1355
ctcatgattg caaagc 16

<210> SEQ ID NO 1356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1356
ctcagcagtc aaaacc 16

<210> SEQ ID NO 1357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1357
gttcctagaa gaagcc 16

<210> SEQ ID NO 1358
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1358
gagggtatat gaaagt 16

<210> SEQ ID NO 1359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1359
tagctggtga tagcca 16

<210> SEQ ID NO 1360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1360
tgttgcaccc ttgagg 16

<210> SEQ ID NO 1361
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1361
tcatttgcta ggtgcc 16

<210> SEQ ID NO 1362
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1362
ggtcaacctc ctctcc 16

<210> SEQ ID NO 1363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1363
tacattccca cagggc 16

<210> SEQ ID NO 1364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1364
cgccaggtca cacaga 16

<210> SEQ ID NO 1365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1365
ggccctattg tgtggc 16

<210> SEQ ID NO 1366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1366
gatttttctt tgaccg 16

<210> SEQ ID NO 1367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1367
cacgaagcct cctcca 16

<210> SEQ ID NO 1368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1368
ttcacccgat aaacct 16

<210> SEQ ID NO 1369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1369
acccaaacag gcagtt 16

<210> SEQ ID NO 1370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1370
gtattcggag acctcc 16

<210> SEQ ID NO 1371
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1371
aacctgggca aggcta 16

<210> SEQ ID NO 1372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1372
tgcttactcc acacct 16

<210> SEQ ID NO 1373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1373
ccatgtttgg tacaaa 16

<210> SEQ ID NO 1374
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1374
cttgtctcac taaacc 16

<210> SEQ ID NO 1375
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1375
taagaccagt gagatc 16

<210> SEQ ID NO 1376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1376
aaaccacctg taggga 16

<210> SEQ ID NO 1377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1377
atgggtactt ctgtta 16

<210> SEQ ID NO 1378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1378
tagaacagct gtaacc 16

<210> SEQ ID NO 1379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1379
gctggtggat ataaaa 16

<210> SEQ ID NO 1380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1380
gagcgattgt cttgtt 16

-continued

<210> SEQ ID NO 1381
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1381
ttgccgtggc aactct 16

<210> SEQ ID NO 1382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1382
agtttttcct cagtcc 16

<210> SEQ ID NO 1383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1383
aggcacctcc atgttg 16

<210> SEQ ID NO 1384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1384
ggagattcct cctgct 16

<210> SEQ ID NO 1385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1385
cccttatagc ttacct 16

<210> SEQ ID NO 1386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1386
gagagtcacc gcccaa 16

<210> SEQ ID NO 1387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1387
tcttgccgtg cacaca 16

<210> SEQ ID NO 1388
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1388
gtggtttgca gggatc 16

<210> SEQ ID NO 1389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1389
ggtctacaaa gaactc 16

<210> SEQ ID NO 1390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1390
ggactgctcc ctgtaa 16

<210> SEQ ID NO 1391
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1391
gatgtgttta ggcatt 16

<210> SEQ ID NO 1392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1392
atcattgggt tatgaa 16

<210> SEQ ID NO 1393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1393
acatgcctgt tgggtc 16

<210> SEQ ID NO 1394
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 1394
agctcagcac caacat 16

<210> SEQ ID NO 1395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1395
gactccaacc cttttg 16

<210> SEQ ID NO 1396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1396
aattctatta gagggc 16

<210> SEQ ID NO 1397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1397
gaagctttaa actcag 16

<210> SEQ ID NO 1398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1398
acttgtttta tggagt 16

<210> SEQ ID NO 1399
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1399
gagtgcataa cagcca 16

<210> SEQ ID NO 1400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1400
acaggtcctc cagtcc 16

<210> SEQ ID NO 1401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1401
tgtcgctgca gggcct 16

<210> SEQ ID NO 1402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1402
ttttgttgca ccctcg 16

<210> SEQ ID NO 1403
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1403
tgctctctgg gtccat 16

<210> SEQ ID NO 1404
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1404
ccagtttctg tactgc 16

<210> SEQ ID NO 1405
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1405
atctgcaagg gcacgg 16

<210> SEQ ID NO 1406
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1406
ttggcgatgg tggtgc 16

<210> SEQ ID NO 1407
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1407
ccctctgtga agggtg 16

<210> SEQ ID NO 1408
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1408
gtaatcccgg tcaaag 16

<210> SEQ ID NO 1409
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1409
gtgtccacca cttctt 16

<210> SEQ ID NO 1410
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1410
gtattgccag ctaagg 16

<210> SEQ ID NO 1411
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1411
aagattggct ctggct 16

<210> SEQ ID NO 1412
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1412
ccgctttcag ctgaga 16

<210> SEQ ID NO 1413
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1413
gagcttgact cctctg 16

<210> SEQ ID NO 1414
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1414
gccccctcat gtaagt 16

<210> SEQ ID NO 1415
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1415
atatctctcc tggtgg 16

<210> SEQ ID NO 1416
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1416
ataaacttta cctcac 16

<210> SEQ ID NO 1417
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1417
cttctccttg ctgcac 16

<210> SEQ ID NO 1418
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1418
cacccggccc cccaat 16

<210> SEQ ID NO 1419
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1419
atccaactgt tctaac 16

<210> SEQ ID NO 1420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1420
atatgccccc aggagg 16

<210> SEQ ID NO 1421
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1421
caccccaatg accatc 16

<210> SEQ ID NO 1422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1422
tggttctcac atactc 16

<210> SEQ ID NO 1423
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1423
ctagagatct gagctt 16

<210> SEQ ID NO 1424
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1424
cagcttgatg agtagg 16

<210> SEQ ID NO 1425
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1425
gggcctcctc cttgag 16

<210> SEQ ID NO 1426
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1426
aagttggtgc tcagac 16

<210> SEQ ID NO 1427

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1427
acagcgggtc ctccct 16

<210> SEQ ID NO 1428
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1428
tcgcataaaa ctttgc 16

<210> SEQ ID NO 1429
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1429
cagaggacgg gcagcc 16

<210> SEQ ID NO 1430
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1430
agtccatccg ggttct 16

<210> SEQ ID NO 1431
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1431
cccacttgag tcattt 16

<210> SEQ ID NO 1432
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1432
agagcgggag gtgaca 16

<210> SEQ ID NO 1433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1433
tcaggcccga tacatt 16

<210> SEQ ID NO 1434
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1434
attattctca tggtac 16

<210> SEQ ID NO 1435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1435
ccttagggag gcccta 16

<210> SEQ ID NO 1436
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1436
aaaattctat tgggcc 16

<210> SEQ ID NO 1437
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1437
ttttcaccat agcacg 16

<210> SEQ ID NO 1438
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1438
gtccttactg cagttt 16

<210> SEQ ID NO 1439
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1439
cagggatttt ccaaca 16

<210> SEQ ID NO 1440
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1440
gtctcacctg tattcg 16

<210> SEQ ID NO 1441
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1441
ttgcactaaa agctga 16

<210> SEQ ID NO 1442
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1442
ccagaaatcc ttatgc 16

<210> SEQ ID NO 1443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1443
gttccatgta tgccca 16

<210> SEQ ID NO 1444
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1444
acactcaatc ataccc 16

<210> SEQ ID NO 1445
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1445
ccaattcagc taagac 16

<210> SEQ ID NO 1446
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1446
aggagttgct gaaacc 16

<210> SEQ ID NO 1447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1447
gtcatatcag atgggt 16

<210> SEQ ID NO 1448
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1448
ctacgaggcc tttaga 16

<210> SEQ ID NO 1449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1449
cctctggcac taaatc 16

<210> SEQ ID NO 1450
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1450
tggctgggcg agcgat 16

<210> SEQ ID NO 1451
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1451
ctgacttggt tgccgt 16

<210> SEQ ID NO 1452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1452
gggcctgtta ttaaac 16

<210> SEQ ID NO 1453
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1453
tgatccttga ggcacc 16

<210> SEQ ID NO 1454
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1454
aactaccatg caaagg 16

<210> SEQ ID NO 1455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1455
actccttatg ttttga 16

<210> SEQ ID NO 1456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1456
ccagacagcg agagtc 16

<210> SEQ ID NO 1457
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1457
gcatgatgta aaattg 16

<210> SEQ ID NO 1458
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1458
aggattactc ctgaag 16

<210> SEQ ID NO 1459
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1459
aaataatggt aggtct 16

<210> SEQ ID NO 1460
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1460
ggtatattcc tgacca 16

<210> SEQ ID NO 1461
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1461
tggaatccag atgtgt 16

<210> SEQ ID NO 1462
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1462
aatatcaaca catcat 16

<210> SEQ ID NO 1463
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1463
ccagtgatca cttcca 16

<210> SEQ ID NO 1464
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1464
aacattgaaa caccag 16

<210> SEQ ID NO 1465
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1465
agcttccata agccag 16

<210> SEQ ID NO 1466
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1466
ggtagggctc taattc 16

<210> SEQ ID NO 1467
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1467
tagagggaat tgtgtg 16

<210> SEQ ID NO 1468
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1468
gctgtgatgt gggact 16

<210> SEQ ID NO 1469
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1469
gaaagtgtgg gagtgc 16

<210> SEQ ID NO 1470
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1470
gacaggtcct ccagtc 16

<210> SEQ ID NO 1471
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1471
atgtcgctgc agggcc 16

<210> SEQ ID NO 1472
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1472
tactgctctc tgggtc 16

<210> SEQ ID NO 1473
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 1473
accagtttct gtactg 16

<210> SEQ ID NO 1474
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1474
catctgcaag ggcacg 16

<210> SEQ ID NO 1475
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1475
attggcgatg gtggtg 16

<210> SEQ ID NO 1476
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1476
tccctctgtg aagggt 16

<210> SEQ ID NO 1477
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1477
ctggtaatcc cggtca 16

<210> SEQ ID NO 1478
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1478
tgtgtccacc acttct 16

<210> SEQ ID NO 1479
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1479
agtattgcca gctaag 16

<210> SEQ ID NO 1480
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1480
gaagattggc tctggc 16

<210> SEQ ID NO 1481
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1481
accgctttca gctgag 16

<210> SEQ ID NO 1482
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1482
tgagcttgac tcctct 16

<210> SEQ ID NO 1483
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1483
tgccccctca tgtaag 16

<210> SEQ ID NO 1484
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1484
gcatatctct cctggt 16

<210> SEQ ID NO 1485
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1485
ctcagttcca taaact 16

<210> SEQ ID NO 1486
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1486
gccttctcct tgctgc 16

<210> SEQ ID NO 1487
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1487
acacccggcc ccccaa 16

<210> SEQ ID NO 1488
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1488
tatccaactg ttctaa 16

<210> SEQ ID NO 1489
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1489
gatatgcccc caggag 16

<210> SEQ ID NO 1490
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1490
ccaccccaat gaccat 16

<210> SEQ ID NO 1491
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1491
ttggttctca catact 16

<210> SEQ ID NO 1492
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1492
tctagagatc tgagct 16

<210> SEQ ID NO 1493
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1493
ccagcttgat gagtag 16

<210> SEQ ID NO 1494
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1494
caagttggtg ctcaga 16

<210> SEQ ID NO 1495
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1495
tcaactagga tacagc 16

<210> SEQ ID NO 1496
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1496
atccttcttc gcataa 16

<210> SEQ ID NO 1497
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1497
aatcagagga cgggca 16

<210> SEQ ID NO 1498
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1498
ctagtccatc cgggtt 16

<210> SEQ ID NO 1499
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1499
ccccacttga gtcatt 16

<210> SEQ ID NO 1500
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1500
cagagcggga ggtgac 16

<210> SEQ ID NO 1501
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1501
atcaggcccg atacat 16

<210> SEQ ID NO 1502
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1502
ctcaagacaa catggg 16

<210> SEQ ID NO 1503
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1503
cccttaggga ggccct 16

<210> SEQ ID NO 1504
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1504
cttactcaat taactc 16

<210> SEQ ID NO 1505
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1505
actttttcac catagc 16

<210> SEQ ID NO 1506

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1506
tgtccttact gcagtt 16

<210> SEQ ID NO 1507
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1507
ccagggattt tccaac 16

<210> SEQ ID NO 1508
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1508
ggtctcacct gtattc 16

<210> SEQ ID NO 1509
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1509
tttgcactaa aagctg 16

<210> SEQ ID NO 1510
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1510
cccagaaatc cttatg 16

<210> SEQ ID NO 1511
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1511
cgttccatgt atgccc 16

<210> SEQ ID NO 1512
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1512
cacactcaat catacc 16

<210> SEQ ID NO 1513
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1513
ggccaattca gctaag 16

<210> SEQ ID NO 1514
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1514
cctacgaggc ctttag 16

<210> SEQ ID NO 1515
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1515
acctctggca ctaaat 16

<210> SEQ ID NO 1516
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1516
ttggctgggc gagcga 16

<210> SEQ ID NO 1517
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1517
gctgacttgg ttgccg 16

<210> SEQ ID NO 1518
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1518
tgggcctgtt attaaa 16

<210> SEQ ID NO 1519
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1519
ctgatccttg aggcac 16

<210> SEQ ID NO 1520
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1520
caactaccat gcaaag 16

<210> SEQ ID NO 1521
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1521
aactccttat gttttg 16

<210> SEQ ID NO 1522
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1522
tccagacagc gagagt 16

<210> SEQ ID NO 1523
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1523
ggcatgatgt aaaatt 16

<210> SEQ ID NO 1524
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1524
gcaggattac tcctga 16

<210> SEQ ID NO 1525
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1525
acagtgaaac aagcaa 16

<210> SEQ ID NO 1526
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1526
tggtatattc ctgacc 16

<210> SEQ ID NO 1527
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1527
ccttaatgta aattcc 16

<210> SEQ ID NO 1528
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1528
atgtgaatat caacac 16

<210> SEQ ID NO 1529
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1529
cccagtgatc acttcc 16

<210> SEQ ID NO 1530
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1530
gaacattgaa acacca 16

<210> SEQ ID NO 1531
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1531
cagcttccat aagcca 16

<210> SEQ ID NO 1532
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1532
gagatcacaa gggtag 16

<210> SEQ ID NO 1533
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1533
atagagggaa ttgtgt 16

<210> SEQ ID NO 1534
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1534
agctgtgatg tgggac 16

<210> SEQ ID NO 1535
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1535
gttggaggaa agtgtg 16

<210> SEQ ID NO 1536
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1536
tctgacataa gcccag 16

<210> SEQ ID NO 1537
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1537
agaaccacct atataa 16

<210> SEQ ID NO 1538
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1538
atataccgag gaattc 16

<210> SEQ ID NO 1539
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1539
atcccacctc cagtta 16

<210> SEQ ID NO 1540
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1540
ccaaggaaaa gtgcac 16

<210> SEQ ID NO 1541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1541
ttgaggatct ccagta 16

<210> SEQ ID NO 1542
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1542
gtgccagttt ttgtct 16

<210> SEQ ID NO 1543
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1543
gccttcttat gttatc 16

<210> SEQ ID NO 1544
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1544
cctttgtgga ccttct 16

<210> SEQ ID NO 1545
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1545
cccatgccga cgaggg 16

<210> SEQ ID NO 1546
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1546
ggctgtgatt cccaac 16

<210> SEQ ID NO 1547
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1547
ccgtagtcca tggtac 16

<210> SEQ ID NO 1548
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1548
ttgtcaaggc ttttga 16

<210> SEQ ID NO 1549
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1549
cggatgtcct tcccaa 16

<210> SEQ ID NO 1550
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1550
tggctcagtg acccgg 16

<210> SEQ ID NO 1551
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1551
ttcattaacc ctctcc 16

<210> SEQ ID NO 1552
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 1552
aggtagacta catcca 16

<210> SEQ ID NO 1553
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1553
ttggtccgcc tgcaga 16

<210> SEQ ID NO 1554
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1554
ttgggtcaaa agcgat 16

<210> SEQ ID NO 1555
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1555
tcagctatgg aaatgc 16

<210> SEQ ID NO 1556
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1556
ctaaagtaaa ctgctt 16

<210> SEQ ID NO 1557
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1557
gttccttcaa gcctcc 16

<210> SEQ ID NO 1558
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1558

-continued cttcggagga cattga 16

<210> SEQ ID NO 1559
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1559
gaagccgctg cctgac 16

<210> SEQ ID NO 1560
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1560
cccttcagtg ttcaag 16

<210> SEQ ID NO 1561
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1561
tttacttacc gggtaa 16

<210> SEQ ID NO 1562
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1562
atcctgggcg gcgaca 16

<210> SEQ ID NO 1563
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1563
aggcaccatt ctgcaa 16

<210> SEQ ID NO 1564
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1564
tgagctgttt ccccaa 16

<210> SEQ ID NO 1565
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1565
ccagtccaat tgtgca 16

<210> SEQ ID NO 1566
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1566
tgttcactgt gtgatc 16

<210> SEQ ID NO 1567
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1567
gcctcttaca tgtgtc 16

<210> SEQ ID NO 1568
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1568
tgtgagccac cagtgg 16

<210> SEQ ID NO 1569
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1569
gggccgtgtc acccta 16

<210> SEQ ID NO 1570
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1570
cccccccgct gattcc 16

<210> SEQ ID NO 1571
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1571
accagcctca ggtgga 16

<210> SEQ ID NO 1572
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1572
caaaggacag accggg 16

<210> SEQ ID NO 1573
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1573
aggccaggta gccgtg 16

<210> SEQ ID NO 1574
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1574
ttagatgact gaactc 16

<210> SEQ ID NO 1575
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1575
agcctcctcc agtttg 16

<210> SEQ ID NO 1576
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1576
cgataaacct tgtctc 16

<210> SEQ ID NO 1577
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1577
cagttttgta agtgca 16

<210> SEQ ID NO 1578
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1578
cggagacctc cctaaa 16

<210> SEQ ID NO 1579
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1579
gggcaaggct aagttc 16

<210> SEQ ID NO 1580
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1580
ccagcaaaga caagaa 16

<210> SEQ ID NO 1581
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1581
ggtacaaaac tgcatt 16

<210> SEQ ID NO 1582
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1582
tcactaaacc ccacac 16

<210> SEQ ID NO 1583
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1583
cagtgagatc caactc 16

<210> SEQ ID NO 1584
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1584
atgggcccac aggatc 16

<210> SEQ ID NO 1585

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1585
tacttctgtt agatac 16

<210> SEQ ID NO 1586
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1586
tgtaaccccc tgaaac 16

<210> SEQ ID NO 1587
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1587
tgaaacattc ctggac 16

<210> SEQ ID NO 1588
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1588
acccaggttt ggatgg 16

<210> SEQ ID NO 1589
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1589
gtggcaactc tgtaag 16

<210> SEQ ID NO 1590
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1590
ggctgagtgc tctcgg 16

<210> SEQ ID NO 1591
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1591
agggtacacg gctctc 16

<210> SEQ ID NO 1592
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1592
ggtcttgggc actctc 16

<210> SEQ ID NO 1593
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1593
ataatgtctc aaactc 16

<210> SEQ ID NO 1594
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1594
caccgcccaa aaccat 16

<210> SEQ ID NO 1595
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1595
cgtgcacaca caagag 16

<210> SEQ ID NO 1596
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1596
gggaattatg gaattg 16

<210> SEQ ID NO 1597
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1597
gaactcaagt cagtac 16

<210> SEQ ID NO 1598
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1598
ctccctgtaa tcacac 16

<210> SEQ ID NO 1599
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1599
taggcattca gaattt 16

<210> SEQ ID NO 1600
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1600
attattggtt caaaag 16

<210> SEQ ID NO 1601
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1601
cctgttgggt caaaca 16

<210> SEQ ID NO 1602
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1602
ccaacatgaa gtgagc 16

<210> SEQ ID NO 1603
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1603
cttttggcac cttcac 16

<210> SEQ ID NO 1604
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1604
tattagaggg ctagtg 16

<210> SEQ ID NO 1605
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1605
taaactcagg tgacta 16

<210> SEQ ID NO 1606
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1606
atggagtcat tagtgc 16

<210> SEQ ID NO 1607
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1607
taacagccat tgcata 16

<210> SEQ ID NO 1608
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1608
gatataccga ggaatt 16

<210> SEQ ID NO 1609
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1609
gatcccacct ccagtt 16

<210> SEQ ID NO 1610
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1610
caccaaggaa aagtgc 16

<210> SEQ ID NO 1611
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1611
actttgagga tctcca 16

<210> SEQ ID NO 1612
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1612
cgtgccagtt tttgtc 16

<210> SEQ ID NO 1613
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1613
agccttctta tgttat 16

<210> SEQ ID NO 1614
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1614
gcctttgtgg accttc 16

<210> SEQ ID NO 1615
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1615
acccatgccg acgagg 16

<210> SEQ ID NO 1616
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1616
cggctgtgat tcccaa 16

<210> SEQ ID NO 1617
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1617
tccgtagtcc atggta 16

<210> SEQ ID NO 1618
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1618
tcaatttgtc aaggct 16

<210> SEQ ID NO 1619
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1619
acggatgtcc ttccca 16

<210> SEQ ID NO 1620
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1620
ttggctcagt gacccg 16

<210> SEQ ID NO 1621
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1621
ggttcattaa ccctct 16

<210> SEQ ID NO 1622
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1622
gaggtagact acatcc 16

<210> SEQ ID NO 1623
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1623
cttggtccgc ctgcag 16

<210> SEQ ID NO 1624
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1624
tttgggtcaa aagcga 16

<210> SEQ ID NO 1625
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1625
gctcagctat ggaaat 16

<210> SEQ ID NO 1626
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1626
gtctaaagta aactgc 16

<210> SEQ ID NO 1627
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1627
tggttccttc aagcct 16

<210> SEQ ID NO 1628
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1628
tcttcggagg acattg 16

<210> SEQ ID NO 1629
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1629
ggaagccgct gcctga 16

<210> SEQ ID NO 1630
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1630
gcccttcagt gttcaa 16

<210> SEQ ID NO 1631
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 1631
gtttacttac cgggta 16

<210> SEQ ID NO 1632
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1632
aatcctgggc ggcgac 16

<210> SEQ ID NO 1633
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1633
acaggcacca ttctgc 16

<210> SEQ ID NO 1634
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1634
ccatctgagc tgtttc 16

<210> SEQ ID NO 1635
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1635
cccagtccaa ttgtgc 16

<210> SEQ ID NO 1636
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1636
ttgctgtaag ggacaa 16

<210> SEQ ID NO 1637
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1637
cagagcctct tacatg                                                     16

<210> SEQ ID NO 1638
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1638
atgtgagcca ccagtg                                                     16

<210> SEQ ID NO 1639
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1639
tgggccgtgt caccct                                                     16

<210> SEQ ID NO 1640
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1640
ccccccccgc tgattc                                                     16

<210> SEQ ID NO 1641
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1641
ggaccagcct caggtg                                                     16

<210> SEQ ID NO 1642
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1642
gcaaaggaca gaccgg                                                     16

<210> SEQ ID NO 1643
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1643
caggccaggt agccgt                                                     16

<210> SEQ ID NO 1644
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1644
tttagatgac tgaact 16

<210> SEQ ID NO 1645
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1645
aagcctcctc cagttt 16

<210> SEQ ID NO 1646
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1646
ccgataaacc ttgtct 16

<210> SEQ ID NO 1647
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1647
gcagttttgt aagtgc 16

<210> SEQ ID NO 1648
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1648
tcggagacct ccctaa 16

<210> SEQ ID NO 1649
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1649
tgggcaaggc taagtt 16

<210> SEQ ID NO 1650
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1650
actccacacc ttaatt 16

<210> SEQ ID NO 1651
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1651
tggtacaaaa ctgcat 16

<210> SEQ ID NO 1652
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1652
ctcactaaac cccaca 16

<210> SEQ ID NO 1653
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1653
ccagtgagat ccaact 16

<210> SEQ ID NO 1654
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1654
gatgggccca caggat 16

<210> SEQ ID NO 1655
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1655
gtacttctgt tagata 16

<210> SEQ ID NO 1656
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1656
gctgtaaccc cctgaa 16

<210> SEQ ID NO 1657
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1657
gccctgaaac attcct 16

<210> SEQ ID NO 1658
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1658
aacccaggtt tggatg 16

<210> SEQ ID NO 1659
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1659
cgtggcaact ctgtaa 16

<210> SEQ ID NO 1660
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1660
tcggctgagt gctctc 16

<210> SEQ ID NO 1661
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1661
cagggtacac ggctct 16

<210> SEQ ID NO 1662
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1662
tggtcttggg cactct 16

<210> SEQ ID NO 1663
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1663
atagcttacc tgtggg 16

<210> SEQ ID NO 1664

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1664
tcaccgccca aaacca 16

<210> SEQ ID NO 1665
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1665
ccgtgcacac acaaga 16

<210> SEQ ID NO 1666
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1666
gatctgggaa ttatgg 16

<210> SEQ ID NO 1667
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1667
agaactcaag tcagta 16

<210> SEQ ID NO 1668
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1668
gctccctgta atcaca 16

<210> SEQ ID NO 1669
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1669
tgtttaggca ttcaga 16

<210> SEQ ID NO 1670
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1670
tgaaattatt ggttca 16

<210> SEQ ID NO 1671
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1671
gcctgttggg tcaaac 16

<210> SEQ ID NO 1672
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1672
accaacatga agtgag 16

<210> SEQ ID NO 1673
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1673
ccttttggca ccttca 16

<210> SEQ ID NO 1674
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1674
ctattagagg gctagt 16

<210> SEQ ID NO 1675
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1675
tttaaactca ggtgac 16

<210> SEQ ID NO 1676
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1676
tatggagtca ttagtg 16

<210> SEQ ID NO 1677
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1677
ataacagcca ttgcat 16

<210> SEQ ID NO 1678
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1678
gttttgttgc accctc 16

<210> SEQ ID NO 1679
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1679
attctgtgtg ctcact 16

<210> SEQ ID NO 1680
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1680
cagattctgt gtgctc 16

<210> SEQ ID NO 1681
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1681
gtcagcagga gtagca 16

<210> SEQ ID NO 1682
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1682
cagtcagcag gagtag 16

<210> SEQ ID NO 1683
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1683
tcagtcagca ggagta 16

<210> SEQ ID NO 1684
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1684
ctcattatca gtcagc 16

<210> SEQ ID NO 1685
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1685
caggcctcat tatcag 16

<210> SEQ ID NO 1686
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1686
ccaggcctca ttatca 16

<210> SEQ ID NO 1687
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1687
tccaggcctc attatc 16

<210> SEQ ID NO 1688
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1688
ttccaggcct cattat 16

<210> SEQ ID NO 1689
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1689
gttccaggcc tcatta 16

<210> SEQ ID NO 1690
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1690
cgttccaggc ctcatt 16

<210> SEQ ID NO 1691
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1691
ccgttccagg cctcat 16

<210> SEQ ID NO 1692
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1692
tccgttccag gcctca 16

<210> SEQ ID NO 1693
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1693
aatccgttcc aggcct 16

<210> SEQ ID NO 1694
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1694
gaatccgttc caggcc 16

<210> SEQ ID NO 1695
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1695
cgaatccgtt ccaggc 16

<210> SEQ ID NO 1696
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1696
acgaatccgt tccagg 16

<210> SEQ ID NO 1697
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1697
cacgaatccg ttccag 16

<210> SEQ ID NO 1698
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1698
gccacgaatc cgttcc 16

<210> SEQ ID NO 1699
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1699
agccacgaat ccgttc 16

<210> SEQ ID NO 1700
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1700
cagccacgaa tccgtt 16

<210> SEQ ID NO 1701
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1701
gcagccacga atccgt 16

<210> SEQ ID NO 1702
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1702
agcagccacg aatccg 16

<210> SEQ ID NO 1703
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1703
tcctgggcag ttcagc 16

<210> SEQ ID NO 1704
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1704
attcctgggc agttca 16

<210> SEQ ID NO 1705
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1705
tcattcctgg gcagtt 16

<210> SEQ ID NO 1706
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1706
gtccagagct ttacgg 16

<210> SEQ ID NO 1707
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1707
gttgtccaga gcttta 16

<210> SEQ ID NO 1708
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1708
ggttgtccag agcttt 16

<210> SEQ ID NO 1709
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1709
aggttgtcca gagctt 16

<210> SEQ ID NO 1710
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 1710
aaggttgtcc agagct 16

<210> SEQ ID NO 1711
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1711
caaggttgtc cagagc 16

<210> SEQ ID NO 1712
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1712
gcaaggttgt ccagag 16

<210> SEQ ID NO 1713
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1713
tgtcttgcaa ggttgt 16

<210> SEQ ID NO 1714
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1714
ttgtcttgca aggttg 16

<210> SEQ ID NO 1715
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1715
tgttatcctc aagctc 16

<210> SEQ ID NO 1716
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1716
gcctgcagaa tcttat 16

<210> SEQ ID NO 1717
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1717
cccctgccag gcatat 16

<210> SEQ ID NO 1718
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1718
tgggtcaaaa gcgatg 16

<210> SEQ ID NO 1719
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1719
ttattgcagg ctccaa 16

<210> SEQ ID NO 1720
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1720
ttacttaccg ggtaag 16

<210> SEQ ID NO 1721
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1721
cagcaaacac gctccc 16

<210> SEQ ID NO 1722
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1722
ggccgtgtca ccctaa 16

<210> SEQ ID NO 1723
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1723
ggccaggtag ccgtgt 16

<210> SEQ ID NO 1724
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1724
gctgggtctg acccac 16

<210> SEQ ID NO 1725
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1725
aaggagttgc tgaaac 16

<210> SEQ ID NO 1726
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1726
gcaggttcac atgaca 16

<210> SEQ ID NO 1727
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1727
tctgttagat acaaac 16

<210> SEQ ID NO 1728
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1728
tgggaaactc aactgg 16

<210> SEQ ID NO 1729
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1729
tggatggaag gaacct 16

<210> SEQ ID NO 1730
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1730
cattcagaat ttccac 16

<210> SEQ ID NO 1731
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1731
cccaccattg atgggt 16

<210> SEQ ID NO 1732
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1732
tcactatcga tcaaat 16

<210> SEQ ID NO 1733
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1733
cactttacat gcacga 16

<210> SEQ ID NO 1734
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1734
tcatcataga tactcc 16

<210> SEQ ID NO 1735
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1735
ggaggtgtgc ctgtca 16

<210> SEQ ID NO 1736
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1736
gctactcact gccagc 16

<210> SEQ ID NO 1737
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1737
agaaatgacc ctgttc 16

<210> SEQ ID NO 1738
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1738
cacgatctca tttttc 16

<210> SEQ ID NO 1739
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1739
atgcacgatc tcattt 16

<210> SEQ ID NO 1740
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1740
acatgcacga tctcat 16

<210> SEQ ID NO 1741
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1741
tttacatgca cgatct 16

<210> SEQ ID NO 1742
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1742
actttacatg cacgat 16

<210> SEQ ID NO 1743

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1743
gtgtcagtca ttatgc 16

<210> SEQ ID NO 1744
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1744
gttaactgtg caccta 16

<210> SEQ ID NO 1745
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1745
agcttgtaag atgtta 16

<210> SEQ ID NO 1746
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1746
gaagatcctt aaccct 16

<210> SEQ ID NO 1747
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1747
acattggtta ggtcag 16

<210> SEQ ID NO 1748
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1748
acacattggt taggtc 16

<210> SEQ ID NO 1749
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1749
ggaattcctc agatga 16

<210> SEQ ID NO 1750
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1750
gtttatggaa ttcctc 16

<210> SEQ ID NO 1751
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1751
ggtcctgccg tgttta 16

<210> SEQ ID NO 1752
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1752
tcctatcaca ttgagt 16

<210> SEQ ID NO 1753
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1753
tgcctctaag gccttc 16

<210> SEQ ID NO 1754
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1754
atcttggtgt tggttc 16

<210> SEQ ID NO 1755
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1755
ttaagtttca agccct 16

<210> SEQ ID NO 1756
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1756
gttcatgacc tcctta 16

<210> SEQ ID NO 1757
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1757
gtcctctgca agttca 16

<210> SEQ ID NO 1758
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1758
gatcatccag acaggg 16

<210> SEQ ID NO 1759
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1759
gaacttgcca gttcca 16

<210> SEQ ID NO 1760
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1760
tgcttgtcaa tgtcag 16

<210> SEQ ID NO 1761
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1761
agacatactg cttgtc 16

<210> SEQ ID NO 1762
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1762
tactatgaaa atggtc 16

<210> SEQ ID NO 1763
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1763
agcaactaat tctact 16

<210> SEQ ID NO 1764
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1764
acaaattggc agcaac 16

<210> SEQ ID NO 1765
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1765
acacaaattg gcagca 16

<210> SEQ ID NO 1766
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1766
cacctatata aattgc 16

<210> SEQ ID NO 1767
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1767
gcaattttat ggaacc 16

<210> SEQ ID NO 1768
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1768
cttagtagtg acagct 16

<210> SEQ ID NO 1769
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1769
agcctaactg atgcct 16

<210> SEQ ID NO 1770
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1770
ggtctcactc gcaggt 16

<210> SEQ ID NO 1771
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1771
ggctattcat tctggc 16

<210> SEQ ID NO 1772
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1772
ggagatctgg ctattc 16

<210> SEQ ID NO 1773
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1773
gctactggtt ctggcc 16

<210> SEQ ID NO 1774
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1774
gagtactttg aattca 16

<210> SEQ ID NO 1775
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1775
gtctggctat ctctga 16

<210> SEQ ID NO 1776
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1776
agacattgca gtctgg 16

<210> SEQ ID NO 1777
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1777
taaatttgca ggtggt 16

<210> SEQ ID NO 1778
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1778
cttaaatttg caggtg 16

<210> SEQ ID NO 1779
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1779
ggatttagaa atcccc 16

<210> SEQ ID NO 1780
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1780
tgtgttcttt ccgtgt 16

<210> SEQ ID NO 1781
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1781
gacaatgaag cttcac 16

<210> SEQ ID NO 1782
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1782
ttaactgggt gagctt 16

<210> SEQ ID NO 1783
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1783
taatgtgatt cacagg 16

<210> SEQ ID NO 1784
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1784
ggtttaatgt gattca 16

<210> SEQ ID NO 1785
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1785
cctgaaaaaa ggcttc 16

<210> SEQ ID NO 1786
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1786
tgtaacaaca atcctg 16

<210> SEQ ID NO 1787
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1787
ttactatatt tggagc 16

<210> SEQ ID NO 1788
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1788
tgtctcctat cagtcc 16

<210> SEQ ID NO 1789
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 1789
caatttagca ggaacc 16

<210> SEQ ID NO 1790
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1790
gattatgctc ttcacc 16

<210> SEQ ID NO 1791
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1791
tatctgatta tgctct 16

<210> SEQ ID NO 1792
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1792
tgattacgct ttgcta 16

<210> SEQ ID NO 1793
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1793
tctgattacg ctttgc 16

<210> SEQ ID NO 1794
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1794
agatactctg gacact 16

<210> SEQ ID NO 1795
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1795
ggcagcttgt gatcca 16

<210> SEQ ID NO 1796
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1796
ccgtatagga atctga 16

<210> SEQ ID NO 1797
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1797
ggtgatttgg ccacgg 16

<210> SEQ ID NO 1798
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1798
agtgatctcc aggccc 16

<210> SEQ ID NO 1799
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1799
gtgactgcca aagtgt 16

<210> SEQ ID NO 1800
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1800
ttgataaaga tgcctc 16

<210> SEQ ID NO 1801
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1801
tttcatggta ggtgtt 16

<210> SEQ ID NO 1802
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1802
atactcctca atattt 16

<210> SEQ ID NO 1803
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1803
tagatactcc tcaata 16

<210> SEQ ID NO 1804
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1804
catcatagat actcct 16

<210> SEQ ID NO 1805
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1805
gttcatcata gatact 16

<210> SEQ ID NO 1806
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1806
gatctctatc ctgtgt 16

<210> SEQ ID NO 1807
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1807
gactcgaaca agtcca 16

<210> SEQ ID NO 1808
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1808
cttcatcggt ccatcg 16

<210> SEQ ID NO 1809
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1809
tccaggtacc cttcta 16

<210> SEQ ID NO 1810
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1810
agacatcacc ttgtcc 16

<210> SEQ ID NO 1811
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1811
attcttcctg gagtgc 16

<210> SEQ ID NO 1812
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1812
tgaggctact cactgc 16

<210> SEQ ID NO 1813
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1813
gtaactggca aagttc 16

<210> SEQ ID NO 1814
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1814
tgcacgatct catttt 16

<210> SEQ ID NO 1815
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1815
catgcacgat ctcatt 16

<210> SEQ ID NO 1816
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1816
tacatgcacg atctca 16

<210> SEQ ID NO 1817
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1817
ctttacatgc acgatc 16

<210> SEQ ID NO 1818
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1818
gcactttaca tgcacg 16

<210> SEQ ID NO 1819
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1819
gtgtgtcagt cattat 16

<210> SEQ ID NO 1820
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1820
cgttaactgt gcacct 16

<210> SEQ ID NO 1821
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1821
tccttaaccc tggttc 16

<210> SEQ ID NO 1822

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1822
tcaagaagaa gatcct 16

<210> SEQ ID NO 1823
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1823
cacattggtt aggtca 16

<210> SEQ ID NO 1824
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1824
acacacattg gttagg 16

<210> SEQ ID NO 1825
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1825
tatggaattc ctcaga 16

<210> SEQ ID NO 1826
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1826
cgtgtttatg gaattc 16

<210> SEQ ID NO 1827
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1827
tcacattgag ttgcta 16

<210> SEQ ID NO 1828
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1828
gcctctaagg ccttca 16

<210> SEQ ID NO 1829
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1829
ggtgttggtt ccccac 16

<210> SEQ ID NO 1830
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1830
gctgatcccg gtctct 16

<210> SEQ ID NO 1831
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1831
tccttaagtt tcaagc 16

<210> SEQ ID NO 1832
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1832
tgcaagttca tgacct 16

<210> SEQ ID NO 1833
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1833
gaaatatccc tctccc 16

<210> SEQ ID NO 1834
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1834
ccctatatgc ccatga 16

<210> SEQ ID NO 1835
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1835
agaacttgcc agttcc 16

<210> SEQ ID NO 1836
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1836
gacatactgc ttgtca 16

<210> SEQ ID NO 1837
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1837
gtcactaaga catact 16

<210> SEQ ID NO 1838
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1838
gcaactaatt ctacta 16

<210> SEQ ID NO 1839
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1839
caaattggca gcaact 16

<210> SEQ ID NO 1840
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1840
cacaaattgg cagcaa 16

<210> SEQ ID NO 1841
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1841
acctatataa attgct 16

<210> SEQ ID NO 1842
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1842
attttatgga acctct 16

<210> SEQ ID NO 1843
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1843
agcttcacct gtgtgc 16

<210> SEQ ID NO 1844
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1844
tgccttagta gtgaca 16

<210> SEQ ID NO 1845
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1845
tcactcgcag gtgtca 16

<210> SEQ ID NO 1846
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1846
gctattcatt ctggct 16

<210> SEQ ID NO 1847
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1847
tggctattca ttctgg 16

<210> SEQ ID NO 1848
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1848
tggttctggc cactgc 16

<210> SEQ ID NO 1849
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1849
ggagttcact ttgcct 16

<210> SEQ ID NO 1850
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1850
gctatctctg agtact 16

<210> SEQ ID NO 1851
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1851
gacattgcag tctggc 16

<210> SEQ ID NO 1852
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1852
tcagacattg cagtct 16

<210> SEQ ID NO 1853
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1853
ttaaatttgc aggtgg 16

<210> SEQ ID NO 1854
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1854
cccttaaatt tgcagg 16

<210> SEQ ID NO 1855
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1855
tggatttaga aatccc 16

<210> SEQ ID NO 1856
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1856
tgaagcttca cactta 16

<210> SEQ ID NO 1857
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1857
aggacaatga agcttc 16

<210> SEQ ID NO 1858
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1858
tccttaactg ggtgag 16

<210> SEQ ID NO 1859
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1859
gtttaatgtg attcac 16

<210> SEQ ID NO 1860
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1860
tggtttaatg tgattc 16

<210> SEQ ID NO 1861
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1861
gtaacaacaa tcctga 16

<210> SEQ ID NO 1862
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1862
tactatattt ggagct 16

<210> SEQ ID NO 1863
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1863
gtctttacta tatttg 16

<210> SEQ ID NO 1864
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1864
aatttagcag gaaccc 16

<210> SEQ ID NO 1865
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1865
gagaatcctg ttaggc 16

<210> SEQ ID NO 1866
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1866
tgattatgct cttcac 16

<210> SEQ ID NO 1867
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1867
gctatctgat tatgct 16

<210> SEQ ID NO 1868
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 1868
ctgattacgc tttgct 16

<210> SEQ ID NO 1869
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1869
gacactaagg catggg 16

<210> SEQ ID NO 1870
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1870
gcagatactc tggaca 16

<210> SEQ ID NO 1871
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1871
gggctatttg gtgtct 16

<210> SEQ ID NO 1872
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1872
tgatttggcc acggga 16

<210> SEQ ID NO 1873
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1873
gaacatctgt ctttgc 16

<210> SEQ ID NO 1874
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1874
agcatgaact ttaccc 16

<210> SEQ ID NO 1875
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1875
caggtcaaca ccgtga 16

<210> SEQ ID NO 1876
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1876
gtttgataaa gatgcc 16

<210> SEQ ID NO 1877
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1877
tactcctcaa tattta 16

<210> SEQ ID NO 1878
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1878
gatactcctc aatatt 16

<210> SEQ ID NO 1879
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1879
atcatagata ctcctc 16

<210> SEQ ID NO 1880
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1880
ttcatcatag atactc 16

<210> SEQ ID NO 1881
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1881
gtgtaaattg cagagc 16

<210> SEQ ID NO 1882
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1882
tgtgaaatga gctcca 16

<210> SEQ ID NO 1883
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1883
atgactcgaa caagtc 16

<210> SEQ ID NO 1884
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1884
tggaacttca tcggtc 16

<210> SEQ ID NO 1885
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1885
gacatcacct tgtcca 16

<210> SEQ ID NO 1886
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1886
ggaagtcagg caccca 16

<210> SEQ ID NO 1887
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1887
tgttatattt gatcct 16

<210> SEQ ID NO 1888
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1888
gaacgcaatg ctgact 16

<210> SEQ ID NO 1889
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1889
cagcattgag tacaac 16

<210> SEQ ID NO 1890
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1890
ctttatacca gtgtct 16

<210> SEQ ID NO 1891
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1891
gagaacattg aaacac 16

<210> SEQ ID NO 1892
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1892
tagtgctata gaggga 16

<210> SEQ ID NO 1893
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1893
ttacatgcac gatctc 16

<210> SEQ ID NO 1894
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1894
aattttatgg aacctc 16

<210> SEQ ID NO 1895
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1895
tcatagatac tcctca 16

<210> SEQ ID NO 1896
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1896
ccctaacact cagttc 16

<210> SEQ ID NO 1897
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1897
tccgtcaata tattct 16

<210> SEQ ID NO 1898
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1898
ggtaagagcg atggga 16

<210> SEQ ID NO 1899
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1899
gagtattgtt tttgtg 16

<210> SEQ ID NO 1900
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1900
gttatatttg atcctc 16

<210> SEQ ID NO 1901

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1901
ctaattttct gactgt 16

<210> SEQ ID NO 1902
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1902
attcagaatt tccact 16

<210> SEQ ID NO 1903
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1903
gcaatgctga cttggc 16

<210> SEQ ID NO 1904
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1904
tatttcttga tgtggt 16

<210> SEQ ID NO 1905
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1905
acgcaatgct gacttg 16

<210> SEQ ID NO 1906
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1906
cgtgttatat ttgatc 16

<210> SEQ ID NO 1907
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1907
caacacatca ttgggt 16

<210> SEQ ID NO 1908
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1908
cactttatac cagtgt 16

<210> SEQ ID NO 1909
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1909
ttatatttga tcctca 16

<210> SEQ ID NO 1910
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1910
ttatgaaatt attggt 16

<210> SEQ ID NO 1911
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1911
aagtattgcc agctaa 16

<210> SEQ ID NO 1912
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1912
atgctaattt tctgac 16

<210> SEQ ID NO 1913
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1913
ggcattcaga atttcc 16

<210> SEQ ID NO 1914
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1914

tttataccag tgtctt                                                     16

<210> SEQ ID NO 1915
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1915

tattctcatg gtacag                                                     16

<210> SEQ ID NO 1916
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1916

tgagtattgt ttttgt                                                     16

<210> SEQ ID NO 1917
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1917

agttttgtaa gtgcaa                                                     16

<210> SEQ ID NO 1918
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1918

taagtattgc cagcta                                                     16

<210> SEQ ID NO 1919
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1919

aacgcaatgc tgactt                                                     16

<210> SEQ ID NO 1920
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1920

agctttaaac tcaggt                                                     16
```

<210> SEQ ID NO 1921
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1921
gtattgtttt tgtggg 16

<210> SEQ ID NO 1922
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1922
agtattgttt ttgtgg 16

<210> SEQ ID NO 1923
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1923
aattatggaa ttgcag 16

<210> SEQ ID NO 1924
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1924
cgcaatgctg acttgg 16

<210> SEQ ID NO 1925
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1925
cgtcaatata ttcttt 16

<210> SEQ ID NO 1926
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1926
tgtatttctt gatgtg 16

<210> SEQ ID NO 1927
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1927
ttattctcat ggtaca 16

<210> SEQ ID NO 1928
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1928
gtgagtattg tttttg 16

<210> SEQ ID NO 1929
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1929
tgggaattat ggaatt 16

<210> SEQ ID NO 1930
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1930
ggttatgaaa ttattg 16

<210> SEQ ID NO 1931
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1931
tgaagattgg ctctgg 16

<210> SEQ ID NO 1932
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1932
tatatttgat cctcaa 16

<210> SEQ ID NO 1933
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1933
gtaagtattg ccagct 16

<210> SEQ ID NO 1934
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1934
gtgttatatt tgatcc 16

<210> SEQ ID NO 1935
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1935
gggttatgaa attatt 16

<210> SEQ ID NO 1936
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1936
ccgtcaatat attctt 16

<210> SEQ ID NO 1937
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1937
gcattcagaa tttcca 16

<210> SEQ ID NO 1938
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1938
ttataccagt gtcttc 16

<210> SEQ ID NO 1939
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1939
ctgaagattg gctctg 16

<210> SEQ ID NO 1940
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1940
gtgtatttct tgatgt 16

<210> SEQ ID NO 1941
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1941
actttatacc agtgtc 16

<210> SEQ ID NO 1942
<211> LENGTH: 21
<212> TYPE: DNA
<213> ORGANISM: Artificial sequence
<220> FEATURE:
<223> OTHER INFORMATION: Primer

<400> SEQUENCE: 1942
ggcagccttg tactcttgga a 21

<210> SEQ ID NO 1943
<211> LENGTH: 20
<212> TYPE: DNA
<213> ORGANISM: Artificial sequence
<220> FEATURE:
<223> OTHER INFORMATION: Primer

<400> SEQUENCE: 1943
gctggtaatc ccggtcaaag 20

<210> SEQ ID NO 1944
<211> LENGTH: 26
<212> TYPE: DNA
<213> ORGANISM: Artificial sequence
<220> FEATURE:
<223> OTHER INFORMATION: Probe

<400> SEQUENCE: 1944
ctgggatgga gttgggaatc acagcc 26

<210> SEQ ID NO 1945
<211> LENGTH: 22
<212> TYPE: DNA
<213> ORGANISM: Artificial sequence
<220> FEATURE:
<223> OTHER INFORMATION: Primer

<400> SEQUENCE: 1945
ctcctgctga gtgaccataa ag 22

<210> SEQ ID NO 1946
<211> LENGTH: 20
<212> TYPE: DNA
<213> ORGANISM: Artificial sequence
<220> FEATURE:
<223> OTHER INFORMATION: Primer

<400> SEQUENCE: 1946
ggacttcttc gagccagttt 20

<210> SEQ ID NO 1947
<211> LENGTH: 24

<212> TYPE: DNA
<213> ORGANISM: Artificial sequence
<220> FEATURE:
<223> OTHER INFORMATION: Probe

<400> SEQUENCE: 1947
agagtggtgg ctactgctga actg 24

<210> SEQ ID NO 1948
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1948
ggctactacg ccgtca 16

<210> SEQ ID NO 1949
<211> LENGTH: 14654
<212> TYPE: DNA
<213> ORGANISM: Macaca fascicularis

<400> SEQUENCE: 1949
catgccagca gggaagggga gctggcatgt caatggtaag catgggaaca agaggaggga 60
ggcagagctc tcacactctt ttaaacaatc agatgttgca tgaattgagt caaaactcac 120
tcagctccaa ggggatgacg ctcagccatt catgaggaat ctgcccccat gatccaatac 180
ctcccactag gccccccttcc aatgctgaag gtcacatttc ctcatgaagt ttgaagggga 240
cacatattca aatcatatca ttcaacacaa cccccccatc acatgttctt ctcacattgc 300
aaaacacagt catcccttcc caggggtctc ccaaagtcat aatttgttcc aacctcaagt 360
ccaaagttct aaatcacatt caaagacccc tccttccagc taggggcctg taaaatcaaa 420
acaagttact ccaggataaa atggtggcat agacattgca taaacactcc cattccaaaa 480
gaaagaagtc ggccaaaaga aagaggcaac atgcccccat gcaagtccca aacccagcag 540
ggcagacgtg aaactttaac tctccagaac aatctttgaa tccatgtccc atacctaggg 600
cacgctggca caagtgttgg tcccccgagg ctttgagcag ctctgcccct gtggcttttc 660
agggggcagc tgctgtggct gctgctacag atggattaca gttgagtgca tgtggccttt 720
ccaggctcag gatggaagct actcgtggct ctaaaattac gggatctgga gggtgactgc 780
cctcttccca cagcctcact aggtagtgcc ctggtgggga ctctgtgtag gcgctcctac 840
cctacctttc ccctcagcac tgtcctagta gattatctct gtggggaatt tgtcctgctg 900
caggcttcta cctgggcacc caggcttttc cacaaaccct ctgaaatcta gatagaagct 960
accaagtctc cttcactctt gaattctgca cacctgaaga cctaaaccat atacggaagc 1020
tgccaaggtg gcttgcaccc tctggggcgg tgtcccaagc cacctttaaa ctgagggtgt 1080
aactggagca accagtaggt gaggagcagg gtcctgaggc tgagaagggg accaacatcc 1140
caaagctggg cccttaaatc atttttcctc tctgagttgt tggatgaaag caacttcctc 1200
tcctcttgct tcggtttcct catcagcaaa atcagatcat aatcctggcc cattgagggg 1260
atgattataa aactcaatca aatggagaag tatttgcaaa tggaatgtat tgcaacgtgt 1320
attgtgcagt ccctgtgtaa tcaccttttt gttcctgcct cacaagctgg gttatgtgtg 1380
taggggtggg gggaggtggc cacgatgccc ccagagatgt ttgctgagga tgaaataggc 1440
ttccatgaaa gggtcagttt ggcttctgtg gttcagctgt ctttgaggcc cttctgcctg 1500
gggcaaagca caaaagtcca acagcaatct ggttgcctga cttcttagcc atggaagtgt 1560
ggtgagcagt ggtctctagt ccctccaccc agtgtgcctc gggagtggaa catggggcgg 1620
tggcctctgc tggggaggat gctgggggtt ctctgaaagg aggcaatgcc tgattttgtc 1680
attgaaggat gagcatgatt tttccagatg gtggaagcag gtgcttctgg cagaagaccc 1740
cacataagca aatgtgtaaa atccacaagg catggccttc aacaagagca ggtctggggc 1800
ggtggctcat gtcaaggtgg gaggctcact tgaggccagg agttcaagag tagcccagtc 1860
aatatagtga gatcccatct ctaacatatt ttttcaaaaa attagctggg tggctggatc 1920
atgcctgtag aaccagctac tcaggaggct gaggtgggag gatggcttga gcccaggagt 1980
ttgaagctgt agttcgctgt gattgtggca ctgcacttca gccttggcta cagagtgaga 2040
ccctgtctcc aaaacataaa caaaataacc ccaacagcat tacaataaat atacaataag 2100
catccacacg gcatgtgtgg gagactgtgc ttatgctgat ggcatgggca ggaggaaggc 2160
aggcatctgg ggagtgtggg tgcacgggag gacagggagg gtcccacagg ctgtcagtgg 2220
caggtctttc ttcctgaaga ccactgcaga cccccaaccc tgaggatgcg aggcaggtgg 2280
gttggatgag agggacctgg gtgtttcgtc tgcggctgct cctctaagta caacagcaaa 2340
gagggtgggc ctggactgaa ggtggtgctg gggagcagcc tgtttgctgt gcttgatcac 2400
gagttgctgg gaagttgtga cattcacctt ccctttccaa tttcatagtt atctgggagg 2460
ccagaggacg tgtctggtta ttacacaggt gcacagctgg agatgggatc cacaaagctc 2520
ggaacagctg gatcttgctc agtctctgtc aggggaagat tcctcggtaa gtcggggacc 2580
gttgacctgc cccatctcc ttattctcaa caatagctcc atgaaggaag gatcattccg 2640
cttttgtaga taagttcaga gacgttagta actggttcag atcagacagg aaagcagtag 2700
cagagtcggg atttgcaccc aggcttgagt ctgatgctcc ctccctcctg ctgtgccctt 2760
aaacagtaga gagaggccgg gaaacaggtc agatgggttc acaaagctcc ctgggctcag 2820
ctctggttta gactgtggag acacagctgg gggaccccag aaggaaggtc tgtgttgggg 2880
gtgcctgact ctttaggaaa tttgaaggaa ccaaagaagg tggaggtggg gaggtgaccc 2940
ggactctggt ctgtccttat ggcctggaaa cacccaggct ggccccaggg tgctgctgct 3000
gaggcccaat gggaacgaca aatttatttt gagatacaag gaacctagag gtcatctcac 3060 caccccccc tccaagtctg agcaccaact tgtgccaggc cctgtgggga aactgaggcc 3120
ctgggagggg agtgacttgc ccagggtcct gtgtctggag gctgagcagg tagctcgtag 3180
gactccacgt ctctggccct cacctctgtc cctctcttca gacctctggg gggatggaga 3240
agaaacaggc tgtgctgtgt ccctaatggg aaacgtggct gagacagggg agtgagaagg 3300
gcgtgctgtg gaatagtgtc tgtggcatga tgccagcttt gcaatcaaga gattcaagaa 3360
ccacactgtg gaattgtgga tataactaca ggagtgacag cttagatctc tgtgtttgta 3420
gaagcagaat caaacctgga aactcttgga ttatcaaaat tatacatttt tgcttctata 3480
tcagagtcat aaggccagat gttggcctcc cctctgccct ccaagagctg tgtgactctg 3540
ggcaagtcac ctccgctctc agcctgagta ttctcccctc tcaaaaacct gatagagctg 3600
ccaaaagtac atgaaatcgg ggggaaattt ctgtgaaatc tgagtcatgg tcttcttttt 3660
cttcactaag aagagatgcc cgtcaagata gaaagcacta tggctgtggc ttgtaacccc 3720
agtgctgtgg gaggtagagg cgggaggatc actagaggct gggagttcaa gacagcctgg 3780
aaaacacagg agatgctgtc tctatgaaat taaaaatgaa caaattagcc cagcatggtg 3840
gcgtgcacct gtagtcccag ctactcagag ggttgaagga ggaggatctc ttgagcccag 3900

-continued tagatctagg ctgcaatgag ctaggatggc gccaaagcac tccagcctgg gtgacagagc 3960
aaaaccgttt ctcaaaaatg aaatgaaaat ggtgatttct caggaggacc acactgtgtc 4020
gaccctctat tcctgcccaa ggaggaggcc ccgcagtgac atggagggtg ctgctttgct 4080
gagactcttt gtcctctgca tctggtgagc ttggctcaga gtgctgaggt gggagggagg 4140
tccccggtct gggctgcaca gttgggcagg gcttgggctg ggcctgggcc atctgggttt 4200
ctttcaggaa ccaaagtccc ttcccagaat tgaccaacca gcagactcgc ccagggagaa 4260
cctgctgtat cctagtcaag gctaacgggc aatatccagc ctcaattctc agcagaggcc 4320
ccagatcagg gtctgagcca ggccaacaat gaccaaagag gatgggatcc tgggtgcagc 4380
tcctcacaag tgtcgggcga gtctgaggcc tcagctctct ctgccctcct gctcctctgc 4440
tctctcctgg tcctcctgtg tcctcatgga tcatgagatg gctgtcctgg cccagggggt 4500
catacagtga gcaaagcagg aacaagggga agggaacccc ctctcctgtc acccctgtcc 4560
cttatagcaa gaagcaccca gacacccctc tgcatactgc cctggtgaac tgctgcccag 4620
gactgggtcc cccttctacc cttgctgcgt ggggtcccag aagacagaca tctgtgtgtc 4680
tgaaccctgg gataaaggca ggaaggggaa agagggaggc gagtggcttt tgagaggggg 4740
cttttgtatg agagctggag gatggaaccc catcaggggg cccggaaacc actgagctgt 4800
taaaataaag gctgcaaaca aagaccagct gctggaagtg ggtgtgccag ggagggagca 4860
gagacacacg gtgagaaaag agaaatggta atgcctggag ccgcccctga ctgcgatggg 4920
cctgaagccg tattattagt agtaattata gtatcattat tagtcatttt catcttattt 4980
gtatcctccg tctatctctc ctctccacct tttcctaaca ttctatcacc agttttatgt 5040
cttccattag caactttgta gctgtaaaca gtttacttac aactttctca tgccctcagt 5100
agtacccagt atttcttgac ttctctcttt aaaaaatgac gatattaatc ttccttctcc 5160
ttccttcagt gtttcacatc ccaactgcta cctttgtgct ttaaattttg tactaattgg 5220
tattagtaac aagtatattt agttctcaca tttacatgtt gtgtatatgg ttttttgtcc 5280
taaagaagag actactgaga accagtgaga ctgagagaat gggcatcttc acgtactgct 5340
agtttgagtg tgaatttggt acaatgtgca tacagtgtgg ctgtaggtat aaaacctaat 5400
tctactccta cgaatatctt aaggaaataa tctcaaatgt gagcaaagtt ttaggagaag 5460
gaggatgttc tttgtagcat aaattacatg aagaattaga aataccctaa ggtccatcag 5520
ccagagagga cagcagaggg gacagggcag caccaggagg gctcggcagc cacagcaggg 5580
gctgcgccgg catctggcag gatccaggtc tttgtgggac agaggacctt agagaagcga 5640
cggggacaca ggctgtccgc tgcagcagca gtgaattcac caagacgaag agttgagcac 5700
agagtgtgag acacggattt gcaatgagga gtcatttccc atgagcgtgt atacatgact 5760
caatattgta tattgaaggg agtagagcac agtcattgaa gacatggggt tgaagcagaa 5820
gtcctggctc tagcactatt gtgaaaacac gggcaggttc cctaactttt gtggattcct 5880
ctgtgtttga aagggaaggt ggtacccatc tcccgggctg tgtgtgatca tcgaatgaga 5940
cacgtgtaag gagccctgca catcacagac actcaataca cactggctat catcaaccag 6000
ttatcacaca tgttcccagg cccaggtcat tgtcagaacc ttcctcccca tctctattcc 6060
tgtgtatgga ctctgtagtt ttctgtaatg atcaggtggc tgcccctcct ctgattatct 6120
tctcctcata ccccaacagg acaagcggac ttttccttgc tgtgggagtg agggcagagg 6180
aagctgcagc gaggtgagtg tctgtaaata gcaggtgatg ggactcagt gacagagaaa 6240

-continued caatctgggt taggttggtc ttgacatttg ctgccaccct agaaggatgt gcagagcccc 6300
ggctgctcaa gcctccctct gtccacaggt ggctcacatt caatcccaca atttgttttc 6360
tcctcctcaa gggtgcagca aaaccatcca ggtgggacag atacaggaga tcctcaaggt 6420
aagcccctca gtgaccgggc tgctggcacc atggacccag gtaggctcgc ctcctcttcc 6480
ctggctggtt cccactcgca cctagcacgg agggtggtgc ctccacagct gagtgaaccc 6540
cagaggaacc cagatggaca aggaggccaa tgagtctgct ccaagcccca agagaagccg 6600
catagagtcc cccgacccag gggtctgtgg ggccatctgc atcctgactt ctcctcaggg 6660
ggggcacggc ccaggagccc acttcctctc taccctggca ctagcaaatg tctcaagtgg 6720
ggcaggaggg ccttggggaa atggaaccag caggggaggg gagtgggggg agagcagggt 6780
ccaggagggg agggctggga gagcaggttg accagcagcc ccgacctgtc acctcccgct 6840
ctgctcccag ctgaccctgg gtgtttctag ccgaggctgg tcccctccct ccagctcttg 6900
ccctgcacca gcccctctgc tctgagtggc cttgtgggaa tgtatcaggc ctgatccagc 6960
ttccaactta actggacccc ggtctggcct ttgccacgtc ccctctgtgt gacctggcgc 7020
gccttacctc ccctctcctg taccatgaga ataatatttc cccatgttgt cttgaggatc 7080
aaatatgaca cagctatctg gcctggccgg tgcctgccac acggtagggc ctccctaagg 7140
gctggttccc atcccctcta cctgtcccct gttgattcca ggtggaaggc acccagtcct 7200
cccagctgtg ttaggggcac ccgccctgcc ctgcccacca caagcgcctg ctgaccaggg 7260
atgactgccc cgggcagggg ttgagtccag tcatctaaaa taccccctggt caaagaaaaa 7320 tctgaggccc agtagaattt taaagagttt atttgagtaa gaaagaattc ttgaattggg 7380
aaacagcaaa ctggaggagg cttcgtgcta tggtgaaaaa gtgtgggaga caatgtttag 7440
cgggtgaata tgaaactgca ataaggacat gacttgattg gttgcactta caaaacttcc 7500
tgttttggtt tactttgttg gaaaatccct ggtcacattg gtgttggtga gtttagggag 7560
gtctccgaat gcaggtgaga ccggacctta gccttgccca ggtttttgac atccaagaga 7620
gaaaaaggtt aagtccaagc aaaagcaaaa gcaaaagcaa aagcaaatca gcttttattg 7680
caaagcggac gctcaggctc gggggtggga gtgcaggcgg actcagaaga gccagtcggg 7740
cccagtgtgg tttggggttt ctgcctttgc tggtttatta aattaagggg tggagtaagc 7800
atgaagattt ctgggaagag gtggggattt cttggaactt ggcggggagg ggtgggtacc 7860
acacagtttt gtaccaaaca caggcataca tggaactgct gtggcgcggg tgggggtggg 7920
gtttagtgag acaaggaggg tatgattgag tgtgaggcga atcgtgagtc cgacccagca 7980
ctgagttgga tcttactggt cttcgccgga ttggccactt cctgtttgtc agggtcctgt 8040
aggcctgtcg cctccccctg tccctgcagc tggtttcagc agctccttct gtgtctgtca 8100
tgggaaccag ctgcctggag ttcttgtttc ttctatgacc tcccagtatt cccatctcag 8160
catggcccgc tgtcagctgg ctgctcgtga ctggccgagg ttaagttttg tttgtgtcta 8220
acagaagcgc ccatctgatg tgaccccagt tcagtttccc acagcttgca gtttaagggg 8280
ggtgacagcc gttctcaagg cctcgtaggt attgtttgcc caggaatgtt tcagagctgg 8340
attttgtttt aattttgctt ttatatccac cagccccacc ccaccaagaa atatacagat 8400
ttagtgctgg aggttccttc catccaaccc tgggtttcct tcttcctttt ggtgaagaag 8460
gaaaaagaaa aaaccagaca agtcctcgcc cagccgagtc agcactgcgt tcatttccct 8520
aagccccatt tccttaggat ggcttcctcc cctcactgag ttgcagtggc aaccaagtca 8580
gctctgctca ggagccgccc tgtacagcaa actgggctgt gctgaatcct gtccaagacc 8640
aggggagggc agggaagatt agaagccagg agctcctagg ccaccccgga ttcctgggct 8700
gggctgggct agggggccaa ggaagaaact gtccctccca aacaggatga tctgtggttt 8760
aataccaaat cacaggcatt tttaaaacac aaggagtctt cgaagcaatg tcaaggaaac 8820
gttggccttg gagtcaaatc ctgagcttcc tgcttgctgg ttttgggcgg tgactctcgc 8880
tgtctggatt ttactttctt cttctgtgaa ttaagaatga ggccccttgt gtgtccacag 8940
caggaaacaa ttttacatca tgtctcggtg cacacacaaa tacatactgg tccccagtcc 9000
attatctgta attccataat ttccagatcc ctgcaaacca cacattttgg gggcagctga 9060
cttcaggagt aatcctgctc tgtactgact cgagttcttt gtaggcctac cattatttac 9120
cccatttaat gtgaatattt gcttgtttca ctgttgaaac atgtgtgggt ttgattacgg 9180
ggagcagtct agcctctgct gggaatggtc aggaatatac catatgcacc ccgtgtcctt 9240
tctaaaatag tgaaaattcg gaatgcctaa acacatctgg attccaggaa tttacattaa 9300
gggatatata tttgaaataa ctcacaaaaa acaatactca tccctgctgt gattgctata 9360
ttctgatatt ttcaaatcga ttttcttttc aaaatgctgc tcttgaacca ataaactaat 9420
ttcataaccc aatgatgtgt tgaaactcac attttgaaga cacaggtata aagtgtttga 9480
cacccaacag gcacgtggca gatagaagtg atcactggga tgtttcctct tccttggcct 9540
ggaaggctca ctttgtgttg gttctgagct gaaaaggatt cattcctccc caaagcactg 9600
tggcactccc ctggtgtttc aatattctca ggctgccatg gtaaaatatc acaggctggg 9660
tgacttcaac atctggtttt tcttttctca cacttccaga ggcaagaagt ccaaggcgaa 9720
ggtgccggca gggttggagt ctggggagga ctctcttgct ggcttgtgga ggctgccttt 9780
gtgctgtgtg atcacgtggc ttgcttgtgt ctctttcact tcctacaata ggacactagc 9840
cctctaacag gattagagtc ctacccttgc gatctcattc agtctttttt tttttttttt 9900
ttttgagacg gagtctcgct ctgtcaccca ggctggagtg cagtggccgg atctcagctc 9960
actgcaagct ccgcctcctg ggttcacgcc attctcctgc ctcagcctcc cgagtagctg 10020
ggactacagg cgcctgtcac ctcgcccggc taagtttttg tatttttagt agagacgggg 10080
tttcactgtg ttagccagga tggtctcgat ctcctgacct cgtgatccgc ccgtctcggc 10140
ctcccaaagt gctgggatta caggcttgag ccaccgcgcc cagccctcat tcagtcttaa 10200
ttgcttcctt aaaggcctga tctccaaata tagtcacctg actttagggc ttcagcatat 10260
gaattttggg ggcatacaat tcccttgata gcactgatga ctccatcaaa cgtatcccac 10320
accacagctg tcctggaaaa ttaacacgta accatctttt acgcaatggc tgttatctcc 10380
tctacacttt cctccaacct gatccttttt tctttccaac tagagagcaa catttctctt 10440
gaggattacc ttaattattt ccagaaaaac gtgagcccac aggagctgct actcctgctg 10500
agtgaccata aagcctggga gagagtggtg gctactgctg aactgcccag gtaacctcca 10560
tggggttatc tccattggga accctggtga tgccacccag atctcccttg ggctagtttt 10620
ccctgacaga cacacctcct ccaggcaggc ccctctgctg ggcttgagga tgaccttctc 10680
ggcagtccag gaggaacatt tcctcccaat ccttcgctgg cagtgagtag cctcaggctg 10740
aggggacagg aagcccacag ggacagggtc atttctgcca tctgctggtg atgggaaatt 10800
tgcgagttac tttcccactt tcagcctttc ttcatccatg gagttttatt gtgagaaaaa 10860
tgagatcatg catgtaaagt actcagcata atgactgaca catagtaggt gcacagttaa 10920
cgttaacatc ttacaaggtt ggtggaaata gaccagggtc aagggtcttc ctcttgaagt 10980

-continued

```
ccagcagcac ttcctttggg acaagtccga aaaatcctga cttaattgat gtgtgttcct  11040
ggggatgctg gctggggcct tttttctcat ctgaggaatt ccataaacac ggcaggaccc  11100
ttctgctggt ccaggatgct gagaggctgg agtggacttg gacagcgatg ggtctctttc  11160
cggctctgtc tgtgcccagt ccctgggctc taggcttatg tcatggagac tgggaactgt  11220
catctgtcca atagaaatag caagtcaatg tcataggagt atggtgaagg ccttagagtg  11280
aactccaggt caaaggtggg gaaccaagac caagatcctg gccaaaggcc aagagagacc  11340
aagaccagtg tcaaagcctg ggtcaggat ggagcaagag tcagccttgg ttgtaggaca  11400
agtaggaagg ttgaggcacc agggctggga ctagggtgtg gcaagagagg caccaagggc  11460
ttgaaactta aggaggtcat gaacttgcag aggacatgtg agtgggagag gaatatttct  11520
tctctgtctg ggagaggaat atttcttctc tgtctggatg atcccaacac tcatggacat  11580
agagggtcat ggttgcctgt gtctctcaca ccctgcctgg gaactggcaa gttctgggct  11640
accctttggg accttcttct cttctacaca aagaagcccc tgacaatggc aagcagtatg  11700
ccttagtgac catctccata gtagaatgag ttgctgtcaa tgtatataat ttcaggggta  11760
ctgagcagac tcacaagtcc ccaaccaaga aggaaaacac ttcctctacc atcttgtcca  11820
aattcaggtc ttttcagcgt tagcaattta tatagatggt tctgaaagtg tcccgagtct  11880
tctagaggtt ccataaaatt gcacacggcc ttggcgtaca cacaggtgaa gctgtcactg  11940
ctaaggcatc agttaggctg gtgacatctg cgagtgagac ctggaaggtt gggggtgcag  12000
ggggcaggtc aggaggcggt aaggtggctg gagagtccat gtggagccag aatgaatacc  12060
cagatctccc actccggtca actggggcag tgcccggacc cagtagcctt cagccagaaa  12120
gtgaaagggc atgaggcctt ggaagggagc acatgccagg caaagtgagc tcctgtctct  12180
ctgaggtttg gtttcgtttg aattcaaagt actcagaggt agccagacgg caatgtctga  12240
gggcacctta cctttgacgc cacctgaaca ttaatgggga ttcctaaaat catctttaga  12300
ttttataatt cactagaagg attcatataa ctcactaaaa actgctattt cacgatcgtg  12360
gtttatcaca cagaaagaac acagattaaa atcagcctaa ggaagagaca cacagggcag  12420
agtctgggag ggcttcaggt gtgaagcttc attgtcctca ggacgctgtg atctcctgtg  12480
ccaatgtggg acaagacaca tggggtgctg ccaaccaggg aagctcaccc agttaaggaa  12540
acattcctgt gaatcacaag aaatcaggaa ggaagccttt attcaggatg gttgttacag  12600
gggagggaga ccgagtccag ctccaaacac agtaaagaca gagagggagt cacagccaac  12660
accagggtga ggggcggcag atggaacagg actaacagga gacaccagag tgggatgttc  12720
ctgccaaact gtcctaacag gattctcgct aaaggcaggt cagacactca cccatcaacg  12780
gtgggagtga ggagcatgat cagatagcaa agagtgctca gacagcaagc agggaggacc  12840
ctccctaaac cgacttgggg agattcttgc tgagctgggc agtgcaagtc cagcaagcag  12900
tgggtgggtg tggaaggcca aggtcggcgc ctagtggaga agaagctctg aagcgccccg  12960
ctggagctgg tcaagcagaa agtctttctc aacccatgtc ttagtgtcca gaatatttgc  13020
tggggttgga tcacaagctg ccctcatgac tgacctgtag tctccagccc ctccctgagg  13080
tctcacacct ttagtcccca ggtcctctgg aagtcaggaa agacaccaaa tagccccaaa  13140
ccccatcatc catcacattg ctgtactgtc ccgtggccaa atcaccagac aaagaaagat  13200
gttcctacca ggcaggacac tccaggagcc tggagatcac ttcccaggag ctgaggacaa  13260
agggaaggcc tctctttggg aaaagttcat gcttcacttt gctaccatcc tgggaataag  13320
gtgtctttgt cccactctca cggctctttg ttcatctgca gagttttccc ctctccaaac  13380
```

-continued

```
actttggcaa tcacagtgtt ggcctgccct tgagtgagga ggcatcttta tcaaacacct  13440

accacgaaag agcatctgag atgcctttaa gatatttatt tccatatgga ataagtactg  13500

aggggtatct atgatgaaca aagcatgttt gagcttaaat tctcttcatt tgtaaaattt  13560

gtttctattt gattgatagt gagagctctg caatttacac aggatagaga tcgcatggag  13620

ccgatttcac agacagggaa actgcatttc ttaatccttt aaactttcct tgtgcaggga  13680

tgaggcagat gagctctata aagctctgaa caagcttata agacacatgg tcatgaaaga  13740

caaaaactgg ctcgaagaag tccagcagca cagaaagcgg tttttggaag agtttcctca  13800

gttggaaagg gagcttcagg ataaaataag aaggctctgc gaccttgcag gtgaggttca  13860

gaaggtccac aaaggcgcca ccatcgccaa tgcgttctcc agcactctcg gcgttgcctc  13920

tggtgtcctg accttcctcg gcatgggtct ggcacccttc acagcgggga gcagccttgt  13980

gctcttggaa cctgtgacgg ggttgggaat cgcagccacc ttgaccggga ttaccagcgg  14040

tagcgtggaa tacgcaaaga agcggtcggc acaagccgaa gcccatgaac tggtcaacaa  14100

aagccttgac accgtggagg agatgaacga gtttctgtat cacaacatac ccaactttat  14160

ttccttacgt gtcaatcttg tcaaattcac agaagacact gggaaggcca tccgtgccat  14220

caggcaagcc agagccaacc ctcactcagt accacatgtc ccagcctcac tccaccgggt  14280

cactgagcca gtctcagcta caagctttga agagatggag agatggagag agttggagag  14340

atggagagag ttgctgaatc ccgcaccacg ggggtgatca gaggagccaa gatcgttgat  14400

aaggtctttg aaggcgccct tttcgtgctg gacgtagtca gcctcgtgtg ccagttaaag  14460

cacttacatg agggggcaaa gtcaaagaca gctgaggagc tgaagaaggt ggctcaggag  14520

ctggagaaga agctaaacat tctcaacaag aagtatgaga ctctgcgcca agaaccgtga  14580

ccacagggca gggcaaccac caggggagat atgcctggga cgggccaaga caaaatgcaa  14640

acttttttt tttt                                                    14654
```

MODULATORS OF APOL1 EXPRESSION

SEQUENCE LISTING

The present application is being filed along with a Sequence Listing in electronic format. The Sequence Listing is provided as a file entitled 200779-US-CNT-SeqListing.txt created May 20, 2019, which is 465 kb in size. The information in the electronic format of the sequence listing is incorporated herein by reference in its entirety.

FIELD

The present embodiments provide methods, compounds, and compositions useful for inhibiting APOL1 (apolipoprotein L, 1) expression, and in certain instances, reducing the amount of APOL1 protein in a cell or animal, which can be useful for treating, preventing, or ameliorating a disease associated with APOL1.

BACKGROUND

End-stage kidney disease (ESKD) affects over half a million individuals in the United States. In the US, the likelihood that individuals of African ancestry will develop ESKD is approximately twice that observed among other ethnic ancestry patients (McClellan W. et al. Am. J. Kidney Dis. 1988. 12: 285-290; Cowie C C. et al. N. Engl. J. Med. 1989. 321: 1074-1079). There are no specific therapies for the vast majority of kidney diseases. Anti-hypertensive and anti-inflamatory treatments have been found to slow progression and reduce symptoms in some patients for some types of chronic kidney disease (CKD), but they neither result in disease resolution nor completely halt disease progression.

Recent data has suggested the association of two common variants (G1 and G2) in the last exon of APOL1 among African ancestry patients and increased risk for developing CKD (Kao W H et al. Nat. Genet. 2008. 40: 1185-1192; Lipkowitz M S et al. Kidney Int. 2013. 83: 114-120; Genovese G. et al. Science. 2010. 329: 841-845; Tzur et al. *Hum Genet.* 2010; Kopp et al. *J Am Soc Nephrol.* 2011). In a 2013 study, G1 and G2 risk variants in APOL1 were associated with higher rates of ESKD and progression of CKD that were observed in African ancestry patients as compared to other ethnic ancestry groups, regardless of diabetes status (Parsa A et al. N. Engl. J. Med. 2013. 369: 2183-2196). Approximately 50% of African ancestry subjects carry one risk allelle in APOL1 whilst approximately 13% of African ancestry subjects (~five million individuals) carry two risk alleles in APOL1, a substantial fraction of which will develop APOL1-associated CKD. Studies in African ancestry subjects with two APOL1 risk alleles have demonstrated increased odds ratios for developing many forms of renal disease including but not limited to focal segmental glomerularsclerosis (FSGS) (OR=10.5), hypertension attributed ESKD (OR=7.3), HIV associated nephropathy (HIVAN) (OR=29), sickle cell nephropathy (OR=3.4) and membranous lupus nephropathy (OR=5.4) (Genovese et al. *Science,* 2010; Tzur et al. *Hum Genet.* 2010; Kopp et al. *J Am Soc Nephrol.* 2011).

SUMMARY

Certain embodiments provided herein are compounds and methods for reducing the amount or activity of APOL1 mRNA, and in certain embodiments, reducing the amount of APOL1 protein in a cell or animal. In certain embodiments, the animal has a APOL1-associated nephropathy, including for example HIV associated nephropathy, focal segmental gomerulosclerosis (FSGS), collapsing nephropathy, sickle cell nephropathy, arterionephro-sclerosis, lupus nephritis, hypertension associated nephropathy, and other forms of APOL1 associated proteinuric disease. In certain embodiments, the disease is focal segmental glomerulosclerosis (FSGS). In certain embodiments, the disease is CKD. In certain embodiments, the disease is aterionephro-sclerosis. In certain embodiments, the disease is lupus nephritis. In certain embodiments the disease is hypertension-attributed CKD. In certain embodiments, the disease is end stage renal disease (ESRD). In certain embodiments, the disease is HIV-associated nephropathy. In certain embodiments, the disease is sickle cell nephropathy. In certain embodiments, the disease is membranous lupus nephropathy.

Certain embodiments provided herein are directed to potent and tolerable compounds and compositions useful for inhibiting APOL1 expression, which can be useful for treating, preventing, ameliorating, or slowing progression of APOL1-associated nephropathy. Certain embodiments provided herein are directed to compounds and compositions that are more potent or have greater therapeutic value than compounds publicly disclosed.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ION/ISIS number indicate a combination of nucleobase sequence, chemical modification, and motif.

Definitions

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE) refers to a 2'-O $(CH_2)_2$ —$OCH_3$) in the place of the 2'-OH group of a ribosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of APOL1", it is implied that APOL1 levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"APOL1" means any nucleic acid or protein of APOL1. "APOL1 nucleic acid" means any nucleic acid encoding APOL1. For example, in certain embodiments, a APOL1 nucleic acid includes a DNA sequence encoding APOL1, an RNA sequence transcribed from DNA encoding APOL1 (including genomic DNA comprising introns and exons), and an mRNA sequence encoding APOL1. "APOL1 mRNA" means an mRNA encoding a APOL1 protein. The target may be referred to in either upper or lower case.

"APOL1 specific inhibitor" refers to any agent capable of specifically inhibiting APOL1 RNA and/or APOL1 protein expression or activity at the molecular level. For example, APOL1 specific inhibitors include nucleic acids (including antisense compounds), peptides, antibodies, small molecules, and other agents capable of inhibiting the expression of APOL1 RNA and/or APOL1 protein.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"cEt" or "constrained ethyl" means a ribosyl bicyclic sugar moiety wherein the second ring of the bicyclic sugar is formed via a bridge connecting the 4'-carbon and the 2'-carbon, wherein the bridge has the formula: 4'-CH$(CH_3)$—O-2', and wherein the methyl group of the bridge is in the S configuration.

"cEt nucleoside" means a nucleoside comprising a cEt modified sugar moiety.

"Chemical modification" in a compound describes the substitutions or changes through chemical reaction, of any of the units in the compound relative to the original state of such unit. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^{m}$C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Designing" or "Designed to" refer to the process of designing a compound that specifically hybridizes with a selected nucleic acid molecule.

"Diluent" means an ingredient in a composition that lacks pharmacological activity, but is pharmaceutically necessary or desirable. For example, the diluent in an injected composition can be a liquid, e.g. saline solution.

"Differently modified" means chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded antisense compound" means an antisense compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to, the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Lengthened oligonucleotides" are those that have one or more additional nucleosides relative to an oligonucleotide disclosed herein, e.g. a parent oligonucleotide.

"Linked nucleosides" means adjacent nucleosides linked together by an internucleoside linkage.

"Linker-nucleoside" means a nucleoside that links an oligonucleotide to a conjugate moiety. Linker-nucleosides are located within the conjugate linker of a compound. Linker-nucleosides are not considered part of the oligonucleotide portion of a compound even if they are contiguous with the oligonucleotide.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating APOL1 RNA can mean to increase or decrease the level of APOL1 RNA and/or APOL1 protein in a cell, tissue, organ or organism. A "modulator" effects the change in the cell, tissue, organ or organism. For example, a APOL1 compound can be a modulator that decreases the amount of APOL1 RNA and/or APOL1 protein in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an individual. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites" are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" with reference to a target nucleic acid means to reduce or block expression of the target nucleic acid while exhibiting fewer, minimal, or no effects on non-target nucleic acids. Reduction does not necessarily indicate a total elimination of the target nucleic acid's expression.

"Standard cell assay" means assay(s) described in the Examples and reasonable variations thereof "Standard in vivo experiment" means the procedure(s) described in the Example(s) and reasonable variations thereof.

"Stereorandom chiral center" in the context of a population of molecules of identical molecular formula means a chiral center having a random stereochemical configuration. For example, in a population of molecules comprising a stereorandom chiral center, the number of molecules having the (5) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

"Sugar moiety" means an unmodified sugar moiety or a modified sugar moiety. "Unmodified sugar moiety" or "unmodified sugar" means a 2'-OH(H) ribosyl moiety, as found in RNA (an "unmodified RNA sugar moiety"), or a 2'-H(H) moiety, as found in DNA (an "unmodified DNA sugar moiety"). "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen or hydroxyl of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary compounds or nucleic acids.

"Synergy" or "synergize" refers to an effect of a combination that is greater than additive of the effects of each component alone at the same doses.

"Target gene" refers to a gene encoding a target.

"Targeting" means the specific hybridization of a compound to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an animal in order to effect an alteration or improvement of a disease, disorder, or condition in the animal.

Certain Embodiments

Certain embodiments provide methods, compounds and compositions for inhibiting APOL1 (APOL1) expression.

Certain embodiments provide compounds targeted to a APOL1 nucleic acid. In certain embodiments, the APOL1 nucleic acid has the sequence set forth in RefSeq or GENBANK Accession No. NM_003661.3 (incorporated by reference, disclosed herein as SEQ ID NO: 1), NT_011520.9 truncated from nucleotides 15986452 to Ser. No. 16/001,905 (SEQ ID NO: 2), NM_001136541.1 (SEQ ID NO: 3), NM_001136540.1 (SEQ ID NO: 4), NM_145343.2 (SEQ ID NO: 5), DC339680.1 (SEQ ID NO: 6), AK309143.1 (SEQ ID NO: 7), NT_011520.13 truncated from nucleotides 17543446 to Ser. No. 17/543,655 (SEQ ID NO: 8), or NC_000022.11 truncated from nucleotides 36250001 to 36271000 (SEQ ID NO: 9). In certain embodiments, the compound is an antisense compound or oligomeric compound. In certain embodiments, the compound is single-stranded. In certain embodiments, the compound is double-stranded.

Certain embodiments provide a compound comprising a modified oligonucleotide 8 to 80 linked nucleosides in length and having a nucleobase sequence comprising at least 8 contiguous nucleobases of any of the nucleobase sequences of SEQ ID NOs: 13-1941. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 12 to 80 linked nucleosides in length and having a nucleobase sequence comprising at least 12 contiguous nucleobases of any of the nucleobase sequences of SEQ ID NOs: 13-1941. In certain embodiments, the compound is an antisense compound or oligomeric compound. In certain embodiments, the compound is single-stranded. In certain embodiments, the compound is double-stranded. In certain embodiments, the modified oligonucleotide is 12 to 30 linked nucleosides in length.

In certain embodiments, the compound comprises a modified oligonucleotide 16 linked nucleosides in length. In certain embodiments, the compound is an antisense compound or oligomeric compound.

Certain embodiments provide a compound comprising a modified oligonucleotide 16 to 30 linked nucleosides in length and having a nucleobase sequence comprising the nucleobase sequence of any one of SEQ ID NOs: 13-1941. In certain embodiments, the compound is an antisense compound or oligomeric compound. In certain embodiments, the compound is single-stranded. In certain embodiments, the compound is double-stranded.

Certain embodiments provide a compound comprising a modified oligonucleotide consisting of the nucleobase sequence of any one of SEQ ID NOs: 13-1941. In certain embodiments, the compound is an antisense compound or oligomeric compound. In certain embodiments, the compound is single-stranded. In certain embodiments, the compound is double-stranded.

In certain embodiments, compounds target nucleotides 5849-5907, 5853-5869, 5855-5873, 8145-8180, 8168-8216, 8306-8321, 8320-8338, 8723-8847, 8743-8760, 8829-8847, 8755-8840, 14342-14390, and 14342-14370 of a APOL1 nucleic acid. In certain embodiments, compounds target within nucleotides 5849-5907, 5853-5869, 5855-5873, 8145-8180, 8168-8216, 8306-8321, 8320-8338, 8723-8847, 8743-8760, 8829-8847, 8755-8840, 14342-14390, and 14342-14370 of a APOL1 nucleic acid having the nucleobase sequence of SEQ ID NO: 2. In certain embodiments, compounds have at least an 8, 9, 10, 11, 12, 13, 14, 15, or 16 contiguous nucleobase portion complementary to an equal length portion within nucleotides 5849-5907, 5853-5869, 5855-5873, 8145-8180, 8168-8216, 8306-8321, 8320-8338, 8723-8847, 8743-8760, 8829-8847, 8755-8840, 14342-14390, and 14342-14370 of a APOL1 nucleic acid having the nucleobase sequence of SEQ ID NO: 2. In certain embodiments, these compounds are antisense compounds, oligomeric compounds, or oligonucleotides.

In certain embodiments, compounds target a region of a APOL1 nucleic acid having the nucleobase sequence of SEQ ID NO: 2 within nucleobases 5849-5907, 5853-5869, 5855-5873, 8145-8180, 8168-8216, 8306-8321, 8320-8338, 8723-8847, 8743-8760, 8829-8847, 8755-8840, 14342-14390, and 14342-14370. In certain embodiments, compounds target at least an 8, 9, 10, 11, 12, 13, 14, 15, or 16 contiguous nucleobases within the aforementioned nucleobase regions. In certain embodiments, these compounds are antisense compounds, oligomeric compounds, or oligonucleotides. In certain embodiments, the modified oligonucleotide is 10 to 30 linked nucleosides in length.

In certain embodiments, a compound comprises a modified oligonucleotide 12 to 30 linked nucleosides in length and complementary within nucleotides 5854-5869, 5855-5870, 8164-8179, 8306-8321, 8321-8336, 8744-8759, 8829-8844, or 14342-14357 of SEQ ID NO: 2. In certain embodiments, the modified oligonucleotide is 16 to 30 linked nucleosides in length.

In certain embodiments, a compound comprises a modified oligonucleotide 12 to 30 linked nucleosides in length and having a nucleobase sequence comprising at least an 8, 9, 10, 11, 12, 13, 14, 15, or 16 contiguous nucleobase portion any one of SEQ ID NOs: 1164, 13, 76, 81, 1095, 1326, 1730, and 1925. In certain embodiments, the modified oligonucleotide is 16 to 30 linked nucleosides in length.

In certain embodiments, a compound comprises a modified oligonucleotide 12 to 30 linked nucleosides in length and having a nucleobase sequence comprising any one of SEQ ID NOs: 1164, 13, 76, 81, 1095, 1326, 1730, and 1925. In certain embodiments, the modified oligonucleotide is 16 to 30 linked nucleosides in length.

In certain embodiments, a compound comprises a modified oligonucleotide having a nucleobase sequence consisting of any one of SEQ ID NOs: 1164, 13, 76, 81, 1095, 1326, 1730, and 1925.

In certain embodiments, any of the foregoing modified oligonucleotides comprises at least one modified internucleoside linkage, at least one modified sugar, and/or at least one modified nucleobase.

In certain embodiments, any of the foregoing modified oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH3)-O-2' group, a 4'-CH2-O-2' group, or a 4'-(CH2)2-O-2' group.

In certain embodiments, the modified oligonucleotide comprises at least one modified internucleoside linkage, such as a phosphorothioate internucleoside linkage.

In certain embodiments, any of the foregoing modified oligonucleotides comprises at least one modified nucleobase, such as 5-methylcytosine.

In certain embodiments, any of the foregoing modified oligonucleotides comprises:

a gap segment consisting of linked deoxynucleosides;

a 5' wing segment consisting of linked nucleosides; and a 3' wing segment consisting of linked nucleosides;

wherein the gap segment is positioned between the 5' wing segment and the 3' wing segment and wherein each nucleoside of each wing segment comprises a modified sugar. In certain embodiments, the modified oligonucleotide is 16 to 80 linked nucleosides in length having a nucleobase sequence comprising the sequence recited in any one of SEQ ID NOs: 1164, 13, 76, 81, 1095, 1326, 1730, and 1925. In certain embodiments, the modified oligonucleotide is 16 to 30 linked nucleosides in length having a nucleobase sequence comprising the sequence recited in any one of SEQ ID NOs: 1164, 13, 76, 81, 1095, 1326, 1730, and 1925. In certain embodiments, the modified oligonucleotide is 16 linked nucleosides in length having a nucleobase sequence consisting of the sequence recited in any one of SEQ ID NOs: 1164, 13, 76, 81, 1095, 1326, 1730, and 1925.

In certain embodiments, a compound comprises or consists of a modified oligonucleotide 16-30 linked nucleobases in length having a nucleobase sequence comprising the sequence recited in any one of SEQ ID NOs: 13, 1095, 1730, 76, 1326, and 81, wherein the modified oligonucleotide comprises a gap segment consisting of ten linked deoxynucleosides;

a 5' wing segment consisting of three linked nucleosides; and a 3' wing segment consisting of three linked nucleosides;

wherein the gap segment is positioned between the 5' wing segment and the 3' wing segment, wherein the 5' and 3' wing segments comprise a cEt nucleoside; wherein each internucleoside linkage is a phosphorothioate linkage; and wherein each cytosine is a 5-methylcytosine. In certain embodiments, the modified oligonucleotide is 16-80 linked nucleosides in length. In certain embodiments, the modified oligonucleotide is 16-30 linked nucleosides in length.

In certain embodiments, a compound comprises or consists of a modified oligonucleotide 16-30 linked nucleobases in length having a nucleobase sequence comprising or consisting of the sequence recited in any one of SEQ ID NOs: 1164 and 1925, wherein the modified oligonucleotide comprises:

a gap segment consisting of nine linked deoxynucleosides;

a 5' wing segment consisting of three linked nucleoside; and a 3' wing segment consisting of four linked nucleosides;

wherein the gap segment is positioned between the 5' wing segment and the 3' wing segment;

wherein the 5' wing segment comprises cEt nucleosides; wherein the 3' wing segment comprises a cEt nucleoside, a a cEt nucleoside, a cEt nucleoside, and 2'-O-methoxyethyl nucleoside in the 5' to 3' direction;

wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In certain embodiments, a compound comprises or consists of a modified oligonucleotide 16-30 linked nucleobases in length having a nucleobase sequence comprising or consisting of the sequence recited in SEQ ID NO: 1164, wherein the modified oligonucleotide comprises:

a gap segment consisting of nine linked deoxynucleosides;

a 5' wing segment consisting of three linked nucleoside; and a 3' wing segment consisting of four linked nucleosides;

wherein the gap segment is positioned between the 5' wing segment and the 3' wing segment;

wherein the 5' wing segment comprises cEt nucleosides; wherein the 3' wing segment comprises a cEt nucleoside, a a cEt nucleoside, a cEt nucleoside, and 2'-O-methoxyethyl nucleoside in the 5' to 3' direction;

wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In certain embodiments, a compound comprises or consists of the following formula Tks Tks Tks Tds Gds Tds Ads Ads Gds Tds Gds mCds Aks Aks mCks mCe, wherein, A=an adenine, mC=a 5-methylcytosine G=a guanine, T=a thymine, e=a 2'-O-methoxyethyl modified nucleoside, k=a cEt modified nucleoside, d=a 2'-deoxynucleoside, and s=a phosphorothioate internucleoside linkage.

In certain embodiments, a compound comprises or consists of ION 972190 or salt thereof, having the following chemical structure:

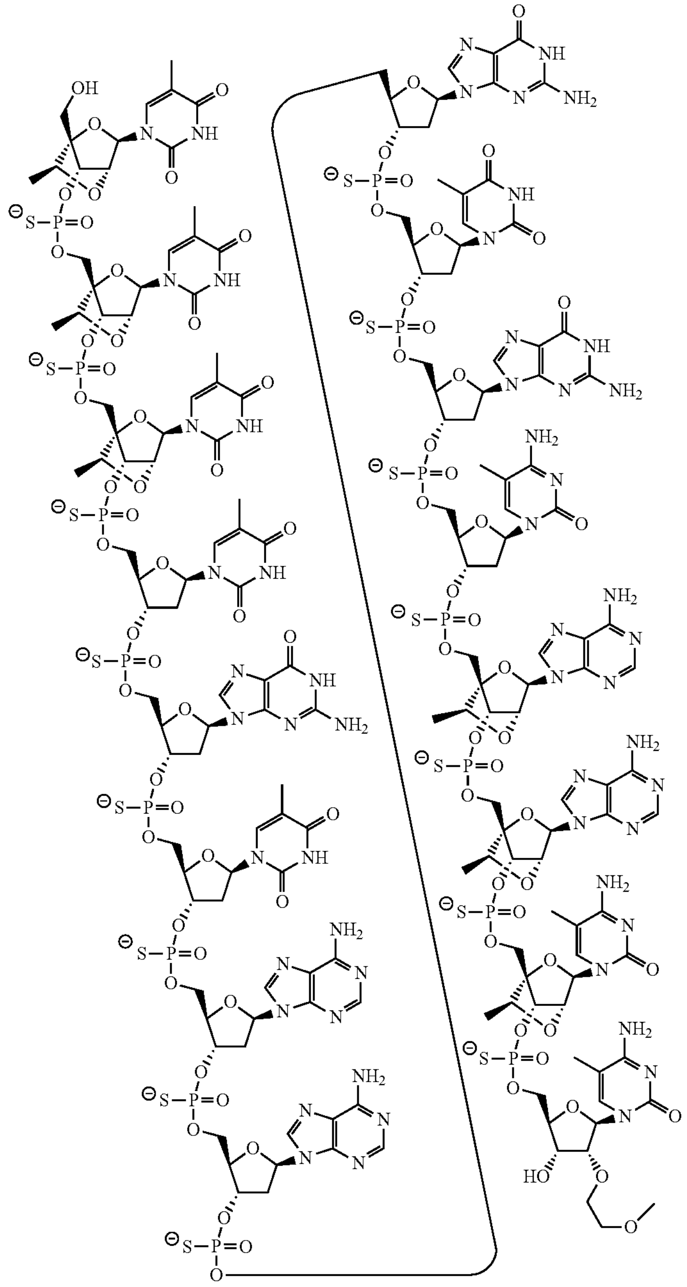

In certain embodiments, a compound comprises or consists of the sodium salt of ION 972190, having the following chemical structure:

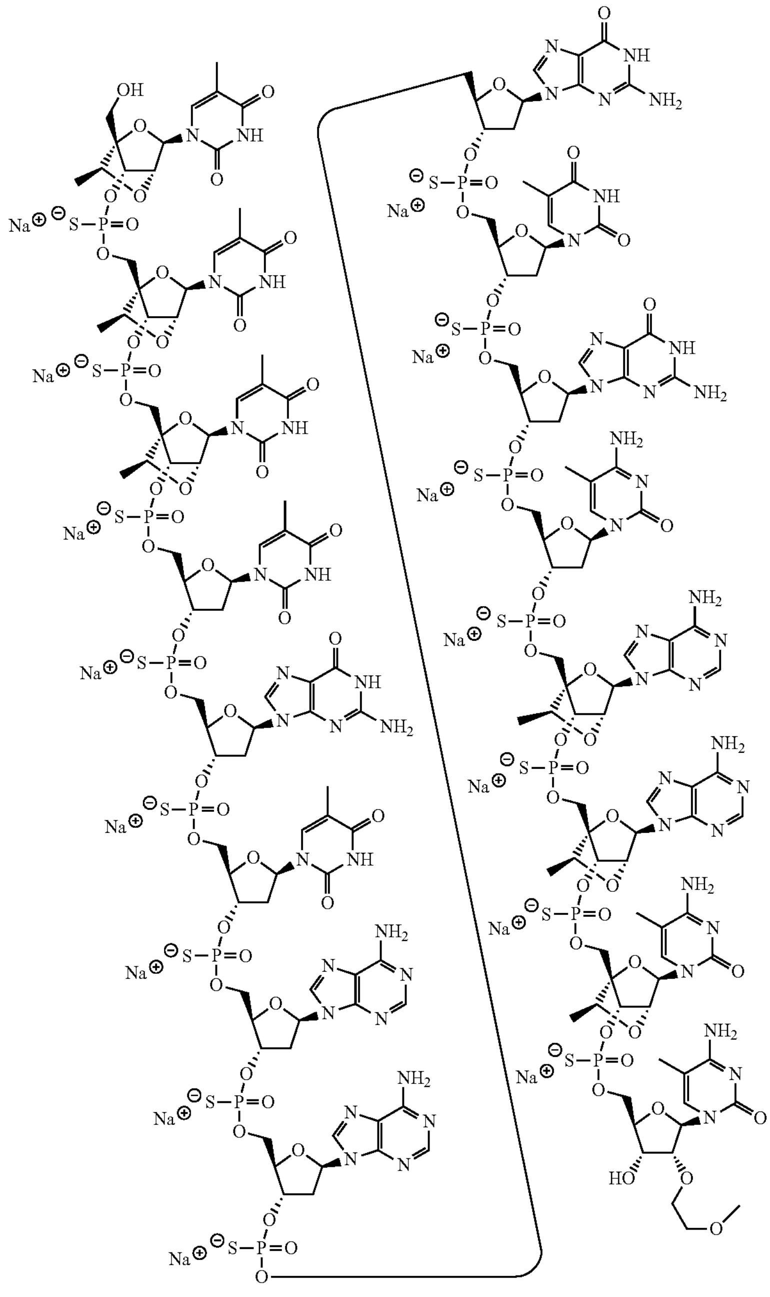

In any of the foregoing embodiments, the compound or oligonucleotide can be at least 85%, at least 90%, at least 95%, at least 98%, at least 99%, or 100% complementary to a nucleic acid encoding APOL1.

In any of the foregoing embodiments, the compound can be single-stranded. In certain embodiments, the compound comprises deoxyribonucleotides. In certain embodiments, the compound is double-stranded. In certain embodiments, the compound is double-stranded and comprises ribonucleotides. In any of the foregoing embodiments, the compound can be an antisense compound or oligomeric compound.

In any of the foregoing embodiments, the compound can be 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides in length. In certain embodiments, the compound comprises or consists of an oligonucleotide.

In certain embodiments, compounds or compositions provided herein comprise a pharmaceutically acceptable salt of the modified oligonucleotide. In certain embodiments, the salt is a sodium salt. In certain embodiments, the salt is a potassium salt.

In certain embodiments, the compounds or compositions as described herein are highly tolerable as demonstrated by having at least one of an increase an alanine transaminase (ALT) or aspartate transaminase (AST) value of no more than 4 fold, 3 fold, or 2 fold over saline treated animals or an increase in liver, spleen, or kidney weight of no more than 30%, 20%, 15%, 12%, 10%, 5%, or 2% compared to control treated animals. In certain embodiments, the compounds or compositions as described herein are highly tolerable as demonstrated by having no increase of ALT or AST over control treated animals. In certain embodiments, the compounds or compositions as described herein are highly tolerable as demonstrated by having no increase in liver, spleen, or kidney weight over control animals.

Certain embodiments provide a composition comprising the compound of any of the aforementioned embodiments or any pharmaceutically acceptable salt thereof and at least one of a pharmaceutically acceptable carrier or diluent. In certain embodiments, the composition has a viscosity less than about 40 centipoise (cP), less than about 30 centipose (cP), less than about 20 centipose (cP), less than about 15 centipose (cP), or less than about 10 centipose (cP). In certain embodiments, the composition having any of the aforementioned viscosities comprises a compound provided herein at a concentration of about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In certain embodiments, the composition having any of the aforementioned viscosities and/or compound concentrations has a temperature of room temperature or about 20° C., about 21° C., about 22° C., about 23° C., about 24° C., about 25° C., about 26° C., about 27° C., about 28° C., about 29° C., or about 30° C.

Certain Indications

Certain embodiments provided herein relate to methods of inhibiting APOL1 expression, which can be useful for treating, preventing, or ameliorating a disease associated with APOL1 in an individual, by administration of a compound that targets APOL1. In certain embodiments, the compound can be a APOL1 specific inhibitor. In certain embodiments, the compound can be an antisense compound, oligomeric compound, or oligonucleotide targeted to APOL1.

Examples of diseases associated with APOL1 treatable, preventable, and/or ameliorable with the methods provided herein include APOL-1-associated nephropathy, focal segmental glomerulosclerosis (FSGS), collapsing nephropathy, CKD, hypertension attributed nephropathy, HIV-associated nephropathy, sickle cell nephropathy, ESKD, glomerular damage, ESRD, arterionephro-sclerosis, lupus nephritis, and other forms of APOL1 associated proteinuric disease.

In certain embodiments, a method of treating, preventing, or ameliorating a disease associated with APOL1 in an individual comprises administering to the individual a compound comprising a APOL1 specific inhibitor, thereby treating, preventing, or ameliorating the disease. In certain embodiments, the individual is identified as having or at risk of having a disease associated with APOL1. In certain embodiments, the disease is a APOL1-associated nephropathy. In certain embodiments, the APOL1-associated nephropathy is one of focal segmental glomerulosclerosis (FSGS), collapsing nephropathy, CKD, hypertension attributed nephropathy, HIV-associated nephropathy, sickle cell nephropathy, arterionephro-sclerosis, lupus nephritis, and other forms of APOL1-associated proteinuric disease. In certain embodiments, the compound comprises an antisense compound targeted to APOL1. In certain embodiments, the compound comprises an oligonucleotide targeted to APOL1. In certain embodiments, a compound comprises a modified oligonucleotide 16 to 30 linked nucleosides in length and having a nucleobase sequence comprising at least 8 contiguous nucleobases of any of the nucleobase sequences of SEQ ID NOs: 13-1941. In certain embodiments, a compound comprises a modified oligonucleotide 16 to 30 linked nucleosides in length and having a nucleobase sequence comprising the nucleobase sequence of any one of SEQ ID NOs: 13-1941. In certain embodiments, a compound comprises a modified oligonucleotide consisting of the nucleobase sequence of any one of SEQ ID NOs: 13-1941. In certain embodiments, a compound comprises a modified oligonucleotide 16 to 30 linked nucleosides in length having a nucleobase sequence comprising any one of SEQ ID NOs: 1164, 13, 76, 81, 1095, 1326, 1730, and 1925. In certain embodiments, a compound comprises a modified oligonucleotide having a nucleobase sequence consisting of any one of SEQ ID NOs: 1164, 13, 76, 81, 1095, 1326, 1730, and 1925. In certain embodiments, the compound is ION #793406, 904763, 905469, 905505, 905634, 905665, 972190, and 972163. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound improves, preserves, or prevents edema, proteinuria, albuminuria, GFR decline, high lipid levels, high cholesterol levels, nephrotic syndrome, high blood pressure or hypertension, kidney damage, glomerular damage, and kidney failure.

In certain embodiments, a method of treating, preventing, or ameliorating edema, proteinuria, albuminuria, GFR decline, high lipid levels, high cholesterol levels, nephrotic syndrome, high blood pressure or hypertension, kidney damage, glomerular damage, and kidney failure comprises administering to the individual a compound comprising a APOL1 specific inhibitor, thereby treating, preventing, or ameliorating edema, proteinuria, albuminuria, GFR decline, high lipid levels, high cholesterol levels, nephrotic syndrome, high blood pressure or hypertension, kidney damage, glomerular damage, and kidney failure. In certain embodiments, the compound comprises an antisense compound targeted to APOL1. In certain embodiments, the compound comprises an oligonucleotide targeted to APOL1. In certain embodiments, a compound comprises a modified oligonucleotide 16 to 30 linked nucleosides in length and having a nucleobase sequence comprising at least 8 contiguous nucleobases of any of the nucleobase sequences of SEQ ID NOs: 13-1941. In certain embodiments, a compound comprises a modified oligonucleotide 16 to 30 linked nucleosides in length and having a nucleobase sequence comprising the nucleobase sequence of any one of SEQ ID NOs: 13-1941. In certain embodiments, a compound comprises a modified oligonucleotide consisting of the nucleobase sequence of any one of SEQ ID NOs: 13-1941. In certain embodiments, a compound comprises a modified oligonucleotide 16 to 30 linked nucleosides in length having a nucleobase sequence comprising any one of SEQ ID NOs: 1164, 13, 76, 81, 1095, 1326, 1730, and 1925. In certain embodiments, a compound comprises a modified oligonucleotide having a nucleobase sequence consisting of any one of SEQ ID NOs: 1164, 13, 76, 81, 1095, 1326, 1730, and 1925. In certain embodiments, the compound is ION #793406, 904763, 905469, 905505, 905634, 905665, 972190, and 972163. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound improves, preserves, or prevents edema, proteinuria, albuminuria, GFR decline, high lipid levels, high cholesterol levels, nephrotic syndrome, high blood pressure or hypertension, kidney damage, glomerular damage, and kidney failure. In certain embodiments, the individual is identified as having or at risk of having a disease associated with APOL1.

In certain embodiments, a method of inhibiting expression of APOL1 in an individual having, or at risk of having, a disease associated with APOL1 comprises administering to the individual a compound comprising a APOL1 specific inhibitor, thereby inhibiting expression of APOL1 in the individual. In certain embodiments, administering the compound inhibits expression of APOL1 in the kidney. In certain embodiments, the disease is a APOL1-associated nephropathy. In certain embodiments, the APOL1-associated nephropathy is one of focal segmental glomerulosclerosis (FSGS), collapsing nephropathy, CKD, hypertension attributed nephropathy, HIV-associated nephropathy, sickle cell nephropathy, arterionephro-sclerosis, lupus nephritis, ESKD, and other forms of APOL1-associated proteinuric disease. In certain embodiments, the individual has, or is at risk of having edema, proteinuria, albuminuria, GFR decline, high lipid levels, high cholesterol levels, nephrotic syndrome, high blood pressure or hypertension, kidney damage, glomerular damage, or kidney failure, or a combination of these symptoms. In certain embodiments, the compound comprises an antisense compound targeted to APOL1. In certain embodiments, the compound comprises an oligonucleotide targeted to APOL1. In certain embodiments, the compound comprises an oligonucleotide targeted to APOL1. In certain embodiments, a compound comprises a modified oligonucleotide 16 to 30 linked nucleosides in length and having a nucleobase sequence comprising at least 8 contiguous nucleobases of any of the nucleobase sequences of SEQ ID NOs: 13-1941. In certain embodiments, a compound comprises a modified oligonucleotide 16 to 30 linked nucleosides in length and having a nucleobase sequence comprising the nucleobase sequence of any one of SEQ ID NOs: 13-1941. In certain embodiments, a compound comprises a modified oligonucleotide consisting of the nucleobase sequence of any one of SEQ ID NOs: 13-1941. In certain embodiments, a compound comprises a modified oligonucleotide 16 to 30 linked nucleosides in length having a nucleobase sequence comprising any one of SEQ ID NOs: 1164, 13, 76, 81, 1095, 1326, 1730, and 1925. In certain embodiments, a compound comprises a modified oligonucleotide having a nucleobase sequence consisting of any one of SEQ ID NOs: 1164, 13, 76, 81, 1095, 1326, 1730, and 1925. In certain embodiments, the compound is ION #793406, 904763, 905469, 905505, 905634, 905665, 972190, and 972163. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound improves, preserves, or prevents edema, proteinuria, albuminuria, GFR decline, high lipid levels, high cholesterol levels, nephrotic syndrome, high blood pressure or hypertension, kidney damage, glomerular damage, and kidney failure.

In certain embodiments, a method of inhibiting expression of APOL1 in a cell comprises contacting the cell with a compound comprising a APOL1 specific inhibitor, thereby inhibiting expression of APOL1 in the cell. In certain embodiments, the cell is a glomerulus. In certain embodiments, the cell is in the kidney. In certain embodiments, the cell is in the kidney of an individual who has, or is at risk of having an APOL1-associated nephropathy. In certain embodiments, the APOL1-associated nephropathy is one of focal segmental glomerulosclerosis (FSGS), collapsing nephropathy, CKD, hypertension attributed nephropathy, HIV-associated nephropathy, sickle cell nephropathy, arterionephro-sclerosis, lupus nephritis, ESKD, and other forms of APOL1-associated proteinuric disease. In certain embodiments, the compound comprises an antisense compound targeted to APOL1. In certain embodiments, the compound comprises an oligonucleotide targeted to APOL1. In certain embodiments, a compound comprises a modified oligonucleotide 16 to 30 linked nucleosides in length and having a nucleobase sequence comprising at least 8 contiguous nucleobases of any of the nucleobase sequences of SEQ ID NOs: 13-1941. In certain embodiments, a compound comprises a modified oligonucleotide 16 to 30 linked nucleosides in length and having a nucleobase sequence comprising the nucleobase sequence of any one of SEQ ID NOs: 13-1941. In certain embodiments, a compound comprises a modified oligonucleotide consisting of the nucleobase sequence of any one of SEQ ID NOs: 13-1941. In certain embodiments, a compound comprises a modified oligonucleotide 16 to 30 linked nucleosides in length having a nucleobase sequence comprising any one of SEQ ID NOs: 1164, 13, 76, 81, 1095, 1326, 1730, and 1925. In certain embodiments, a compound comprises a modified oligonucleotide having a nucleobase sequence consisting of any one of SEQ ID NOs: 1164, 13, 76, 81, 1095, 1326, 1730, and 1925. In certain embodiments, the compound is ION #793406, 904763, 905469, 905505, 905634, 905665, 972190, and 972163. In any of the foregoing embodiments, the compound can be single-stranded or double-stranded. In any of the foregoing embodiments, the compound can be an antisense compound or oligomeric compound.

In certain embodiments, a method of reducing or inhibiting edema, proteinuria, albuminuria, GFR decline, high lipid levels, high cholesterol levels, nephrotic syndrome, high blood pressure or hypertension, kidney damage, glomerular damage, or kidney failure in the kidney of an individual having, or at risk of having, a disease associated with APOL1 comprises administering to the individual a compound comprising a APOL1 specific inhibitor, thereby reducing or inhibiting edema, proteinuria, GFR decline, high lipid levels, high cholesterol levels, nephrotic syndrome, high blood pressure or hypertension, kidney damage, glomerular damage, or kidney failure in the individual. In certain embodiments, the individual has, or is at risk of having, an APOL1-associated nephropathy. In certain embodiments, the APOL1-associated nephropathy is one of focal segmental glomerulosclerosis (FSGS), collapsing nephropathy, CKD, hypertension attributed nephropathy, HIV-associated nephropathy, sickle cell nephropathy, arterionephro-sclerosis, lupus nephritis, ESKD, and other forms of APOL1-associated proteinuric disease. In certain embodiments, the compound comprises an antisense compound targeted to APOL1. In certain embodiments, the compound comprises an oligonucleotide targeted to APOL1. In certain embodiments, the compound comprises an antisense compound targeted to APOL1. In certain embodiments, the compound comprises an oligonucleotide targeted to APOL1. In certain embodiments, a compound comprises a modified oligonucleotide 16 to 30 linked nucleosides in length and having a nucleobase sequence comprising at least 8 contiguous nucleobases of any of the nucleobase sequences of SEQ ID NOs: 13-1941. In certain embodiments, a compound comprises a modified oligonucleotide 16 to 30 linked nucleosides in length and having a nucleobase sequence comprising the nucleobase sequence of any one of SEQ ID NOs: 13-1941. In certain embodiments, a compound comprises a modified oligonucleotide consisting of the nucleobase sequence of any one of SEQ ID NOs: 13-1941. In certain embodiments, a compound comprises a modified oligonucleotide 16 to 30 linked nucleosides in length having a nucleobase sequence comprising any one of SEQ ID NOs: 1164, 13, 76, 81, 1095, 1326, 1730, and 1925. In certain embodiments, a compound comprises a modified oligonucleotide having a nucleobase sequence consisting of any one of SEQ ID NOs: 1164, 13, 76, 81, 1095, 1326, 1730, and 1925. In certain embodiments, the compound is ION #793406, 904763, 905469, 905505, 905634, 905665, 972190, and 972163. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, the individual is identified as having or at risk of having a disease associated with APOL1.

Certain embodiments are drawn to a compound comprising a APOL1 specific inhibitor for use in treating a disease associated with APOL1. In certain embodiments, the disease is focal segmental glomerulosclerosis (FSGS), collapsing nephropathy, CKD, hypertension attributed nephropathy, HIV-associated nephropathy, sickle cell nephropathy, arterionephro-sclerosis, lupus nephritis, ESKD, or other forms of APOL1-associated proteinuric disease. In certain embodiments, the compound comprises an antisense compound targeted to APOL1. In certain embodiments, the compound comprises an oligonucleotide targeted to APOL1. In certain embodiments, a compound comprises a modified oligonucleotide 16 to 30 linked nucleosides in length and having a nucleobase sequence comprising at least 8 contiguous nucleobases of any of the nucleobase sequences of SEQ ID NOs: 13-1941. In certain embodiments, a compound comprises a modified oligonucleotide 16 to 30 linked nucleosides in length and having a nucleobase sequence comprising the nucleobase sequence of any one of SEQ ID NOs: 13-1941. In certain embodiments, a compound comprises a modified oligonucleotide consisting of the nucleobase sequence of any one of SEQ ID NOs: 13-1941. In certain embodiments, a compound comprises a modified oligonucleotide 16 to 30 linked nucleosides in length having a nucleobase sequence comprising any one of SEQ ID NOs: 1164, 13, 76, 81, 1095, 1326, 1730, and 1925. In certain embodiments, a compound comprises a modified oligonucleotide having a nucleobase sequence consisting of any one of SEQ ID NOs: 1164, 13, 76, 81, 1095, 1326, 1730, and 1925. In certain embodiments, the compound is ION #793406, 904763, 905469, 905505, 905634, 905665, 972190, and 972163. In any of the foregoing embodiments, the compound can be single-stranded or double-stranded. In any of the foregoing embodiments, the compound can be an antisense compound or oligomeric compound. In certain embodiments, the compound is administered to the individual parenterally.

Certain embodiments are drawn to a compound comprising a APOL1 specific inhibitor for use in reducing or inhibiting edema, proteinuria, albuminuria, GFR decline, high lipid levels, high cholesterol levels, nephrotic syndrome, high blood pressure or hypertension, kidney damage, glomerular damage, or kidney failure in an individual having or at risk of having an APOL1-associated nephropathy. In certain embodiments, the APOL1-associated nephropathy is one of focal segmental glomerulosclerosis (FSGS), collapsing nephropathy, CKD, hypertension attributed nephropathy, HIV-associated nephropathy, sickle cell nephropathy, arterionephro-sclerosis, lupus nephritis, ESKD, and other forms of APOL1-associated proteinuric disease. In certain embodiments, the compound comprises an antisense compound targeted to APOL1. In certain embodiments, the compound comprises an oligonucleotide targeted to APOL1. In certain embodiments, a compound comprises a modified oligonucleotide 16 to 30 linked nucleosides in length and having a nucleobase sequence comprising at least 8 contiguous nucleobases of any of the nucleobase sequences of SEQ ID NOs: 13-1941. In certain embodiments, a compound comprises a modified oligonucleotide 16 to 30 linked nucleosides in length and having a nucleobase sequence comprising the nucleobase sequence of any one of SEQ ID NOs: 13-1941. In certain embodiments, a compound comprises a modified oligonucleotide consisting of the nucleobase sequence of any one of SEQ ID NOs: 13-1941. In certain embodiments, a compound comprises a modified oligonucleotide 16 to 30 linked nucleosides in length having a nucleobase sequence comprising any one of SEQ ID NOs: 1164, 13, 76, 81, 1095, 1326, 1730, and 1925. In certain embodiments, a compound comprises a modified oligonucleotide having a nucleobase sequence consisting of any one of SEQ ID NOs: 1164, 13, 76, 81, 1095, 1326, 1730, and 1925. In certain embodiments, the compound is ION #793406, 904763, 905469, 905505, 905634, 905665, 972190, and 972163. In any of the foregoing embodiments, the compound can be single-stranded or double-stranded. In any of the foregoing embodiments, the compound can be an antisense compound or oligomeric compound.

Certain embodiments are drawn to use of a compound comprising a APOL1 specific inhibitor for the manufacture or preparation of a medicament for treating a disease associated with APOL1. Certain embodiments are drawn to use of a compound comprising a APOL1 specific inhibitor for the preparation of a medicament for treating a disease associated with APOL1. In certain embodiments, the disease is a APOL1-associated nephropathy. In certain embodiments, the disease is one of focal segmental glomerulosclerosis (FSGS), collapsing nephropathy, CKD, hypertension attributed nephropathy, HIV-associated nephropathy, sickle cell nephropathy, arterionephro-sclerosis, lupus nephritis, ESKD, and other forms of APOL1-associated proteinuric disease. In certain embodiments, the compound comprises an antisense compound targeted to APOL1. In certain embodiments, the compound comprises an oligonucleotide targeted to APOL1. In certain embodiments, the compound comprises an antisense compound targeted to APOL1. In certain embodiments, the compound comprises an oligonucleotide targeted to APOL1. In certain embodiments, a compound comprises a modified oligonucleotide 16 to 30 linked nucleosides in length and having a nucleobase sequence comprising at least 8 contiguous nucleobases of any of the nucleobase sequences of SEQ ID NOs: 13-1941. In certain embodiments, a compound comprises a modified oligonucleotide 16 to 30 linked nucleosides in length and having a nucleobase sequence comprising the nucleobase sequence of any one of SEQ ID NOs: 13-1941. In certain embodiments, a compound comprises a modified oligonucleotide consisting of the nucleobase sequence of any one of SEQ ID NOs: 13-1941. In certain embodiments, a compound comprises a modified oligonucleotide 16 to 30 linked nucleosides in length having a nucleobase sequence comprising any one of SEQ ID NOs: 1164, 13, 76, 81, 1095, 1326, 1730, and 1925. In certain embodiments, a compound comprises a modified oligonucleotide having a nucleobase sequence consisting of any one of SEQ ID NOs: 1164, 13, 76, 81, 1095, 1326, 1730, and 1925. In certain embodiments, the compound is ION #793406, 904763, 905469, 905505, 905634, 905665, 972190, and 972163. In any of the foregoing embodiments, the compound can be single-stranded or double-stranded. In any of the foregoing embodiments, the compound can be an antisense compound or oligomeric compound.

Certain embodiments are drawn to use of a compound comprising a APOL1 specific inhibitor for the manufacture or preparation of a medicament for reducing or inhibiting edema, proteinuria, albuminuria, GFR decline, high lipid levels, high cholesterol levels, nephrotic syndrome, high blood pressure or hypertension, kidney damage, glomerular damage, or kidney failure in an individual having or at risk of having a APOL1-associated nephropathy associated with APOL1. In certain embodiments, the APOL1-associated nephropathy is one of focal segmental glomerulosclerosis (FSGS), collapsing nephropathy, CKD, hypertension attributed nephropathy, HIV-associated nephropathy, sickle cell nephropathy, arterionephro-sclerosis, lupus nephritis, ESKD, and other forms of APOL1-associated proteinuric disease. Certain embodiments are drawn to use of a compound comprising a APOL1 specific inhibitor for the preparation of a medicament for treating a disease associated with APOL1. In certain embodiments, the disease is one of focal segmental glomerulosclerosis (FSGS), collapsing nephropathy, CKD, hypertension attributed nephropathy, HIV-associated nephropathy, sickle cell nephropathy, arterionephrosclerosis, lupus nephritis, ESKD, and other forms of APOL1-associated proteinuric disease. In certain embodiments, the compound comprises an antisense compound targeted to APOL1. In certain embodiments, the compound comprises an oligonucleotide targeted to APOL1. In certain embodiments, a compound comprises a modified oligonucleotide 16 to 30 linked nucleosides in length and having a nucleobase sequence comprising at least 8 contiguous nucleobases of any of the nucleobase sequences of SEQ ID NOs: 13-1941. In certain embodiments, a compound comprises a modified oligonucleotide 16 to 30 linked nucleosides in length and having a nucleobase sequence comprising the nucleobase sequence of any one of SEQ ID NOs: 13-1941. In certain embodiments, a compound comprises a modified oligonucleotide consisting of the nucleobase sequence of any one of SEQ ID NOs: 13-1941. In certain embodiments, a compound comprises a modified oligonucleotide 16 to 30 linked nucleosides in length having a nucleobase sequence comprising any one of SEQ ID NOs: 1164, 13, 76, 81, 1095, 1326, 1730, and 1925. In certain embodiments, a compound comprises a modified oligonucleotide having a nucleobase sequence consisting of any one of SEQ ID NOs: 1164, 13, 76, 81, 1095, 1326, 1730, and 1925. In certain embodiments, the compound is ION #793406, 904763, 905469, 905505, 905634, 905665, 972190, and 972163. In any of the foregoing embodiments, the compound can be single-stranded or double-stranded. In any of the foregoing embodiments, the compound can be an antisense compound or oligomeric compound.

In any of the foregoing methods or uses, the compound can be targeted to APOL1. In certain embodiments, the compound comprises or consists of a modified oligonucleotide, for example a modified oligonucleotide 8 to 80 linked nucleosides in length, 10 to 30 linked nucleosides in length, 12 to 30 linked nucleosides in length, or 16 linked nucleosides in length. In certain embodiments, the modified oligonucleotide is at least 80%, 85%, 90%, 95% or 100% complementary to any of the nucleobase sequences recited in SEQ ID NOs: 1-9. In certain embodiments, the modified oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing embodiments, the modified oligonucleotide is 12 to 30, 15 to 30, 15 to 25, 15 to 24, 16 to 24, 17 to 24, 18 to 24, 19 to 24, 20 to 24, 19 to 22, 20 to 22, 16 to 20, or 17 or 20 linked nucleosides in length. In certain embodiments, the modified oligonucleotide is at least 80%, 85%, 90%, 95% or 100% complementary to any of the nucleobase sequences recited in SEQ ID NOs: 1-9. In certain embodiments, the modified oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing methods or uses, the compound comprises or consists of a modified oligonucleotide 16 to 30 linked nucleosides in length and having a nucleobase sequence comprising any one of SEQ ID NOs: 13-1941, wherein the modified oligonucleotide comprises:

a gap segment consisting of linked 2'-deoxynucleosides;

a 5' wing segment consisting of linked nucleosides; and a 3' wing segment consisting of linked nucleosides;

wherein the gap segment is positioned between the 5' wing segment and the 3' wing segment and wherein each nucleoside of each wing segment comprises a modified sugar.

In any of the foregoing methods or uses, the compound comprises or consists of a modified oligonucleotide 16-30 linked nucleobases in length having a nucleobase sequence comprising the sequence recited in any one of SEQ ID NOs: 13, 1095, 1730, 76, 1326, and 81, wherein the modified oligonucleotide comprises a gap segment consisting of ten linked deoxynucleosides;

a 5' wing segment consisting of three linked nucleosides; and a 3' wing segment consisting of three linked nucleosides;

wherein the gap segment is positioned between the 5' wing segment and the 3' wing segment, wherein the 5' and 3' wing segments comprise a cEt nucleoside; wherein each internucleoside linkage is a phosphorothioate linkage; and wherein each cytosine is a 5-methylcytosine. In certain embodiments, the modified oligonucleotide is 16-30 linked nucleosides in length.

In any of the foregoing methods or uses, the compound comprises or consists of a modified oligonucleotide 16-30 linked nucleobases in length having a nucleobase sequence comprising or consisting of the sequence recited in any one of SEQ ID NOs: 1164 and 1925, wherein the modified oligonucleotide comprises:

a gap segment consisting of nine linked deoxynucleosides;

a 5' wing segment consisting of three linked nucleoside; and a 3' wing segment consisting of four linked nucleosides;

wherein the gap segment is positioned between the 5' wing segment and the 3' wing segment; wherein the 5' wing segment comprises a cEt nucleosides; wherein the 3' wing segment comprises a cEt nucleoside, a a cEt nucleoside, a cEt nucleoside, and 2'-O-methoxyethyl nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In any of the foregoing methods or uses, the compound comprises or consists of ION 972190 or salt thereof, having the following chemical structure:

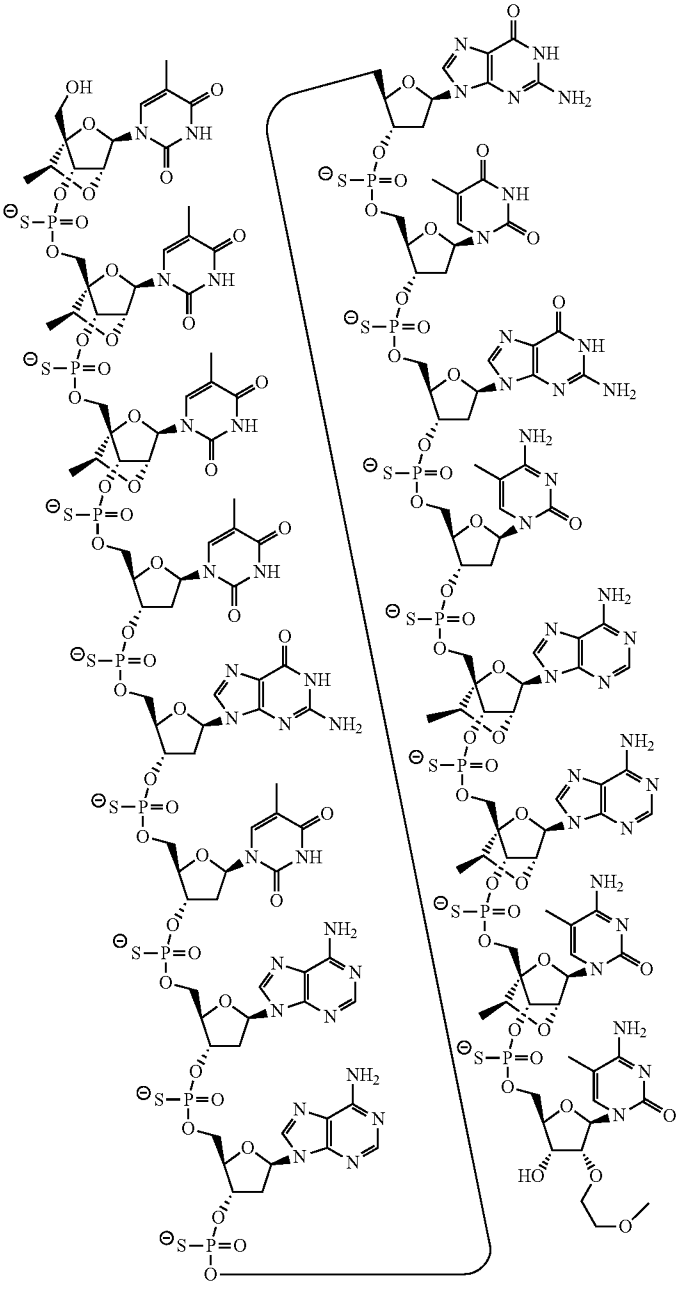

In any of the foregoing methods or uses, the compound comprises or consists of the sodium salt of ION 972190, having the following chemical structure:

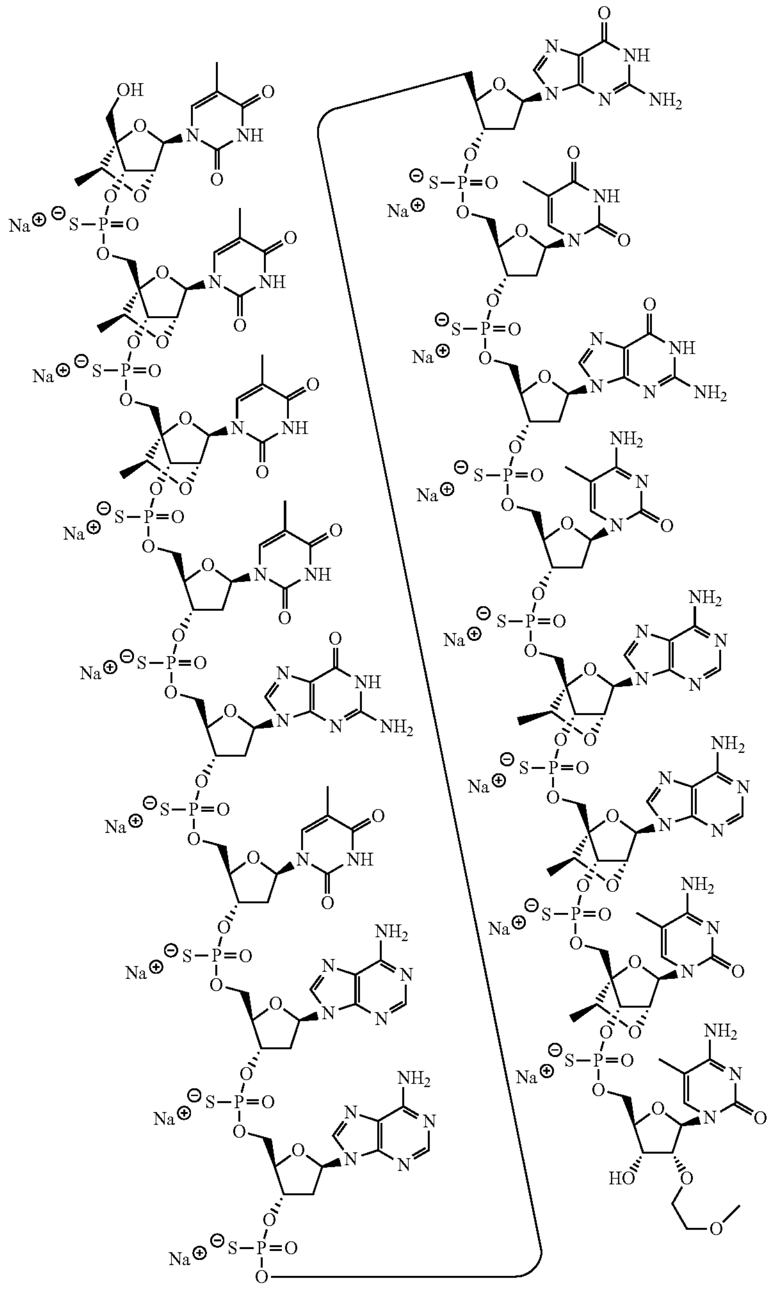

In any of the foregoing methods or uses, the compound can be administered parenterally. For example, in certain embodiments the compound can be administered through injection or infusion. Parenteral administration includes subcutaneous administration, intravenous administration, intramuscular administration, intraarterial administration, intraperitoneal administration, or intracranial administration, e.g. intrathecal or intracerebroventricular administration.

Certain Compounds

In certain embodiments, compounds described herein can be antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide and optionally a conjugate group. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, one of the modified oligonucleotides is conjugated. In certain embodiments, both the modified oligonucleotides are conjugated. In certain embodiments, the first modified oligonucleotide is conjugated. In certain embodiments, the second modified oligonucleotide is conjugated. In certain embodiments, the first modified oligonucleotide is 12-30 linked nucleosides in length and the second modified oligonucleotide is 12-30 linked nucleosides in length. In certain embodiments, one of the modified oligonucleotides has a nucleobase sequence comprising at least 8 contiguous nucleobases of any of SEQ ID NOs: 13-1941.

In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, a compound described herein comprises an oligonucleotide 12 to 30 linked subunits in length. In certain embodiments, a compound described herein comprises an oligonucleotide 12 to 22 linked subunits in length. In certain embodiments, compound escribed herein comprises an oligonucleotide 14 to 30 linked subunits in length. In certain embodiments, compound described herein comprises an oligonucleotide 14 to 20 linked subunits in length. In certain embodiments, a compound described herein comprises an oligonucleotide 15 to 30 linked subunits in length. In certain embodiments, a compound described herein comprises an oligonucleotide 15 to 20 linked subunits in length. In certain embodiments, a compound described herein comprises an oligonucleotide 16 to 30 linked subunits in length. In certain embodiments, a compound described herein comprises an oligonucleotide 16 to 20 linked subunits in length. In certain embodiments, a compound described herein comprises an oligonucleotide 17 to 30 linked subunits in length. In certain embodiments, a compound described herein comprises an oligonucleotide 17 to 20 linked subunits in length. In certain embodiments, a compound described herein comprises an oligonucleotide 18 to 30 linked subunits in length. In certain embodiments, a compound described herein comprises an oligonucleotide 18 to 21 linked subunits in length. In certain embodiments, a compound described herein comprises an oligonucleotide 18 to 20 linked subunits in length. In certain embodiments, a compound described herein comprises an oligonucleotide 20 to 30 linked subunits in length. In other words, such oligonucleotides are 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits in length, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, the compound may further comprise additional features or elements, such as a conjugate group, that are attached to the oligonucleotide. In certain embodiments, such compounds are antisense compounds. In certain embodiments, such compounds are oligomeric compounds. In embodiments where a conjugate group comprises a nucleoside (i.e. a nucleoside that links the conjugate group to the oligonucleotide), the nucleoside of the conjugate group is not counted in the length of the oligonucleotide.

In certain embodiments, compounds may be shortened or truncated. For example, a single subunit may be deleted from the 5' end (5' truncation), or alternatively from the 3' end (3' truncation). A shortened or truncated compound targeted to an APOL1 nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. Proc. Natl. Acad. Sci. USA 1992, 89:7305-7309; Gautschi et al. *J. Natl. Cancer Inst*. March 2001, 93:463-471; Maher and Dolnick Nuc. Acid. Res. 1998, 16:3341-3358). However, seemingly small changes in oligonucleotide sequence, chemistry and motif can make large differences in one or more of the many properties required for clinical development (Seth et al. *J. Med. Chem*. 2009, 52, 10; Egli et al. *J. Am. Chem. Soc*. 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term “RNAi” is meant to be equivalent to other terms used to describe sequence specific RNA interference, such as post transcriptional gene silencing, translational inhibition, or epigenetics.

In certain embodiments, a compound described herein can comprise any of the oligonucleotide sequences targeted to APOL1 described herein. In certain embodiments, the compound can be double-stranded. In certain embodiments, the compound comprises a first strand comprising at least an 8, 9, 10, 11, 12, 13, 14, 15, 16, 17, 18, 19, or 20 contiguous nucleobase portion of any one of SEQ ID NOs: 13-1941 and a second strand. In certain embodiments, the compound comprises a first strand comprising the nucleobase sequence of any one of SEQ ID NOs: 13-1941 and a second strand. In certain embodiments, the compound comprises ribonucleotides in which the first strand has uracil (U) in place of thymine (T) in any one of SEQ ID NOs13-1941. In certain embodiments, the compound comprises (i) a first strand comprising a nucleobase sequence complementary to the site on APOL1 to which any of SEQ ID NOs: 13-1941 is targeted, and (ii) a second strand. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains one or two capped strands, as disclosed, for example, by WO 00/63364, filed Apr. 19, 2000.

In certain embodiments, the first strand of the compound is an siRNA guide strand and the second strand of the compound is an siRNA passenger strand. In certain embodiments, the second strand of the compound is complementary to the first strand. In certain embodiments, each strand of the compound is 16, 17, 18, 19, 20, 21, 22, or 23 linked nucleosides in length. In certain embodiments, the first or second strand of the compound can comprise a conjugate group.

In certain embodiments, a compound described herein can comprise any of the oligonucleotide sequences targeted to APOL1 described herein. In certain embodiments, the compound is single stranded. In certain embodiments, such a compound is a single-stranded RNAi (ssRNAi) compound. In certain embodiments, the compound comprises at least an 8, 9, 10, 11, 12, 13, 14, 15, 16, 17, 18, 19, or 20 contiguous nucleobase portion of any one of SEQ ID NOs: 13-1941. In certain embodiments, the compound comprises the nucleobase sequence of any one of SEQ ID NOs: 13-1941. In certain embodiments, the compound comprises ribonucleotides in which uracil (U) is in place of thymine (T) in any one of SEQ ID NOs: 13-1941. In certain embodiments, the compound comprises a nucleobase sequence complementary to the site on APOL1 to which any of SEQ ID NOs: 13-1941 is targeted. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains a capped strand, as disclosed, for example, by WO 00/63364, filed Apr. 19, 2000. In certain embodiments, the compound consists of 16, 17, 18, 19, 20, 21, 22, or 23 linked nucleosides. In certain embodiments, the compound can comprise a conjugate group.

Certain Mechanisms

In certain embodiments, compounds described herein comprise or consist of modified oligonucleotides. In certain embodiments, compounds described herein are antisense compounds. In certain embodiments, compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

Nucleotide sequences that encode APOL1 include, without limitation, the following: RefSEQ No. NM_003661.3 (incorporated by reference, disclosed herein as SEQ ID NO: 1), NT_011520.9 truncated from nucleotides 15986452 to Ser. No. 16/001,905 (SEQ ID NO: 2), NM_001136541.1 (SEQ ID NO: 3), NM_001136540.1 (SEQ ID NO: 4), NM_145343.2 (SEQ ID NO: 5), DC339680.1 (SEQ ID NO: 6), AK309143.1 (SEQ ID NO: 7), NT_011520.13 truncated from nucleotides 17543446 to Ser. No. 17/543,655 (SEQ ID NO: 8), or NC_000022.11 truncated from nucleotides 36250001 to 36271000 (SEQ ID NO: 9).

Hybridization

In some embodiments, hybridization occurs between a compound disclosed herein and a APOL1 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a APOL1 nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a APOL1 nucleic acid may be tolerated provided that the compound remains able to specifically hybridize to a target nucleic acid. Moreover, a compound may hybridize over one or more segments of a APOL1 nucleic acid such that intervening or adjacent segments are not involved in the hybridization event (e.g., a loop structure, mismatch or hairpin structure).

In certain embodiments, the compounds provided herein, or a specified portion thereof, are, are at least, or are up to 70%, 80%, 85%, 86%, 87%, 88%, 89%, 90%, 91%, 92%, 93%, 94%, 95%, 96%, 97%, 98%, 99%, or 100% complementary to a APOL1 nucleic acid, a target region, target segment, or specified portion thereof. In certain embodiments, the compounds provided herein, or a specified portion thereof, are 70% to 75%, 75% to 80%, 80% to 85%, 85% to 90%, 90% to 95%, 95% to 100%, or any number in between these ranges, complementary to a APOL1 nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid. Percent complementarity of a compound with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a APOL1 nucleic acid, or a target region, or a target segment or target sequence thereof. As used herein, "fully complementary" means each nucleobase of a compound is complementary to the corresponding nucleobase of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a APOL1 nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a APOL1 nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the compounds, are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific ION number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of an compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific ION number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

In certain embodiments, compounds described herein comprise or consist of antisense compounds. In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein comprise or consist of oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified furanosyl sugar moieties comprising one or more acyclic substituent, including but not limited to substituents at the 2', 4', and/or 5' positions. In certain embodiments, the furanosyl sugar moiety is a ribosyl sugar moiety. In certain embodiments one or more acyclic substituent of non-bicyclic modified sugar moieties is branched. Examples of 2'-substituent groups suitable for non-bicyclic modified sugar moieties include but are not limited to: 2'-F, 2'-$OCH_3$ ("OMe" or "O-methyl"), and 2'-$O(CH_2)_2OCH_3$ ("MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, O—$C_1$-$C_{10}$ alkyl, O—$C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—$N(R_m)(R_n)$, where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for linearly non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a linear 2'-substituent group selected from: F, $NH_2$, $N_3$, $OCF_3$, $OCH_3$, $O(CH_2)_3NH_2$, $CH_2CH{=}CH_2$, $OCH_2CH{=}CH_2$, $OCH_2CH_2OCH_3$, $O(CH_2)_2SCH_3$, $O(CH_2)_2$ $ON(R_m)(R_n)$, $O(CH_2)_2O(CH_2)_2N(CH_3)_2$, and N-substituted acetamide ($OCH_2C(=O)$—$N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted nucleoside or 2'-non-bicyclic modified nucleoside comprises a sugar moiety comprising a linear 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)$—$N(H)CH_3$ ("NMA").

In certain embodiments, a 2'-substituted nucleoside or 2'-non-bicyclic modified nucleoside comprises a sugar moiety comprising a linear 2'-substituent group selected from: F, $OCH_3$, and $OCH_2CH_2OCH_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of such 4' to 2' bridging sugar substituents include but are not limited to: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-CH$(CH_3)$—O-2' (referred to as "constrained ethyl" or "cEt" when in the S configuration), 4'-$CH_2$—O—$CH_2$-2', 4'-$CH_2$—N(R)-2', 4'-CH$(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C$(CH_3)(CH_3)$—O-2' and analogs thereof (see, e.g., Seth et al., U.S. Pat. No. 8,278,283), 4'-$CH_2$—N$(OCH_3)$-2' and analogs thereof (see, e.g., Prakash et al., U.S. Pat. No. 8,278,425), 4'-$CH_2$—O—N$(CH_3)$-2' (see, e.g., Allerson et al., U.S. Pat. No. 7,696,345 and Allerson et al., U.S. Pat. No. 8,124,745), 4'-$CH_2$—C(H)$(CH_3)$-2' (see, e.g., Zhou, et al., *J. Org. Chem.*, 2009, 74, 118-134), 4'-$CH_2$—C(=$CH_2$)-2' and analogs thereof (see e.g., Seth et al., U.S. Pat. No. 8,278,426), 4'-C$(R_aR_b)$—N(R)—O-2', 4'-C$(R_aR_b)$—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —$[C(R_a)(R_b)]_n$—, —$[C(R_a)(R_b)]_n$—O—, —C$(R_a)$=C$(R_b)$—, —C$(R_a)$=N—, —C(=N$R_a$)—, —C(=O)—, —C(=S)—, —O—, —Si$(R_a)_2$—, —S(=O)$_x$—, and —N$(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, COM, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research,* 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron,* 1998, 54, 3607-3630; Wahlestedt et al., *Proc. Natl. Acad. Sci.* U S. A., 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129, 8362-8379; Elayadi et al., *Curr. Opinion Invens. Drugs,* 2001, 2, 558-561; Braasch et al., *Chem. Biol.*, 2001, 8, 1-7; Orum et al., *Curr. Opinion Mol. Ther.*, 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; Allerson et al., US2008/0039618; and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

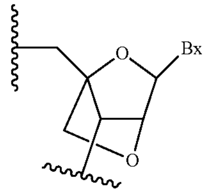

LNA (β-D-configuration)
bridge = 4'-$CH_2$—O-2'

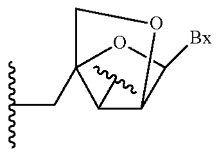

α-L-LNA (α-L-configuration)
bridge = 4'-$CH_2$—O-2'

α-L-methyleneoxy (4'-$CH_2$—O-2') or α-L-LNA bicyclic nucleosides have been incorporated into oligonucleotides that showed antisense activity (Frieden et al., *Nucleic Acids Research,* 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see e.g., Leumann, C J. *Bioorg. & Med. Chem.* 2002, 10, 841-854), fluoro HNA:

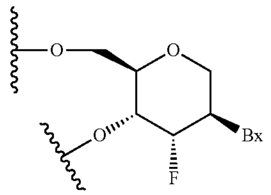

F-HNA ("F-HNA", see e.g., Swayze et al., U.S. Pat. No. 8,088,904; Swayze et al., U.S. Pat. No. 8,440,803; and Swayze et al., U.S. Pat. No. 9,005,906, F-HNA can also be referred to as a F-THP or 3'-fluoro tetrahydropyran), and nucleosides comprising additional modified THP compounds having the formula:

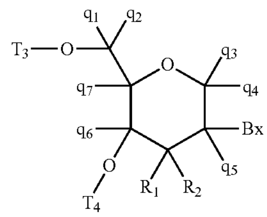

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is 0, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and R2 is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

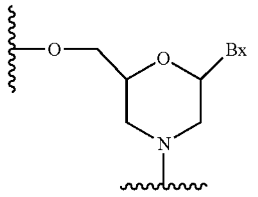

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.,* 2013, 11, 5853-5865), and nucleosides and oligonucleotides described in Manoharan et al., US2013/130378.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimi¬dines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp).

Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948, 903; Cook et al., U.S. Pat. No. 5,587,470; Cook et al., U.S. Pat. No. 5,457,191; Matteucci et al., U.S. Pat. No. 5,763, 588; Froehler et al., U.S. Pat. No. 5,830,653; Cook et al., U.S. Pat. No. 5,808,027; Cook et al., U.S. Pat. No. 6,166, 199; and Matteucci et al., U.S. Pat. No. 6,005,096.

In certain embodiments, compounds targeted to a APOL1 nucleic acid comprise one or more modified nucleobases. In certain embodiments, the modified nucleobase is 5-methylcytosine. In certain embodiments, each cytosine is a 5-methylcytosine.

Modified Internucleoside Linkages

The naturally occurring internucleoside linkage of RNA and DNA is a 3' to 5' phosphodiester linkage In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

($R_p$)

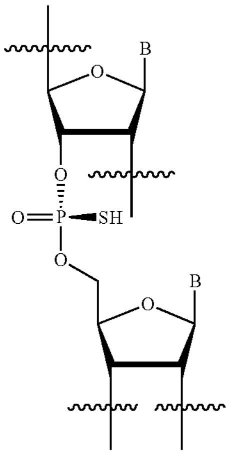

-continued ($S_p$)

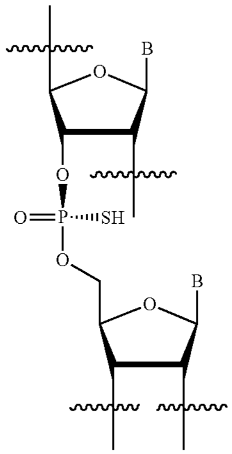

Unless otherwise indicated, chiral internucleoside linkages of modified oligonucleotides described herein can be stereorandom or in a particular stereochemical configuration.

In certain embodiments, compounds targeted to an APOL1 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS—P═S"). Representative non-phosphorus containing internucleoside linking groups include but are not limited to methylenemethylimino (—CH2-N(CH3)-O—CH2-), thiodiester, thionocarbamate (—O—C(═O)(NH)—S—); siloxane (—O—$SiH_2$-O—); and N,N'-dimethylhydrazine (—CH2-N(CH3)-N(CH3)-). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH2-N(CH3)-O-5'), amide-3 (3'-CH2-C(═O)—N(H)-5'), amide-4 (3'-CH2-N(H)—C(═O)-5'), formacetal (3'-O—CH2-O-5), methoxypropyl, and thioformacetal (3'-S—CH2-O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

3. Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

a. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

b. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

c. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P═O). In certain embodiments, each internucleoside linking group of a modified oligonucleotide is a phosphorothioate (P═S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

4. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Certain Conjugated Compounds

In certain embodiments, the compounds described herein comprise or consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

In certain embodiments, the oligonucleotide is modified. In certain embodiments, the oligonucleotide of a compound has a nucleobase sequence that is complementary to a target nucleic acid. In certain embodiments, oligonucleotides are complementary to a messenger RNA (mRNA). In certain embodiments, oligonucleotides are complementary to a sense transcript.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO* 1, 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, i, 923-937), a tocopherol group (Nishina et al., *Molecular Therapy Nucleic Acids,* 2015, 4, e220; doi:10.1038/mtna.2014.72 and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain compounds, a conjugate group is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the compound after it reaches a target tissue. Accordingly, linker-nucleosides are typically linked to one another and to the remainder of the compound through cleavable bonds. In certain embodiments, such cleavable bonds are phosphodiester bonds.

Herein, linker-nucleosides are not considered to be part of the oligonucleotide. Accordingly, in embodiments in which a compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, a compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, an compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances compounds comprising a particular conjugate moiety are better taken up by a particular cell type, but once the compound has been taken up, it is desirable that the conjugate group be cleaved to release the unconjugated or parent oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to APOL1 nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to APOL1 nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound. In certain embodiments, the compounds or compositions further comprise a pharmaceutically acceptable carrier or diluent.

Certain Selected Compounds

Approximately 1930 newly designed compounds and a few previously disclosed compounds of various lengths, chemistries, and motifs were tested for their effect on human APOL1 mRNA in vitro in several cell types (Example 1). Of 1930 compounds tested for potency at a single dose in vitro, 373 selected compounds were tested for dose dependent inhibition in A431 cells (Example 2). Of the 373 compounds tested by dose response assays, 86 oligonucleotides were selected for in vivo efficacy and tolerability in rodents.

In the in vivo rodent tolerability models, body weights and organ weights, liver function markers (such as alanine transaminase, aspartate transaminase and bilirubin), hematology markers (such as HCT, white blood cell counts, platelet counts, RBC counts, MCH, and MCHC), and kidney function markers (such as BUN and creatinine) were measured. In the hAPOL1 transgenic mouse model, in vivo reduction of hAPOL1 mRNA was measured.

ION #s 793406, 904763, 905469, 905505, 905634, 905665, 972190, and 972163 were tested for activity, pharmacokinetic profile and tolerability in cynomolgus monkeys (Example 9). Treatment with some of the compounds caused reduction of APOL1 mRNA expression in liver tissue. Specifically, treatment with ION 904763 and ION 972190, which were cross-reactive with the APOL1 cynomolgus monkey gene sequence, caused significant reduction of APOL1 mRNA expression in liver tissue, compared to the PBS control. It was noted that ION 972190 caused the highest reduction of APOL1 mRNA expression compared to the PBS control. Treatment with the compounds was well tolerated in the monkeys, in particular, treatment with ION 972190.

Accordingly, provided herein are compounds with any one or more of the improved properties. In certain embodiments, the compounds as described herein are potent and tolerable.

EXAMPLES

The Examples below describe the screening process to identify lead compounds targeted to APOL1. ION 793406, 904763, 905469, 905505, 905634, 905665, 972190, and 972163 resulted in high potency and tolerability, for instance. ION 972190 exhibited high potency and tolerability.

Non-Limiting Disclosure and Incorporation by Reference

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and compounds having other modified nucleobases, such as "AT$^{m}$CGAUCG," wherein $^{m}$C indicates a cytosine base comprising a methyl group at the 5-position.

Certain compounds described herein (e.g. modified oligonucleotides) have one or more asymmetric centers and thus give rise to enantiomers, diastereomers, and other stereoisomeric configurations that may be defined, in terms of absolute stereochemistry, as (R) or (S), as a or (3, such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms. Likewise, all tautomeric forms of the compounds provided herein are included unless otherwise indicated. Unless otherwise indicated, oligomeric compounds and modified oligonucleotides described herein are intended to include corresponding salt forms.

Compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}H$ hydrogen atoms. Isotopic substitutions encompassed by the compounds herein include but are not limited to: $^{2}H$ or $^{3}H$ in place of $^{1}H$, $^{13}C$ or $^{14}C$ in place of $^{12}C$, $^{15}N$ in place of $^{14}N$, $^{17}O$ or $^{18}O$ in place of $^{16}O$, and $^{33}S$, $^{34}S$, $^{35}S$, or $^{36}S$ in place of $^{32}S$.

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human APOL1 in A431 Cells

Antisense oligonucleotides with various chemistry motifs were designed targeting an APOL1 nucleic acid and were tested for their effects on APOL1 mRNA in vitro.

3-10-3 cEt Gapmers

The newly designed chimeric antisense oligonucleotides in the Tables below were designed as 3-10-3 cEt gapmers. The gapmers are 16 nucleosides in length, wherein the central gap segment comprises of ten 2'-deoxynucleosides and is flanked by wing segments on the 5' direction and the 3' direction comprising three nucleosides each. Each nucleoside in the 5' wing segment and each nucleoside in the 3' wing segment has a cEt modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human APOL1 mRNA, designated herein as SEQ ID NO: 1 (GENBANK Accession No. NM_003661.3) or the human APOL1 genomic sequence, designated herein as SEQ ID NO: 2 (GENBANK Accession No. NT_011520.9 truncated from nucleotides 15986452 to Ser. No. 16/001,905). 'n/a' indicates that the antisense oligonucleotide does not target that particular gene sequence with 100% complementarity.

The antisense oligonucleotides were tested in a series of experiments that had similar culture conditions. The results for each experiment are presented in separate tables shown below. Cultured A431 cells at a density of 10,000 cells per well were transfected by free uptake with 4,000 nM antisense oligonucleotide. After a treatment period of approximately 24 hours, RNA was isolated from the cells and APOL1 mRNA levels were measured by quantitative real-time PCR. Human primer probe set RTS35962 (forward sequence GCTACTCCTGCTGACTGATAATG, designated herein as SEQ ID NO: 10; reverse sequence AAGGTTGTCCAGAGCTTTACG, designated herein as SEQ ID NO: 11; probe sequence TGCCCAGGAAT-GAGGCAGATGAG, designated herein as SEQ ID NO: 12) was used to measure mRNA levels. APOL1 mRNA levels were adjusted according to total RNA content, as measured by RIBOGREEN®. Results are presented as percent inhibition of APOL1, relative to untreated control cells. Oligonucleotides listed in Table 28 were screened in later experiments.

TABLE 1

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 793406 | N/A | N/A | 8306 | 8321 | GTTCAAAAGCAGCATT | 83 | 13 |
| 903425 | 23 | 38 | 516 | 531 | AAGATATACCGAGGAA | 24 | 14 |
| 903457 | 124 | 139 | 617 | 632 | TCCCCTGGCAGAGACT | 54 | 15 |
| 903489 | 250 | 265 | 4543 | 4558 | TCGCTCCAGCTTCCTC | 55 | 16 |
| 903521 | 302 | 317 | 4777 | 4792 | TTACTTTGAGGATCTC | 48 | 17 |
| 903617 | 559 | 574 | 12650 | 12665 | ACTGCTGGCCTTTATC | 76 | 18 |
| 903649 | 628 | 643 | 12719 | 12734 | GGAGCCTTCTTATGTT | 8 | 19 |
| 903681 | 669 | 684 | 12760 | 12775 | GGTGCCTTTGTGGACC | 0 | 20 |
| 903713 | 740 | 755 | 12831 | 12846 | AGACCCATGCCGACGA | 30 | 21 |
| 903745 | 810 | 825 | 12901 | 12916 | AGCGGCTGTGATTCCC | 46 | 22 |
| 903777 | 849 | 864 | 12940 | 12955 | CTTTCCGTAGTCCATG | 17 | 23 |
| 903809 | 930 | 945 | 13021 | 13036 | ACCCAAAAACTCCCTC | 82 | 24 |
| 903841 | 1007 | 1022 | 13098 | 13113 | GCACGGATGTCCTTCC | 57 | 25 |
| 903873 | 1083 | 1098 | 13174 | 13189 | GATTGGCTCAGTGACC | 59 | 26 |
| 903905 | 1126 | 1141 | 13217 | 13232 | TGGGTTCATTAACCCT | 3 | 27 |
| 903937 | 1211 | 1226 | 13302 | 13317 | ACGAGGTAGACTACAT | 76 | 28 |
| 903969 | 1344 | 1359 | 13435 | 13450 | TTCTTGGTCCGCCTGC | 84 | 29 |
| 904001 | 1719 | 1734 | 13810 | 13825 | AATGTTTGCATTTGGG | 98 | 30 |
| 904033 | 1798 | 1813 | 13889 | 13904 | GTGCTCAGCTATGGAA | 90 | 31 |
| 904065 | 1925 | 1940 | 14016 | 14031 | TAGTCTAAAGTAAACT | 26 | 32 |
| 904097 | 2283 | 2298 | 14374 | 14389 | GCTGGTTCCTTCAAGC | 25 | 33 |
| 904129 | 2412 | 2427 | 14503 | 14518 | CATTCTTCGGAGGACA | 78 | 34 |
| 904161 | 2510 | 2525 | 14601 | 14616 | TCAGGAAGCCGCTGCC | 58 | 35 |
| 904193 | 2599 | 2614 | 14690 | 14705 | ACCTGCCCTTCAGTGT | 52 | 36 |
| 904225 | 2723 | 2738 | 14814 | 14829 | CTGTTTACTTACCGGG | 83 | 37 |
| 904257 | 2804 | 2819 | 14895 | 14910 | TCAATCCTGGGCGGCG | 85 | 38 |
| 904321 | N/A | N/A | 1373 | 1388 | CATGATTGCAAAGCTG | 89 | 39 |
| 904353 | N/A | N/A | 836 | 851 | GCTTTGTGAACCCATC | 58 | 40 |
| 904385 | N/A | N/A | 2479 | 2494 | CAAGCCCAGTCCAATT | 23 | 41 |
| 904417 | N/A | N/A | 2988 | 3003 | GATGTTTGTCTTCTGG | 88 | 42 |
| 904449 | N/A | N/A | 4339 | 4354 | GCCAGTGTGTATTGCA | 40 | 43 |
| 904481 | N/A | N/A | 4711 | 4726 | ACAAATTGTGGGATCA | 0 | 44 |
| 904513 | N/A | N/A | 5057 | 5072 | CTAGGTGCCAGGGTAG | 47 | 45 |

TABLE 1 -continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904545 | N/A | N/A | 5114 | 5129 | CCCCCCCCCCGCTGAT | 9 | 46 |
| 904577 | N/A | N/A | 5292 | 5307 | GGGCCACTCAGAGCAA | 0 | 47 |
| 904609 | N/A | N/A | 5357 | 5372 | GTGGCAAAGGACAGAC | 72 | 48 |
| 904641 | N/A | N/A | 5489 | 5504 | CCCTATTGTGTGGCAG | 66 | 49 |
| 904673 | N/A | N/A | 5681 | 5696 | TTTTTCTTTGACCGGG | 74 | 50 |
| 904705 | N/A | N/A | 5765 | 5780 | CGAAGCCTCCTCCAGT | 65 | 51 |
| 904737 | N/A | N/A | 5806 | 5821 | CACCCGATAAACCTTG | 67 | 52 |
| 904769 | N/A | N/A | 5861 | 5876 | AGGCAGTTTTGTAAGT | 76 | 53 |
| 904801 | N/A | N/A | 5932 | 5947 | ATTCGGAGACCTCCCT | 5 | 54 |
| 904833 | N/A | N/A | 5964 | 5979 | CCTGGGCAAGGCTAAG | 35 | 55 |
| 904865 | N/A | N/A | 6137 | 6152 | TTACTCCACACCTTAA | 39 | 56 |
| 904897 | N/A | N/A | 6205 | 6220 | TTTGGTACAAAACTGC | 71 | 57 |
| 904929 | N/A | N/A | 6260 | 6275 | TGTCTCACTAAACCCC | 69 | 58 |
| 904961 | N/A | N/A | 6328 | 6343 | GACCAGTGAGATCCAA | 85 | 59 |
| 904993 | N/A | N/A | 6401 | 6416 | ACCACCTGTAGGGACA | 50 | 60 |
| 905025 | N/A | N/A | 6541 | 6556 | GGGTACTTCTGTTAGA | 82 | 61 |
| 905057 | N/A | N/A | 6599 | 6614 | CAGCTGTAACCCCCTG | 44 | 62 |
| 905089 | N/A | N/A | 6647 | 6662 | CAGCCCTGAAACATTC | 13 | 63 |
| 905121 | N/A | N/A | 6793 | 6808 | GCGATTGTCTTGTTTT | 93 | 64 |
| 905153 | N/A | N/A | 6878 | 6893 | GCCGTGGCAACTCTGT | 0 | 65 |
| 905185 | N/A | N/A | 6994 | 7009 | GGGTCGGCTGAGTGCT | 61 | 66 |
| 905217 | N/A | N/A | 7156 | 7171 | ACCTCCATGTTGCCTC | 42 | 67 |
| 905249 | N/A | N/A | 7243 | 7258 | GCTGGTCTTGGGCACT | 34 | 68 |
| 905281 | N/A | N/A | 7338 | 7353 | CTTATAGCTTACCTGT | 27 | 69 |
| 905313 | N/A | N/A | 7474 | 7489 | GAGTCACCGCCCAAAA | 59 | 70 |
| 905345 | N/A | N/A | 7842 | 7857 | TTGCCGTGCACACACA | 19 | 71 |
| 905377 | N/A | N/A | 7937 | 7952 | GTTTGCAGGGATCTGG | 86 | 72 |
| 905409 | N/A | N/A | 8000 | 8015 | CAAAGAACTCAAGTCA | 85 | 73 |
| 905441 | N/A | N/A | 8087 | 8102 | ACTGCTCCCTGTAATC | 38 | 74 |
| 905473 | N/A | N/A | 8174 | 8189 | TGTGTTTAGGCATTCA | 87 | 75 |
| 905505 | N/A | N/A | 8321 | 8336 | GTTATGAAATTATTGG | 96 | 76 |
| 905537 | N/A | N/A | 8385 | 8400 | ATGCCTGTTGGGTCAA | 64 | 77 |
| 905569 | N/A | N/A | 8455 | 8470 | GCACCAACATGAAGTG | 71 | 78 |
| 905601 | N/A | N/A | 8625 | 8640 | ACCCTTTTGGCACCTT | 94 | 79 |
| 905633 | N/A | N/A | 8743 | 8758 | TTCTATTAGAGGGCTA | 94 | 80 |
| 905665 | N/A | N/A | 8829 | 8844 | GCTTTAAACTCAGGTG | 93 | 81 |

TABLE 1 -continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 905697 | N/A | N/A | 8890 | 8905 | GTTTTATGGAGTCATT | 95 | 82 |
| 905729 | N/A | N/A | 8959 | 8974 | GTGCATAACAGCCATT | 19 | 83 |

TABLE 2

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 793406 | N/A | N/A | 8306 | 8321 | GTTCAAAAGCAGCATT | 85 | 13 |
| 903424 | 22 | 37 | 515 | 530 | AGATATACCGAGGAAT | 3 | 84 |
| 903456 | 79 | 94 | 572 | 587 | GGATCCCACCTCCAGT | 9 | 85 |
| 903488 | 227 | 242 | 4520 | 4535 | ACTCCCACACCAAGGA | 27 | 86 |
| 903520 | 301 | 316 | 4776 | 4791 | TACTTTGAGGATCTCC | 65 | 87 |
| 903616 | 558 | 573 | 12649 | 12664 | CTGCTGGCCTTTATCG | 0 | 88 |
| 903648 | 627 | 642 | 12718 | 12733 | GAGCCTTCTTATGTTA | 27 | 89 |
| 903680 | 668 | 683 | 12759 | 12774 | GTGCCTTTGTGGACCT | 24 | 90 |
| 903712 | 739 | 754 | 12830 | 12845 | GACCCATGCCGACGAG | 46 | 91 |
| 903744 | 809 | 824 | 12900 | 12915 | GCGGCTGTGATTCCCA | 0 | 92 |
| 903776 | 848 | 863 | 12939 | 12954 | TTTCCGTAGTCCATGG | 20 | 93 |
| 903808 | 914 | 929 | 13005 | 13020 | ACCTCCTTCAATTTGT | 61 | 94 |
| 903840 | 1006 | 1021 | 13097 | 13112 | CACGGATGTCCTTCCC | 69 | 95 |
| 903872 | 1082 | 1097 | 13173 | 13188 | ATTGGCTCAGTGACCC | 88 | 96 |
| 903904 | 1125 | 1140 | 13216 | 13231 | GGGTTCATTAACCCTC | 22 | 97 |
| 903936 | 1210 | 1225 | 13301 | 13316 | CGAGGTAGACTACATC | 63 | 98 |
| 903968 | 1343 | 1358 | 13434 | 13449 | TCTTGGTCCGCCTGCA | 66 | 99 |
| 904000 | 1717 | 1732 | 13808 | 13823 | TGTTTGCATTTGGGTC | 99 | 100 |
| 904032 | 1797 | 1812 | 13888 | 13903 | TGCTCAGCTATGGAAA | 77 | 101 |
| 904064 | 1924 | 1939 | 14015 | 14030 | AGTCTAAAGTAAACTG | 18 | 102 |
| 904096 | 2282 | 2297 | 14373 | 14388 | CTGGTTCCTTCAAGCC | 77 | 103 |
| 904128 | 2411 | 2426 | 14502 | 14517 | ATTCTTCGGAGGACAT | 71 | 104 |
| 904160 | 2508 | 2523 | 14599 | 14614 | AGGAAGCCGCTGCCTG | 0 | 105 |
| 904192 | 2596 | 2611 | 14687 | 14702 | TGCCCTTCAGTGTTCA | 47 | 106 |
| 904224 | 2722 | 2737 | 14813 | 14828 | TGTTTACTTACCGGGT | 91 | 107 |
| 904256 | 2803 | 2818 | 14894 | 14909 | CAATCCTGGGCGGCGA | 79 | 108 |
| 904320 | N/A | N/A | 1372 | 1387 | ATGATTGCAAAGCTGG | 75 | 109 |
| 904352 | N/A | N/A | 828 | 843 | AACCCATCTGAGCTGT | 34 | 110 |

TABLE 2-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904384 | N/A | N/A | 2476 | 2491 | GCCCAGTCCAATTGTG | 14 | 111 |
| 904416 | N/A | N/A | 2970 | 2985 | ACTCCATGCAGCAAGG | 71 | 112 |
| 904448 | N/A | N/A | 4322 | 4337 | GTCTGCGATGTGCAGA | 21 | 113 |
| 904480 | N/A | N/A | 4705 | 4720 | TGTGGGATCAAATGTG | 0 | 114 |
| 904512 | N/A | N/A | 5056 | 5071 | TAGGTGCCAGGGTAGG | 68 | 115 |
| 904544 | N/A | N/A | 5113 | 5128 | CCCCCCCCCGCTGATT | 16 | 116 |
| 904576 | N/A | N/A | 5291 | 5306 | GGCCACTCAGAGCAAA | 0 | 117 |
| 904608 | N/A | N/A | 5355 | 5370 | GGCAAAGGACAGACCG | 9 | 118 |
| 904640 | N/A | N/A | 5466 | 5481 | CCAGGCCAGGTAGCCG | 21 | 119 |
| 904672 | N/A | N/A | 5666 | 5681 | GGGTATTTTAGATGAC | 76 | 120 |
| 904704 | N/A | N/A | 5764 | 5779 | GAAGCCTCCTCCAGTT | 68 | 121 |
| 904736 | N/A | N/A | 5805 | 5820 | ACCCGATAAACCTTGT | 73 | 122 |
| 904768 | N/A | N/A | 5860 | 5875 | GGCAGTTTTGTAAGTG | 81 | 123 |
| 904800 | N/A | N/A | 5931 | 5946 | TTCGGAGACCTCCCTA | 33 | 124 |
| 904832 | N/A | N/A | 5963 | 5978 | CTGGGCAAGGCTAAGT | 1 | 125 |
| 904864 | N/A | N/A | 6136 | 6151 | TACTCCACACCTTAAT | 18 | 126 |
| 904896 | N/A | N/A | 6204 | 6219 | TTGGTACAAAACTGCA | 68 | 127 |
| 904928 | N/A | N/A | 6259 | 6274 | GTCTCACTAAACCCCA | 71 | 128 |
| 904960 | N/A | N/A | 6327 | 6342 | ACCAGTGAGATCCAAC | 87 | 129 |
| 904992 | N/A | N/A | 6377 | 6392 | GGATGGGCCCACAGGA | 39 | 130 |
| 905024 | N/A | N/A | 6540 | 6555 | GGTACTTCTGTTAGAT | 37 | 131 |
| 905056 | N/A | N/A | 6598 | 6613 | AGCTGTAACCCCCTGA | 54 | 132 |
| 905088 | N/A | N/A | 6646 | 6661 | AGCCCTGAAACATTCC | 39 | 133 |
| 905120 | N/A | N/A | 6792 | 6807 | CGATTGTCTTGTTTTT | 96 | 134 |
| 905152 | N/A | N/A | 6877 | 6892 | CCGTGGCAACTCTGTA | 22 | 135 |
| 905184 | N/A | N/A | 6992 | 7007 | GTCGGCTGAGTGCTCT | 35 | 136 |
| 905216 | N/A | N/A | 7152 | 7167 | CCATGTTGCCTCTGTC | 62 | 137 |
| 905248 | N/A | N/A | 7242 | 7257 | CTGGTCTTGGGCACTC | 25 | 138 |
| 905280 | N/A | N/A | 7336 | 7351 | TATAGCTTACCTGTGG | 59 | 139 |
| 905312 | N/A | N/A | 7472 | 7487 | GTCACCGCCCAAAACC | 51 | 140 |
| 905344 | N/A | N/A | 7840 | 7855 | GCCGTGCACACACAAG | 29 | 141 |
| 905376 | N/A | N/A | 7929 | 7944 | GGATCTGGGAATTATG | 65 | 142 |
| 905408 | N/A | N/A | 7999 | 8014 | AAAGAACTCAAGTCAG | 91 | 143 |
| 905440 | N/A | N/A | 8085 | 8100 | TGCTCCCTGTAATCAC | 55 | 144 |
| 905472 | N/A | N/A | 8173 | 8188 | GTGTTTAGGCATTCAG | 72 | 145 |
| 905504 | N/A | N/A | 8318 | 8333 | ATGAAATTATTGGTTC | 82 | 146 |

TABLE 2-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 905536 | N/A | N/A | 8384 | 8399 | TGCCTGTTGGGTCAAA | 43 | 147 |
| 905568 | N/A | N/A | 8454 | 8469 | CACCAACATGAAGTGA | 0 | 148 |
| 905600 | N/A | N/A | 8624 | 8639 | CCCTTTTGGCACCTTC | 95 | 149 |
| 905632 | N/A | N/A | 8742 | 8757 | TCTATTAGAGGGCTAG | 57 | 150 |
| 905664 | N/A | N/A | 8828 | 8843 | CTTTAAACTCAGGTGA | 62 | 151 |
| 905696 | N/A | N/A | 8887 | 8902 | TTATGGAGTCATTAGT | 79 | 152 |
| 905728 | N/A | N/A | 8958 | 8973 | TGCATAACAGCCATTG | 0 | 153 |

TABLE 3

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 793406 | N/A | N/A | 8306 | 8321 | GTTCAAAAGCAGCATT | 81 | 13 |
| 903428 | 26 | 41 | 519 | 534 | CCCAAGATATACCGAG | 24 | 154 |
| 903460 | 130 | 145 | 623 | 638 | GAATCTTCCCCTGGCA | 55 | 155 |
| 903492 | 255 | 270 | N/A | N/A | CACCCTCGCTCCAGCT | 44 | 156 |
| 903524 | 322 | 337 | 4797 | 4812 | CAGCCCAGTCACCGAG | 14 | 157 |
| 903620 | 562 | 577 | 12653 | 12668 | TGTACTGCTGGCCTTT | 68 | 158 |
| 903652 | 631 | 646 | 12722 | 12737 | CACGGAGCCTTCTTAT | 31 | 159 |
| 903684 | 672 | 687 | 12763 | 12778 | GGTGGTGCCTTTGTGG | 0 | 160 |
| 903716 | 743 | 758 | 12834 | 12849 | GCCAGACCCATGCCGA | 39 | 161 |
| 903748 | 813 | 828 | 12904 | 12919 | CAAAGCGGCTGTGATT | 21 | 162 |
| 903780 | 852 | 867 | 12943 | 12958 | CTTCTTTCCGTAGTCC | 32 | 163 |
| 903812 | 936 | 951 | 13027 | 13042 | GTTCTCACCCAAAAAC | 20 | 164 |
| 903844 | 1011 | 1026 | 13102 | 13117 | GAGGGCACGGATGTCC | 39 | 165 |
| 903876 | 1086 | 1101 | 13177 | 13192 | TGAGATTGGCTCAGTG | 64 | 166 |
| 903908 | 1129 | 1144 | 13220 | 13235 | TGCTGGGTTCATTAAC | 6 | 167 |
| 903940 | 1231 | 1246 | 13322 | 13337 | GTAAGTGCTTTGATTC | 93 | 168 |
| 903972 | 1347 | 1362 | 13438 | 13453 | CAGTTCTTGGTCCGCC | 79 | 169 |
| 904004 | 1743 | 1758 | 13834 | 13849 | TCACCCTCTTTATCCC | 76 | 170 |
| 904036 | 1801 | 1816 | 13892 | 13907 | GCTGTGCTCAGCTATG | 35 | 171 |
| 904068 | 1929 | 1944 | 14020 | 14035 | TCTTTAGTCTAAAGTA | 0 | 172 |
| 904100 | 2336 | 2351 | 14427 | 14442 | TAACTCTTGGGCTTTC | 73 | 173 |
| 904132 | 2415 | 2430 | 14506 | 14521 | CTTCATTCTTCGGAGG | 34 | 174 |

TABLE 3-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904164 | 2513 | 2528 | 14604 | 14619 | TCATCAGGAAGCCGCT | 73 | 175 |
| 904196 | 2613 | 2628 | 14704 | 14719 | GGCCATGGCCCACCAC | 0 | 176 |
| 904228 | 2766 | 2781 | 14857 | 14872 | AGCTTCCTCCCAATGC | 24 | 177 |
| 904260 | 2807 | 2822 | 14898 | 14913 | AGGTCAATCCTGGGCG | 58 | 178 |
| 904324 | N/A | N/A | 1376 | 1391 | TCTCATGATTGCAAAG | 69 | 179 |
| 904356 | N/A | N/A | 871 | 886 | GTCTCAGCAGTCAAAA | 62 | 180 |
| 904388 | N/A | N/A | 2518 | 2533 | TTGGTTCCTAGAAGAA | 36 | 181 |
| 904420 | N/A | N/A | 3414 | 3429 | ACTGAGGGTATATGAA | 82 | 182 |
| 904452 | N/A | N/A | 4361 | 4376 | GTGTGATAACTAGCTG | 86 | 183 |
| 904484 | N/A | N/A | 4738 | 4753 | TTTTGTTGCACCCTTG | 83 | 184 |
| 904516 | N/A | N/A | 5065 | 5080 | GTCATTTGCTAGGTGC | 90 | 185 |
| 904548 | N/A | N/A | 5173 | 5188 | TGGTCAACCTCCTCTC | 0 | 186 |
| 904580 | N/A | N/A | 5305 | 5320 | ATACATTCCCACAGGG | 22 | 187 |
| 904612 | N/A | N/A | 5393 | 5408 | AGGGAGGTAAGGAGCG | 26 | 188 |
| 904644 | N/A | N/A | 5492 | 5507 | AGGCCCTATTGTGTGG | 0 | 189 |
| 904676 | N/A | N/A | 5694 | 5709 | ATTGGGCCTCAGATTT | 57 | 190 |
| 904708 | N/A | N/A | 5768 | 5783 | GCACGAAGCCTCCTCC | 60 | 191 |
| 904740 | N/A | N/A | 5809 | 5824 | ATTCACCCGATAAACC | 47 | 192 |
| 904772 | N/A | N/A | 5870 | 5885 | AACCCAAACAGGCAGT | 69 | 193 |
| 904804 | N/A | N/A | 5935 | 5950 | TGTATTCGGAGACCTC | 47 | 194 |
| 904836 | N/A | N/A | 5967 | 5982 | AAACCTGGGCAAGGCT | 23 | 195 |
| 904868 | N/A | N/A | 6141 | 6156 | ATGCTTACTCCACACC | 75 | 196 |
| 904900 | N/A | N/A | 6211 | 6226 | CCCATGTTTGGTACAA | 54 | 197 |
| 904932 | N/A | N/A | 6263 | 6278 | CCTTGTCTCACTAAAC | 73 | 198 |
| 904964 | N/A | N/A | 6332 | 6347 | CTAAGACCAGTGAGAT | 58 | 199 |
| 904996 | N/A | N/A | 6404 | 6419 | GAAACCACCTGTAGGG | 53 | 200 |
| 905028 | N/A | N/A | 6544 | 6559 | GATGGGTACTTCTGTT | 88 | 201 |
| 905060 | N/A | N/A | 6605 | 6620 | TTAGAACAGCTGTAAC | 50 | 202 |
| 905092 | N/A | N/A | 6684 | 6699 | GGGCTGGTGGATATAA | 0 | 203 |
| 905124 | N/A | N/A | 6796 | 6811 | CGAGCGATTGTCTTGT | 76 | 204 |
| 905156 | N/A | N/A | 6881 | 6896 | GTTGCCGTGGCAACTC | 21 | 205 |
| 905188 | N/A | N/A | 7039 | 7054 | GAGTTTTTCCTCAGTC | 49 | 206 |
| 905220 | N/A | N/A | 7161 | 7176 | GAGGCACCTCCATGTT | 41 | 207 |
| 905252 | N/A | N/A | 7260 | 7275 | CAAAGGAGATTCCTCC | 35 | 208 |
| 905284 | N/A | N/A | 7342 | 7357 | CTCCCTTATAGCTTAC | 62 | 209 |
| 905316 | N/A | N/A | 7477 | 7492 | CGAGAGTCACCGCCCA | 72 | 210 |

TABLE 3-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 905348 | N/A | N/A | 7845 | 7860 | TTCTTGCCGTGCACAC | 10 | 211 |
| 905380 | N/A | N/A | 7943 | 7958 | CGTGTGGTTTGCAGGG | 72 | 212 |
| 905412 | N/A | N/A | 8008 | 8023 | TAGGTCTACAAAGAAC | 71 | 213 |
| 905444 | N/A | N/A | 8090 | 8105 | TGGACTGCTCCCTGTA | 13 | 214 |
| 905476 | N/A | N/A | 8177 | 8192 | AGATGTGTTTAGGCAT | 96 | 215 |
| 905508 | N/A | N/A | 8330 | 8345 | CATCATTGGGTTATGA | 37 | 216 |
| 905540 | N/A | N/A | 8388 | 8403 | CACATGCCTGTTGGGT | 48 | 217 |
| 905572 | N/A | N/A | 8466 | 8481 | TTTTCAGCTCAGCACC | 49 | 218 |
| 905604 | N/A | N/A | 8633 | 8648 | AGACTCCAACCCTTTT | 53 | 219 |
| 905636 | N/A | N/A | 8746 | 8761 | TAATTCTATTAGAGGG | 83 | 220 |
| 905668 | N/A | N/A | 8833 | 8848 | TGAAGCTTTAAACTCA | 18 | 221 |
| 905700 | N/A | N/A | 8895 | 8910 | GACTTGTTTTATGGAG | 87 | 222 |
| 905732 | N/A | N/A | 8962 | 8977 | GGAGTGCATAACAGCC | 0 | 223 |

TABLE 4

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 793406 | N/A | N/A | 8306 | 8321 | GTTCAAAAGCAGCATT | 85 | 13 |
| 903429 | 27 | 42 | 520 | 535 | CCCCAAGATATACCGA | 0 | 224 |
| 903461 | 131 | 146 | 624 | 639 | GGAATCTTCCCCTGGC | 51 | 225 |
| 903493 | 256 | 271 | N/A | N/A | GCACCCTCGCTCCAGC | 24 | 226 |
| 903525 | 323 | 338 | 4798 | 4813 | GCAGCCCAGTCACCGA | 0 | 227 |
| 903621 | 563 | 578 | 12654 | 12669 | CTGTACTGCTGGCCTT | 87 | 228 |
| 903653 | 632 | 647 | 12723 | 12738 | GCACGGAGCCTTCTTA | 33 | 229 |
| 903685 | 673 | 688 | 12764 | 12779 | TGGTGGTGCCTTTGTG | 0 | 230 |
| 903717 | 744 | 759 | 12835 | 12850 | TGCCAGACCCATGCCG | 48 | 231 |
| 903749 | 817 | 832 | 12908 | 12923 | CGGTCAAAGCGGCTGT | 71 | 232 |
| 903781 | 853 | 868 | 12944 | 12959 | ACTTCTTTCCGTAGTC | 6 | 233 |
| 903813 | 940 | 955 | 13031 | 13046 | ATATGTTCTCACCCAA | 77 | 234 |
| 903845 | 1012 | 1027 | 13103 | 13118 | TGAGGGCACGGATGTC | 67 | 235 |
| 903877 | 1090 | 1105 | 13181 | 13196 | CAGCTGAGATTGGCTC | 19 | 236 |
| 903909 | 1130 | 1145 | 13221 | 13236 | ATGCTGGGTTCATTAA | 28 | 237 |
| 903941 | 1233 | 1248 | 13324 | 13339 | ATGTAAGTGCTTTGAT | 74 | 238 |
| 903973 | 1348 | 1363 | 13439 | 13454 | ACAGTTCTTGGTCCGC | 92 | 239 |

TABLE 4-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904005 | 1744 | 1759 | 13835 | 13850 | CTCACCCTCTTTATCC | 50 | 240 |
| 904037 | 1827 | 1842 | 13918 | 13933 | CTGCCATCTGCATTAA | 54 | 241 |
| 904069 | 1942 | 1957 | 14033 | 14048 | CCCCCCAATATATTCT | 67 | 242 |
| 904101 | 2340 | 2355 | 14431 | 14446 | GTTCTAACTCTTGGGC | 90 | 243 |
| 904133 | 2416 | 2431 | 14507 | 14522 | ACTTCATTCTTCGGAG | 27 | 244 |
| 904165 | 2514 | 2529 | 14605 | 14620 | ATCATCAGGAAGCCGC | 92 | 245 |
| 904197 | 2614 | 2629 | 14705 | 14720 | TGGCCATGGCCCACCA | 10 | 246 |
| 904229 | 2767 | 2782 | 14858 | 14873 | GAGCTTCCTCCCAATG | 0 | 247 |
| 904261 | 2839 | 2854 | 14930 | 14945 | ATGAGTAGGTGAGTTT | 84 | 248 |
| 904325 | N/A | N/A | 1378 | 1393 | AATCTCATGATTGCAA | 70 | 249 |
| 904357 | N/A | N/A | 872 | 887 | TGTCTCAGCAGTCAAA | 69 | 250 |
| 904389 | N/A | N/A | 2519 | 2534 | TTTGGTTCCTAGAAGA | 25 | 251 |
| 904421 | N/A | N/A | 3417 | 3432 | ACAACTGAGGGTATAT | 80 | 252 |
| 904453 | N/A | N/A | 4366 | 4381 | AGCATGTGTGATAACT | 88 | 253 |
| 904485 | N/A | N/A | 4818 | 4833 | TACCTGGGTCCATGGT | 6 | 254 |
| 904517 | N/A | N/A | 5067 | 5082 | GAGTCATTTGCTAGGT | 90 | 255 |
| 904549 | N/A | N/A | 5175 | 5190 | GCTGGTCAACCTCCTC | 40 | 256 |
| 904581 | N/A | N/A | 5306 | 5321 | GATACATTCCCACAGG | 60 | 257 |
| 904613 | N/A | N/A | 5394 | 5409 | AAGGGAGGTAAGGAGC | 15 | 258 |
| 904645 | N/A | N/A | 5493 | 5508 | GAGGCCCTATTGTGTG | 13 | 259 |
| 904677 | N/A | N/A | 5695 | 5710 | TATTGGGCCTCAGATT | 17 | 260 |
| 904709 | N/A | N/A | 5769 | 5784 | AGCACGAAGCCTCCTC | 60 | 261 |
| 904741 | N/A | N/A | 5813 | 5828 | TCATATTCACCCGATA | 76 | 262 |
| 904773 | N/A | N/A | 5872 | 5887 | TAAACCCAAACAGGCA | 76 | 263 |
| 904805 | N/A | N/A | 5936 | 5951 | CTGTATTCGGAGACCT | 54 | 264 |
| 904837 | N/A | N/A | 5970 | 5985 | CAAAAACCTGGGCAAG | 56 | 265 |
| 904869 | N/A | N/A | 6142 | 6157 | TATGCTTACTCCACAC | 57 | 266 |
| 904901 | N/A | N/A | 6213 | 6228 | TGCCCATGTTTGGTAC | 7 | 267 |
| 904933 | N/A | N/A | 6265 | 6280 | CTCCTTGTCTCACTAA | 50 | 268 |
| 904965 | N/A | N/A | 6333 | 6348 | GCTAAGACCAGTGAGA | 67 | 269 |
| 904997 | N/A | N/A | 6405 | 6420 | TGAAACCACCTGTAGG | 38 | 270 |
| 905029 | N/A | N/A | 6545 | 6560 | AGATGGGTACTTCTGT | 89 | 271 |
| 905061 | N/A | N/A | 6607 | 6622 | CTTTAGAACAGCTGTA | 57 | 272 |
| 905093 | N/A | N/A | 6698 | 6713 | TTCTTGATGTGGTGGG | 92 | 273 |
| 905125 | N/A | N/A | 6797 | 6812 | GCGAGCGATTGTCTTG | 59 | 274 |
| 905157 | N/A | N/A | 6882 | 6897 | GGTTGCCGTGGCAACT | 0 | 275 |

TABLE 4-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 905189 | N/A | N/A | 7043 | 7058 | GGGAGAGTTTTTCCTC | 14 | 276 |
| 905221 | N/A | N/A | 7162 | 7177 | TGAGGCACCTCCATGT | 0 | 277 |
| 905253 | N/A | N/A | 7261 | 7276 | GCAAAGGAGATTCCTC | 61 | 278 |
| 905285 | N/A | N/A | 7343 | 7358 | TCTCCCTTATAGCTTA | 71 | 279 |
| 905317 | N/A | N/A | 7478 | 7493 | GCGAGAGTCACCGCCC | 0 | 280 |
| 905349 | N/A | N/A | 7846 | 7861 | TTTCTTGCCGTGCACA | 17 | 281 |
| 905381 | N/A | N/A | 7957 | 7972 | AGCTGCCACCAAAACG | 25 | 282 |
| 905413 | N/A | N/A | 8009 | 8024 | GTAGGTCTACAAAGAA | 79 | 283 |
| 905445 | N/A | N/A | 8091 | 8106 | CTGGACTGCTCCCTGT | 20 | 284 |
| 905477 | N/A | N/A | 8178 | 8193 | CAGATGTGTTTAGGCA | 97 | 285 |
| 905509 | N/A | N/A | 8331 | 8346 | ACATCATTGGGTTATG | 82 | 286 |
| 905541 | N/A | N/A | 8389 | 8404 | CCACATGCCTGTTGGG | 1 | 287 |
| 905573 | N/A | N/A | 8472 | 8487 | GAATCCTTTTCAGCTC | 63 | 288 |
| 905605 | N/A | N/A | 8634 | 8649 | CAGACTCCAACCCTTT | 49 | 289 |
| 905637 | N/A | N/A | 8747 | 8762 | CTAATTCTATTAGAGG | 35 | 290 |
| 905669 | N/A | N/A | 8835 | 8850 | GCTGAAGCTTTAAACT | 7 | 291 |
| 905701 | N/A | N/A | 8899 | 8914 | GTGGGACTTGTTTTAT | 72 | 292 |
| 905733 | N/A | N/A | 8963 | 8978 | GGGAGTGCATAACAGC | 30 | 293 |

TABLE 5

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ SEQ ID NO |
|---|---|---|---|---|---|---|---|
| 793406 | N/A | N/A | 8306 | 8321 | GTTCAAAAGCAGCATT | 85 | 13 |
| 903430 | 28 | 43 | 521 | 536 | TCCCCAAGATATACCG | 0 | 294 |
| 903462 | 132 | 147 | 625 | 640 | AGGAATCTTCCCCTGG | 0 | 295 |
| 903494 | 257 | 272 | N/A | N/A | TGCACCCTCGCTCCAG | 6 | 296 |
| 903526 | 324 | 339 | 4799 | 4814 | AGCAGCCCAGTCACCG | 0 | 297 |
| 903622 | 564 | 579 | 12655 | 12670 | TCTGTACTGCTGGCCT | 46 | 298 |
| 903654 | 633 | 648 | 12724 | 12739 | GGCACGGAGCCTTCTT | 13 | 299 |
| 903686 | 674 | 689 | 12765 | 12780 | ATGGTGGTGCCTTTGT | 0 | 300 |
| 903718 | 745 | 760 | 12836 | 12851 | GTGCCAGACCCATGCC | 32 | 301 |
| 903750 | 818 | 833 | 12909 | 12924 | CCGGTCAAAGCGGCTG | 0 | 302 |
| 903782 | 854 | 869 | 12945 | 12960 | CACTTCTTTCCGTAGT | 0 | 303 |

TABLE 5-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ SEQ ID NO |
|---|---|---|---|---|---|---|---|
| 903814 | 941 | 956 | 13032 | 13047 | GATATGTTCTCACCCA | 94 | 304 |
| 903846 | 1013 | 1028 | 13104 | 13119 | CTGAGGGCACGGATGT | 65 | 305 |
| 903878 | 1091 | 1106 | 13182 | 13197 | TCAGCTGAGATTGGCT | 0 | 306 |
| 903910 | 1131 | 1146 | 13222 | 13237 | GATGCTGGGTTCATTA | 0 | 307 |
| 903942 | 1235 | 1250 | 13326 | 13341 | TCATGTAAGTGCTTTG | 85 | 308 |
| 903974 | 1349 | 1364 | 13440 | 13455 | CACAGTTCTTGGTCCG | 89 | 309 |
| 904006 | 1747 | 1762 | 13838 | 13853 | TACCTCACCCTCTTTA | 66 | 310 |
| 904038 | 1828 | 1843 | 13919 | 13934 | ACTGCCATCTGCATTA | 0 | 311 |
| 904070 | 1943 | 1958 | 14034 | 14049 | GCCCCCCAATATATTC | 29 | 312 |
| 904102 | 2341 | 2356 | 14432 | 14447 | TGTTCTAACTCTTGGG | 90 | 313 |
| 904134 | 2417 | 2432 | 14508 | 14523 | GACTTCATTCTTCGGA | 85 | 314 |
| 904166 | 2515 | 2530 | 14606 | 14621 | CATCATCAGGAAGCCG | 88 | 315 |
| 904198 | 2615 | 2630 | 14706 | 14721 | ATGGCCATGGCCCACC | 0 | 316 |
| 904230 | 2768 | 2783 | 14859 | 14874 | TGAGCTTCCTCCCAAT | 35 | 317 |
| 904262 | 2840 | 2855 | 14931 | 14946 | GATGAGTAGGTGAGTT | 82 | 318 |
| 904326 | N/A | N/A | 1379 | 1394 | GAATCTCATGATTGCA | 68 | 319 |
| 904358 | N/A | N/A | 919 | 934 | AGATGGGCACCCCCAA | 3 | 320 |
| 904390 | N/A | N/A | 2533 | 2548 | TTCCGGGAAGTGACTT | 27 | 321 |
| 904422 | N/A | N/A | 3539 | 3554 | AACACCAATTAGTACA | 64 | 322 |
| 904454 | N/A | N/A | 4384 | 4399 | CAATGACCAGGGCCTG | 30 | 323 |
| 904486 | N/A | N/A | 4822 | 4837 | AGCCTACCTGGGTCCA | 0 | 324 |
| 904518 | N/A | N/A | 5068 | 5083 | TGAGTCATTTGCTAGG | 48 | 325 |
| 904550 | N/A | N/A | 5194 | 5209 | GAGGTGACAGGTCGGG | 33 | 326 |
| 904582 | N/A | N/A | 5307 | 5322 | CGATACATTCCCACAG | 29 | 327 |
| 904614 | N/A | N/A | 5406 | 5421 | ATGGTACAGGAGAAGG | 89 | 328 |
| 904646 | N/A | N/A | 5494 | 5509 | GGAGGCCCTATTGTGT | 10 | 329 |
| 904678 | N/A | N/A | 5696 | 5711 | CTATTGGGCCTCAGAT | 49 | 330 |
| 904710 | N/A | N/A | 5771 | 5786 | ATAGCACGAAGCCTCC | 72 | 331 |
| 904742 | N/A | N/A | 5814 | 5829 | TTCATATTCACCCGAT | 66 | 332 |
| 904774 | N/A | N/A | 5873 | 5888 | GTAAACCCAAACAGGC | 71 | 333 |
| 904806 | N/A | N/A | 5937 | 5952 | CCTGTATTCGGAGACC | 66 | 334 |
| 904838 | N/A | N/A | 5972 | 5987 | ATCAAAAACCTGGGCA | 75 | 335 |
| 904870 | N/A | N/A | 6143 | 6158 | TTATGCTTACTCCACA | 71 | 336 |
| 904902 | N/A | N/A | 6214 | 6229 | ATGCCCATGTTTGGTA | 0 | 337 |
| 904934 | N/A | N/A | 6266 | 6281 | CCTCCTTGTCTCACTA | 0 | 338 |
| 904966 | N/A | N/A | 6334 | 6349 | AGCTAAGACCAGTGAG | 21 | 339 |

TABLE 5-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ SEQ ID NO |
|---|---|---|---|---|---|---|---|
| 904998 | N/A | N/A | 6406 | 6421 | CTGAAACCACCTGTAG | 47 | 340 |
| 905030 | N/A | N/A | 6546 | 6561 | CAGATGGGTACTTCTG | 41 | 341 |
| 905062 | N/A | N/A | 6609 | 6624 | GCCTTTAGAACAGCTG | 23 | 342 |
| 905094 | N/A | N/A | 6700 | 6715 | ATTTCTTGATGTGGTG | 98 | 343 |
| 905126 | N/A | N/A | 6798 | 6813 | GGCGAGCGATTGTCTT | 84 | 344 |
| 905158 | N/A | N/A | 6883 | 6898 | TGGTTGCCGTGGCAAC | 0 | 345 |
| 905190 | N/A | N/A | 7059 | 7074 | ATCATCTTGTTTTGGG | 80 | 346 |
| 905222 | N/A | N/A | 7163 | 7178 | TTGAGGCACCTCCATG | 0 | 347 |
| 905254 | N/A | N/A | 7263 | 7278 | ATGCAAAGGAGATTCC | 28 | 348 |
| 905286 | N/A | N/A | 7344 | 7359 | TTCTCCCTTATAGCTT | 33 | 349 |
| 905318 | N/A | N/A | 7479 | 7494 | AGCGAGAGTCACCGCC | 4 | 350 |
| 905350 | N/A | N/A | 7847 | 7862 | GTTTCTTGCCGTGCAC | 22 | 351 |
| 905382 | N/A | N/A | 7960 | 7975 | GTCAGCTGCCACCAAA | 76 | 352 |
| 905414 | N/A | N/A | 8010 | 8025 | GGTAGGTCTACAAAGA | 78 | 353 |
| 905446 | N/A | N/A | 8095 | 8110 | GAGGCTGGACTGCTCC | 0 | 354 |
| 905478 | N/A | N/A | 8179 | 8194 | CCAGATGTGTTTAGGC | 87 | 355 |
| 905510 | N/A | N/A | 8332 | 8347 | CACATCATTGGGTTAT | 92 | 356 |
| 905542 | N/A | N/A | 8390 | 8405 | GCCACATGCCTGTTGG | 0 | 357 |
| 905574 | N/A | N/A | 8481 | 8496 | GAGAGGAATGAATCCT | 37 | 358 |
| 905606 | N/A | N/A | 8644 | 8659 | GAGTCCTCCCCAGACT | 0 | 359 |
| 905638 | N/A | N/A | 8750 | 8765 | GCTCTAATTCTATTAG | 0 | 360 |
| 905670 | N/A | N/A | 8836 | 8851 | TGCTGAAGCTTTAAAC | 13 | 361 |
| 905702 | N/A | N/A | 8900 | 8915 | TGTGGGACTTGTTTTA | 64 | 362 |
| 905734 | N/A | N/A | 8965 | 8980 | GTGGGAGTGCATAACA | 0 | 363 |

TABLE 6

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 793406 | N/A | N/A | 8306 | 8321 | GTTCAAAAGCAGCATT | 80 | 13 |
| 903431 | 29 | 44 | 522 | 537 | GTCCCCAAGATATACC | 2 | 364 |
| 903463 | 135 | 150 | 628 | 643 | CCAAGGAATCTTCCCC | 53 | 365 |
| 903495 | 258 | 273 | N/A | N/A | TTGCACCCTCGCTCCA | 25 | 366 |
| 903527 | 329 | 344 | 4804 | 4819 | GTGCCAGCAGCCCAGT | 0 | 367 |
| 903623 | 565 | 580 | 12656 | 12671 | TTCTGTACTGCTGGCC | 15 | 368 |

TABLE 6-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 903655 | 634 | 649 | 12725 | 12740 | GGGCACGGAGCCTTCT | 0 | 369 |
| 903687 | 675 | 690 | 12766 | 12781 | GATGGTGGTGCCTTTG | 0 | 370 |
| 903719 | 746 | 761 | 12837 | 12852 | GGTGCCAGACCCATGC | 0 | 371 |
| 903751 | 819 | 834 | 12910 | 12925 | CCCGGTCAAAGCGGCT | 0 | 372 |
| 903783 | 855 | 870 | 12946 | 12961 | CCACTTCTTTCCGTAG | 51 | 373 |
| 903815 | 946 | 961 | 13037 | 13052 | AGTTGGATATGTTCTC | 81 | 374 |
| 903847 | 1014 | 1029 | 13105 | 13120 | TCTGAGGGCACGGATG | 24 | 375 |
| 903879 | 1092 | 1107 | 13183 | 13198 | TTCAGCTGAGATTGGC | 49 | 376 |
| 903911 | 1132 | 1147 | 13223 | 13238 | GGATGCTGGGTTCATT | 41 | 377 |
| 903943 | 1236 | 1251 | 13327 | 13342 | CTCATGTAAGTGCTTT | 81 | 378 |
| 903975 | 1351 | 1366 | 13442 | 13457 | GTCACAGTTCTTGGTC | 54 | 379 |
| 904007 | 1748 | 1763 | 13839 | 13854 | TTACCTCACCCTCTTT | 64 | 380 |
| 904039 | 1829 | 1844 | 13920 | 13935 | CACTGCCATCTGCATT | 57 | 381 |
| 904071 | 1944 | 1959 | 14035 | 14050 | GGCCCCCCAATATATT | 0 | 382 |
| 904103 | 2342 | 2357 | 14433 | 14448 | CTGTTCTAACTCTTGG | 93 | 383 |
| 904135 | 2418 | 2433 | 14509 | 14524 | AGACTTCATTCTTCGG | 69 | 384 |
| 904167 | 2516 | 2531 | 14607 | 14622 | CCATCATCAGGAAGCC | 87 | 385 |
| 904199 | 2620 | 2635 | 14711 | 14726 | GGACCATGGCCATGGC | 0 | 386 |
| 904231 | 2772 | 2787 | 14863 | 14878 | GATCTGAGCTTCCTCC | 44 | 387 |
| 904263 | 2841 | 2856 | 14932 | 14947 | TGATGAGTAGGTGAGT | 81 | 388 |
| 904327 | N/A | N/A | 1380 | 1395 | TGAATCTCATGATTGC | 75 | 389 |
| 904359 | N/A | N/A | 1002 | 1017 | GTGTGGCCTGGCCATA | 0 | 390 |
| 904391 | N/A | N/A | 2544 | 2559 | CGGTTGGTCAATTCCG | 0 | 391 |
| 904423 | N/A | N/A | 3741 | 3756 | CAGAGGCTATCAACAA | 90 | 392 |
| 904455 | N/A | N/A | 4391 | 4406 | GTTCTGACAATGACCA | 50 | 393 |
| 904487 | N/A | N/A | 4830 | 4845 | AGGAGGTGAGCCTACC | 0 | 394 |
| 904519 | N/A | N/A | 5069 | 5084 | TTGAGTCATTTGCTAG | 47 | 395 |
| 904551 | N/A | N/A | 5196 | 5211 | GGGAGGTGACAGGTCG | 36 | 396 |
| 904583 | N/A | N/A | 5309 | 5324 | CCCGATACATTCCCAC | 50 | 397 |
| 904615 | N/A | N/A | 5407 | 5422 | CATGGTACAGGAGAAG | 32 | 398 |
| 904647 | N/A | N/A | 5495 | 5510 | GGGAGGCCCTATTGTG | 14 | 399 |
| 904679 | N/A | N/A | 5697 | 5712 | TCTATTGGGCCTCAGA | 15 | 400 |
| 904711 | N/A | N/A | 5772 | 5787 | CATAGCACGAAGCCTC | 70 | 401 |
| 904743 | N/A | N/A | 5815 | 5830 | TTTCATATTCACCCGA | 87 | 402 |
| 904775 | N/A | N/A | 5874 | 5889 | GGTAAACCCAAACAGG | 54 | 403 |
| 904807 | N/A | N/A | 5938 | 5953 | ACCTGTATTCGGAGAC | 58 | 404 |
| 904839 | N/A | N/A | 5974 | 5989 | GCATCAAAAACCTGGG | 52 | 405 |

TABLE 6-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904871 | N/A | N/A | 6144 | 6159 | CTTATGCTTACTCCAC | 85 | 406 |
| 904903 | N/A | N/A | 6215 | 6230 | TATGCCCATGTTTGGT | 51 | 407 |
| 904935 | N/A | N/A | 6268 | 6283 | ACCCTCCTTGTCTCAC | 37 | 408 |
| 904967 | N/A | N/A | 6335 | 6350 | CAGCTAAGACCAGTGA | 65 | 409 |
| 904999 | N/A | N/A | 6407 | 6422 | GCTGAAACCACCTGTA | 66 | 410 |
| 905031 | N/A | N/A | 6547 | 6562 | TCAGATGGGTACTTCT | 89 | 411 |
| 905063 | N/A | N/A | 6610 | 6625 | GGCCTTTAGAACAGCT | 0 | 412 |
| 905095 | N/A | N/A | 6702 | 6717 | GTATTTCTTGATGTGG | 98 | 413 |
| 905127 | N/A | N/A | 6799 | 6814 | GGGCGAGCGATTGTCT | 16 | 414 |
| 905159 | N/A | N/A | 6884 | 6899 | TTGGTTGCCGTGGCAA | 6 | 415 |
| 905191 | N/A | N/A | 7060 | 7075 | GATCATCTTGTTTTGG | 51 | 416 |
| 905223 | N/A | N/A | 7164 | 7179 | CTTGAGGCACCTCCAT | 35 | 417 |
| 905255 | N/A | N/A | 7264 | 7279 | CATGCAAAGGAGATTC | 0 | 418 |
| 905287 | N/A | N/A | 7345 | 7360 | ATTCTCCCTTATAGCT | 15 | 419 |
| 905319 | N/A | N/A | 7480 | 7495 | CAGCGAGAGTCACCGC | 0 | 420 |
| 905351 | N/A | N/A | 7848 | 7863 | TGTTTCTTGCCGTGCA | 34 | 421 |
| 905383 | N/A | N/A | 7963 | 7978 | GAAGTCAGCTGCCACC | 87 | 422 |
| 905415 | N/A | N/A | 8011 | 8026 | TGGTAGGTCTACAAAG | 76 | 423 |
| 905447 | N/A | N/A | 8109 | 8124 | GACCATTCCCAGCAGA | 65 | 424 |
| 905479 | N/A | N/A | 8180 | 8195 | TCCAGATGTGTTTAGG | 83 | 425 |
| 905511 | N/A | N/A | 8333 | 8348 | ACACATCATTGGGTTA | 85 | 426 |
| 905543 | N/A | N/A | 8404 | 8419 | GATCACTTCCATCTGC | 0 | 427 |
| 905575 | N/A | N/A | 8492 | 8507 | ATGGTGCTTTGGAGAG | 5 | 428 |
| 905607 | N/A | N/A | 8649 | 8664 | CAAGAGAGTCCTCCCC | 57 | 429 |
| 905639 | N/A | N/A | 8751 | 8766 | GGCTCTAATTCTATTA | 0 | 430 |
| 905671 | N/A | N/A | 8862 | 8877 | GGAATTGTGTGCCCCC | 43 | 431 |
| 905703 | N/A | N/A | 8902 | 8917 | GATGTGGGACTTGTTT | 82 | 432 |
| 905735 | N/A | N/A | 8966 | 8981 | TGTGGGAGTGCATAAC | 0 | 433 |

TABLE 7

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 793406 | N/A | N/A | 8306 | 8321 | GTTCAAAAGCAGCATT | 86 | 13 |
| 903432 | 30 | 45 | 523 | 538 | AGTCCCCAAGATATAC | 0 | 434 |

TABLE 7-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 903464 | 142 | 157 | N/A | N/A | GCCTCCTCCAAGGAAT | 9 | 435 |
| 903496 | 259 | 274 | N/A | N/A | GTTGCACCCTCGCTCC | 13 | 436 |
| 903528 | 331 | 346 | 4806 | 4821 | TGGTGCCAGCAGCCCA | 0 | 437 |
| 903624 | 566 | 581 | 12657 | 12672 | TTTCTGTACTGCTGGC | 64 | 438 |
| 903656 | 635 | 650 | 12726 | 12741 | AGGGCACGGAGCCTTC | 0 | 439 |
| 903688 | 676 | 691 | 12767 | 12782 | CGATGGTGGTGCCTTT | 0 | 440 |
| 903720 | 747 | 762 | 12838 | 12853 | GGGTGCCAGACCCATG | 5 | 441 |
| 903752 | 820 | 835 | 12911 | 12926 | TCCCGGTCAAAGCGGC | 0 | 442 |
| 903784 | 856 | 871 | 12947 | 12962 | ACCACTTCTTTCCGTA | 23 | 443 |
| 903816 | 947 | 962 | 13038 | 13053 | AAGTTGGATATGTTCT | 74 | 444 |
| 903848 | 1015 | 1030 | 13106 | 13121 | GTCTGAGGGCACGGAT | 37 | 445 |
| 903880 | 1093 | 1108 | 13184 | 13199 | TTTCAGCTGAGATTGG | 56 | 446 |
| 903912 | 1133 | 1148 | 13224 | 13239 | AGGATGCTGGGTTCAT | 66 | 447 |
| 903944 | 1237 | 1252 | 13328 | 13343 | CCTCATGTAAGTGCTT | 70 | 448 |
| 903976 | 1353 | 1368 | 13444 | 13459 | TGGTCACAGTTCTTGG | 89 | 449 |
| 904008 | 1751 | 1766 | 13842 | 13857 | ACTTTACCTCACCCTC | 80 | 450 |
| 904040 | 1830 | 1845 | 13921 | 13936 | GCACTGCCATCTGCAT | 23 | 451 |
| 904072 | 1945 | 1960 | 14036 | 14051 | CGGCCCCCCAATATAT | 0 | 452 |
| 904104 | 2343 | 2358 | 14434 | 14449 | ACTGTTCTAACTCTTG | 90 | 453 |
| 904136 | 2419 | 2434 | 14510 | 14525 | AAGACTTCATTCTTCG | 23 | 454 |
| 904168 | 2517 | 2532 | 14608 | 14623 | ACCATCATCAGGAAGC | 82 | 455 |
| 904200 | 2621 | 2636 | 14712 | 14727 | GGGACCATGGCCATGG | 74 | 456 |
| 904232 | 2773 | 2788 | 14864 | 14879 | AGATCTGAGCTTCCTC | 9 | 457 |
| 904264 | 2842 | 2857 | 14933 | 14948 | TTGATGAGTAGGTGAG | 93 | 458 |
| 904328 | N/A | N/A | 1381 | 1396 | TTGAATCTCATGATTG | 48 | 459 |
| 904360 | N/A | N/A | 1049 | 1064 | TGTTGCCCCCATTGGG | 3 | 460 |
| 904392 | N/A | N/A | 2549 | 2564 | TCTGCCGGTTGGTCAA | 18 | 461 |
| 904424 | N/A | N/A | 3753 | 3768 | GAATGAGCAGGTCAGA | 95 | 462 |
| 904456 | N/A | N/A | 4392 | 4407 | GGTTCTGACAATGACC | 37 | 463 |
| 904488 | N/A | N/A | 4831 | 4846 | GAGGAGGTGAGCCTAC | 35 | 464 |
| 904520 | N/A | N/A | 5070 | 5085 | CTTGAGTCATTTGCTA | 63 | 465 |
| 904552 | N/A | N/A | 5197 | 5212 | CGGGAGGTGACAGGTC | 41 | 466 |
| 904584 | N/A | N/A | 5310 | 5325 | GCCCGATACATTCCCA | 16 | 467 |
| 904616 | N/A | N/A | 5409 | 5424 | CTCATGGTACAGGAGA | 56 | 468 |
| 904648 | N/A | N/A | 5496 | 5511 | AGGGAGGCCCTATTGT | 14 | 469 |
| 904680 | N/A | N/A | 5698 | 5713 | TTCTATTGGGCCTCAG | 90 | 470 |
| 904712 | N/A | N/A | 5773 | 5788 | CCATAGCACGAAGCCT | 72 | 471 |

TABLE 7-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904744 | N/A | N/A | 5816 | 5831 | GTTTCATATTCACCCG | 95 | 472 |
| 904776 | N/A | N/A | 5875 | 5890 | AGGTAAACCCAAACAG | 59 | 473 |
| 904808 | N/A | N/A | 5939 | 5954 | CACCTGTATTCGGAGA | 16 | 474 |
| 904840 | N/A | N/A | 5975 | 5990 | AGCATCAAAAACCTGG | 88 | 475 |
| 904872 | N/A | N/A | 6145 | 6160 | CCTTATGCTTACTCCA | 92 | 476 |
| 904904 | N/A | N/A | 6216 | 6231 | GTATGCCCATGTTTGG | 34 | 477 |
| 904936 | N/A | N/A | 6269 | 6284 | TACCCTCCTTGTCTCA | 54 | 478 |
| 904968 | N/A | N/A | 6336 | 6351 | TCAGCTAAGACCAGTG | 89 | 479 |
| 905000 | N/A | N/A | 6409 | 6424 | TTGCTGAAACCACCTG | 74 | 480 |
| 905032 | N/A | N/A | 6548 | 6563 | ATCAGATGGGTACTTC | 94 | 481 |
| 905064 | N/A | N/A | 6611 | 6626 | AGGCCTTTAGAACAGC | 26 | 482 |
| 905096 | N/A | N/A | 6714 | 6729 | CACTAAATCTGTGTAT | 8 | 483 |
| 905128 | N/A | N/A | 6800 | 6815 | TGGGCGAGCGATTGTC | 87 | 484 |
| 905160 | N/A | N/A | 6885 | 6900 | CTTGGTTGCCGTGGCA | 27 | 485 |
| 905192 | N/A | N/A | 7076 | 7091 | CTGTTATTAAACCACA | 67 | 486 |
| 905224 | N/A | N/A | 7165 | 7180 | CCTTGAGGCACCTCCA | 35 | 487 |
| 905256 | N/A | N/A | 7265 | 7280 | CCATGCAAAGGAGATT | 68 | 488 |
| 905288 | N/A | N/A | 7346 | 7361 | CATTCTCCCTTATAGC | 42 | 489 |
| 905320 | N/A | N/A | 7481 | 7496 | ACAGCGAGAGTCACCG | 78 | 490 |
| 905352 | N/A | N/A | 7849 | 7864 | TTGTTTCTTGCCGTGC | 57 | 491 |
| 905384 | N/A | N/A | 7964 | 7979 | TGAAGTCAGCTGCCAC | 79 | 492 |
| 905416 | N/A | N/A | 8012 | 8027 | ATGGTAGGTCTACAAA | 64 | 493 |
| 905448 | N/A | N/A | 8115 | 8130 | ATTCCTGACCATTCCC | 75 | 494 |
| 905480 | N/A | N/A | 8181 | 8196 | ATCCAGATGTGTTTAG | 86 | 495 |
| 905512 | N/A | N/A | 8334 | 8349 | AACACATCATTGGGTT | 27 | 496 |
| 905544 | N/A | N/A | 8405 | 8420 | TGATCACTTCCATCTG | 0 | 497 |
| 905576 | N/A | N/A | 8493 | 8508 | CATGGTGCTTTGGAGA | 40 | 498 |
| 905608 | N/A | N/A | 8659 | 8674 | CATAAGCCAGCAAGAG | 40 | 499 |
| 905640 | N/A | N/A | 8752 | 8767 | GGGCTCTAATTCTATT | 0 | 500 |
| 905672 | N/A | N/A | 8863 | 8878 | GGGAATTGTGTGCCCC | 24 | 501 |
| 905704 | N/A | N/A | 8903 | 8918 | TGATGTGGGACTTGTT | 92 | 502 |
| 905736 | N/A | N/A | 8967 | 8982 | GTGTGGGAGTGCATAA | 0 | 503 |

TABLE 8

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 793406 | N/A | N/A | 8306 | 8321 | GTTCAAAAGCAGCATT | 80 | 13 |
| 903433 | 31 | 46 | 524 | 539 | CAGTCCCCAAGATATA | 24 | 504 |
| 903465 | 144 | 159 | N/A | N/A | GGGCCTCCTCCAAGGA | 0 | 505 |
| 903497 | 260 | 275 | N/A | N/A | TGTTGCACCCTCGCTC | 42 | 506 |
| 903529 | 332 | 347 | 4807 | 4822 | ATGGTGCCAGCAGCCC | 0 | 507 |
| 903625 | 567 | 582 | 12658 | 12673 | GTTTCTGTACTGCTGG | 72 | 508 |
| 903657 | 636 | 651 | 12727 | 12742 | AAGGGCACGGAGCCTT | 61 | 509 |
| 903689 | 677 | 692 | 12768 | 12783 | GCGATGGTGGTGCCTT | 32 | 510 |
| 903721 | 748 | 763 | 12839 | 12854 | AGGGTGCCAGACCCAT | 0 | 511 |
| 903753 | 821 | 836 | 12912 | 12927 | ATCCCGGTCAAAGCGG | 0 | 512 |
| 903785 | 857 | 872 | 12948 | 12963 | CACCACTTCTTTCCGT | 22 | 513 |
| 903817 | 949 | 964 | 13040 | 13055 | GAAAGTTGGATATGTT | 83 | 514 |
| 903849 | 1016 | 1031 | 13107 | 13122 | CGTCTGAGGGCACGGA | 15 | 515 |
| 903881 | 1094 | 1109 | 13185 | 13200 | CTTTCAGCTGAGATTG | 57 | 516 |
| 903913 | 1134 | 1149 | 13225 | 13240 | CAGGATGCTGGGTTCA | 76 | 517 |
| 903945 | 1238 | 1253 | 13329 | 13344 | CCCTCATGTAAGTGCT | 67 | 518 |
| 903977 | 1354 | 1369 | 13445 | 13460 | GTGGTCACAGTTCTTG | 0 | 519 |
| 904009 | 1752 | 1767 | 13843 | 13858 | AACTTTACCTCACCCT | 87 | 520 |
| 904041 | 1838 | 1853 | 13929 | 13944 | TCCTTGCTGCACTGCC | 94 | 521 |
| 904073 | 1946 | 1961 | 14037 | 14052 | CCGGCCCCCCAATATA | 3 | 522 |
| 904105 | 2345 | 2360 | 14436 | 14451 | CAACTGTTCTAACTCT | 74 | 523 |
| 904137 | 2482 | 2497 | 14573 | 14588 | GCCCCCAGGAGGACAA | 5 | 524 |
| 904169 | 2518 | 2533 | 14609 | 14624 | GACCATCATCAGGAAG | 79 | 525 |
| 904201 | 2672 | 2687 | 14763 | 14778 | CACATACTCTCTGGGA | 47 | 526 |
| 904233 | 2774 | 2789 | 14865 | 14880 | GAGATCTGAGCTTCCT | 88 | 527 |
| 904265 | 2843 | 2858 | 14934 | 14949 | CTTGATGAGTAGGTGA | 78 | 528 |
| 904361 | N/A | N/A | 1052 | 1067 | TTCTGTTGCCCCCATT | 68 | 529 |
| 904393 | N/A | N/A | 2558 | 2573 | CTGGGCGAGTCTGCCG | 0 | 530 |
| 904425 | N/A | N/A | 3756 | 3771 | GTAGAATGAGCAGGTC | 97 | 531 |
| 904457 | N/A | N/A | 4426 | 4441 | AGAGTCTATACACAGA | 75 | 532 |
| 904489 | N/A | N/A | 4851 | 4866 | GAGTAGGAACCAGCAG | 84 | 533 |
| 904521 | N/A | N/A | 5071 | 5086 | ACTTGAGTCATTTGCT | 85 | 534 |
| 904553 | N/A | N/A | 5198 | 5213 | GCGGGAGGTGACAGGT | 33 | 535 |
| 904585 | N/A | N/A | 5311 | 5326 | GGCCCGATACATTCCC | 0 | 536 |
| 904617 | N/A | N/A | 5410 | 5425 | TCTCATGGTACAGGAG | 75 | 537 |
| 904649 | N/A | N/A | 5497 | 5512 | TAGGGAGGCCCTATTG | 14 | 538 |
| 904681 | N/A | N/A | 5699 | 5714 | ATTCTATTGGGCCTCA | 89 | 539 |

TABLE 8-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904713 | N/A | N/A | 5775 | 5790 | CACCATAGCACGAAGC | 90 | 540 |
| 904745 | N/A | N/A | 5817 | 5832 | AGTTTCATATTCACCC | 95 | 541 |
| 904777 | N/A | N/A | 5877 | 5892 | CAAGGTAAACCCAAAC | 30 | 542 |
| 904809 | N/A | N/A | 5940 | 5955 | TCACCTGTATTCGGAG | 32 | 543 |
| 904841 | N/A | N/A | 6017 | 6032 | CTAAAAGCTGATTTGC | 52 | 544 |
| 904873 | N/A | N/A | 6146 | 6161 | TCCTTATGCTTACTCC | 93 | 545 |
| 904905 | N/A | N/A | 6219 | 6234 | CATGTATGCCCATGTT | 61 | 546 |
| 904937 | N/A | N/A | 6270 | 6285 | ATACCCTCCTTGTCTC | 39 | 547 |
| 904969 | N/A | N/A | 6337 | 6352 | TTCAGCTAAGACCAGT | 89 | 548 |
| 905001 | N/A | N/A | 6410 | 6425 | GTTGCTGAAACCACCT | 64 | 549 |
| 905033 | N/A | N/A | 6549 | 6564 | TATCAGATGGGTACTT | 66 | 550 |
| 905065 | N/A | N/A | 6612 | 6627 | GAGGCCTTTAGAACAG | 0 | 551 |
| 905097 | N/A | N/A | 6715 | 6730 | GCACTAAATCTGTGTA | 24 | 552 |
| 905129 | N/A | N/A | 6801 | 6816 | CTGGGCGAGCGATTGT | 61 | 553 |
| 905161 | N/A | N/A | 6886 | 6901 | ACTTGGTTGCCGTGGC | 27 | 554 |
| 905193 | N/A | N/A | 7077 | 7092 | CCTGTTATTAAACCAC | 81 | 555 |
| 905225 | N/A | N/A | 7166 | 7181 | TCCTTGAGGCACCTCC | 32 | 556 |
| 905257 | N/A | N/A | 7266 | 7281 | ACCATGCAAAGGAGAT | 30 | 557 |
| 905289 | N/A | N/A | 7347 | 7362 | GCATTCTCCCTTATAG | 75 | 558 |
| 905321 | N/A | N/A | 7482 | 7497 | GACAGCGAGAGTCACC | 29 | 559 |
| 905353 | N/A | N/A | 7850 | 7865 | ATTGTTTCTTGCCGTG | 55 | 560 |
| 905385 | N/A | N/A | 7967 | 7982 | TCCTGAAGTCAGCTGC | 56 | 561 |
| 905417 | N/A | N/A | 8013 | 8028 | AATGGTAGGTCTACAA | 85 | 562 |
| 905449 | N/A | N/A | 8116 | 8131 | TATTCCTGACCATTCC | 77 | 563 |
| 905481 | N/A | N/A | 8182 | 8197 | AATCCAGATGTGTTTA | 81 | 564 |
| 905513 | N/A | N/A | 8336 | 8351 | TCAACACATCATTGGG | 88 | 565 |
| 905545 | N/A | N/A | 8406 | 8421 | GTGATCACTTCCATCT | 84 | 566 |
| 905577 | N/A | N/A | 8494 | 8509 | CCATGGTGCTTTGGAG | 4 | 567 |
| 905609 | N/A | N/A | 8660 | 8675 | CCATAAGCCAGCAAGA | 53 | 568 |
| 905641 | N/A | N/A | 8753 | 8768 | AGGGCTCTAATTCTAT | 0 | 569 |
| 905673 | N/A | N/A | 8864 | 8879 | AGGGAATTGTGTGCCC | 11 | 570 |
| 905705 | N/A | N/A | 8904 | 8919 | GTGATGTGGGACTTGT | 80 | 571 |
| 905737 | N/A | N/A | 8968 | 8983 | AGTGTGGGAGTGCATA | 0 | 572 |

TABLE 9

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 793406 | N/A | N/A | 8306 | 8321 | GTTCAAAAGCAGCATT | 83 | 13 |
| 903434 | 32 | 47 | 525 | 540 | CCAGTCCCCAAGATAT | 31 | 573 |
| 903466 | 152 | 167 | 2362 | 2377 | TCGCTGCAGGGCCTCC | 26 | 574 |
| 903498 | 261 | 276 | N/A | N/A | TTGTTGCACCCTCGCT | 61 | 575 |
| 903530 | 343 | 358 | N/A | N/A | TCTCTGGGTCCATGGT | 0 | 576 |
| 903626 | 568 | 583 | 12659 | 12674 | AGTTTCTGTACTGCTG | 58 | 577 |
| 903658 | 637 | 652 | 12728 | 12743 | CAAGGGCACGGAGCCT | 1 | 578 |
| 903690 | 678 | 693 | 12769 | 12784 | GGCGATGGTGGTGCCT | 17 | 579 |
| 903722 | 756 | 771 | 12847 | 12862 | CTCTGTGAAGGGTGCC | 39 | 580 |
| 903754 | 822 | 837 | 12913 | 12928 | AATCCCGGTCAAAGCG | 21 | 581 |
| 903786 | 858 | 873 | 12949 | 12964 | CCACCACTTCTTTCCG | 48 | 582 |
| 903818 | 966 | 981 | 13057 | 13072 | ATTGCCAGCTAAGGAA | 51 | 583 |
| 903850 | 1030 | 1045 | 13121 | 13136 | GATTGGCTCTGGCTCG | 56 | 584 |
| 903882 | 1095 | 1110 | 13186 | 13201 | GCTTTCAGCTGAGATT | 6 | 585 |
| 903914 | 1152 | 1167 | 13243 | 13258 | GACTCCTCTGCTCATT | 84 | 586 |
| 903946 | 1239 | 1254 | 13330 | 13345 | CCCCTCATGTAAGTGC | 43 | 587 |
| 903978 | 1359 | 1374 | 13450 | 13465 | GCCCTGTGGTCACAGT | 31 | 588 |
| 904010 | 1753 | 1768 | 13844 | 13859 | AAACTTTACCTCACCC | 71 | 589 |
| 904042 | 1840 | 1855 | 13931 | 13946 | TCTCCTTGCTGCACTG | 92 | 590 |
| 904074 | 1947 | 1962 | 14038 | 14053 | CCCGGCCCCCCAATAT | 0 | 591 |
| 904106 | 2346 | 2361 | 14437 | 14452 | CCAACTGTTCTAACTC | 89 | 592 |
| 904138 | 2484 | 2499 | 14575 | 14590 | ATGCCCCCAGGAGGAC | 29 | 593 |
| 904170 | 2522 | 2537 | 14613 | 14628 | CAATGACCATCATCAG | 45 | 594 |
| 904202 | 2673 | 2688 | 14764 | 14779 | TCACATACTCTCTGGG | 79 | 595 |
| 904234 | 2775 | 2790 | 14866 | 14881 | AGAGATCTGAGCTTCC | 74 | 596 |
| 904266 | 2844 | 2859 | 14935 | 14950 | GCTTGATGAGTAGGTG | 54 | 597 |
| 904298 | N/A | N/A | 2349 | 2364 | TCCTCCTTGAGCAGGA | 29 | 598 |
| 904362 | N/A | N/A | 1077 | 1092 | TGAACTCCTTGTACCT | 51 | 599 |
| 904394 | N/A | N/A | 2565 | 2580 | GTCCTCCCTGGGCGAG | 33 | 600 |
| 904426 | N/A | N/A | 3793 | 3808 | CCACATTTGAGATTAT | 88 | 601 |
| 904458 | N/A | N/A | 4457 | 4472 | CGGGCAGCCATCTGAT | 0 | 602 |
| 904490 | N/A | N/A | 4870 | 4885 | CACCCTCCATTCTAAG | 0 | 603 |
| 904522 | N/A | N/A | 5072 | 5087 | CACTTGAGTCATTTGC | 84 | 604 |
| 904554 | N/A | N/A | 5199 | 5214 | AGCGGGAGGTGACAGG | 34 | 605 |
| 904586 | N/A | N/A | 5312 | 5327 | AGGCCCGATACATTCC | 26 | 606 |
| 904618 | N/A | N/A | 5411 | 5426 | TTCTCATGGTACAGGA | 65 | 607 |
| 904650 | N/A | N/A | 5498 | 5513 | TTAGGGAGGCCCTATT | 6 | 608 |

TABLE 9-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 904682 | N/A | N/A | 5700 | 5715 | AATTCTATTGGGCCTC | 64 | 609 |
| 904714 | N/A | N/A | 5776 | 5791 | TCACCATAGCACGAAG | 86 | 610 |
| 904746 | N/A | N/A | 5819 | 5834 | GCAGTTTCATATTCAC | 96 | 611 |
| 904778 | N/A | N/A | 5887 | 5902 | GATTTTCCAACAAGGT | 84 | 612 |
| 904810 | N/A | N/A | 5941 | 5956 | CTCACCTGTATTCGGA | 27 | 613 |
| 904842 | N/A | N/A | 6020 | 6035 | GCACTAAAAGCTGATT | 70 | 614 |
| 904874 | N/A | N/A | 6150 | 6165 | GAAATCCTTATGCTTA | 69 | 615 |
| 904906 | N/A | N/A | 6220 | 6235 | CCATGTATGCCCATGT | 79 | 616 |
| 904938 | N/A | N/A | 6271 | 6286 | CATACCCTCCTTGTCT | 21 | 617 |
| 904970 | N/A | N/A | 6339 | 6354 | AATTCAGCTAAGACCA | 77 | 618 |
| 905002 | N/A | N/A | 6411 | 6426 | AGTTGCTGAAACCACC | 68 | 619 |
| 905034 | N/A | N/A | 6550 | 6565 | ATATCAGATGGGTACT | 74 | 620 |
| 905066 | N/A | N/A | 6613 | 6628 | CGAGGCCTTTAGAACA | 19 | 621 |
| 905098 | N/A | N/A | 6716 | 6731 | GGCACTAAATCTGTGT | 0 | 622 |
| 905130 | N/A | N/A | 6802 | 6817 | GCTGGGCGAGCGATTG | 39 | 623 |
| 905162 | N/A | N/A | 6887 | 6902 | GACTTGGTTGCCGTGG | 79 | 624 |
| 905194 | N/A | N/A | 7078 | 7093 | GCCTGTTATTAAACCA | 52 | 625 |
| 905226 | N/A | N/A | 7167 | 7182 | ATCCTTGAGGCACCTC | 64 | 626 |
| 905258 | N/A | N/A | 7268 | 7283 | CTACCATGCAAAGGAG | 38 | 627 |
| 905290 | N/A | N/A | 7348 | 7363 | TGCATTCTCCCTTATA | 19 | 628 |
| 905322 | N/A | N/A | 7483 | 7498 | AGACAGCGAGAGTCAC | 1 | 629 |
| 905354 | N/A | N/A | 7851 | 7866 | AATTGTTTCTTGCCGT | 41 | 630 |
| 905386 | N/A | N/A | 7973 | 7988 | GATTACTCCTGAAGTC | 53 | 631 |
| 905418 | N/A | N/A | 8015 | 8030 | ATAATGGTAGGTCTAC | 87 | 632 |
| 905450 | N/A | N/A | 8117 | 8132 | ATATTCCTGACCATTC | 72 | 633 |
| 905482 | N/A | N/A | 8183 | 8198 | GAATCCAGATGTGTTT | 80 | 634 |
| 905514 | N/A | N/A | 8337 | 8352 | ATCAACACATCATTGG | 62 | 635 |
| 905546 | N/A | N/A | 8407 | 8422 | AGTGATCACTTCCATC | 0 | 636 |
| 905578 | N/A | N/A | 8495 | 8510 | GCCATGGTGCTTTGGA | 0 | 637 |
| 905610 | N/A | N/A | 8663 | 8678 | CTTCCATAAGCCAGCA | 48 | 638 |
| 905642 | N/A | N/A | 8754 | 8769 | TAGGGCTCTAATTCTA | 32 | 639 |
| 905674 | N/A | N/A | 8865 | 8880 | GAGGGAATTGTGTGCC | 58 | 640 |
| 905706 | N/A | N/A | 8905 | 8920 | TGTGATGTGGGACTTG | 82 | 641 |
| 905738 | N/A | N/A | 8969 | 8984 | AAGTGTGGGAGTGCAT | 0 | 642 |

TABLE 10

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 793406 | N/A | N/A | 8306 | 8321 | GTTCAAAAGCAGCATT | 84 | 13 |
| 903435 | 39 | 54 | 532 | 547 | AGGTCCTCCAGTCCCC | 0 | 643 |
| 903467 | 153 | 168 | 2363 | 2378 | GTCGCTGCAGGGCCTC | 4 | 644 |
| 903499 | 262 | 277 | N/A | N/A | TTTGTTGCACCCTCGC | 91 | 645 |
| 903531 | 345 | 360 | N/A | N/A | GCTCTCTGGGTCCATG | 8 | 646 |
| 903627 | 569 | 584 | 12660 | 12675 | CAGTTTCTGTACTGCT | 14 | 647 |
| 903659 | 638 | 653 | 12729 | 12744 | GCAAGGGCACGGAGCC | 0 | 648 |
| 903691 | 679 | 694 | 12770 | 12785 | TGGCGATGGTGGTGCC | 0 | 649 |
| 903723 | 757 | 772 | 12848 | 12863 | CCTCTGTGAAGGGTGC | 24 | 650 |
| 903755 | 823 | 838 | 12914 | 12929 | TAATCCCGGTCAAAGC | 18 | 651 |
| 903787 | 861 | 876 | 12952 | 12967 | TGTCCACCACTTCTTT | 49 | 652 |
| 903819 | 967 | 982 | 13058 | 13073 | TATTGCCAGCTAAGGA | 33 | 653 |
| 903851 | 1031 | 1046 | 13122 | 13137 | AGATTGGCTCTGGCTC | 87 | 654 |
| 903883 | 1096 | 1111 | 13187 | 13202 | CGCTTTCAGCTGAGAT | 0 | 655 |
| 903915 | 1156 | 1171 | 13247 | 13262 | GCTTGACTCCTCTGCT | 6 | 656 |
| 903947 | 1240 | 1255 | 13331 | 13346 | CCCCCTCATGTAAGTG | 25 | 657 |
| 903979 | 1380 | 1395 | 13471 | 13486 | ATCTCTCCTGGTGGCT | 82 | 658 |
| 904011 | 1754 | 1769 | 13845 | 13860 | TAAACTTTACCTCACC | 65 | 659 |
| 904043 | 1841 | 1856 | 13932 | 13947 | TTCTCCTTGCTGCACT | 89 | 660 |
| 904075 | 1948 | 1963 | 14039 | 14054 | ACCCGGCCCCCCAATA | 13 | 661 |
| 904107 | 2347 | 2362 | 14438 | 14453 | TCCAACTGTTCTAACT | 66 | 662 |
| 904139 | 2485 | 2500 | 14576 | 14591 | TATGCCCCCAGGAGGA | 24 | 663 |
| 904171 | 2525 | 2540 | 14616 | 14631 | CCCCAATGACCATCAT | 27 | 664 |
| 904203 | 2678 | 2693 | 14769 | 14784 | GGTTCTCACATACTCT | 96 | 665 |
| 904235 | 2776 | 2791 | 14867 | 14882 | TAGAGATCTGAGCTTC | 43 | 666 |
| 904267 | 2845 | 2860 | 14936 | 14951 | AGCTTGATGAGTAGGT | 0 | 667 |
| 904299 | N/A | N/A | 2352 | 2367 | GCCTCCTCCTTGAGCA | 0 | 668 |
| 904363 | N/A | N/A | 1086 | 1101 | GATGACCTCTGAACTC | 65 | 669 |
| 904395 | N/A | N/A | 2566 | 2581 | GGTCCTCCCTGGGCGA | 7 | 670 |
| 904427 | N/A | N/A | 3795 | 3810 | GCCCACATTTGAGATT | 23 | 671 |
| 904459 | N/A | N/A | 4461 | 4476 | AGGACGGGCAGCCATC | 9 | 672 |
| 904491 | N/A | N/A | 4871 | 4886 | CCACCCTCCATTCTAA | 11 | 673 |
| 904523 | N/A | N/A | 5073 | 5088 | CCACTTGAGTCATTTG | 89 | 674 |
| 904555 | N/A | N/A | 5200 | 5215 | GAGCGGGAGGTGACAG | 16 | 675 |
| 904587 | N/A | N/A | 5313 | 5328 | CAGGCCCGATACATTC | 8 | 676 |
| 904619 | N/A | N/A | 5412 | 5427 | ATTCTCATGGTACAGG | 92 | 677 |
| 904651 | N/A | N/A | 5499 | 5514 | CTTAGGGAGGCCCTAT | 3 | 678 |

TABLE 10-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 904683 | N/A | N/A | 5701 | 5716 | AAATTCTATTGGGCCT | 19 | 679 |
| 904715 | N/A | N/A | 5777 | 5792 | TTCACCATAGCACGAA | 24 | 680 |
| 904747 | N/A | N/A | 5826 | 5841 | CCTTACTGCAGTTTCA | 91 | 681 |
| 904779 | N/A | N/A | 5889 | 5904 | GGGATTTTCCAACAAG | 42 | 682 |
| 904811 | N/A | N/A | 5942 | 5957 | TCTCACCTGTATTCGG | 28 | 683 |
| 904843 | N/A | N/A | 6021 | 6036 | TGCACTAAAAGCTGAT | 21 | 684 |
| 904875 | N/A | N/A | 6152 | 6167 | CAGAAATCCTTATGCT | 25 | 685 |
| 904907 | N/A | N/A | 6221 | 6236 | TCCATGTATGCCCATG | 77 | 686 |
| 904939 | N/A | N/A | 6279 | 6294 | CACTCAATCATACCCT | 43 | 687 |
| 904971 | N/A | N/A | 6340 | 6355 | CAATTCAGCTAAGACC | 54 | 688 |
| 905003 | N/A | N/A | 6413 | 6428 | GGAGTTGCTGAAACCA | 35 | 689 |
| 905035 | N/A | N/A | 6551 | 6566 | CATATCAGATGGGTAC | 65 | 690 |
| 905067 | N/A | N/A | 6614 | 6629 | ACGAGGCCTTTAGAAC | 49 | 691 |
| 905099 | N/A | N/A | 6720 | 6735 | CTCTGGCACTAAATCT | 38 | 692 |
| 905131 | N/A | N/A | 6803 | 6818 | GGCTGGGCGAGCGATT | 44 | 693 |
| 905163 | N/A | N/A | 6888 | 6903 | TGACTTGGTTGCCGTG | 67 | 694 |
| 905195 | N/A | N/A | 7079 | 7094 | GGCCTGTTATTAAACC | 2 | 695 |
| 905227 | N/A | N/A | 7168 | 7183 | GATCCTTGAGGCACCT | 4 | 696 |
| 905259 | N/A | N/A | 7269 | 7284 | ACTACCATGCAAAGGA | 38 | 697 |
| 905291 | N/A | N/A | 7379 | 7394 | CTCCTTATGTTTTGAA | 81 | 698 |
| 905323 | N/A | N/A | 7484 | 7499 | CAGACAGCGAGAGTCA | 22 | 699 |
| 905355 | N/A | N/A | 7852 | 7867 | AAATTGTTTCTTGCCG | 46 | 700 |
| 905387 | N/A | N/A | 7974 | 7989 | GGATTACTCCTGAAGT | 33 | 701 |
| 905419 | N/A | N/A | 8016 | 8031 | AATAATGGTAGGTCTA | 82 | 702 |
| 905451 | N/A | N/A | 8118 | 8133 | TATATTCCTGACCATT | 63 | 703 |
| 905483 | N/A | N/A | 8184 | 8199 | GGAATCCAGATGTGTT | 86 | 704 |
| 905515 | N/A | N/A | 8338 | 8353 | TATCAACACATCATTG | 37 | 705 |
| 905547 | N/A | N/A | 8408 | 8423 | CAGTGATCACTTCCAT | 38 | 706 |
| 905579 | N/A | N/A | 8516 | 8531 | ACATTGAAACACCAGG | 92 | 707 |
| 905611 | N/A | N/A | 8664 | 8679 | GCTTCCATAAGCCAGC | 35 | 708 |
| 905643 | N/A | N/A | 8755 | 8770 | GTAGGGCTCTAATTCT | 56 | 709 |
| 905675 | N/A | N/A | 8866 | 8881 | AGAGGGAATTGTGTGC | 78 | 710 |
| 905707 | N/A | N/A | 8906 | 8921 | CTGTGATGTGGGACTT | 91 | 711 |
| 905739 | N/A | N/A | 8970 | 8985 | AAAGTGTGGGAGTGCA | 0 | 712 |

TABLE 11

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 793406 | N/A | N/A | 8306 | 8321 | GTTCAAAAGCAGCATT | 93 | 13 |
| 903414 | 12 | 27 | 505 | 520 | AGGAATTCGAAAGGGA | 0 | 713 |
| 903446 | 52 | 67 | 545 | 560 | ATAATAACCAGACAGG | 48 | 714 |
| 903478 | 206 | 221 | N/A | N/A | GCACTCATCCAGATGC | 29 | 715 |
| 903510 | 288 | 303 | 4763 | 4778 | TCCAGTATCTGTCCCA | 57 | 716 |
| 903542 | 397 | 412 | 9060 | 9075 | GTGTGCTCACTTTTTC | 91 | 717 |
| 903638 | 615 | 630 | 12706 | 12721 | GTTATCCTCAAGCTCA | 81 | 718 |
| 903670 | 656 | 671 | 12747 | 12762 | ACCTTCTGAACCCCAT | 85 | 719 |
| 903702 | 729 | 744 | 12820 | 12835 | GACGAGGGTCAGGATG | 51 | 720 |
| 903734 | 789 | 804 | 12880 | 12895 | CATCCCAGGTTCCAAG | 63 | 721 |
| 903766 | 836 | 851 | 12927 | 12942 | ATGGTACTGCTGGTAA | 76 | 722 |
| 903798 | 873 | 888 | 12964 | 12979 | GGCTTGGGCTTGTGTC | 57 | 723 |
| 903830 | 982 | 997 | 13073 | 13088 | GTGTGAGTTGGTAAGT | 98 | 724 |
| 903862 | 1047 | 1062 | 13138 | 13153 | ATGCGGTACTGACTGA | 92 | 725 |
| 903894 | 1107 | 1122 | 13198 | 13213 | CACCTGTTCACCGCTT | 94 | 726 |
| 903926 | 1169 | 1184 | 13260 | 13275 | GCCACATCCGTGAGCT | 25 | 727 |
| 903958 | 1333 | 1348 | 13424 | 13439 | CCTGCAGAATCTTATA | 0 | 728 |
| 903990 | 1393 | 1408 | 13484 | 13499 | CCCTGCCAGGCATATC | 20 | 729 |
| 904022 | 1779 | 1794 | 13870 | 13885 | CCAAAGTCCCTAACAC | 74 | 730 |
| 904054 | 1866 | 1881 | 13957 | 13972 | TATTGCAGGCTCCAAT | 18 | 731 |
| 904086 | 2256 | 2271 | 14347 | 14362 | TCTTCCGTCAATATAT | 79 | 732 |
| 904118 | 2383 | 2398 | 14474 | 14489 | TGGGTCTGTAGTGGAG | 76 | 733 |
| 904150 | 2498 | 2513 | 14589 | 14604 | TGCCTGACTGAGATAT | 64 | 734 |
| 904182 | 2542 | 2557 | 14633 | 14648 | CCATCACATGACAACC | 83 | 735 |
| 904214 | 2712 | 2727 | 14803 | 14818 | CCGGGTAAGAGCGATG | 29 | 736 |
| 904246 | 2793 | 2808 | 14884 | 14899 | CGGCGACAAGACAGCT | 53 | 737 |
| 904278 | N/A | N/A | 448 | 463 | AGCAAACACGCTCCCC | 32 | 738 |
| 904310 | N/A | N/A | 1333 | 1348 | GCAACGCACCCTTCTC | 67 | 739 |
| 904374 | N/A | N/A | 1715 | 1730 | ACAGGCTTCATCATCT | 72 | 740 |
| 904406 | N/A | N/A | 2624 | 2639 | AGCCTCTGCTGAATAT | 25 | 741 |
| 904438 | N/A | N/A | 3956 | 3971 | GATCTTGCCAGATGCC | 38 | 742 |
| 904470 | N/A | N/A | 4584 | 4599 | ATCACTGAGCCCCCAT | 55 | 743 |
| 904502 | N/A | N/A | 5016 | 5031 | TCACCCTAAGGAGAGG | 68 | 744 |
| 904534 | N/A | N/A | 5095 | 5110 | ACTTCCCCAAGGATGT | 25 | 745 |
| 904566 | N/A | N/A | 5217 | 5232 | AGGGTCAGCTTGGAGC | 73 | 746 |
| 904598 | N/A | N/A | 5332 | 5347 | GTTAAGCTGGAAGCTG | 41 | 747 |
| 904630 | N/A | N/A | 5455 | 5470 | AGCCGTGTTATATTTG | 88 | 748 |

TABLE 11-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 904662 | N/A | N/A | 5580 | 5595 | TGCCCTAACACAGCTG | 8 | 749 |
| 904694 | N/A | N/A | 5742 | 5757 | TTCCCAATTCAGCAAT | 54 | 750 |
| 904726 | N/A | N/A | 5793 | 5808 | TTGTCTCCGACACTTT | 43 | 751 |
| 904758 | N/A | N/A | 5849 | 5864 | AAGTGCAACCAATCAA | 94 | 752 |
| 904790 | N/A | N/A | 5918 | 5933 | CTAAACTCACACTGGC | 67 | 753 |
| 904822 | N/A | N/A | 5953 | 5968 | CTAAGTTCCGGTCTCA | 87 | 754 |
| 904854 | N/A | N/A | 6090 | 6105 | ACTCCACTGGGCCCGA | 16 | 755 |
| 904886 | N/A | N/A | 6191 | 6206 | GCATTGCCCTCCCAAT | 57 | 756 |
| 904918 | N/A | N/A | 6233 | 6248 | CACCACAGCCGTTCCA | 26 | 757 |
| 904950 | N/A | N/A | 6305 | 6320 | CTGGGTCTGACCCACG | 0 | 758 |
| 904982 | N/A | N/A | 6366 | 6381 | CAGGATCCTGACAAAC | 0 | 759 |
| 905014 | N/A | N/A | 6437 | 6452 | CAGGTTCACATGACAG | 77 | 760 |
| 905046 | N/A | N/A | 6582 | 6597 | AACTGCAAGCTATGGG | 91 | 761 |
| 905078 | N/A | N/A | 6628 | 6643 | GACAGGCAATACCTAC | 6 | 762 |
| 905110 | N/A | N/A | 6733 | 6748 | GGATGGAAGGAACCTC | 91 | 763 |
| 905142 | N/A | N/A | 6821 | 6836 | TGAACGCAATGCTGAC | 97 | 764 |
| 905174 | N/A | N/A | 6981 | 6996 | GCTCTCGGCTTCTAAT | 21 | 765 |
| 905206 | N/A | N/A | 7111 | 7126 | CGGCTCTCCACTGTCA | 46 | 766 |
| 905238 | N/A | N/A | 7232 | 7247 | GCACTCTCAGATGGGC | 20 | 767 |
| 905270 | N/A | N/A | 7284 | 7299 | ACAGCATTGAGTACAA | 96 | 768 |
| 905302 | N/A | N/A | 7456 | 7471 | ATCAAGCAGGAAGCTC | 70 | 769 |
| 905334 | N/A | N/A | 7527 | 7542 | CCGGCCACCTCATTCT | 16 | 770 |
| 905366 | N/A | N/A | 7889 | 7904 | CCAGTATGTATTTGTG | 52 | 771 |
| 905398 | N/A | N/A | 7986 | 8001 | CAGTACAGAGCAGGAT | 96 | 772 |
| 905430 | N/A | N/A | 8064 | 8079 | CACATGTTTCAACAGT | 78 | 773 |
| 905462 | N/A | N/A | 8145 | 8160 | TTTAGAAAGGACACGG | 94 | 774 |
| 905494 | N/A | N/A | 8268 | 8283 | AATATCAGAGTGTACC | 94 | 775 |
| 905526 | N/A | N/A | 8373 | 8388 | TCAAACACTTTATACC | 63 | 776 |
| 905558 | N/A | N/A | 8424 | 8439 | GGAAGTGGAAACATCC | 50 | 777 |
| 905590 | N/A | N/A | 8561 | 8576 | GTTGAAGTCACCCAGC | 48 | 778 |
| 905622 | N/A | N/A | 8692 | 8707 | GACTGTGTGAGCACAC | 25 | 779 |
| 905654 | N/A | N/A | 8809 | 8824 | CATTTGGAGATCTGGC | 90 | 780 |
| 905686 | N/A | N/A | 8877 | 8892 | ATTAGTGCTATAGAGG | 87 | 781 |
| 905718 | N/A | N/A | 8945 | 8960 | TTGCATAAGAGATGAC | 84 | 782 |

TABLE 12

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 793406 | N/A | N/A | 8306 | 8321 | GTTCAAAAGCAGCATT | 89 | 13 |
| 903415 | 13 | 28 | 506 | 521 | GAGGAATTCGAAAGGG | 47 | 783 |
| 903447 | 54 | 69 | 547 | 562 | GTATAATAACCAGACA | 30 | 784 |
| 903479 | 207 | 222 | N/A | N/A | TGCACTCATCCAGATG | 15 | 785 |
| 903511 | 289 | 304 | 4764 | 4779 | CTCCAGTATCTGTCCC | 70 | 786 |
| 903671 | 658 | 673 | 12749 | 12764 | GGACCTTCTGAACCCC | 20 | 787 |
| 903703 | 730 | 745 | 12821 | 12836 | CGACGAGGGTCAGGAT | 53 | 788 |
| 903735 | 790 | 805 | 12881 | 12896 | CCATCCCAGGTTCCAA | 51 | 789 |
| 903767 | 837 | 852 | 12928 | 12943 | CATGGTACTGCTGGTA | 83 | 790 |
| 903799 | 891 | 906 | 12982 | 12997 | TTTGATGACCAGGTCG | 74 | 791 |
| 903831 | 983 | 998 | 13074 | 13089 | CGTGTGAGTTGGTAAG | 86 | 792 |
| 903863 | 1048 | 1063 | 13139 | 13154 | CATGCGGTACTGACTG | 44 | 793 |
| 903895 | 1108 | 1123 | 13199 | 13214 | CCACCTGTTCACCGCT | 92 | 794 |
| 903927 | 1171 | 1186 | 13262 | 13277 | GGGCCACATCCGTGAG | 0 | 795 |
| 904023 | 1780 | 1795 | 13871 | 13886 | GCCAAAGTCCCTAACA | 87 | 796 |
| 904087 | 2257 | 2272 | 14348 | 14363 | TTCTTCCGTCAATATA | 91 | 797 |
| 904119 | 2385 | 2400 | 14476 | 14491 | GCTGGGTCTGTAGTGG | 88 | 798 |
| 904151 | 2499 | 2514 | 14590 | 14605 | CTGCCTGACTGAGATA | 86 | 799 |
| 904183 | 2543 | 2558 | 14634 | 14649 | CCCATCACATGACAAC | 85 | 800 |
| 904215 | 2713 | 2728 | 14804 | 14819 | ACCGGGTAAGAGCGAT | 76 | 801 |
| 904247 | 2794 | 2809 | 14885 | 14900 | GCGGCGACAAGACAGC | 24 | 802 |
| 904311 | N/A | N/A | 1336 | 1351 | TCTGCAACGCACCCTT | 54 | 803 |
| 904343 | N/A | N/A | 631 | 646 | TTACCAAGGAATCTTC | 42 | 804 |
| 904375 | N/A | N/A | 1885 | 1900 | CGCCTCCTTCAACCTT | 68 | 805 |
| 904407 | N/A | N/A | 2637 | 2652 | GACCCTGACCTGGAGC | 48 | 806 |
| 904439 | N/A | N/A | 4015 | 4030 | GCACTGGACAGCCTGT | 41 | 807 |
| 904471 | N/A | N/A | 4590 | 4605 | TTGTCTATCACTGAGC | 66 | 808 |
| 904503 | N/A | N/A | 5017 | 5032 | GTCACCCTAAGGAGAG | 40 | 809 |
| 904535 | N/A | N/A | 5104 | 5119 | GCTGATTCCACTTCCC | 66 | 810 |
| 904567 | N/A | N/A | 5221 | 5236 | CCCCAGGGTCAGCTTG | 48 | 811 |
| 904599 | N/A | N/A | 5333 | 5348 | AGTTAAGCTGGAAGCT | 18 | 812 |
| 904631 | N/A | N/A | 5456 | 5471 | TAGCCGTGTTATATTT | 73 | 813 |
| 904663 | N/A | N/A | 5650 | 5665 | TGAACTCAGCCCCTGC | 43 | 814 |
| 904695 | N/A | N/A | 5743 | 5758 | TTTCCCAATTCAGCAA | 63 | 815 |
| 904727 | N/A | N/A | 5794 | 5809 | CTTGTCTCCGACACTT | 81 | 816 |
| 904759 | N/A | N/A | 5850 | 5865 | TAAGTGCAACCAATCA | 92 | 817 |
| 904791 | N/A | N/A | 5919 | 5934 | CCTAAACTCACACTGG | 47 | 818 |

TABLE 12-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 904823 | N/A | N/A | 5954 | 5969 | GCTAAGTTCCGGTCTC | 87 | 819 |
| 904855 | N/A | N/A | 6091 | 6106 | AACTCCACTGGGCCCG | 0 | 820 |
| 904887 | N/A | N/A | 6194 | 6209 | ACTGCATTGCCCTCCC | 80 | 821 |
| 904919 | N/A | N/A | 6234 | 6249 | GCACCACAGCCGTTCC | 37 | 822 |
| 904983 | N/A | N/A | 6367 | 6382 | ACAGGATCCTGACAAA | 8 | 823 |
| 905047 | N/A | N/A | 6583 | 6598 | AAACTGCAAGCTATGG | 71 | 824 |
| 905079 | N/A | N/A | 6630 | 6645 | TGGACAGGCAATACCT | 1 | 825 |
| 905143 | N/A | N/A | 6822 | 6837 | ATGAACGCAATGCTGA | 96 | 826 |
| 905175 | N/A | N/A | 6982 | 6997 | TGCTCTCGGCTTCTAA | 65 | 827 |
| 905207 | N/A | N/A | 7112 | 7127 | ACGGCTCTCCACTGTC | 58 | 828 |
| 905239 | N/A | N/A | 7233 | 7248 | GGCACTCTCAGATGGG | 13 | 829 |
| 905271 | N/A | N/A | 7285 | 7300 | CACAGCATTGAGTACA | 88 | 830 |
| 905303 | N/A | N/A | 7459 | 7474 | ACCATCAAGCAGGAAG | 90 | 831 |
| 905335 | N/A | N/A | 7528 | 7543 | CCCGGCCACCTCATTC | 0 | 832 |
| 905367 | N/A | N/A | 7890 | 7905 | ACCAGTATGTATTTGT | 75 | 833 |
| 905399 | N/A | N/A | 7987 | 8002 | TCAGTACAGAGCAGGA | 96 | 834 |
| 905431 | N/A | N/A | 8065 | 8080 | ACACATGTTTCAACAG | 70 | 835 |
| 905463 | N/A | N/A | 8146 | 8161 | TTTTAGAAAGGACACG | 93 | 836 |
| 905495 | N/A | N/A | 8269 | 8284 | AAATATCAGAGTGTAC | 75 | 837 |
| 905527 | N/A | N/A | 8374 | 8389 | GTCAAACACTTTATAC | 52 | 838 |
| 905559 | N/A | N/A | 8442 | 8457 | GTGAGCCTTCCAGGCC | 0 | 839 |
| 905591 | N/A | N/A | 8564 | 8579 | GATGTTGAAGTCACCC | 60 | 840 |
| 905623 | N/A | N/A | 8694 | 8709 | AAGACTGTGTGAGCAC | 54 | 841 |
| 905655 | N/A | N/A | 8811 | 8826 | TACATTTGGAGATCTG | 95 | 842 |
| 905687 | N/A | N/A | 8878 | 8893 | CATTAGTGCTATAGAG | 76 | 843 |
| 905719 | N/A | N/A | 8946 | 8961 | ATTGCATAAGAGATGA | 83 | 844 |

TABLE 13

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 793406 | N/A | N/A | 8306 | 8321 | GTTCAAAAGCAGCATT | 79 | 13 |
| 903416 | 14 | 29 | 507 | 522 | CGAGGAATTCGAAAGG | 22 | 845 |
| 903448 | 55 | 70 | 548 | 563 | TGTATAATAACCAGAC | 27 | 846 |
| 903480 | 208 | 223 | N/A | N/A | GTGCACTCATCCAGAT | 0 | 847 |

TABLE 13-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 903512 | 291 | 306 | 4766 | 4781 | ATCTCCAGTATCTGTC | 20 | 848 |
| 903544 | 403 | 418 | 9066 | 9081 | GATTCTGTGTGCTCAC | 90 | 849 |
| 903640 | 617 | 632 | 12708 | 12723 | ATGTTATCCTCAAGCT | 47 | 850 |
| 903672 | 659 | 674 | 12750 | 12765 | TGGACCTTCTGAACCC | 6 | 851 |
| 903704 | 731 | 746 | 12822 | 12837 | CCGACGAGGGTCAGGA | 25 | 852 |
| 903736 | 793 | 808 | 12884 | 12899 | ACTCCATCCCAGGTTC | 20 | 853 |
| 903768 | 838 | 853 | 12929 | 12944 | CCATGGTACTGCTGGT | 0 | 854 |
| 903800 | 892 | 907 | 12983 | 12998 | TTTTGATGACCAGGTC | 57 | 855 |
| 903832 | 997 | 1012 | 13088 | 13103 | CCTTCCCAATGCCTCG | 78 | 856 |
| 903864 | 1049 | 1064 | 13140 | 13155 | GCATGCGGTACTGACT | 4 | 857 |
| 903896 | 1109 | 1124 | 13200 | 13215 | TCCACCTGTTCACCGC | 78 | 858 |
| 903928 | 1200 | 1215 | 13291 | 13306 | TACATCCAGCACAAGA | 72 | 859 |
| 903960 | 1335 | 1350 | 13426 | 13441 | CGCCTGCAGAATCTTA | 63 | 860 |
| 903992 | 1395 | 1410 | 13486 | 13501 | GCCCCTGCCAGGCATA | 20 | 861 |
| 904024 | 1781 | 1796 | 13872 | 13887 | TGCCAAAGTCCCTAAC | 83 | 862 |
| 904056 | 1872 | 1887 | 13963 | 13978 | TTCCCTTATTGCAGGC | 77 | 863 |
| 904088 | 2258 | 2273 | 14349 | 14364 | ATTCTTCCGTCAATAT | 77 | 864 |
| 904120 | 2386 | 2401 | 14477 | 14492 | GGCTGGGTCTGTAGTG | 66 | 865 |
| 904152 | 2500 | 2515 | 14591 | 14606 | GCTGCCTGACTGAGAT | 33 | 866 |
| 904184 | 2544 | 2559 | 14635 | 14650 | ACCCATCACATGACAA | 80 | 867 |
| 904216 | 2714 | 2729 | 14805 | 14820 | TACCGGGTAAGAGCGA | 84 | 868 |
| 904248 | 2795 | 2810 | 14886 | 14901 | GGCGGCGACAAGACAG | 58 | 869 |
| 904280 | N/A | N/A | 450 | 465 | ACAGCAAACACGCTCC | 18 | 870 |
| 904312 | N/A | N/A | 1338 | 1353 | ATTCTGCAACGCACCC | 61 | 871 |
| 904344 | N/A | N/A | 642 | 657 | CTGTCCCCAACTTACC | 7 | 872 |
| 904376 | N/A | N/A | 1887 | 1902 | TCCGCCTCCTTCAACC | 45 | 873 |
| 904408 | N/A | N/A | 2680 | 2695 | CACCCTGGATCCCATC | 26 | 874 |
| 904440 | N/A | N/A | 4044 | 4059 | CTCTTCATCTTGGTGA | 69 | 875 |
| 904472 | N/A | N/A | 4599 | 4614 | CCAGATTGTTTGTCTA | 62 | 876 |
| 904504 | N/A | N/A | 5018 | 5033 | TGTCACCCTAAGGAGA | 36 | 877 |
| 904536 | N/A | N/A | 5105 | 5120 | CGCTGATTCCACTTCC | 17 | 878 |
| 904568 | N/A | N/A | 5222 | 5237 | ACCCCAGGGTCAGCTT | 25 | 879 |
| 904600 | N/A | N/A | 5334 | 5349 | CAGTTAAGCTGGAAGC | 18 | 880 |
| 904632 | N/A | N/A | 5457 | 5472 | GTAGCCGTGTTATATT | 73 | 881 |
| 904664 | N/A | N/A | 5652 | 5667 | ACTGAACTCAGCCCCT | 50 | 882 |
| 904696 | N/A | N/A | 5744 | 5759 | GTTTCCCAATTCAGCA | 64 | 883 |
| 904728 | N/A | N/A | 5795 | 5810 | CCTTGTCTCCGACACT | 88 | 884 |

TABLE 13-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 904760 | N/A | N/A | 5851 | 5866 | GTAAGTGCAACCAATC | 98 | 885 |
| 904792 | N/A | N/A | 5920 | 5935 | CCCTAAACTCACACTG | 28 | 886 |
| 904824 | N/A | N/A | 5955 | 5970 | GGCTAAGTTCCGGTCT | 48 | 887 |
| 904856 | N/A | N/A | 6092 | 6107 | AAACTCCACTGGGCCC | 9 | 888 |
| 904888 | N/A | N/A | 6195 | 6210 | AACTGCATTGCCCTCC | 72 | 889 |
| 904920 | N/A | N/A | 6236 | 6251 | CCGCACCACAGCCGTT | 26 | 890 |
| 904952 | N/A | N/A | 6307 | 6322 | CGCTGGGTCTGACCCA | 22 | 891 |
| 904984 | N/A | N/A | 6368 | 6383 | CACAGGATCCTGACAA | 0 | 892 |
| 905016 | N/A | N/A | 6439 | 6454 | AGCAGGTTCACATGAC | 78 | 893 |
| 905048 | N/A | N/A | 6587 | 6602 | CCTGAAACTGCAAGCT | 41 | 894 |
| 905080 | N/A | N/A | 6631 | 6646 | CTGGACAGGCAATACC | 24 | 895 |
| 905112 | N/A | N/A | 6735 | 6750 | TTGGATGGAAGGAACC | 75 | 896 |
| 905144 | N/A | N/A | 6823 | 6838 | AATGAACGCAATGCTG | 83 | 897 |
| 905176 | N/A | N/A | 6983 | 6998 | GTGCTCTCGGCTTCTA | 59 | 898 |
| 905208 | N/A | N/A | 7113 | 7128 | CACGGCTCTCCACTGT | 30 | 899 |
| 905240 | N/A | N/A | 7234 | 7249 | GGGCACTCTCAGATGG | 44 | 900 |
| 905272 | N/A | N/A | 7286 | 7301 | CCACAGCATTGAGTAC | 58 | 901 |
| 905304 | N/A | N/A | 7460 | 7475 | AACCATCAAGCAGGAA | 70 | 902 |
| 905336 | N/A | N/A | 7532 | 7547 | AGTGCCCGGCCACCTC | 37 | 903 |
| 905368 | N/A | N/A | 7892 | 7907 | GGACCAGTATGTATTT | 34 | 904 |
| 905400 | N/A | N/A | 7988 | 8003 | GTCAGTACAGAGCAGG | 96 | 905 |
| 905432 | N/A | N/A | 8066 | 8081 | CACACATGTTTCAACA | 48 | 906 |
| 905464 | N/A | N/A | 8156 | 8171 | ATTTCCACTATTTTAG | 59 | 907 |
| 905496 | N/A | N/A | 8271 | 8286 | GAAAATATCAGAGTGT | 94 | 908 |
| 905528 | N/A | N/A | 8375 | 8390 | GGTCAAACACTTTATA | 58 | 909 |
| 905560 | N/A | N/A | 8443 | 8458 | AGTGAGCCTTCCAGGC | 11 | 910 |
| 905592 | N/A | N/A | 8565 | 8580 | AGATGTTGAAGTCACC | 67 | 911 |
| 905624 | N/A | N/A | 8704 | 8719 | GGGACACAAGAAGACT | 23 | 912 |
| 905656 | N/A | N/A | 8812 | 8827 | CTACATTTGGAGATCT | 62 | 913 |
| 905688 | N/A | N/A | 8879 | 8894 | TCATTAGTGCTATAGA | 91 | 914 |
| 905720 | N/A | N/A | 8947 | 8962 | CATTGCATAAGAGATG | 19 | 915 |

TABLE 14

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 793406 | N/A | N/A | 8306 | 8321 | GTTCAAAAGCAGCATT | 82 | 13 |
| 903417 | 15 | 30 | 508 | 523 | CCGAGGAATTCGAAAG | 12 | 916 |
| 903449 | 56 | 71 | 549 | 564 | CTGTATAATAACCAGA | 47 | 917 |
| 903481 | 209 | 224 | N/A | N/A | AGTGCACTCATCCAGA | 0 | 918 |
| 903513 | 292 | 307 | 4767 | 4782 | GATCTCCAGTATCTGT | 28 | 919 |
| 903641 | 618 | 633 | 12709 | 12724 | TATGTTATCCTCAAGC | 52 | 920 |
| 903673 | 660 | 675 | 12751 | 12766 | GTGGACCTTCTGAACC | 0 | 921 |
| 903705 | 732 | 747 | 12823 | 12838 | GCCGACGAGGGTCAGG | 11 | 922 |
| 903737 | 794 | 809 | 12885 | 12900 | AACTCCATCCCAGGTT | 0 | 923 |
| 903769 | 839 | 854 | 12930 | 12945 | TCCATGGTACTGCTGG | 0 | 924 |
| 903801 | 893 | 908 | 12984 | 12999 | CTTTTGATGACCAGGT | 60 | 925 |
| 903833 | 999 | 1014 | 13090 | 13105 | GTCCTTCCCAATGCCT | 28 | 926 |
| 903865 | 1050 | 1065 | 13141 | 13156 | GGCATGCGGTACTGAC | 37 | 927 |
| 903897 | 1110 | 1125 | 13201 | 13216 | CTCCACCTGTTCACCG | 57 | 928 |
| 903929 | 1201 | 1216 | 13292 | 13307 | CTACATCCAGCACAAG | 72 | 929 |
| 903961 | 1336 | 1351 | 13427 | 13442 | CCGCCTGCAGAATCTT | 91 | 930 |
| 903993 | 1405 | 1420 | 13496 | 13511 | TTTTGTCCTGGCCCCT | 83 | 931 |
| 904025 | 1782 | 1797 | 13873 | 13888 | ATGCCAAAGTCCCTAA | 96 | 932 |
| 904057 | 1873 | 1888 | 13964 | 13979 | TTTCCCTTATTGCAGG | 77 | 933 |
| 904089 | 2259 | 2274 | 14350 | 14365 | TATTCTTCCGTCAATA | 50 | 934 |
| 904121 | 2401 | 2416 | 14492 | 14507 | GGACATTGAACCTGGG | 86 | 935 |
| 904153 | 2501 | 2516 | 14592 | 14607 | CGCTGCCTGACTGAGA | 58 | 936 |
| 904185 | 2545 | 2560 | 14636 | 14651 | GACCCATCACATGACA | 59 | 937 |
| 904217 | 2715 | 2730 | 14806 | 14821 | TTACCGGGTAAGAGCG | 76 | 938 |
| 904249 | 2796 | 2811 | 14887 | 14902 | GGGCGGCGACAAGACA | 82 | 939 |
| 904281 | N/A | N/A | 451 | 466 | CACAGCAAACACGCTC | 30 | 940 |
| 904313 | N/A | N/A | 1339 | 1354 | CATTCTGCAACGCACC | 54 | 941 |
| 904345 | N/A | N/A | 651 | 666 | GCAGGTCAACTGTCCC | 0 | 942 |
| 904377 | N/A | N/A | 1888 | 1903 | ATCCGCCTCCTTCAAC | 17 | 943 |
| 904409 | N/A | N/A | 2706 | 2721 | ATTCCCCCGACACTTG | 62 | 944 |
| 904441 | N/A | N/A | 4045 | 4060 | ACTCTTCATCTTGGTG | 73 | 945 |
| 904473 | N/A | N/A | 4607 | 4622 | AACCTAAACCAGATTG | 0 | 946 |
| 904505 | N/A | N/A | 5019 | 5034 | GTGTCACCCTAAGGAG | 29 | 947 |
| 904537 | N/A | N/A | 5106 | 5121 | CCGCTGATTCCACTTC | 35 | 948 |
| 904569 | N/A | N/A | 5233 | 5248 | CAGGTGGAAACACCCC | 1 | 949 |
| 904601 | N/A | N/A | 5335 | 5350 | CCAGTTAAGCTGGAAG | 4 | 950 |
| 904633 | N/A | N/A | 5458 | 5473 | GGTAGCCGTGTTATAT | 74 | 951 |

TABLE 14-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 904665 | N/A | N/A | 5653 | 5668 | GACTGAACTCAGCCCC | 57 | 952 |
| 904697 | N/A | N/A | 5745 | 5760 | TGTTTCCCAATTCAGC | 67 | 953 |
| 904729 | N/A | N/A | 5796 | 5811 | ACCTTGTCTCCGACAC | 71 | 954 |
| 904761 | N/A | N/A | 5852 | 5867 | TGTAAGTGCAACCAAT | 85 | 955 |
| 904793 | N/A | N/A | 5921 | 5936 | TCCCTAAACTCACACT | 18 | 956 |
| 904825 | N/A | N/A | 5956 | 5971 | AGGCTAAGTTCCGGTC | 35 | 957 |
| 904857 | N/A | N/A | 6093 | 6108 | CAAACTCCACTGGGCC | 16 | 958 |
| 904889 | N/A | N/A | 6196 | 6211 | AAACTGCATTGCCCTC | 64 | 959 |
| 904921 | N/A | N/A | 6237 | 6252 | CCCGCACCACAGCCGT | 44 | 960 |
| 904953 | N/A | N/A | 6308 | 6323 | GCGCTGGGTCTGACCC | 0 | 961 |
| 904985 | N/A | N/A | 6369 | 6384 | CCACAGGATCCTGACA | 14 | 962 |
| 905017 | N/A | N/A | 6512 | 6527 | TAAAGCCAGCTGACAG | 47 | 963 |
| 905049 | N/A | N/A | 6588 | 6603 | CCCTGAAACTGCAAGC | 32 | 964 |
| 905081 | N/A | N/A | 6632 | 6647 | CCTGGACAGGCAATAC | 0 | 965 |
| 905113 | N/A | N/A | 6736 | 6751 | TTTGGATGGAAGGAAC | 71 | 966 |
| 905145 | N/A | N/A | 6824 | 6839 | AAATGAACGCAATGCT | 65 | 967 |
| 905177 | N/A | N/A | 6984 | 6999 | AGTGCTCTCGGCTTCT | 39 | 968 |
| 905209 | N/A | N/A | 7114 | 7129 | ACACGGCTCTCCACTG | 55 | 969 |
| 905241 | N/A | N/A | 7235 | 7250 | TGGGCACTCTCAGATG | 25 | 970 |
| 905273 | N/A | N/A | 7289 | 7304 | ACTCCACAGCATTGAG | 4 | 971 |
| 905305 | N/A | N/A | 7461 | 7476 | AAACCATCAAGCAGGA | 63 | 972 |
| 905337 | N/A | N/A | 7829 | 7844 | ACAAGAGACCTCATTC | 48 | 973 |
| 905369 | N/A | N/A | 7893 | 7908 | GGGACCAGTATGTATT | 21 | 974 |
| 905401 | N/A | N/A | 7990 | 8005 | AAGTCAGTACAGAGCA | 94 | 975 |
| 905433 | N/A | N/A | 8067 | 8082 | CCACACATGTTTCAAC | 62 | 976 |
| 905465 | N/A | N/A | 8158 | 8173 | GAATTTCCACTATTTT | 74 | 977 |
| 905497 | N/A | N/A | 8307 | 8322 | GGTTCAAAAGCAGCAT | 96 | 978 |
| 905529 | N/A | N/A | 8376 | 8391 | GGGTCAAACACTTTAT | 78 | 979 |
| 905561 | N/A | N/A | 8444 | 8459 | AAGTGAGCCTTCCAGG | 30 | 980 |
| 905593 | N/A | N/A | 8566 | 8581 | CAGATGTTGAAGTCAC | 56 | 981 |
| 905625 | N/A | N/A | 8723 | 8738 | CCTATTGTAAGAACAG | 58 | 982 |
| 905657 | N/A | N/A | 8820 | 8835 | TCAGGTGACTACATTT | 89 | 983 |
| 905689 | N/A | N/A | 8880 | 8895 | GTCATTAGTGCTATAG | 95 | 984 |
| 905721 | N/A | N/A | 8948 | 8963 | CCATTGCATAAGAGAT | 84 | 985 |

TABLE 15

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 793406 | N/A | N/A | 8306 | 8321 | GTTCAAAAGCAGCATT | 86 | 13 |
| 903418 | 16 | 31 | 509 | 524 | ACCGAGGAATTCGAAA | 22 | 986 |
| 903450 | 59 | 74 | 552 | 567 | CGTCTGTATAATAACC | 37 | 987 |
| 903482 | 210 | 225 | N/A | N/A | AAGTGCACTCATCCAG | 50 | 988 |
| 903514 | 293 | 308 | 4768 | 4783 | GGATCTCCAGTATCTG | 15 | 989 |
| 903642 | 619 | 634 | 12710 | 12725 | TTATGTTATCCTCAAG | 67 | 990 |
| 903674 | 661 | 676 | 12752 | 12767 | TGTGGACCTTCTGAAC | 16 | 991 |
| 903706 | 733 | 748 | 12824 | 12839 | TGCCGACGAGGGTCAG | 42 | 992 |
| 903738 | 795 | 810 | 12886 | 12901 | CAACTCCATCCCAGGT | 37 | 993 |
| 903770 | 841 | 856 | 12932 | 12947 | AGTCCATGGTACTGCT | 21 | 994 |
| 903802 | 894 | 909 | 12985 | 13000 | GCTTTTGATGACCAGG | 87 | 995 |
| 903834 | 1000 | 1015 | 13091 | 13106 | TGTCCTTCCCAATGCC | 38 | 996 |
| 903866 | 1052 | 1067 | 13143 | 13158 | GAGGCATGCGGTACTG | 53 | 997 |
| 903898 | 1111 | 1126 | 13202 | 13217 | TCTCCACCTGTTCACC | 63 | 998 |
| 903930 | 1204 | 1219 | 13295 | 13310 | AGACTACATCCAGCAC | 81 | 999 |
| 903962 | 1337 | 1352 | 13428 | 13443 | TCCGCCTGCAGAATCT | 76 | 1000 |
| 903994 | 1406 | 1421 | 13497 | 13512 | ATTTTGTCCTGGCCCC | 64 | 1001 |
| 904026 | 1787 | 1802 | 13878 | 13893 | TGGAAATGCCAAAGTC | 97 | 1002 |
| 904058 | 1884 | 1899 | 13975 | 13990 | CAGTTCCCATTTTTCC | 93 | 1003 |
| 904090 | 2260 | 2275 | 14351 | 14366 | CTATTCTTCCGTCAAT | 67 | 1004 |
| 904122 | 2402 | 2417 | 14493 | 14508 | AGGACATTGAACCTGG | 65 | 1005 |
| 904154 | 2502 | 2517 | 14593 | 14608 | CCGCTGCCTGACTGAG | 81 | 1006 |
| 904186 | 2546 | 2561 | 14637 | 14652 | GGACCCATCACATGAC | 55 | 1007 |
| 904218 | 2716 | 2731 | 14807 | 14822 | CTTACCGGGTAAGAGC | 49 | 1008 |
| 904250 | 2797 | 2812 | 14888 | 14903 | TGGGCGGCGACAAGAC | 74 | 1009 |
| 904282 | N/A | N/A | 457 | 472 | ACCAAGCACAGCAAAC | 0 | 1010 |
| 904314 | N/A | N/A | 1341 | 1356 | ACCATTCTGCAACGCA | 68 | 1011 |
| 904346 | N/A | N/A | 655 | 670 | GGAGGCAGGTCAACTG | 5 | 1012 |
| 904378 | N/A | N/A | 2051 | 2066 | TGACCACCTGTCTTGG | 0 | 1013 |
| 904410 | N/A | N/A | 2716 | 2731 | GGTGCCTCGGATTCCC | 9 | 1014 |
| 904442 | N/A | N/A | 4052 | 4067 | GTGCTCAACTCTTCAT | 76 | 1015 |
| 904474 | N/A | N/A | 4615 | 4630 | CCAAGACCAACCTAAA | 29 | 1016 |
| 904506 | N/A | N/A | 5020 | 5035 | CGTGTCACCCTAAGGA | 51 | 1017 |
| 904538 | N/A | N/A | 5107 | 5122 | CCCGCTGATTCCACTT | 36 | 1018 |
| 904570 | N/A | N/A | 5234 | 5249 | TCAGGTGGAAACACCC | 11 | 1019 |
| 904602 | N/A | N/A | 5336 | 5351 | TCCAGTTAAGCTGGAA | 0 | 1020 |
| 904634 | N/A | N/A | 5460 | 5475 | CAGGTAGCCGTGTTAT | 41 | 1021 |

TABLE 15-continued

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| Inhibition of APOL1 mRNA by 3-10-3 cEt gapmers targeting SEQ ID NO: 1 and 2 | | | | | | | |
| 904666 | N/A | N/A | 5654 | 5669 | TGACTGAACTCAGCCC | 43 | 1022 |
| 904698 | N/A | N/A | 5747 | 5762 | GCTGTTTCCCAATTCA | 57 | 1023 |
| 904730 | N/A | N/A | 5797 | 5812 | AACCTTGTCTCCGACA | 46 | 1024 |
| 904762 | N/A | N/A | 5853 | 5868 | TTGTAAGTGCAACCAA | 76 | 1025 |
| 904794 | N/A | N/A | 5925 | 5940 | GACCTCCCTAAACTCA | 13 | 1026 |
| 904826 | N/A | N/A | 5957 | 5972 | AAGGCTAAGTTCCGGT | 47 | 1027 |
| 904858 | N/A | N/A | 6104 | 6119 | GACAAGAACCCCAAAC | 0 | 1028 |
| 904890 | N/A | N/A | 6197 | 6212 | AAAACTGCATTGCCCT | 72 | 1029 |
| 904922 | N/A | N/A | 6238 | 6253 | ACCCGCACCACAGCCG | 12 | 1030 |
| 904954 | N/A | N/A | 6320 | 6335 | AGATCCAACTCGGCGC | 7 | 1031 |
| 904986 | N/A | N/A | 6370 | 6385 | CCCACAGGATCCTGAC | 25 | 1032 |
| 905018 | N/A | N/A | 6514 | 6529 | CTTAAAGCCAGCTGAC | 25 | 1033 |
| 905050 | N/A | N/A | 6590 | 6605 | CCCCCTGAAACTGCAA | 34 | 1034 |
| 905082 | N/A | N/A | 6633 | 6648 | TCCTGGACAGGCAATA | 32 | 1035 |
| 905114 | N/A | N/A | 6739 | 6754 | AGGTTTGGATGGAAGG | 90 | 1036 |
| 905146 | N/A | N/A | 6825 | 6840 | GAAATGAACGCAATGC | 87 | 1037 |
| 905178 | N/A | N/A | 6985 | 7000 | GAGTGCTCTCGGCTTC | 47 | 1038 |
| 905210 | N/A | N/A | 7115 | 7130 | TACACGGCTCTCCACT | 73 | 1039 |
| 905242 | N/A | N/A | 7236 | 7251 | TTGGGCACTCTCAGAT | 8 | 1040 |
| 905274 | N/A | N/A | 7290 | 7305 | AACTCCACAGCATTGA | 53 | 1041 |
| 905306 | N/A | N/A | 7466 | 7481 | GCCCAAAACCATCAAG | 3 | 1042 |
| 905338 | N/A | N/A | 7830 | 7845 | CACAAGAGACCTCATT | 15 | 1043 |
| 905370 | N/A | N/A | 7917 | 7932 | TATGGAATTGCAGATA | 85 | 1044 |
| 905402 | N/A | N/A | 7991 | 8006 | CAAGTCAGTACAGAGC | 93 | 1045 |
| 905434 | N/A | N/A | 8068 | 8083 | CCCACACATGTTTCAA | 58 | 1046 |
| 905466 | N/A | N/A | 8159 | 8174 | AGAATTTCCACTATTT | 82 | 1047 |
| 905498 | N/A | N/A | 8308 | 8323 | TGGTTCAAAAGCAGCA | 90 | 1048 |
| 905530 | N/A | N/A | 8377 | 8392 | TGGGTCAAACACTTTA | 63 | 1049 |
| 905562 | N/A | N/A | 8445 | 8460 | GAAGTGAGCCTTCCAG | 60 | 1050 |
| 905594 | N/A | N/A | 8567 | 8582 | CCAGATGTTGAAGTCA | 76 | 1051 |
| 905626 | N/A | N/A | 8724 | 8739 | TCCTATTGTAAGAACA | 54 | 1052 |
| 905658 | N/A | N/A | 8821 | 8836 | CTCAGGTGACTACATT | 87 | 1053 |
| 905690 | N/A | N/A | 8881 | 8896 | AGTCATTAGTGCTATA | 90 | 1054 |
| 905722 | N/A | N/A | 8949 | 8964 | GCCATTGCATAAGAGA | 29 | 1055 |

TABLE 16

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 903419 | 17 | 32 | 510 | 525 | TACCGAGGAATTCGAA | 13 | 1056 |
| 903451 | 73 | 88 | 566 | 581 | CACCTCCAGTTATGCG | 51 | 1057 |
| 903483 | 211 | 226 | N/A | N/A | AAAGTGCACTCATCCA | 71 | 1058 |
| 903515 | 294 | 309 | 4769 | 4784 | AGGATCTCCAGTATCT | 24 | 1059 |
| 903643 | 620 | 635 | 12711 | 12726 | CTTATGTTATCCTCAA | 81 | 1060 |
| 903675 | 662 | 677 | 12753 | 12768 | TTGTGGACCTTCTGAA | 58 | 1061 |
| 903707 | 734 | 749 | 12825 | 12840 | ATGCCGACGAGGGTCA | 49 | 1062 |
| 903739 | 801 | 816 | 12892 | 12907 | GATTCCCAACTCCATC | 10 | 1063 |
| 903771 | 842 | 857 | 12933 | 12948 | TAGTCCATGGTACTGC | 4 | 1064 |
| 903803 | 896 | 911 | 12987 | 13002 | AGGCTTTTGATGACCA | 24 | 1065 |
| 903835 | 1001 | 1016 | 13092 | 13107 | ATGTCCTTCCCAATGC | 32 | 1066 |
| 903867 | 1053 | 1068 | 13144 | 13159 | TGAGGCATGCGGTACT | 88 | 1067 |
| 903899 | 1115 | 1130 | 13206 | 13221 | ACCCTCTCCACCTGTT | 41 | 1068 |
| 903931 | 1205 | 1220 | 13296 | 13311 | TAGACTACATCCAGCA | 72 | 1069 |
| 903963 | 1338 | 1353 | 13429 | 13444 | GTCCGCCTGCAGAATC | 82 | 1070 |
| 903995 | 1701 | 1716 | 13792 | 13807 | AAAAGCGATGGCTCAC | 57 | 1071 |
| 904027 | 1791 | 1806 | 13882 | 13897 | GCTATGGAAATGCCAA | 90 | 1072 |
| 904059 | 1886 | 1901 | 13977 | 13992 | TCCAGTTCCCATTTTT | 90 | 1073 |
| 904091 | 2264 | 2279 | 14355 | 14370 | CTCTCTATTCTTCCGT | 92 | 1074 |
| 904123 | 2404 | 2419 | 14495 | 14510 | GGAGGACATTGAACCT | 62 | 1075 |
| 904155 | 2503 | 2518 | 14594 | 14609 | GCCGCTGCCTGACTGA | 48 | 1076 |
| 904187 | 2589 | 2604 | 14680 | 14695 | CAGTGTTCAAGCAGGG | 83 | 1077 |
| 904219 | 2717 | 2732 | 14808 | 14823 | ACTTACCGGGTAAGAG | 49 | 1078 |
| 904251 | 2798 | 2813 | 14889 | 14904 | CTGGGCGGCGACAAGA | 39 | 1079 |
| 904283 | N/A | N/A | 458 | 473 | GACCAAGCACAGCAAA | 0 | 1080 |
| 904315 | N/A | N/A | 1342 | 1357 | CACCATTCTGCAACGC | 74 | 1081 |
| 904347 | N/A | N/A | 767 | 782 | CAATCAGACTCAAGCC | 19 | 1082 |
| 904379 | N/A | N/A | 2053 | 2068 | CGTGACCACCTGTCTT | 16 | 1083 |
| 904411 | N/A | N/A | 2721 | 2736 | GAGCTGGTGCCTCGGA | 30 | 1084 |
| 904443 | N/A | N/A | 4081 | 4096 | CCTCATTGCAAATCCT | 96 | 1085 |
| 904475 | N/A | N/A | 4648 | 4663 | GCTCTGCAAATCTCTC | 15 | 1086 |
| 904507 | N/A | N/A | 5021 | 5036 | CCGTGTCACCCTAAGG | 54 | 1087 |
| 904539 | N/A | N/A | 5108 | 5123 | CCCCGCTGATTCCACT | 16 | 1088 |
| 904571 | N/A | N/A | 5235 | 5250 | CTCAGGTGGAAACACC | 34 | 1089 |
| 904603 | N/A | N/A | 5337 | 5352 | GTCCAGTTAAGCTGGA | 9 | 1090 |
| 904635 | N/A | N/A | 5461 | 5476 | CCAGGTAGCCGTGTTA | 74 | 1091 |
| 904667 | N/A | N/A | 5655 | 5670 | ATGACTGAACTCAGCC | 32 | 1092 |

TABLE 16-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 904699 | N/A | N/A | 5757 | 5772 | CCTCCAGTTTGCTGTT | 48 | 1093 |
| 904731 | N/A | N/A | 5798 | 5813 | AAACCTTGTCTCCGAC | 66 | 1094 |
| 904763 | N/A | N/A | 5854 | 5869 | TTTGTAAGTGCAACCA | 96 | 1095 |
| 904795 | N/A | N/A | 5926 | 5941 | AGACCTCCCTAAACTC | 8 | 1096 |
| 904827 | N/A | N/A | 5958 | 5973 | CAAGGCTAAGTTCCGG | 64 | 1097 |
| 904859 | N/A | N/A | 6106 | 6121 | AAGACAAGAACCCCAA | 68 | 1098 |
| 904891 | N/A | N/A | 6198 | 6213 | CAAAACTGCATTGCCC | 50 | 1099 |
| 904923 | N/A | N/A | 6242 | 6257 | ACCCACCCGCACCACA | 16 | 1100 |
| 904955 | N/A | N/A | 6321 | 6336 | GAGATCCAACTCGGCG | 11 | 1101 |
| 904987 | N/A | N/A | 6371 | 6386 | GCCCACAGGATCCTGA | 0 | 1102 |
| 905051 | N/A | N/A | 6592 | 6607 | AACCCCCTGAAACTGC | 65 | 1103 |
| 905083 | N/A | N/A | 6634 | 6649 | TTCCTGGACAGGCAAT | 31 | 1104 |
| 905115 | N/A | N/A | 6740 | 6755 | CAGGTTTGGATGGAAG | 74 | 1105 |
| 905147 | N/A | N/A | 6826 | 6841 | GGAAATGAACGCAATG | 91 | 1106 |
| 905179 | N/A | N/A | 6986 | 7001 | TGAGTGCTCTCGGCTT | 62 | 1107 |
| 905211 | N/A | N/A | 7116 | 7131 | GTACACGGCTCTCCAC | 7 | 1108 |
| 905243 | N/A | N/A | 7237 | 7252 | CTTGGGCACTCTCAGA | 44 | 1109 |
| 905275 | N/A | N/A | 7291 | 7306 | AAACTCCACAGCATTG | 30 | 1110 |
| 905307 | N/A | N/A | 7467 | 7482 | CGCCCAAAACCATCAA | 44 | 1111 |
| 905339 | N/A | N/A | 7833 | 7848 | ACACACAAGAGACCTC | 0 | 1112 |
| 905371 | N/A | N/A | 7918 | 7933 | TTATGGAATTGCAGAT | 93 | 1113 |
| 905403 | N/A | N/A | 7992 | 8007 | TCAAGTCAGTACAGAG | 92 | 1114 |
| 905435 | N/A | N/A | 8070 | 8085 | CACCCACACATGTTTC | 49 | 1115 |
| 905467 | N/A | N/A | 8160 | 8175 | CAGAATTTCCACTATT | 85 | 1116 |
| 905499 | N/A | N/A | 8309 | 8324 | TTGGTTCAAAAGCAGC | 92 | 1117 |
| 905531 | N/A | N/A | 8378 | 8393 | TTGGGTCAAACACTTT | 69 | 1118 |
| 905563 | N/A | N/A | 8448 | 8463 | CATGAAGTGAGCCTTC | 56 | 1119 |
| 905595 | N/A | N/A | 8568 | 8583 | GCCAGATGTTGAAGTC | 34 | 1120 |
| 905627 | N/A | N/A | 8725 | 8740 | GTCCTATTGTAAGAAC | 24 | 1121 |
| 905659 | N/A | N/A | 8822 | 8837 | ACTCAGGTGACTACAT | 71 | 1122 |
| 905691 | N/A | N/A | 8882 | 8897 | GAGTCATTAGTGCTAT | 92 | 1123 |
| 905723 | N/A | N/A | 8951 | 8966 | CAGCCATTGCATAAGA | 46 | 1124 |

TABLE 17

| Inhibition of APOL1 mRNA by 3-10-3 cEt gapmers targeting SEQ ID NO: 1 and 2 | | | | | | | |
|---|---|---|---|---|---|---|---|
| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
| 793406 | N/A | N/A | 8306 | 8321 | GTTCAAAAGCAGCATT | 84 | 13 |
| 903420 | 18 | 33 | 511 | 526 | ATACCGAGGAATTCGA | 5 | 1125 |
| 903452 | 74 | 89 | 567 | 582 | CCACCTCCAGTTATGC | 70 | 1126 |
| 903484 | 212 | 227 | 4505 | 4520 | AAAAGTGCACTCATCC | 65 | 1127 |
| 903516 | 295 | 310 | 4770 | 4785 | GAGGATCTCCAGTATC | 60 | 1128 |
| 903644 | 623 | 638 | 12714 | 12729 | CTTCTTATGTTATCCT | 90 | 1129 |
| 903676 | 663 | 678 | 12754 | 12769 | TTTGTGGACCTTCTGA | 76 | 1130 |
| 903708 | 735 | 750 | 12826 | 12841 | CATGCCGACGAGGGTC | 25 | 1131 |
| 903740 | 805 | 820 | 12896 | 12911 | CTGTGATTCCCAACTC | 66 | 1132 |
| 903772 | 843 | 858 | 12934 | 12949 | GTAGTCCATGGTACTG | 15 | 1133 |
| 903804 | 897 | 912 | 12988 | 13003 | AAGGCTTTTGATGACC | 64 | 1134 |
| 903836 | 1002 | 1017 | 13093 | 13108 | GATGTCCTTCCCAATG | 29 | 1135 |
| 903868 | 1054 | 1069 | 13145 | 13160 | CTGAGGCATGCGGTAC | 78 | 1136 |
| 903900 | 1116 | 1131 | 13207 | 13222 | AACCCTCTCCACCTGT | 48 | 1137 |
| 903932 | 1206 | 1221 | 13297 | 13312 | GTAGACTACATCCAGC | 63 | 1138 |
| 903964 | 1339 | 1354 | 13430 | 13445 | GGTCCGCCTGCAGAAT | 70 | 1139 |
| 903996 | 1706 | 1721 | 13797 | 13812 | GGGTCAAAAGCGATGG | 94 | 1140 |
| 904028 | 1792 | 1807 | 13883 | 13898 | AGCTATGGAAATGCCA | 62 | 1141 |
| 904060 | 1888 | 1903 | 13979 | 13994 | TCTCCAGTTCCCATTT | 73 | 1142 |
| 904092 | 2270 | 2285 | 14361 | 14376 | AGCCTCCTCTCTATTC | 49 | 1143 |
| 904124 | 2405 | 2420 | 14496 | 14511 | CGGAGGACATTGAACC | 89 | 1144 |
| 904156 | 2504 | 2519 | 14595 | 14610 | AGCCGCTGCCTGACTG | 54 | 1145 |
| 904188 | 2590 | 2605 | 14681 | 14696 | TCAGTGTTCAAGCAGG | 92 | 1146 |
| 904220 | 2718 | 2733 | 14809 | 14824 | TACTTACCGGGTAAGA | 47 | 1147 |
| 904252 | 2799 | 2814 | 14890 | 14905 | CCTGGGCGGCGACAAG | 53 | 1148 |
| 904284 | N/A | N/A | 459 | 474 | TGACCAAGCACAGCAA | 10 | 1149 |
| 904316 | N/A | N/A | 1343 | 1358 | GCACCATTCTGCAACG | 29 | 1150 |
| 904348 | N/A | N/A | 801 | 816 | TCTATAGTTTAAGAGC | 6 | 1151 |
| 904380 | N/A | N/A | 2437 | 2452 | TCCCGCCTCAGGGCTC | 22 | 1152 |
| 904412 | N/A | N/A | 2788 | 2803 | ACACCATCTCATGAGC | 59 | 1153 |
| 904444 | N/A | N/A | 4200 | 4215 | GTTTTTACAATAGTGC | 97 | 1154 |
| 904476 | N/A | N/A | 4667 | 4682 | GCTTGCTTGAGCAGCC | 16 | 1155 |
| 904508 | N/A | N/A | 5022 | 5037 | GCCGTGTCACCCTAAG | 65 | 1156 |
| 904540 | N/A | N/A | 5109 | 5124 | CCCCCGCTGATTCCAC | 43 | 1157 |
| 904572 | N/A | N/A | 5236 | 5251 | CCTCAGGTGGAAACAC | 0 | 1158 |
| 904604 | N/A | N/A | 5338 | 5353 | GGTCCAGTTAAGCTGG | 12 | 1159 |
| 904636 | N/A | N/A | 5462 | 5477 | GCCAGGTAGCCGTGTT | 61 | 1160 |

TABLE 17-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 904668 | N/A | N/A | 5656 | 5671 | GATGACTGAACTCAGC | 63 | 1161 |
| 904700 | N/A | N/A | 5760 | 5775 | CCTCCTCCAGTTTGCT | 50 | 1162 |
| 904732 | N/A | N/A | 5799 | 5814 | TAAACCTTGTCTCCGA | 87 | 1163 |
| 904764 | N/A | N/A | 5855 | 5870 | TTTTGTAAGTGCAACC | 94 | 1164 |
| 904796 | N/A | N/A | 5927 | 5942 | GAGACCTCCCTAAACT | 26 | 1165 |
| 904828 | N/A | N/A | 5959 | 5974 | GCAAGGCTAAGTTCCG | 97 | 1166 |
| 904860 | N/A | N/A | 6108 | 6123 | CAAAGACAAGAACCCC | 68 | 1167 |
| 904892 | N/A | N/A | 6199 | 6214 | ACAAAACTGCATTGCC | 50 | 1168 |
| 904924 | N/A | N/A | 6254 | 6269 | ACTAAACCCCACACCC | 6 | 1169 |
| 904956 | N/A | N/A | 6322 | 6337 | TGAGATCCAACTCGGC | 65 | 1170 |
| 904988 | N/A | N/A | 6372 | 6387 | GGCCCACAGGATCCTG | 0 | 1171 |
| 905020 | N/A | N/A | 6536 | 6551 | CTTCTGTTAGATACAA | 93 | 1172 |
| 905052 | N/A | N/A | 6593 | 6608 | TAACCCCCTGAAACTG | 61 | 1173 |
| 905084 | N/A | N/A | 6635 | 6650 | ATTCCTGGACAGGCAA | 62 | 1174 |
| 905116 | N/A | N/A | 6741 | 6756 | CCAGGTTTGGATGGAA | 73 | 1175 |
| 905148 | N/A | N/A | 6827 | 6842 | GGGAAATGAACGCAAT | 89 | 1176 |
| 905180 | N/A | N/A | 6987 | 7002 | CTGAGTGCTCTCGGCT | 77 | 1177 |
| 905212 | N/A | N/A | 7117 | 7132 | GGTACACGGCTCTCCA | 29 | 1178 |
| 905244 | N/A | N/A | 7238 | 7253 | TCTTGGGCACTCTCAG | 80 | 1179 |
| 905276 | N/A | N/A | 7298 | 7313 | ATGTCTCAAACTCCAC | 90 | 1180 |
| 905308 | N/A | N/A | 7468 | 7483 | CCGCCCAAAACCATCA | 58 | 1181 |
| 905340 | N/A | N/A | 7835 | 7850 | GCACACACAAGAGACC | 13 | 1182 |
| 905372 | N/A | N/A | 7921 | 7936 | GAATTATGGAATTGCA | 90 | 1183 |
| 905404 | N/A | N/A | 7994 | 8009 | ACTCAAGTCAGTACAG | 87 | 1184 |
| 905436 | N/A | N/A | 8077 | 8092 | GTAATCACACCCACAC | 50 | 1185 |
| 905468 | N/A | N/A | 8162 | 8177 | TTCAGAATTTCCACTA | 92 | 1186 |
| 905500 | N/A | N/A | 8310 | 8325 | ATTGGTTCAAAAGCAG | 85 | 1187 |
| 905532 | N/A | N/A | 8379 | 8394 | GTTGGGTCAAACACTT | 71 | 1188 |
| 905564 | N/A | N/A | 8449 | 8464 | ACATGAAGTGAGCCTT | 88 | 1189 |
| 905596 | N/A | N/A | 8620 | 8635 | TTTGGCACCTTCACCT | 53 | 1190 |
| 905628 | N/A | N/A | 8738 | 8753 | TTAGAGGGCTAGTGTC | 82 | 1191 |
| 905660 | N/A | N/A | 8823 | 8838 | AACTCAGGTGACTACA | 68 | 1192 |
| 905692 | N/A | N/A | 8883 | 8898 | GGAGTCATTAGTGCTA | 82 | 1193 |
| 905724 | N/A | N/A | 8952 | 8967 | ACAGCCATTGCATAAG | 50 | 1194 |

TABLE 18

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 793406 | N/A | N/A | 8306 | 8321 | GTTCAAAAGCAGCATT | 87 | 13 |
| 903421 | 19 | 34 | 512 | 527 | TATACCGAGGAATTCG | 23 | 1195 |
| 903453 | 75 | 90 | 568 | 583 | CCCACCTCCAGTTATG | 45 | 1196 |
| 903485 | 217 | 232 | 4510 | 4525 | CAAGGAAAAGTGCACT | 33 | 1197 |
| 903517 | 296 | 311 | 4771 | 4786 | TGAGGATCTCCAGTAT | 69 | 1198 |
| 903613 | 527 | 542 | 12618 | 12633 | TTCATGATCATTTGTC | 88 | 1199 |
| 903645 | 624 | 639 | 12715 | 12730 | CCTTCTTATGTTATCC | 82 | 1200 |
| 903677 | 664 | 679 | 12755 | 12770 | CTTTGTGGACCTTCTG | 74 | 1201 |
| 903709 | 736 | 751 | 12827 | 12842 | CCATGCCGACGAGGGT | 25 | 1202 |
| 903741 | 806 | 821 | 12897 | 12912 | GCTGTGATTCCCAACT | 59 | 1203 |
| 903773 | 844 | 859 | 12935 | 12950 | CGTAGTCCATGGTACT | 25 | 1204 |
| 903805 | 898 | 913 | 12989 | 13004 | CAAGGCTTTTGATGAC | 88 | 1205 |
| 903837 | 1003 | 1018 | 13094 | 13109 | GGATGTCCTTCCCAAT | 46 | 1206 |
| 903869 | 1079 | 1094 | 13170 | 13185 | GGCTCAGTGACCCGGG | 17 | 1207 |
| 903901 | 1119 | 1134 | 13210 | 13225 | ATTAACCCTCTCCACC | 27 | 1208 |
| 903933 | 1207 | 1222 | 13298 | 13313 | GGTAGACTACATCCAG | 59 | 1209 |
| 903965 | 1340 | 1355 | 13431 | 13446 | TGGTCCGCCTGCAGAA | 83 | 1210 |
| 904029 | 1793 | 1808 | 13884 | 13899 | CAGCTATGGAAATGCC | 86 | 1211 |
| 904061 | 1890 | 1905 | 13981 | 13996 | ACTCTCCAGTTCCCAT | 88 | 1212 |
| 904093 | 2272 | 2287 | 14363 | 14378 | CAAGCCTCCTCTCTAT | 81 | 1213 |
| 904125 | 2407 | 2422 | 14498 | 14513 | TTCGGAGGACATTGAA | 19 | 1214 |
| 904157 | 2505 | 2520 | 14596 | 14611 | AAGCCGCTGCCTGACT | 48 | 1215 |
| 904189 | 2591 | 2606 | 14682 | 14697 | TTCAGTGTTCAAGCAG | 92 | 1216 |
| 904253 | 2800 | 2815 | 14891 | 14906 | TCCTGGGCGGCGACAA | 92 | 1217 |
| 904317 | N/A | N/A | 1344 | 1359 | GGCACCATTCTGCAAC | 28 | 1218 |
| 904349 | N/A | N/A | 807 | 822 | CAACCCTCTATAGTTT | 12 | 1219 |
| 904381 | N/A | N/A | 2448 | 2463 | GGAGCCCTCCCTCCCG | 0 | 1220 |
| 904413 | N/A | N/A | 2821 | 2836 | TGTGTGATCCCCTAGG | 22 | 1221 |
| 904445 | N/A | N/A | 4206 | 4221 | GCCAGTGTTTTTACAA | 72 | 1222 |
| 904477 | N/A | N/A | 4691 | 4706 | TGAGCCACCAGTGGAC | 0 | 1223 |
| 904541 | N/A | N/A | 5110 | 5125 | CCCCCCGCTGATTCCA | 31 | 1224 |
| 904573 | N/A | N/A | 5238 | 5253 | AGCCTCAGGTGGAAAC | 53 | 1225 |
| 904605 | N/A | N/A | 5339 | 5354 | GGGTCCAGTTAAGCTG | 14 | 1226 |
| 904669 | N/A | N/A | 5658 | 5673 | TAGATGACTGAACTCA | 79 | 1227 |
| 904701 | N/A | N/A | 5761 | 5776 | GCCTCCTCCAGTTTGC | 34 | 1228 |
| 904733 | N/A | N/A | 5801 | 5816 | GATAAACCTTGTCTCC | 65 | 1229 |
| 904765 | N/A | N/A | 5856 | 5871 | GTTTTGTAAGTGCAAC | 73 | 1230 |

TABLE 18-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 904797 | N/A | N/A | 5928 | 5943 | GGAGACCTCCCTAAAC | 33 | 1231 |
| 904829 | N/A | N/A | 5960 | 5975 | GGCAAGGCTAAGTTCC | 91 | 1232 |
| 904861 | N/A | N/A | 6111 | 6126 | CAGCAAAGACAAGAAC | 53 | 1233 |
| 904893 | N/A | N/A | 6201 | 6216 | GTACAAAACTGCATTG | 31 | 1234 |
| 904925 | N/A | N/A | 6255 | 6270 | CACTAAACCCCACACC | 26 | 1235 |
| 904957 | N/A | N/A | 6323 | 6338 | GTGAGATCCAACTCGG | 77 | 1236 |
| 904989 | N/A | N/A | 6374 | 6389 | TGGGCCCACAGGATCC | 4 | 1237 |
| 905021 | N/A | N/A | 6537 | 6552 | ACTTCTGTTAGATACA | 95 | 1238 |
| 905053 | N/A | N/A | 6594 | 6609 | GTAACCCCCTGAAACT | 45 | 1239 |
| 905085 | N/A | N/A | 6638 | 6653 | AACATTCCTGGACAGG | 31 | 1240 |
| 905117 | N/A | N/A | 6742 | 6757 | CCCAGGTTTGGATGGA | 49 | 1241 |
| 905149 | N/A | N/A | 6828 | 6843 | AGGGAAATGAACGCAA | 86 | 1242 |
| 905181 | N/A | N/A | 6988 | 7003 | GCTGAGTGCTCTCGGC | 57 | 1243 |
| 905213 | N/A | N/A | 7118 | 7133 | GGGTACACGGCTCTCC | 38 | 1244 |
| 905245 | N/A | N/A | 7239 | 7254 | GTCTTGGGCACTCTCA | 89 | 1245 |
| 905277 | N/A | N/A | 7300 | 7315 | TAATGTCTCAAACTCC | 90 | 1246 |
| 905309 | N/A | N/A | 7469 | 7484 | ACCGCCCAAAACCATC | 57 | 1247 |
| 905341 | N/A | N/A | 7836 | 7851 | TGCACACACAAGAGAC | 0 | 1248 |
| 905373 | N/A | N/A | 7922 | 7937 | GGAATTATGGAATTGC | 98 | 1249 |
| 905405 | N/A | N/A | 7995 | 8010 | AACTCAAGTCAGTACA | 81 | 1250 |
| 905437 | N/A | N/A | 8081 | 8096 | CCCTGTAATCACACCC | 71 | 1251 |
| 905501 | N/A | N/A | 8311 | 8326 | TATTGGTTCAAAAGCA | 87 | 1252 |
| 905533 | N/A | N/A | 8381 | 8396 | CTGTTGGGTCAAACAC | 41 | 1253 |
| 905565 | N/A | N/A | 8450 | 8465 | AACATGAAGTGAGCCT | 88 | 1254 |
| 905597 | N/A | N/A | 8621 | 8636 | TTTTGGCACCTTCACC | 76 | 1255 |
| 905629 | N/A | N/A | 8739 | 8754 | ATTAGAGGGCTAGTGT | 73 | 1256 |
| 905661 | N/A | N/A | 8824 | 8839 | AAACTCAGGTGACTAC | 75 | 1257 |
| 905693 | N/A | N/A | 8884 | 8899 | TGGAGTCATTAGTGCT | 91 | 1258 |
| 905725 | N/A | N/A | 8953 | 8968 | AACAGCCATTGCATAA | 10 | 1259 |

TABLE 19

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 793406 | N/A | N/A | 8306 | 8321 | GTTCAAAAGCAGCATT | 74 | 13 |
| 903426 | 24 | 39 | 517 | 532 | CAAGATATACCGAGGA | 0 | 1260 |
| 903458 | 125 | 140 | 618 | 633 | TTCCCCTGGCAGAGAC | 3 | 1261 |
| 903490 | 253 | 268 | N/A | N/A | CCCTCGCTCCAGCTTC | 61 | 1262 |
| 903522 | 303 | 318 | 4778 | 4793 | CTTACTTTGAGGATCT | 68 | 1263 |
| 903618 | 560 | 575 | 12651 | 12666 | TACTGCTGGCCTTTAT | 59 | 1264 |
| 903650 | 629 | 644 | 12720 | 12735 | CGGAGCCTTCTTATGT | 30 | 1265 |
| 903682 | 670 | 685 | 12761 | 12776 | TGGTGCCTTTGTGGAC | 0 | 1266 |
| 903714 | 741 | 756 | 12832 | 12847 | CAGACCCATGCCGACG | 37 | 1267 |
| 903746 | 811 | 826 | 12902 | 12917 | AAGCGGCTGTGATTCC | 60 | 1268 |
| 903778 | 850 | 865 | 12941 | 12956 | TCTTTCCGTAGTCCAT | 14 | 1269 |
| 903810 | 931 | 946 | 13022 | 13037 | CACCCAAAAACTCCCT | 59 | 1270 |
| 903842 | 1008 | 1023 | 13099 | 13114 | GGCACGGATGTCCTTC | 48 | 1271 |
| 903874 | 1084 | 1099 | 13175 | 13190 | AGATTGGCTCAGTGAC | 91 | 1272 |
| 903906 | 1127 | 1142 | 13218 | 13233 | CTGGGTTCATTAACCC | 0 | 1273 |
| 903938 | 1212 | 1227 | 13303 | 13318 | CACGAGGTAGACTACA | 56 | 1274 |
| 903970 | 1345 | 1360 | 13436 | 13451 | GTTCTTGGTCCGCCTG | 62 | 1275 |
| 904002 | 1741 | 1756 | 13832 | 13847 | ACCCTCTTTATCCCCC | 91 | 1276 |
| 904034 | 1799 | 1814 | 13890 | 13905 | TGTGCTCAGCTATGGA | 84 | 1277 |
| 904066 | 1926 | 1941 | 14017 | 14032 | TTAGTCTAAAGTAAAC | 44 | 1278 |
| 904098 | 2284 | 2299 | 14375 | 14390 | TGCTGGTTCCTTCAAG | 76 | 1279 |
| 904130 | 2413 | 2428 | 14504 | 14519 | TCATTCTTCGGAGGAC | 73 | 1280 |
| 904162 | 2511 | 2526 | 14602 | 14617 | ATCAGGAAGCCGCTGC | 52 | 1281 |
| 904194 | 2609 | 2624 | 14700 | 14715 | ATGGCCCACCACCTGC | 0 | 1282 |
| 904226 | 2736 | 2751 | 14827 | 14842 | GCTAATTTTCTGACTG | 96 | 1283 |
| 904258 | 2805 | 2820 | 14896 | 14911 | GTCAATCCTGGGCGGC | 63 | 1284 |
| 904322 | N/A | N/A | 1374 | 1389 | TCATGATTGCAAAGCT | 20 | 1285 |
| 904354 | N/A | N/A | 837 | 852 | AGCTTTGTGAACCCAT | 10 | 1286 |
| 904386 | N/A | N/A | 2482 | 2497 | GCCCAAGCCCAGTCCA | 0 | 1287 |
| 904418 | N/A | N/A | 3410 | 3425 | AGGGTATATGAAAGTT | 77 | 1288 |
| 904450 | N/A | N/A | 4340 | 4355 | AGCCAGTGTGTATTGC | 83 | 1289 |
| 904482 | N/A | N/A | 4733 | 4748 | TTGCACCCTTGAGGAG | 0 | 1290 |
| 904514 | N/A | N/A | 5058 | 5073 | GCTAGGTGCCAGGGTA | 78 | 1291 |
| 904546 | N/A | N/A | 5115 | 5130 | CCCCCCCCCCCGCTGA | 16 | 1292 |
| 904578 | N/A | N/A | 5303 | 5318 | ACATTCCCACAGGGCC | 0 | 1293 |
| 904610 | N/A | N/A | 5361 | 5376 | GGATGTGGCAAAGGAC | 54 | 1294 |
| 904642 | N/A | N/A | 5490 | 5505 | GCCCTATTGTGTGGCA | 0 | 1295 |

TABLE 19-continued

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| Inhibition of APOL1 mRNA by 3-10-3 cEt gapmers targeting SEQ ID NO: 1 and 2 | | | | | | | |
| 904674 | N/A | N/A | 5682 | 5697 | ATTTTTCTTTGACCGG | 64 | 1296 |
| 904706 | N/A | N/A | 5766 | 5781 | ACGAAGCCTCCTCCAG | 55 | 1297 |
| 904738 | N/A | N/A | 5807 | 5822 | TCACCCGATAAACCTT | 82 | 1298 |
| 904770 | N/A | N/A | 5868 | 5883 | CCCAAACAGGCAGTTT | 57 | 1299 |
| 904802 | N/A | N/A | 5933 | 5948 | TATTCGGAGACCTCCC | 5 | 1300 |
| 904834 | N/A | N/A | 5965 | 5980 | ACCTGGGCAAGGCTAA | 52 | 1301 |
| 904866 | N/A | N/A | 6138 | 6153 | CTTACTCCACACCTTA | 72 | 1302 |
| 904898 | N/A | N/A | 6206 | 6221 | GTTTGGTACAAAACTG | 0 | 1303 |
| 904930 | N/A | N/A | 6261 | 6276 | TTGTCTCACTAAACCC | 21 | 1304 |
| 904962 | N/A | N/A | 6330 | 6345 | AAGACCAGTGAGATCC | 50 | 1305 |
| 904994 | N/A | N/A | 6402 | 6417 | AACCACCTGTAGGGAC | 69 | 1306 |
| 905026 | N/A | N/A | 6542 | 6557 | TGGGTACTTCTGTTAG | 62 | 1307 |
| 905058 | N/A | N/A | 6600 | 6615 | ACAGCTGTAACCCCCT | 13 | 1308 |
| 905090 | N/A | N/A | 6680 | 6695 | TGGTGGATATAAAAGC | 39 | 1309 |
| 905122 | N/A | N/A | 6794 | 6809 | AGCGATTGTCTTGTTT | 72 | 1310 |
| 905154 | N/A | N/A | 6879 | 6894 | TGCCGTGGCAACTCTG | 6 | 1311 |
| 905186 | N/A | N/A | 7037 | 7052 | GTTTTTCCTCAGTCCC | 69 | 1312 |
| 905218 | N/A | N/A | 7159 | 7174 | GGCACCTCCATGTTGC | 0 | 1313 |
| 905250 | N/A | N/A | 7244 | 7259 | TGCTGGTCTTGGGCAC | 17 | 1314 |
| 905282 | N/A | N/A | 7339 | 7354 | CCTTATAGCTTACCTG | 64 | 1315 |
| 905314 | N/A | N/A | 7475 | 7490 | AGAGTCACCGCCCAAA | 58 | 1316 |
| 905346 | N/A | N/A | 7843 | 7858 | CTTGCCGTGCACACAC | 10 | 1317 |
| 905378 | N/A | N/A | 7939 | 7954 | TGGTTTGCAGGGATCT | 56 | 1318 |
| 905410 | N/A | N/A | 8001 | 8016 | ACAAAGAACTCAAGTC | 55 | 1319 |
| 905442 | N/A | N/A | 8088 | 8103 | GACTGCTCCCTGTAAT | 0 | 1320 |
| 905474 | N/A | N/A | 8175 | 8190 | ATGTGTTTAGGCATTC | 81 | 1321 |
| 905506 | N/A | N/A | 8327 | 8342 | CATTGGGTTATGAAAT | 48 | 1322 |
| 905538 | N/A | N/A | 8386 | 8401 | CATGCCTGTTGGGTCA | 46 | 1323 |
| 905570 | N/A | N/A | 8460 | 8475 | GCTCAGCACCAACATG | 0 | 1324 |
| 905602 | N/A | N/A | 8631 | 8646 | ACTCCAACCCTTTTGG | 10 | 1325 |
| 905634 | N/A | N/A | 8744 | 8759 | ATTCTATTAGAGGGCT | 85 | 1326 |
| 905666 | N/A | N/A | 8831 | 8846 | AAGCTTTAAACTCAGG | 62 | 1327 |
| 905698 | N/A | N/A | 8893 | 8908 | CTTGTTTTATGGAGTC | 97 | 1328 |
| 905730 | N/A | N/A | 8960 | 8975 | AGTGCATAACAGCCAT | 9 | 1329 |

TABLE 20

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 793406 | N/A | N/A | 8306 | 8321 | GTTCAAAAGCAGCATT | 74 | 13 |
| 903427 | 25 | 40 | 518 | 533 | CCAAGATATACCGAGG | 12 | 1330 |
| 903459 | 129 | 144 | 622 | 637 | AATCTTCCCCTGGCAG | 13 | 1331 |
| 903491 | 254 | 269 | N/A | N/A | ACCCTCGCTCCAGCTT | 50 | 1332 |
| 903523 | 306 | 321 | 4781 | 4796 | GGGCTTACTTTGAGGA | 0 | 1333 |
| 903619 | 561 | 576 | 12652 | 12667 | GTACTGCTGGCCTTTA | 47 | 1334 |
| 903651 | 630 | 645 | 12721 | 12736 | ACGGAGCCTTCTTATG | 34 | 1335 |
| 903683 | 671 | 686 | 12762 | 12777 | GTGGTGCCTTTGTGGA | 0 | 1336 |
| 903715 | 742 | 757 | 12833 | 12848 | CCAGACCCATGCCGAC | 49 | 1337 |
| 903747 | 812 | 827 | 12903 | 12918 | AAAGCGGCTGTGATTC | 29 | 1338 |
| 903779 | 851 | 866 | 12942 | 12957 | TTCTTTCCGTAGTCCA | 38 | 1339 |
| 903811 | 932 | 947 | 13023 | 13038 | TCACCCAAAAACTCCC | 72 | 1340 |
| 903843 | 1010 | 1025 | 13101 | 13116 | AGGGCACGGATGTCCT | 3 | 1341 |
| 903875 | 1085 | 1100 | 13176 | 13191 | GAGATTGGCTCAGTGA | 69 | 1342 |
| 903907 | 1128 | 1143 | 13219 | 13234 | GCTGGGTTCATTAACC | 6 | 1343 |
| 903939 | 1230 | 1245 | 13321 | 13336 | TAAGTGCTTTGATTCG | 89 | 1344 |
| 903971 | 1346 | 1361 | 13437 | 13452 | AGTTCTTGGTCCGCCT | 52 | 1345 |
| 904003 | 1742 | 1757 | 13833 | 13848 | CACCCTCTTTATCCCC | 85 | 1346 |
| 904035 | 1800 | 1815 | 13891 | 13906 | CTGTGCTCAGCTATGG | 73 | 1347 |
| 904067 | 1928 | 1943 | 14019 | 14034 | CTTTAGTCTAAAGTAA | 16 | 1348 |
| 904099 | 2334 | 2349 | 14425 | 14440 | ACTCTTGGGCTTTCTC | 91 | 1349 |
| 904131 | 2414 | 2429 | 14505 | 14520 | TTCATTCTTCGGAGGA | 63 | 1350 |
| 904163 | 2512 | 2527 | 14603 | 14618 | CATCAGGAAGCCGCTG | 23 | 1351 |
| 904195 | 2612 | 2627 | 14703 | 14718 | GCCATGGCCCACCACC | 0 | 1352 |
| 904227 | 2744 | 2759 | 14835 | 14850 | GCTTTCATGCTAATTT | 40 | 1353 |
| 904259 | 2806 | 2821 | 14897 | 14912 | GGTCAATCCTGGGCGG | 58 | 1354 |
| 904323 | N/A | N/A | 1375 | 1390 | CTCATGATTGCAAAGC | 69 | 1355 |
| 904355 | N/A | N/A | 869 | 884 | CTCAGCAGTCAAAACC | 24 | 1356 |
| 904387 | N/A | N/A | 2515 | 2530 | GTTCCTAGAAGAAGCC | 25 | 1357 |
| 904419 | N/A | N/A | 3411 | 3426 | GAGGGTATATGAAAGT | 59 | 1358 |
| 904451 | N/A | N/A | 4351 | 4366 | TAGCTGGTGATAGCCA | 27 | 1359 |
| 904483 | N/A | N/A | 4735 | 4750 | TGTTGCACCCTTGAGG | 23 | 1360 |
| 904515 | N/A | N/A | 5064 | 5079 | TCATTTGCTAGGTGCC | 84 | 1361 |
| 904547 | N/A | N/A | 5172 | 5187 | GGTCAACCTCCTCTCC | 3 | 1362 |
| 904579 | N/A | N/A | 5304 | 5319 | TACATTCCCACAGGGC | 23 | 1363 |
| 904611 | N/A | N/A | 5379 | 5394 | CGCCAGGTCACACAGA | 69 | 1364 |
| 904643 | N/A | N/A | 5491 | 5506 | GGCCCTATTGTGTGGC | 0 | 1365 |

TABLE 20-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904675 | N/A | N/A | 5683 | 5698 | GATTTTTCTTTGACCG | 95 | 1366 |
| 904707 | N/A | N/A | 5767 | 5782 | CACGAAGCCTCCTCCA | 38 | 1367 |
| 904739 | N/A | N/A | 5808 | 5823 | TTCACCCGATAAACCT | 69 | 1368 |
| 904771 | N/A | N/A | 5869 | 5884 | ACCCAAACAGGCAGTT | 2 | 1369 |
| 904803 | N/A | N/A | 5934 | 5949 | GTATTCGGAGACCTCC | 25 | 1370 |
| 904835 | N/A | N/A | 5966 | 5981 | AACCTGGGCAAGGCTA | 21 | 1371 |
| 904867 | N/A | N/A | 6140 | 6155 | TGCTTACTCCACACCT | 65 | 1372 |
| 904899 | N/A | N/A | 6210 | 6225 | CCATGTTTGGTACAAA | 61 | 1373 |
| 904931 | N/A | N/A | 6262 | 6277 | CTTGTCTCACTAAACC | 30 | 1374 |
| 904963 | N/A | N/A | 6331 | 6346 | TAAGACCAGTGAGATC | 41 | 1375 |
| 904995 | N/A | N/A | 6403 | 6418 | AAACCACCTGTAGGGA | 42 | 1376 |
| 905027 | N/A | N/A | 6543 | 6558 | ATGGGTACTTCTGTTA | 79 | 1377 |
| 905059 | N/A | N/A | 6604 | 6619 | TAGAACAGCTGTAACC | 48 | 1378 |
| 905091 | N/A | N/A | 6682 | 6697 | GCTGGTGGATATAAAA | 0 | 1379 |
| 905123 | N/A | N/A | 6795 | 6810 | GAGCGATTGTCTTGTT | 89 | 1380 |
| 905155 | N/A | N/A | 6880 | 6895 | TTGCCGTGGCAACTCT | 0 | 1381 |
| 905187 | N/A | N/A | 7038 | 7053 | AGTTTTTCCTCAGTCC | 56 | 1382 |
| 905219 | N/A | N/A | 7160 | 7175 | AGGCACCTCCATGTTG | 11 | 1383 |
| 905251 | N/A | N/A | 7256 | 7271 | GGAGATTCCTCCTGCT | 0 | 1384 |
| 905283 | N/A | N/A | 7340 | 7355 | CCCTTATAGCTTACCT | 64 | 1385 |
| 905315 | N/A | N/A | 7476 | 7491 | GAGAGTCACCGCCCAA | 65 | 1386 |
| 905347 | N/A | N/A | 7844 | 7859 | TCTTGCCGTGCACACA | 26 | 1387 |
| 905379 | N/A | N/A | 7940 | 7955 | GTGGTTTGCAGGGATC | 82 | 1388 |
| 905411 | N/A | N/A | 8006 | 8021 | GGTCTACAAAGAACTC | 42 | 1389 |
| 905443 | N/A | N/A | 8089 | 8104 | GGACTGCTCCCTGTAA | 17 | 1390 |
| 905475 | N/A | N/A | 8176 | 8191 | GATGTGTTTAGGCATT | 84 | 1391 |
| 905507 | N/A | N/A | 8329 | 8344 | ATCATTGGGTTATGAA | 15 | 1392 |
| 905539 | N/A | N/A | 8387 | 8402 | ACATGCCTGTTGGGTC | 48 | 1393 |
| 905571 | N/A | N/A | 8461 | 8476 | AGCTCAGCACCAACAT | 22 | 1394 |
| 905603 | N/A | N/A | 8632 | 8647 | GACTCCAACCCTTTTG | 19 | 1395 |
| 905635 | N/A | N/A | 8745 | 8760 | AATTCTATTAGAGGGC | 80 | 1396 |
| 905667 | N/A | N/A | 8832 | 8847 | GAAGCTTTAAACTCAG | 83 | 1397 |
| 905699 | N/A | N/A | 8894 | 8909 | ACTTGTTTTATGGAGT | 30 | 1398 |
| 905731 | N/A | N/A | 8961 | 8976 | GAGTGCATAACAGCCA | 9 | 1399 |

TABLE 21

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 793406 | N/A | N/A | 8306 | 8321 | GTTCAAAAGCAGCATT | 84 | 13 |
| 903436 | 41 | 56 | 534 | 549 | ACAGGTCCTCCAGTCC | 37 | 1400 |
| 903468 | 154 | 169 | 2364 | 2379 | TGTCGCTGCAGGGCCT | 35 | 1401 |
| 903500 | 263 | 278 | 12661 | 12676 | TTTTGTTGCACCCTCG | 84 | 1402 |
| 903532 | 346 | 361 | N/A | N/A | TGCTCTCTGGGTCCAT | 8 | 1403 |
| 903628 | 570 | 585 | N/A | N/A | CCAGTTTCTGTACTGC | 23 | 1404 |
| 903660 | 642 | 657 | 12733 | 12748 | ATCTGCAAGGGCACGG | 39 | 1405 |
| 903692 | 680 | 695 | 12771 | 12786 | TTGGCGATGGTGGTGC | 0 | 1406 |
| 903724 | 758 | 773 | 12849 | 12864 | CCCTCTGTGAAGGGTG | 0 | 1407 |
| 903756 | 824 | 839 | 12915 | 12930 | GTAATCCCGGTCAAAG | 41 | 1408 |
| 903788 | 862 | 877 | 12953 | 12968 | GTGTCCACCACTTCTT | 18 | 1409 |
| 903820 | 968 | 983 | 13059 | 13074 | GTATTGCCAGCTAAGG | 94 | 1410 |
| 903852 | 1032 | 1047 | 13123 | 13138 | AAGATTGGCTCTGGCT | 74 | 1411 |
| 903884 | 1097 | 1112 | 13188 | 13203 | CCGCTTTCAGCTGAGA | 39 | 1412 |
| 903916 | 1158 | 1173 | 13249 | 13264 | GAGCTTGACTCCTCTG | 5 | 1413 |
| 903948 | 1241 | 1256 | 13332 | 13347 | GCCCCCTCATGTAAGT | 11 | 1414 |
| 903980 | 1382 | 1397 | 13473 | 13488 | ATATCTCTCCTGGTGG | 69 | 1415 |
| 904012 | 1755 | 1770 | 13846 | 13861 | ATAAACTTTACCTCAC | 62 | 1416 |
| 904044 | 1842 | 1857 | 13933 | 13948 | CTTCTCCTTGCTGCAC | 84 | 1417 |
| 904076 | 1949 | 1964 | 14040 | 14055 | CACCCGGCCCCCCAAT | 36 | 1418 |
| 904108 | 2348 | 2363 | 14439 | 14454 | ATCCAACTGTTCTAAC | 64 | 1419 |
| 904140 | 2486 | 2501 | 14577 | 14592 | ATATGCCCCCAGGAGG | 40 | 1420 |
| 904172 | 2527 | 2542 | 14618 | 14633 | CACCCCAATGACCATC | 63 | 1421 |
| 904204 | 2679 | 2694 | 14770 | 14785 | TGGTTCTCACATACTC | 91 | 1422 |
| 904236 | 2777 | 2792 | 14868 | 14883 | CTAGAGATCTGAGCTT | 14 | 1423 |
| 904268 | 2846 | 2861 | 14937 | 14952 | CAGCTTGATGAGTAGG | 21 | 1424 |
| 904300 | N/A | N/A | 2354 | 2369 | GGGCCTCCTCCTTGAG | 2 | 1425 |
| 904364 | N/A | N/A | 1115 | 1130 | AAGTTGGTGCTCAGAC | 8 | 1426 |
| 904396 | N/A | N/A | 2572 | 2587 | ACAGCGGGTCCTCCCT | 60 | 1427 |
| 904428 | N/A | N/A | 3809 | 3824 | TCGCATAAAACTTTGC | 43 | 1428 |
| 904460 | N/A | N/A | 4464 | 4479 | CAGAGGACGGGCAGCC | 0 | 1429 |
| 904492 | N/A | N/A | 4914 | 4929 | AGTCCATCCGGGTTCT | 27 | 1430 |
| 904524 | N/A | N/A | 5074 | 5089 | CCCACTTGAGTCATTT | 67 | 1431 |
| 904556 | N/A | N/A | 5201 | 5216 | AGAGCGGGAGGTGACA | 25 | 1432 |
| 904588 | N/A | N/A | 5314 | 5329 | TCAGGCCCGATACATT | 0 | 1433 |
| 904620 | N/A | N/A | 5415 | 5430 | ATTATTCTCATGGTAC | 73 | 1434 |
| 904652 | N/A | N/A | 5500 | 5515 | CCTTAGGGAGGCCCTA | 16 | 1435 |

TABLE 21-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904684 | N/A | N/A | 5702 | 5717 | AAAATTCTATTGGGCC | 0 | 1436 |
| 904716 | N/A | N/A | 5779 | 5794 | TTTTCACCATAGCACG | 87 | 1437 |
| 904748 | N/A | N/A | 5828 | 5843 | GTCCTTACTGCAGTTT | 95 | 1438 |
| 904780 | N/A | N/A | 5891 | 5906 | CAGGGATTTTCCAACA | 77 | 1439 |
| 904812 | N/A | N/A | 5943 | 5958 | GTCTCACCTGTATTCG | 34 | 1440 |
| 904844 | N/A | N/A | 6022 | 6037 | TTGCACTAAAAGCTGA | 62 | 1441 |
| 904876 | N/A | N/A | 6153 | 6168 | CCAGAAATCCTTATGC | 35 | 1442 |
| 904908 | N/A | N/A | 6223 | 6238 | GTTCCATGTATGCCCA | 85 | 1443 |
| 904940 | N/A | N/A | 6280 | 6295 | ACACTCAATCATACCC | 64 | 1444 |
| 904972 | N/A | N/A | 6341 | 6356 | CCAATTCAGCTAAGAC | 73 | 1445 |
| 905004 | N/A | N/A | 6414 | 6429 | AGGAGTTGCTGAAACC | 69 | 1446 |
| 905036 | N/A | N/A | 6553 | 6568 | GTCATATCAGATGGGT | 92 | 1447 |
| 905068 | N/A | N/A | 6616 | 6631 | CTACGAGGCCTTTAGA | 23 | 1448 |
| 905100 | N/A | N/A | 6721 | 6736 | CCTCTGGCACTAAATC | 40 | 1449 |
| 905132 | N/A | N/A | 6804 | 6819 | TGGCTGGGCGAGCGAT | 38 | 1450 |
| 905164 | N/A | N/A | 6889 | 6904 | CTGACTTGGTTGCCGT | 60 | 1451 |
| 905196 | N/A | N/A | 7080 | 7095 | GGGCCTGTTATTAAAC | 0 | 1452 |
| 905228 | N/A | N/A | 7169 | 7184 | TGATCCTTGAGGCACC | 28 | 1453 |
| 905260 | N/A | N/A | 7270 | 7285 | AACTACCATGCAAAGG | 38 | 1454 |
| 905292 | N/A | N/A | 7380 | 7395 | ACTCCTTATGTTTTGA | 94 | 1455 |
| 905324 | N/A | N/A | 7485 | 7500 | CCAGACAGCGAGAGTC | 78 | 1456 |
| 905356 | N/A | N/A | 7862 | 7877 | GCATGATGTAAAATTG | 6 | 1457 |
| 905388 | N/A | N/A | 7975 | 7990 | AGGATTACTCCTGAAG | 0 | 1458 |
| 905420 | N/A | N/A | 8017 | 8032 | AAATAATGGTAGGTCT | 77 | 1459 |
| 905452 | N/A | N/A | 8120 | 8135 | GGTATATTCCTGACCA | 25 | 1460 |
| 905484 | N/A | N/A | 8185 | 8200 | TGGAATCCAGATGTGT | 65 | 1461 |
| 905516 | N/A | N/A | 8340 | 8355 | AATATCAACACATCAT | 82 | 1462 |
| 905548 | N/A | N/A | 8409 | 8424 | CCAGTGATCACTTCCA | 78 | 1463 |
| 905580 | N/A | N/A | 8517 | 8532 | AACATTGAAACACCAG | 94 | 1464 |
| 905612 | N/A | N/A | 8665 | 8680 | AGCTTCCATAAGCCAG | 12 | 1465 |
| 905644 | N/A | N/A | 8756 | 8771 | GGTAGGGCTCTAATTC | 60 | 1466 |
| 905676 | N/A | N/A | 8867 | 8882 | TAGAGGGAATTGTGTG | 61 | 1467 |
| 905708 | N/A | N/A | 8907 | 8922 | GCTGTGATGTGGGACT | 89 | 1468 |
| 905740 | N/A | N/A | 8971 | 8986 | GAAAGTGTGGGAGTGC | 8 | 1469 |

TABLE 22

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 793406 | N/A | N/A | 8306 | 8321 | GTTCAAAAGCAGCATT | 82 | 13 |
| 903437 | 42 | 57 | 535 | 550 | GACAGGTCCTCCAGTC | 14 | 1470 |
| 903469 | 155 | 170 | 2365 | 2380 | ATGTCGCTGCAGGGCC | 18 | 1471 |
| 903533 | 349 | 364 | N/A | N/A | TACTGCTCTCTGGGTC | 33 | 1472 |
| 903629 | 571 | 586 | 12662 | 12677 | ACCAGTTTCTGTACTG | 4 | 1473 |
| 903661 | 643 | 658 | 12734 | 12749 | CATCTGCAAGGGCACG | 43 | 1474 |
| 903693 | 681 | 696 | 12772 | 12787 | ATTGGCGATGGTGGTG | 27 | 1475 |
| 903725 | 759 | 774 | 12850 | 12865 | TCCCTCTGTGAAGGGT | 0 | 1476 |
| 903757 | 827 | 842 | 12918 | 12933 | CTGGTAATCCCGGTCA | 63 | 1477 |
| 903789 | 863 | 878 | 12954 | 12969 | TGTGTCCACCACTTCT | 39 | 1478 |
| 903821 | 969 | 984 | 13060 | 13075 | AGTATTGCCAGCTAAG | 98 | 1479 |
| 903853 | 1033 | 1048 | 13124 | 13139 | GAAGATTGGCTCTGGC | 91 | 1480 |
| 903885 | 1098 | 1113 | 13189 | 13204 | ACCGCTTTCAGCTGAG | 10 | 1481 |
| 903917 | 1159 | 1174 | 13250 | 13265 | TGAGCTTGACTCCTCT | 6 | 1482 |
| 903949 | 1242 | 1257 | 13333 | 13348 | TGCCCCCTCATGTAAG | 46 | 1483 |
| 903981 | 1384 | 1399 | 13475 | 13490 | GCATATCTCTCCTGGT | 81 | 1484 |
| 904013 | 1764 | 1779 | 13855 | 13870 | CTCAGTTCCATAAACT | 87 | 1485 |
| 904045 | 1844 | 1859 | 13935 | 13950 | GCCTTCTCCTTGCTGC | 57 | 1486 |
| 904077 | 1950 | 1965 | 14041 | 14056 | ACACCCGGCCCCCCAA | 49 | 1487 |
| 904109 | 2349 | 2364 | 14440 | 14455 | TATCCAACTGTTCTAA | 68 | 1488 |
| 904141 | 2487 | 2502 | 14578 | 14593 | GATATGCCCCCAGGAG | 84 | 1489 |
| 904173 | 2528 | 2543 | 14619 | 14634 | CCACCCCAATGACCAT | 67 | 1490 |
| 904205 | 2680 | 2695 | 14771 | 14786 | TTGGTTCTCACATACT | 84 | 1491 |
| 904237 | 2778 | 2793 | 14869 | 14884 | TCTAGAGATCTGAGCT | 20 | 1492 |
| 904269 | 2847 | 2862 | 14938 | 14953 | CCAGCTTGATGAGTAG | 30 | 1493 |
| 904365 | N/A | N/A | 1116 | 1131 | CAAGTTGGTGCTCAGA | 0 | 1494 |
| 904397 | N/A | N/A | 2583 | 2598 | TCAACTAGGATACAGC | 82 | 1495 |
| 904429 | N/A | N/A | 3817 | 3832 | ATCCTTCTTCGCATAA | 80 | 1496 |
| 904461 | N/A | N/A | 4467 | 4482 | AATCAGAGGACGGGCA | 5 | 1497 |
| 904493 | N/A | N/A | 4916 | 4931 | CTAGTCCATCCGGGTT | 49 | 1498 |
| 904525 | N/A | N/A | 5075 | 5090 | CCCCACTTGAGTCATT | 57 | 1499 |
| 904557 | N/A | N/A | 5202 | 5217 | CAGAGCGGGAGGTGAC | 24 | 1500 |
| 904589 | N/A | N/A | 5315 | 5330 | ATCAGGCCCGATACAT | 0 | 1501 |
| 904621 | N/A | N/A | 5436 | 5451 | CTCAAGACAACATGGG | 43 | 1502 |
| 904653 | N/A | N/A | 5501 | 5516 | CCCTTAGGGAGGCCCT | 13 | 1503 |
| 904685 | N/A | N/A | 5721 | 5736 | CTTACTCAATTAACTC | 77 | 1504 |
| 904717 | N/A | N/A | 5782 | 5797 | ACTTTTTCACCATAGC | 94 | 1505 |

TABLE 22-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904749 | N/A | N/A | 5829 | 5844 | TGTCCTTACTGCAGTT | 82 | 1506 |
| 904781 | N/A | N/A | 5892 | 5907 | CCAGGGATTTTCCAAC | 69 | 1507 |
| 904813 | N/A | N/A | 5944 | 5959 | GGTCTCACCTGTATTC | 32 | 1508 |
| 904845 | N/A | N/A | 6023 | 6038 | TTTGCACTAAAAGCTG | 67 | 1509 |
| 904877 | N/A | N/A | 6154 | 6169 | CCCAGAAATCCTTATG | 37 | 1510 |
| 904909 | N/A | N/A | 6224 | 6239 | CGTTCCATGTATGCCC | 93 | 1511 |
| 904941 | N/A | N/A | 6281 | 6296 | CACACTCAATCATACC | 22 | 1512 |
| 904973 | N/A | N/A | 6343 | 6358 | GGCCAATTCAGCTAAG | 7 | 1513 |
| 905069 | N/A | N/A | 6617 | 6632 | CCTACGAGGCCTTTAG | 59 | 1514 |
| 905101 | N/A | N/A | 6722 | 6737 | ACCTCTGGCACTAAAT | 59 | 1515 |
| 905133 | N/A | N/A | 6805 | 6820 | TTGGCTGGGCGAGCGA | 61 | 1516 |
| 905165 | N/A | N/A | 6890 | 6905 | GCTGACTTGGTTGCCG | 10 | 1517 |
| 905197 | N/A | N/A | 7081 | 7096 | TGGGCCTGTTATTAAA | 14 | 1518 |
| 905229 | N/A | N/A | 7170 | 7185 | CTGATCCTTGAGGCAC | 72 | 1519 |
| 905261 | N/A | N/A | 7271 | 7286 | CAACTACCATGCAAAG | 53 | 1520 |
| 905293 | N/A | N/A | 7381 | 7396 | AACTCCTTATGTTTTG | 89 | 1521 |
| 905325 | N/A | N/A | 7486 | 7501 | TCCAGACAGCGAGAGT | 83 | 1522 |
| 905357 | N/A | N/A | 7863 | 7878 | GGCATGATGTAAAATT | 33 | 1523 |
| 905389 | N/A | N/A | 7977 | 7992 | GCAGGATTACTCCTGA | 10 | 1524 |
| 905421 | N/A | N/A | 8053 | 8068 | ACAGTGAAACAAGCAA | 93 | 1525 |
| 905453 | N/A | N/A | 8121 | 8136 | TGGTATATTCCTGACC | 35 | 1526 |
| 905485 | N/A | N/A | 8201 | 8216 | CCTTAATGTAAATTCC | 90 | 1527 |
| 905517 | N/A | N/A | 8345 | 8360 | ATGTGAATATCAACAC | 74 | 1528 |
| 905549 | N/A | N/A | 8410 | 8425 | CCCAGTGATCACTTCC | 78 | 1529 |
| 905581 | N/A | N/A | 8518 | 8533 | GAACATTGAAACACCA | 93 | 1530 |
| 905613 | N/A | N/A | 8666 | 8681 | CAGCTTCCATAAGCCA | 30 | 1531 |
| 905645 | N/A | N/A | 8767 | 8782 | GAGATCACAAGGGTAG | 98 | 1532 |
| 905677 | N/A | N/A | 8868 | 8883 | ATAGAGGGAATTGTGT | 45 | 1533 |
| 905709 | N/A | N/A | 8908 | 8923 | AGCTGTGATGTGGGAC | 63 | 1534 |
| 905741 | N/A | N/A | 8978 | 8993 | GTTGGAGGAAAGTGTG | 19 | 1535 |
| 905773 | N/A | N/A | 9795 | 9810 | TCTGACATAAGCCCAG | 0 | 1536 |
| 905805 | N/A | N/A | 10425 | 10440 | AGAACCACCTATATAA | 60 | 1537 |

TABLE 23

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 793406 | N/A | N/A | 8306 | 8321 | GTTCAAAAGCAGCATT | 88 | 13 |
| 903422 | 20 | 35 | 513 | 528 | ATATACCGAGGAATTC | 7 | 1538 |
| 903454 | 77 | 92 | 570 | 585 | ATCCCACCTCCAGTTA | 49 | 1539 |
| 903486 | 218 | 233 | 4511 | 4526 | CCAAGGAAAAGTGCAC | 47 | 1540 |
| 903518 | 297 | 312 | 4772 | 4787 | TTGAGGATCTCCAGTA | 55 | 1541 |
| 903614 | 543 | 558 | 12634 | 12649 | GTGCCAGTTTTTGTCT | 0 | 1542 |
| 903646 | 625 | 640 | 12716 | 12731 | GCCTTCTTATGTTATC | 30 | 1543 |
| 903678 | 665 | 680 | 12756 | 12771 | CCTTTGTGGACCTTCT | 71 | 1544 |
| 903710 | 737 | 752 | 12828 | 12843 | CCCATGCCGACGAGGG | 11 | 1545 |
| 903742 | 807 | 822 | 12898 | 12913 | GGCTGTGATTCCCAAC | 28 | 1546 |
| 903774 | 845 | 860 | 12936 | 12951 | CCGTAGTCCATGGTAC | 11 | 1547 |
| 903806 | 902 | 917 | 12993 | 13008 | TTGTCAAGGCTTTTGA | 69 | 1548 |
| 903838 | 1004 | 1019 | 13095 | 13110 | CGGATGTCCTTCCCAA | 23 | 1549 |
| 903870 | 1080 | 1095 | 13171 | 13186 | TGGCTCAGTGACCCGG | 31 | 1550 |
| 903902 | 1122 | 1137 | 13213 | 13228 | TTCATTAACCCTCTCC | 74 | 1551 |
| 903934 | 1208 | 1223 | 13299 | 13314 | AGGTAGACTACATCCA | 40 | 1552 |
| 903966 | 1341 | 1356 | 13432 | 13447 | TTGGTCCGCCTGCAGA | 64 | 1553 |
| 903998 | 1708 | 1723 | 13799 | 13814 | TTGGGTCAAAAGCGAT | 92 | 1554 |
| 904030 | 1794 | 1809 | 13885 | 13900 | TCAGCTATGGAAATGC | 93 | 1555 |
| 904062 | 1921 | 1936 | 14012 | 14027 | CTAAAGTAAACTGCTT | 63 | 1556 |
| 904094 | 2279 | 2294 | 14370 | 14385 | GTTCCTTCAAGCCTCC | 92 | 1557 |
| 904126 | 2408 | 2423 | 14499 | 14514 | CTTCGGAGGACATTGA | 70 | 1558 |
| 904158 | 2506 | 2521 | 14597 | 14612 | GAAGCCGCTGCCTGAC | 78 | 1559 |
| 904190 | 2594 | 2609 | 14685 | 14700 | CCCTTCAGTGTTCAAG | 89 | 1560 |
| 904222 | 2720 | 2735 | 14811 | 14826 | TTTACTTACCGGGTAA | 22 | 1561 |
| 904254 | 2801 | 2816 | 14892 | 14907 | ATCCTGGGCGGCGACA | 84 | 1562 |
| 904318 | N/A | N/A | 1345 | 1360 | AGGCACCATTCTGCAA | 29 | 1563 |
| 904350 | N/A | N/A | 820 | 835 | TGAGCTGTTTCCCCAA | 39 | 1564 |
| 904382 | N/A | N/A | 2474 | 2489 | CCAGTCCAATTGTGCA | 43 | 1565 |
| 904414 | N/A | N/A | 2828 | 2843 | TGTTCACTGTGTGATC | 74 | 1566 |
| 904446 | N/A | N/A | 4306 | 4321 | GCCTCTTACATGTGTC | 52 | 1567 |
| 904478 | N/A | N/A | 4693 | 4708 | TGTGAGCCACCAGTGG | 0 | 1568 |
| 904510 | N/A | N/A | 5024 | 5039 | GGGCCGTGTCACCCTA | 8 | 1569 |
| 904542 | N/A | N/A | 5111 | 5126 | CCCCCCCGCTGATTCC | 19 | 1570 |
| 904574 | N/A | N/A | 5241 | 5256 | ACCAGCCTCAGGTGGA | 12 | 1571 |
| 904606 | N/A | N/A | 5353 | 5368 | CAAAGGACAGACCGGG | 64 | 1572 |
| 904638 | N/A | N/A | 5464 | 5479 | AGGCCAGGTAGCCGTG | 9 | 1573 |

TABLE 23-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904670 | N/A | N/A | 5659 | 5674 | TTAGATGACTGAACTC | 75 | 1574 |
| 904702 | N/A | N/A | 5762 | 5777 | AGCCTCCTCCAGTTTG | 32 | 1575 |
| 904734 | N/A | N/A | 5802 | 5817 | CGATAAACCTTGTCTC | 44 | 1576 |
| 904766 | N/A | N/A | 5858 | 5873 | CAGTTTTGTAAGTGCA | 97 | 1577 |
| 904798 | N/A | N/A | 5929 | 5944 | CGGAGACCTCCCTAAA | 12 | 1578 |
| 904830 | N/A | N/A | 5961 | 5976 | GGGCAAGGCTAAGTTC | 56 | 1579 |
| 904862 | N/A | N/A | 6112 | 6127 | CCAGCAAAGACAAGAA | 87 | 1580 |
| 904894 | N/A | N/A | 6202 | 6217 | GGTACAAAACTGCATT | 78 | 1581 |
| 904926 | N/A | N/A | 6256 | 6271 | TCACTAAACCCCACAC | 0 | 1582 |
| 904958 | N/A | N/A | 6325 | 6340 | CAGTGAGATCCAACTC | 40 | 1583 |
| 904990 | N/A | N/A | 6375 | 6390 | ATGGGCCCACAGGATC | 0 | 1584 |
| 905022 | N/A | N/A | 6538 | 6553 | TACTTCTGTTAGATAC | 92 | 1585 |
| 905054 | N/A | N/A | 6595 | 6610 | TGTAACCCCCTGAAAC | 17 | 1586 |
| 905086 | N/A | N/A | 6641 | 6656 | TGAAACATTCCTGGAC | 85 | 1587 |
| 905118 | N/A | N/A | 6743 | 6758 | ACCCAGGTTTGGATGG | 33 | 1588 |
| 905150 | N/A | N/A | 6875 | 6890 | GTGGCAACTCTGTAAG | 10 | 1589 |
| 905182 | N/A | N/A | 6989 | 7004 | GGCTGAGTGCTCTCGG | 60 | 1590 |
| 905214 | N/A | N/A | 7119 | 7134 | AGGGTACACGGCTCTC | 45 | 1591 |
| 905246 | N/A | N/A | 7240 | 7255 | GGTCTTGGGCACTCTC | 79 | 1592 |
| 905278 | N/A | N/A | 7301 | 7316 | ATAATGTCTCAAACTC | 77 | 1593 |
| 905310 | N/A | N/A | 7470 | 7485 | CACCGCCCAAAACCAT | 25 | 1594 |
| 905342 | N/A | N/A | 7838 | 7853 | CGTGCACACACAAGAG | 0 | 1595 |
| 905374 | N/A | N/A | 7923 | 7938 | GGGAATTATGGAATTG | 83 | 1596 |
| 905406 | N/A | N/A | 7996 | 8011 | GAACTCAAGTCAGTAC | 73 | 1597 |
| 905438 | N/A | N/A | 8083 | 8098 | CTCCCTGTAATCACAC | 40 | 1598 |
| 905470 | N/A | N/A | 8168 | 8183 | TAGGCATTCAGAATTT | 71 | 1599 |
| 905502 | N/A | N/A | 8313 | 8328 | ATTATTGGTTCAAAAG | 35 | 1600 |
| 905534 | N/A | N/A | 8382 | 8397 | CCTGTTGGGTCAAACA | 45 | 1601 |
| 905566 | N/A | N/A | 8452 | 8467 | CCAACATGAAGTGAGC | 79 | 1602 |
| 905598 | N/A | N/A | 8622 | 8637 | CTTTTGGCACCTTCAC | 83 | 1603 |
| 905630 | N/A | N/A | 8740 | 8755 | TATTAGAGGGCTAGTG | 55 | 1604 |
| 905662 | N/A | N/A | 8825 | 8840 | TAAACTCAGGTGACTA | 60 | 1605 |
| 905694 | N/A | N/A | 8885 | 8900 | ATGGAGTCATTAGTGC | 85 | 1606 |
| 905726 | N/A | N/A | 8954 | 8969 | TAACAGCCATTGCATA | 6 | 1607 |

TABLE 24

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi- bition | SEQ ID NO |
|---|---|---|---|---|---|---|---|
| 793406 | N/A | N/A | 8306 | 8321 | GTTCAAAAGCAGCATT | 87 | 13 |
| 903423 | 21 | 36 | 514 | 529 | GATATACCGAGGAATT | 17 | 1608 |
| 903455 | 78 | 93 | 571 | 586 | GATCCCACCTCCAGTT | 29 | 1609 |
| 903487 | 220 | 235 | 4513 | 4528 | CACCAAGGAAAAGTGC | 3 | 1610 |
| 903519 | 300 | 315 | 4775 | 4790 | ACTTTGAGGATCTCCA | 66 | 1611 |
| 903615 | 544 | 559 | 12635 | 12650 | CGTGCCAGTTTTTGTC | 0 | 1612 |
| 903647 | 626 | 641 | 12717 | 12732 | AGCCTTCTTATGTTAT | 44 | 1613 |
| 903679 | 666 | 681 | 12757 | 12772 | GCCTTTGTGGACCTTC | 77 | 1614 |
| 903711 | 738 | 753 | 12829 | 12844 | ACCCATGCCGACGAGG | 19 | 1615 |
| 903743 | 808 | 823 | 12899 | 12914 | CGGCTGTGATTCCCAA | 19 | 1616 |
| 903775 | 846 | 861 | 12937 | 12952 | TCCGTAGTCCATGGTA | 5 | 1617 |
| 903807 | 907 | 922 | 12998 | 13013 | TCAATTTGTCAAGGCT | 94 | 1618 |
| 903839 | 1005 | 1020 | 13096 | 13111 | ACGGATGTCCTTCCCA | 40 | 1619 |
| 903871 | 1081 | 1096 | 13172 | 13187 | TTGGCTCAGTGACCCG | 44 | 1620 |
| 903903 | 1124 | 1139 | 13215 | 13230 | GGTTCATTAACCCTCT | 39 | 1621 |
| 903935 | 1209 | 1224 | 13300 | 13315 | GAGGTAGACTACATCC | 29 | 1622 |
| 903967 | 1342 | 1357 | 13433 | 13448 | CTTGGTCCGCCTGCAG | 42 | 1623 |
| 903999 | 1709 | 1724 | 13800 | 13815 | TTTGGGTCAAAAGCGA | 89 | 1624 |
| 904031 | 1796 | 1811 | 13887 | 13902 | GCTCAGCTATGGAAAT | 77 | 1625 |
| 904063 | 1923 | 1938 | 14014 | 14029 | GTCTAAAGTAAACTGC | 88 | 1626 |
| 904095 | 2281 | 2296 | 14372 | 14387 | TGGTTCCTTCAAGCCT | 35 | 1627 |
| 904127 | 2409 | 2424 | 14500 | 14515 | TCTTCGGAGGACATTG | 64 | 1628 |
| 904159 | 2507 | 2522 | 14598 | 14613 | GGAAGCCGCTGCCTGA | 80 | 1629 |
| 904191 | 2595 | 2610 | 14686 | 14701 | GCCCTTCAGTGTTCAA | 47 | 1630 |
| 904223 | 2721 | 2736 | 14812 | 14827 | GTTTACTTACCGGGTA | 83 | 1631 |
| 904255 | 2802 | 2817 | 14893 | 14908 | AATCCTGGGCGGCGAC | 79 | 1632 |
| 904319 | N/A | N/A | 1347 | 1362 | ACAGGCACCATTCTGC | 38 | 1633 |
| 904351 | N/A | N/A | 825 | 840 | CCATCTGAGCTGTTTC | 30 | 1634 |
| 904383 | N/A | N/A | 2475 | 2490 | CCCAGTCCAATTGTGC | 34 | 1635 |
| 904415 | N/A | N/A | 2885 | 2900 | TTGCTGTAAGGGACAA | 53 | 1636 |
| 904447 | N/A | N/A | 4310 | 4325 | CAGAGCCTCTTACATG | 47 | 1637 |
| 904479 | N/A | N/A | 4694 | 4709 | ATGTGAGCCACCAGTG | 46 | 1638 |
| 904511 | N/A | N/A | 5025 | 5040 | TGGGCCGTGTCACCCT | 9 | 1639 |
| 904543 | N/A | N/A | 5112 | 5127 | CCCCCCCCGCTGATTC | 43 | 1640 |
| 904575 | N/A | N/A | 5243 | 5258 | GGACCAGCCTCAGGTG | 0 | 1641 |
| 904607 | N/A | N/A | 5354 | 5369 | GCAAAGGACAGACCGG | 32 | 1642 |
| 904639 | N/A | N/A | 5465 | 5480 | CAGGCCAGGTAGCCGT | 22 | 1643 |

TABLE 24-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 904671 | N/A | N/A | 5660 | 5675 | TTTAGATGACTGAACT | 69 | 1644 |
| 904703 | N/A | N/A | 5763 | 5778 | AAGCCTCCTCCAGTTT | 23 | 1645 |
| 904735 | N/A | N/A | 5803 | 5818 | CCGATAAACCTTGTCT | 67 | 1646 |
| 904767 | N/A | N/A | 5859 | 5874 | GCAGTTTTGTAAGTGC | 43 | 1647 |
| 904799 | N/A | N/A | 5930 | 5945 | TCGGAGACCTCCCTAA | 25 | 1648 |
| 904831 | N/A | N/A | 5962 | 5977 | TGGGCAAGGCTAAGTT | 49 | 1649 |
| 904863 | N/A | N/A | 6135 | 6150 | ACTCCACACCTTAATT | 36 | 1650 |
| 904895 | N/A | N/A | 6203 | 6218 | TGGTACAAAACTGCAT | 66 | 1651 |
| 904927 | N/A | N/A | 6257 | 6272 | CTCACTAAACCCCACA | 29 | 1652 |
| 904959 | N/A | N/A | 6326 | 6341 | CCAGTGAGATCCAACT | 70 | 1653 |
| 904991 | N/A | N/A | 6376 | 6391 | GATGGGCCCACAGGAT | 2 | 1654 |
| 905023 | N/A | N/A | 6539 | 6554 | GTACTTCTGTTAGATA | 66 | 1655 |
| 905055 | N/A | N/A | 6597 | 6612 | GCTGTAACCCCCTGAA | 85 | 1656 |
| 905087 | N/A | N/A | 6645 | 6660 | GCCCTGAAACATTCCT | 20 | 1657 |
| 905119 | N/A | N/A | 6744 | 6759 | AACCCAGGTTTGGATG | 40 | 1658 |
| 905151 | N/A | N/A | 6876 | 6891 | CGTGGCAACTCTGTAA | 41 | 1659 |
| 905183 | N/A | N/A | 6991 | 7006 | TCGGCTGAGTGCTCTC | 63 | 1660 |
| 905215 | N/A | N/A | 7120 | 7135 | CAGGGTACACGGCTCT | 40 | 1661 |
| 905247 | N/A | N/A | 7241 | 7256 | TGGTCTTGGGCACTCT | 76 | 1662 |
| 905279 | N/A | N/A | 7335 | 7350 | ATAGCTTACCTGTGGG | 38 | 1663 |
| 905311 | N/A | N/A | 7471 | 7486 | TCACCGCCCAAAACCA | 29 | 1664 |
| 905343 | N/A | N/A | 7839 | 7854 | CCGTGCACACACAAGA | 0 | 1665 |
| 905375 | N/A | N/A | 7928 | 7943 | GATCTGGGAATTATGG | 62 | 1666 |
| 905407 | N/A | N/A | 7997 | 8012 | AGAACTCAAGTCAGTA | 92 | 1667 |
| 905439 | N/A | N/A | 8084 | 8099 | GCTCCCTGTAATCACA | 35 | 1668 |
| 905471 | N/A | N/A | 8172 | 8187 | TGTTTAGGCATTCAGA | 86 | 1669 |
| 905503 | N/A | N/A | 8317 | 8332 | TGAAATTATTGGTTCA | 6 | 1670 |
| 905535 | N/A | N/A | 8383 | 8398 | GCCTGTTGGGTCAAAC | 60 | 1671 |
| 905567 | N/A | N/A | 8453 | 8468 | ACCAACATGAAGTGAG | 72 | 1672 |
| 905599 | N/A | N/A | 8623 | 8638 | CCTTTTGGCACCTTCA | 93 | 1673 |
| 905631 | N/A | N/A | 8741 | 8756 | CTATTAGAGGGCTAGT | 78 | 1674 |
| 905663 | N/A | N/A | 8827 | 8842 | TTTAAACTCAGGTGAC | 64 | 1675 |
| 905695 | N/A | N/A | 8886 | 8901 | TATGGAGTCATTAGTG | 81 | 1676 |
| 905727 | N/A | N/A | 8955 | 8970 | ATAACAGCCATTGCAT | 14 | 1677 |

TABLE 25

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 793406 | N/A | N/A | 8306 | 8321 | GTTCAAAAGCAGCATT | 95 | 13 |
| 903501 | 264 | 279 | N/A | N/A | GTTTTGTTGCACCCTC | 98 | 1678 |
| 903543 | 402 | 417 | 9065 | 9080 | ATTCTGTGTGCTCACT | 98 | 1679 |
| 903545 | 405 | 420 | 9068 | 9083 | CAGATTCTGTGTGCTC | 98 | 1680 |
| 903556 | 419 | 434 | 9082 | 9097 | GTCAGCAGGAGTAGCA | 65 | 1681 |
| 903557 | 421 | 436 | 9084 | 9099 | CAGTCAGCAGGAGTAG | 84 | 1682 |
| 903558 | 422 | 437 | 9085 | 9100 | TCAGTCAGCAGGAGTA | 92 | 1683 |
| 903564 | 429 | 444 | 9092 | 9107 | CTCATTATCAGTCAGC | 94 | 1684 |
| 903567 | 434 | 449 | 9097 | 9112 | CAGGCCTCATTATCAG | 40 | 1685 |
| 903568 | 435 | 450 | 9098 | 9113 | CCAGGCCTCATTATCA | 52 | 1686 |
| 903569 | 436 | 451 | 9099 | 9114 | TCCAGGCCTCATTATC | 69 | 1687 |
| 903570 | 437 | 452 | 9100 | 9115 | TTCCAGGCCTCATTAT | 55 | 1688 |
| 903571 | 438 | 453 | 9101 | 9116 | GTTCCAGGCCTCATTA | 74 | 1689 |
| 903572 | 439 | 454 | 9102 | 9117 | CGTTCCAGGCCTCATT | 97 | 1690 |
| 903573 | 440 | 455 | 9103 | 9118 | CCGTTCCAGGCCTCAT | 81 | 1691 |
| 903574 | 441 | 456 | 9104 | 9119 | TCCGTTCCAGGCCTCA | 85 | 1692 |
| 903575 | 443 | 458 | 9106 | 9121 | AATCCGTTCCAGGCCT | 52 | 1693 |
| 903576 | 444 | 459 | 9107 | 9122 | GAATCCGTTCCAGGCC | 55 | 1694 |
| 903577 | 445 | 460 | 9108 | 9123 | CGAATCCGTTCCAGGC | 45 | 1695 |
| 903578 | 446 | 461 | 9109 | 9124 | ACGAATCCGTTCCAGG | 43 | 1696 |
| 903579 | 447 | 462 | 9110 | 9125 | CACGAATCCGTTCCAG | 61 | 1697 |
| 903581 | 449 | 464 | 9112 | 9127 | GCCACGAATCCGTTCC | 35 | 1698 |
| 903582 | 450 | 465 | 9113 | 9128 | AGCCACGAATCCGTTC | 53 | 1699 |
| 903583 | 451 | 466 | 9114 | 9129 | CAGCCACGAATCCGTT | 47 | 1700 |
| 903584 | 452 | 467 | 9115 | 9130 | GCAGCCACGAATCCGT | 40 | 1701 |
| 903585 | 453 | 468 | 9116 | 9131 | AGCAGCCACGAATCCG | 82 | 1702 |
| 903586 | 469 | 484 | N/A | N/A | TCCTGGGCAGTTCAGC | 53 | 1703 |
| 903587 | 471 | 486 | N/A | N/A | ATTCCTGGGCAGTTCA | 89 | 1704 |
| 903589 | 473 | 488 | N/A | N/A | TCATTCCTGGGCAGTT | 74 | 1705 |
| 903592 | 501 | 516 | 12592 | 12607 | GTCCAGAGCTTTACGG | 65 | 1706 |
| 903595 | 504 | 519 | 12595 | 12610 | GTTGTCCAGAGCTTTA | 94 | 1707 |
| 903596 | 505 | 520 | 12596 | 12611 | GGTTGTCCAGAGCTTT | 98 | 1708 |
| 903597 | 506 | 521 | 12597 | 12612 | AGGTTGTCCAGAGCTT | 83 | 1709 |
| 903598 | 507 | 522 | 12598 | 12613 | AAGGTTGTCCAGAGCT | 80 | 1710 |
| 903599 | 508 | 523 | 12599 | 12614 | CAAGGTTGTCCAGAGC | 91 | 1711 |
| 903600 | 509 | 524 | 12600 | 12615 | GCAAGGTTGTCCAGAG | 90 | 1712 |
| 903606 | 515 | 530 | 12606 | 12621 | TGTCTTGCAAGGTTGT | 98 | 1713 |

TABLE 25-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 903607 | 516 | 531 | 12607 | 12622 | TTGTCTTGCAAGGTTG | 96 | 1714 |
| 903639 | 616 | 631 | 12707 | 12722 | TGTTATCCTCAAGCTC | 76 | 1715 |
| 903959 | 1334 | 1349 | 13425 | 13440 | GCCTGCAGAATCTTAT | 65 | 1716 |
| 903991 | 1394 | 1409 | 13485 | 13500 | CCCCTGCCAGGCATAT | 71 | 1717 |
| 903997 | 1707 | 1722 | 13798 | 13813 | TGGGTCAAAAGCGATG | 96 | 1718 |
| 904055 | 1867 | 1882 | 13958 | 13973 | TTATTGCAGGCTCCAA | 96 | 1719 |
| 904221 | 2719 | 2734 | 14810 | 14825 | TTACTTACCGGGTAAG | 57 | 1720 |
| 904279 | N/A | N/A | 449 | 464 | CAGCAAACACGCTCCC | 23 | 1721 |
| 904509 | N/A | N/A | 5023 | 5038 | GGCCGTGTCACCCTAA | 46 | 1722 |
| 904637 | N/A | N/A | 5463 | 5478 | GGCCAGGTAGCCGTGT | 46 | 1723 |
| 904951 | N/A | N/A | 6306 | 6321 | GCTGGGTCTGACCCAC | 0 | 1724 |
| 905005 | N/A | N/A | 6415 | 6430 | AAGGAGTTGCTGAAAC | 75 | 1725 |
| 905015 | N/A | N/A | 6438 | 6453 | GCAGGTTCACATGACA | 88 | 1726 |
| 905019 | N/A | N/A | 6534 | 6549 | TCTGTTAGATACAAAC | 92 | 1727 |
| 905037 | N/A | N/A | 6570 | 6585 | TGGGAAACTCAACTGG | 77 | 1728 |
| 905111 | N/A | N/A | 6734 | 6749 | TGGATGGAAGGAACCT | 73 | 1729 |
| 905469 | N/A | N/A | 8164 | 8179 | CATTCAGAATTTCCAC | 98 | 1730 |
| 905837 | N/A | N/A | 11345 | 11360 | CCCACCATTGATGGGT | 30 | 1731 |
| 905869 | N/A | N/A | 12150 | 12165 | TCACTATCGATCAAAT | 53 | 1732 |

TABLE 26

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhibition | SEQ ID NO |
|---|---|---|---|---|---|---|---|
| 905758 | N/A | N/A | 9461 | 9476 | CACTTTACATGCACGA | 90 | 1733 |
| 905867 | N/A | N/A | 12079 | 12094 | TCATCATAGATACTCC | 87 | 1734 |
| 972204 | N/A | N/A | 9219 | 9234 | GGAGGTGTGCCTGTCA | 49 | 1735 |
| 972206 | N/A | N/A | 9311 | 9326 | GCTACTCACTGCCAGC | 0 | 1736 |
| 972208 | N/A | N/A | 9356 | 9371 | AGAAATGACCCTGTTC | 31 | 1737 |
| 972210 | N/A | N/A | 9450 | 9465 | CACGATCTCATTTTTC | 79 | 1738 |
| 972212 | N/A | N/A | 9453 | 9468 | ATGCACGATCTCATTT | 5 | 1739 |
| 972214 | N/A | N/A | 9455 | 9470 | ACATGCACGATCTCAT | 48 | 1740 |
| 972216 | N/A | N/A | 9458 | 9473 | TTTACATGCACGATCT | 66 | 1741 |
| 972218 | N/A | N/A | 9460 | 9475 | ACTTTACATGCACGAT | 89 | 1742 |
| 972220 | N/A | N/A | 9481 | 9496 | GTGTCAGTCATTATGC | 79 | 1743 |
| 972222 | N/A | N/A | 9501 | 9516 | GTTAACTGTGCACCTA | 25 | 1744 |
| 972224 | N/A | N/A | 9519 | 9534 | AGCTTGTAAGATGTTA | 44 | 1745 |
| 972226 | N/A | N/A | 9551 | 9566 | GAAGATCCTTAACCCT | 46 | 1746 |
| 972228 | N/A | N/A | 9622 | 9637 | ACATTGGTTAGGTCAG | 82 | 1747 |
| 972230 | N/A | N/A | 9624 | 9639 | ACACATTGGTTAGGTC | 55 | 1748 |
| 972232 | N/A | N/A | 9672 | 9687 | GGAATTCCTCAGATGA | 15 | 1749 |
| 972234 | N/A | N/A | 9678 | 9693 | GTTTATGGAATTCCTC | 95 | 1750 |
| 972236 | N/A | N/A | 9689 | 9704 | GGTCCTGCCGTGTTTA | 29 | 1751 |
| 972238 | N/A | N/A | 9846 | 9861 | TCCTATCACATTGAGT | 37 | 1752 |
| 972240 | N/A | N/A | 9869 | 9884 | TGCCTCTAAGGCCTTC | 10 | 1753 |
| 972242 | N/A | N/A | 9904 | 9919 | ATCTTGGTGTTGGTTC | 68 | 1754 |

TABLE 26-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 972244 | N/A | N/A | 10059 | 10074 | TTAAGTTTCAAGCCCT | 77 | 1755 |
| 972246 | N/A | N/A | 10072 | 10087 | GTTCATGACCTCCTTA | 76 | 1756 |
| 972248 | N/A | N/A | 10083 | 10098 | GTCCTCTGCAAGTTCA | 65 | 1757 |
| 972250 | N/A | N/A | 10125 | 10140 | GATCATCCAGACAGGG | 27 | 1758 |
| 972252 | N/A | N/A | 10196 | 10211 | GAACTTGCCAGTTCCA | 32 | 1759 |
| 972254 | N/A | N/A | 10257 | 10272 | TGCTTGTCAATGTCAG | 72 | 1760 |
| 972256 | N/A | N/A | 10265 | 10280 | AGACATACTGCTTGTC | 0 | 1761 |
| 972258 | N/A | N/A | 10285 | 10300 | TACTATGAAAATGGTC | 11 | 1762 |
| 972260 | N/A | N/A | 10297 | 10312 | AGCAACTAATTCTACT | 47 | 1763 |
| 972262 | N/A | N/A | 10307 | 10322 | ACAAATTGGCAGCAAC | 81 | 1764 |
| 972264 | N/A | N/A | 10309 | 10324 | ACACAAATTGGCAGCA | 72 | 1765 |
| 972266 | N/A | N/A | 10420 | 10435 | CACCTATATAAATTGC | 39 | 1766 |
| 972268 | N/A | N/A | 10464 | 10479 | GCAATTTTATGGAACC | 94 | 1767 |
| 972270 | N/A | N/A | 10507 | 10522 | CTTAGTAGTGACAGCT | 40 | 1768 |
| 972272 | N/A | N/A | 10521 | 10536 | AGCCTAACTGATGCCT | 14 | 1769 |
| 972274 | N/A | N/A | 10543 | 10558 | GGTCTCACTCGCAGGT | 52 | 1770 |
| 972276 | N/A | N/A | 10623 | 10638 | GGCTATTCATTCTGGC | 0 | 1771 |
| 972278 | N/A | N/A | 10631 | 10646 | GGAGATCTGGCTATTC | 71 | 1772 |
| 972280 | N/A | N/A | 10669 | 10684 | GCTACTGGTTCTGGCC | 0 | 1773 |
| 972282 | N/A | N/A | 10774 | 10789 | GAGTACTTTGAATTCA | 0 | 1774 |
| 972284 | N/A | N/A | 10788 | 10803 | GTCTGGCTATCTCTGA | 49 | 1775 |
| 972286 | N/A | N/A | 10798 | 10813 | AGACATTGCAGTCTGG | 22 | 1776 |
| 972288 | N/A | N/A | 10835 | 10850 | TAAATTTGCAGGTGGT | 96 | 1777 |
| 972290 | N/A | N/A | 10837 | 10852 | CTTAAATTTGCAGGTG | 89 | 1778 |
| 972292 | N/A | N/A | 10852 | 10867 | GGATTTAGAAATCCCC | 7 | 1779 |
| 972294 | N/A | N/A | 10944 | 10959 | TGTGTTCTTTCCGTGT | 48 | 1780 |
| 972296 | N/A | N/A | 11017 | 11032 | GACAATGAAGCTTCAC | 60 | 1781 |
| 972298 | N/A | N/A | 11097 | 11112 | TTAACTGGGTGAGCTT | 27 | 1782 |
| 972300 | N/A | N/A | 11122 | 11137 | TAATGTGATTCACAGG | 98 | 1783 |
| 972302 | N/A | N/A | 11126 | 11141 | GGTTTAATGTGATTCA | 90 | 1784 |
| 972304 | N/A | N/A | 11148 | 11163 | CCTGAAAAAAGGCTTC | 55 | 1785 |
| 972306 | N/A | N/A | 11160 | 11175 | TGTAACAACAATCCTG | 61 | 1786 |
| 972308 | N/A | N/A | 11196 | 11211 | TTACTATATTTGGAGC | 33 | 1787 |
| 972310 | N/A | N/A | 11264 | 11279 | TGTCTCCTATCAGTCC | 36 | 1788 |
| 972312 | N/A | N/A | 11291 | 11306 | CAATTTAGCAGGAACC | 36 | 1789 |
| 972314 | N/A | N/A | 11361 | 11376 | GATTATGCTCTTCACC | 59 | 1790 |
| 972316 | N/A | N/A | 11366 | 11381 | TATCTGATTATGCTCT | 78 | 1791 |
| 972318 | N/A | N/A | 11380 | 11395 | TGATTACGCTTTGCTA | 15 | 1792 |
| 972320 | N/A | N/A | 11382 | 11397 | TCTGATTACGCTTTGC | 79 | 1793 |
| 972322 | N/A | N/A | 11582 | 11597 | AGATACTCTGGACACT | 50 | 1794 |
| 972324 | N/A | N/A | 11606 | 11621 | GGCAGCTTGTGATCCA | 0 | 1795 |
| 972326 | N/A | N/A | 11731 | 11746 | CCGTATAGGAATCTGA | 37 | 1796 |
| 972328 | N/A | N/A | 11749 | 11764 | GGTGATTTGGCCACGG | 56 | 1797 |
| 972330 | N/A | N/A | 11804 | 11819 | AGTGATCTCCAGGCCC | 25 | 1798 |
| 972332 | N/A | N/A | 11956 | 11971 | GTGACTGCCAAAGTGT | 22 | 1799 |
| 972334 | N/A | N/A | 11996 | 12011 | TTGATAAAGATGCCTC | 76 | 1800 |
| 972336 | N/A | N/A | 12011 | 12026 | TTTCATGGTAGGTGTT | 76 | 1801 |
| 972338 | N/A | N/A | 12070 | 12085 | ATACTCCTCAATATTT | 41 | 1802 |
| 972340 | N/A | N/A | 12073 | 12088 | TAGATACTCCTCAATA | 56 | 1803 |
| 972342 | N/A | N/A | 12078 | 12093 | CATCATAGATACTCCT | 88 | 1804 |
| 972344 | N/A | N/A | 12081 | 12096 | GTTCATCATAGATACT | 26 | 1805 |
| 972346 | N/A | N/A | 12180 | 12195 | GATCTCTATCCTGTGT | 36 | 1806 |
| 972348 | N/A | N/A | 14951 | 14966 | GACTCGAACAAGTCCA | 1 | 1807 |
| 972350 | N/A | N/A | 15111 | 15126 | CTTCATCGGTCCATCG | 30 | 1808 |
| 972352 | N/A | N/A | 15298 | 15313 | TCCAGGTACCCTTCTA | 2 | 1809 |
| 972354 | N/A | N/A | 15311 | 15326 | AGACATCACCTTGTCC | 1 | 1810 |

TABLE 27

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 905758 | N/A | N/A | 9461 | 9476 | CACTTTACATGCACGA | 88 | 1733 |
| 905867 | N/A | N/A | 12079 | 12094 | TCATCATAGATACTCC | 85 | 1734 |

TABLE 27-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 972205 | N/A | N/A | 9277 | 9292 | ATTCTTCCTGGAGTGC | 50 | 1811 |
| 972207 | N/A | N/A | 9315 | 9330 | TGAGGCTACTCACTGC | 0 | 1812 |
| 972209 | N/A | N/A | 9390 | 9405 | GTAACTGGCAAAGTTC | 3 | 1813 |
| 972211 | N/A | N/A | 9452 | 9467 | TGCACGATCTCATTTT | 29 | 1814 |
| 972213 | N/A | N/A | 9454 | 9469 | CATGCACGATCTCATT | 23 | 1815 |
| 972215 | N/A | N/A | 9456 | 9471 | TACATGCACGATCTCA | 83 | 1816 |
| 972217 | N/A | N/A | 9459 | 9474 | CTTTACATGCACGATC | 55 | 1817 |
| 972219 | N/A | N/A | 9462 | 9477 | GCACTTTACATGCACG | 63 | 1818 |
| 972221 | N/A | N/A | 9483 | 9498 | GTGTGTCAGTCATTAT | 94 | 1819 |
| 972223 | N/A | N/A | 9502 | 9517 | CGTTAACTGTGCACCT | 50 | 1820 |
| 972225 | N/A | N/A | 9546 | 9561 | TCCTTAACCCTGGTTC | 21 | 1821 |
| 972227 | N/A | N/A | 9558 | 9573 | TCAAGAAGAAGATCCT | 48 | 1822 |
| 972229 | N/A | N/A | 9623 | 9638 | CACATTGGTTAGGTCA | 82 | 1823 |
| 972231 | N/A | N/A | 9626 | 9641 | ACACACATTGGTTAGG | 75 | 1824 |
| 972233 | N/A | N/A | 9675 | 9690 | TATGGAATTCCTCAGA | 40 | 1825 |
| 972235 | N/A | N/A | 9681 | 9696 | CGTGTTTATGGAATTC | 71 | 1826 |
| 972237 | N/A | N/A | 9841 | 9856 | TCACATTGAGTTGCTA | 85 | 1827 |
| 972239 | N/A | N/A | 9868 | 9883 | GCCTCTAAGGCCTTCA | 7 | 1828 |
| 972241 | N/A | N/A | 9899 | 9914 | GGTGTTGGTTCCCCAC | 31 | 1829 |
| 972243 | N/A | N/A | 9937 | 9952 | GCTGATCCCGGTCTCT | 42 | 1830 |
| 972245 | N/A | N/A | 10062 | 10077 | TCCTTAAGTTTCAAGC | 31 | 1831 |
| 972247 | N/A | N/A | 10077 | 10092 | TGCAAGTTCATGACCT | 41 | 1832 |
| 972249 | N/A | N/A | 10107 | 10122 | GAAATATCCCTCTCCC | 23 | 1833 |
| 972251 | N/A | N/A | 10148 | 10163 | CCCTATATGCCCATGA | 75 | 1834 |
| 972253 | N/A | N/A | 10197 | 10212 | AGAACTTGCCAGTTCC | 0 | 1835 |
| 972255 | N/A | N/A | 10264 | 10279 | GACATACTGCTTGTCA | 0 | 1836 |
| 972257 | N/A | N/A | 10272 | 10287 | GTCACTAAGACATACT | 8 | 1837 |
| 972259 | N/A | N/A | 10296 | 10311 | GCAACTAATTCTACTA | 80 | 1838 |
| 972261 | N/A | N/A | 10306 | 10321 | CAAATTGGCAGCAACT | 61 | 1839 |
| 972263 | N/A | N/A | 10308 | 10323 | CACAAATTGGCAGCAA | 91 | 1840 |
| 972265 | N/A | N/A | 10419 | 10434 | ACCTATATAAATTGCT | 22 | 1841 |
| 972267 | N/A | N/A | 10461 | 10476 | ATTTTATGGAACCTCT | 72 | 1842 |
| 972269 | N/A | N/A | 10495 | 10510 | AGCTTCACCTGTGTGC | 10 | 1843 |
| 972271 | N/A | N/A | 10510 | 10525 | TGCCTTAGTAGTGACA | 34 | 1844 |
| 972273 | N/A | N/A | 10539 | 10554 | TCACTCGCAGGTGTCA | 30 | 1845 |
| 972275 | N/A | N/A | 10622 | 10637 | GCTATTCATTCTGGCT | 0 | 1846 |
| 972277 | N/A | N/A | 10624 | 10639 | TGGCTATTCATTCTGG | 22 | 1847 |

TABLE 27-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 972279 | N/A | N/A | 10664 | 10679 | TGGTTCTGGCCACTGC | 37 | 1848 |
| 972281 | N/A | N/A | 10732 | 10747 | GGAGTTCACTTTGCCT | 0 | 1849 |
| 972283 | N/A | N/A | 10783 | 10798 | GCTATCTCTGAGTACT | 13 | 1850 |
| 972285 | N/A | N/A | 10797 | 10812 | GACATTGCAGTCTGGC | 46 | 1851 |
| 972287 | N/A | N/A | 10800 | 10815 | TCAGACATTGCAGTCT | 0 | 1852 |
| 972289 | N/A | N/A | 10836 | 10851 | TTAAATTTGCAGGTGG | 92 | 1853 |
| 972291 | N/A | N/A | 10839 | 10854 | CCCTTAAATTTGCAGG | 19 | 1854 |
| 972293 | N/A | N/A | 10853 | 10868 | TGGATTTAGAAATCCC | 13 | 1855 |
| 972295 | N/A | N/A | 11012 | 11027 | TGAAGCTTCACACTTA | 29 | 1856 |
| 972297 | N/A | N/A | 11019 | 11034 | AGGACAATGAAGCTTC | 50 | 1857 |
| 972299 | N/A | N/A | 11100 | 11115 | TCCTTAACTGGGTGAG | 25 | 1858 |
| 972301 | N/A | N/A | 11125 | 11140 | GTTTAATGTGATTCAC | 88 | 1859 |
| 972303 | N/A | N/A | 11127 | 11142 | TGGTTTAATGTGATTC | 90 | 1860 |
| 972305 | N/A | N/A | 11159 | 11174 | GTAACAACAATCCTGA | 69 | 1861 |
| 972307 | N/A | N/A | 11195 | 11210 | TACTATATTTGGAGCT | 40 | 1862 |
| 972309 | N/A | N/A | 11200 | 11215 | GTCTTTACTATATTTG | 77 | 1863 |
| 972311 | N/A | N/A | 11290 | 11305 | AATTTAGCAGGAACCC | 53 | 1864 |
| 972313 | N/A | N/A | 11307 | 11322 | GAGAATCCTGTTAGGC | 51 | 1865 |
| 972315 | N/A | N/A | 11362 | 11377 | TGATTATGCTCTTCAC | 36 | 1866 |
| 972317 | N/A | N/A | 11368 | 11383 | GCTATCTGATTATGCT | 18 | 1867 |
| 972319 | N/A | N/A | 11381 | 11396 | CTGATTACGCTTTGCT | 33 | 1868 |
| 972321 | N/A | N/A | 11572 | 11587 | GACACTAAGGCATGGG | 77 | 1869 |
| 972323 | N/A | N/A | 11584 | 11599 | GCAGATACTCTGGACA | 46 | 1870 |
| 972325 | N/A | N/A | 11699 | 11714 | GGGCTATTTGGTGTCT | 22 | 1871 |
| 972327 | N/A | N/A | 11747 | 11762 | TGATTTGGCCACGGGA | 58 | 1872 |
| 972329 | N/A | N/A | 11767 | 11782 | GAACATCTGTCTTTGC | 42 | 1873 |
| 972331 | N/A | N/A | 11856 | 11871 | AGCATGAACTTTACCC | 53 | 1874 |
| 972333 | N/A | N/A | 11968 | 11983 | CAGGTCAACACCGTGA | 0 | 1875 |
| 972335 | N/A | N/A | 11998 | 12013 | GTTTGATAAAGATGCC | 77 | 1876 |
| 972337 | N/A | N/A | 12069 | 12084 | TACTCCTCAATATTTA | 66 | 1877 |
| 972339 | N/A | N/A | 12071 | 12086 | GATACTCCTCAATATT | 37 | 1878 |
| 972341 | N/A | N/A | 12077 | 12092 | ATCATAGATACTCCTC | 93 | 1879 |
| 972343 | N/A | N/A | 12080 | 12095 | TTCATCATAGATACTC | 87 | 1880 |
| 972345 | N/A | N/A | 12168 | 12183 | GTGTAAATTGCAGAGC | 82 | 1881 |
| 972347 | N/A | N/A | 12199 | 12214 | TGTGAAATGAGCTCCA | 78 | 1882 |
| 972349 | N/A | N/A | 14953 | 14968 | ATGACTCGAACAAGTC | 38 | 1883 |

TABLE 27-continued

Inhibition of APOL1 mRNA by 3-10-3 cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | % inhi-bition | SEQ ID NO |
|---|---|---|---|---|---|---|---|
| 972351 | N/A | N/A | 15116 | 15131 | TGGAACTTCATCGGTC | 5 | 1884 |
| 972353 | N/A | N/A | 15310 | 15325 | GACATCACCTTGTCCA | 16 | 1885 |
| 972355 | N/A | N/A | 15432 | 15447 | GGAAGTCAGGCACCCA | 16 | 1886 |

TABLE 28

Gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | SEQ ID NO |
|---|---|---|---|---|---|---|---|
| 904628 | N/A | N/A | 5450 | 5465 | TGTTATATTTGATCCT | kkk-d10-kkk | 1887 |
| 905141 | N/A | N/A | 6820 | 6835 | GAACGCAATGCTGACT | kkk-d10-kkk | 1888 |
| 905269 | N/A | N/A | 7283 | 7298 | CAGCATTGAGTACAAC | kkk-d10-kkk | 1889 |
| 905521 | N/A | N/A | 8366 | 8381 | CTTTATACCAGTGTCT | kkk-d10-kkk | 1890 |
| 905582 | N/A | N/A | 8520 | 8535 | GAGAACATTGAAACAC | kkk-d10-kkk | 1891 |
| 905684 | N/A | N/A | 8875 | 8890 | TAGTGCTATAGAGGGA | kkk-d10-kkk | 1892 |
| 905757 | N/A | N/A | 9457 | 9472 | TTACATGCACGATCTC | kkk-d10-kkk | 1893 |
| 969419 | N/A | N/A | 9460 | 9475 | ACTTTACATGCACGAT | kk-d9-ekeke | 1742 |
| 905758 | N/A | N/A | 9461 | 9476 | CACTTTACATGCACGA | kkk-d10-kkk | 1733 |
| 969219 | N/A | N/A | 9461 | 9476 | CACTTTACATGCACGA | kk-d10-keke | 1733 |
| 971984 | N/A | N/A | 9461 | 9476 | CACTTTACATGCACGA | kk-d9-kekek | 1733 |
| 905808 | N/A | N/A | 10462 | 10477 | AATTTTATGGAACCTC | kkk-d10-kkk | 1894 |
| 971987 | N/A | N/A | 12076 | 12091 | TCATAGATACTCCTCA | kkk-d10-kkk | 1895 |
| 905867 | N/A | N/A | 12079 | 12094 | TCATCATAGATACTCC | kkk-d10-kkk | 1734 |
| 904016 | 1772 | 1787 | 13863 | 13878 | CCCTAACACTCAGTTC | kkk-d10-kkk | 1896 |
| 904084 | 2253 | 2268 | 14344 | 14359 | TCCGTCAATATATTCT | kkk-d10-kkk | 1897 |
| 904212 | 2709 | 2724 | 14800 | 14815 | GGTAAGAGCGATGGGA | kkk-d10-kkk | 1898 |

Deoxy, MOE, and cEt Gapmers

The newly designed chimeric antisense oligonucleotides in the Tables below were designed as deoxy, MOE, and cEt gapmers. The deoxy, MOE and cEt oligonucleotides have nucleosides that have either a MOE sugar modification, an (S)-cEt sugar modification, or a deoxy modification. The ‘Chemistry’ column describes the sugar modifications of each oligonucleotide. 1' indicates an (S)-cEt sugar modification; ‘d’ indicates deoxyribose; and ‘e’ indicates a MOE modification. The internucleoside linkages throughout each gapmer are phosphorothioate (P═S) linkages. All cytosine residues throughout each gapmer are 5-methylcytosines. The sugar motifs of the gapmers are shown in the Chemistry columns of the tables below wherein 1' means cEt sugar; ‘e’ means 2'-MOE sugar; ‘d’ means deoxy sugar, and the number after ‘d’ indicates the number of deoxy nucleosides.

“Start site” indicates the 5'-most nucleoside to which the gapmer is targeted in the human gene sequence. “Stop site” indicates the 3'-most nucleoside to which the gapmer is targeted human gene sequence. Each gapmer listed in the Tables below is targeted to either the human APOL1 mRNA, designated herein as SEQ ID NO: 1 (GENBANK Accession No. NM_003661.3) or the human APOL1 genomic sequence, designated herein as SEQ ID NO: 2 (GENBANK Accession No. NT_011520.9 truncated from nucleotides 15986452 to Ser. No. 16/001,905). ‘n/a’ indicates that the antisense oligonucleotide does not target that a particular gene sequence with 100% complementarity.

The antisense oligonucleotides were tested in a series of experiments that had similar culture conditions. The results for each experiment are presented in separate tables shown below. Cultured A431 cells at a density of 5,000 cells per well were transfected by free uptake with 2,000 nM antisense oligonucleotide. After a treatment period of approximately 24 hours, RNA was isolated from the cells and APOL1 mRNA levels were measured by quantitative real-time PCR. Human primer probe set RTS35962 was used to measure mRNA levels. APOL1 mRNA levels were adjusted according to total RNA content, as measured by RIBOGREEN®. Results are presented as percent inhibition of APOL1, relative to untreated control cells.

TABLE 29

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 793406 | N/A | N/A | 8306 | 8321 | GTTCAAAAGCAGCATT | kkk-d10-kkk | 90 | 13 |
| 905095 | N/A | N/A | 6702 | 6717 | GTATTTCTTGATGTGG | kkk-d10-kkk | 99 | 413 |
| 905491 | N/A | N/A | 8237 | 8252 | GAGTATTGTTTTTGTG | kkk-d10-kkk | 93 | 1899 |
| 905634 | N/A | N/A | 8744 | 8759 | ATTCTATTAGAGGGCT | kkk-d10-kkk | 95 | 1326 |
| 969064 | N/A | N/A | 6700 | 6715 | ATTTCTTGATGTGGTG | k-d10-kekek | 96 | 343 |
| 969084 | N/A | N/A | 5449 | 5464 | GTTATATTTGATCCTC | k-d10-kekek | 95 | 1900 |
| 969094 | N/A | N/A | 8321 | 8336 | GTTATGAAATTATTGG | k-d10-kekek | 73 | 76 |
| 969104 | 1031 | 1046 | 13122 | 13137 | AGATTGGCTCTGGCTC | k-d9-kekeke | 23 | 654 |
| 969114 | N/A | N/A | 8162 | 8177 | TTCAGAATTTCCACTA | k-d9-kekeke | 62 | 1186 |
| 969124 | N/A | N/A | 8306 | 8321 | GTTCAAAAGCAGCATT | k-d9-kekeke | 33 | 13 |
| 969134 | N/A | N/A | 5858 | 5873 | CAGTTTTGTAAGTGCA | k-d9-kekeke | 48 | 1577 |
| 969144 | N/A | N/A | 8743 | 8758 | TTCTATTAGAGGGCTA | k-d9-kekeke | 34 | 80 |
| 969154 | 2340 | 2355 | 14431 | 14446 | GTTCTAACTCTTGGGC | kek-d9-eekk | 86 | 243 |
| 969164 | N/A | N/A | 7922 | 7937 | GGAATTATGGAATTGC | kek-d9-eekk | 98 | 1249 |
| 969184 | N/A | N/A | 6547 | 6562 | TCAGATGGGTACTTCT | kk-d10-keke | 89 | 411 |
| 969194 | N/A | N/A | 8743 | 8758 | TTCTATTAGAGGGCTA | kk-d10-keke | 94 | 80 |
| 969204 | 2736 | 2751 | 14827 | 14842 | GCTAATTTTCTGACTG | kk-d10-keke | 99 | 1283 |
| 969214 | N/A | N/A | 8237 | 8252 | GAGTATTGTTTTTGTG | kk-d10-keke | 96 | 1899 |
| 969224 | 2735 | 2750 | 14826 | 14841 | CTAATTTTCTGACTGT | kk-d8-eeeekk | 88 | 1901 |
| 969234 | N/A | N/A | 8163 | 8178 | ATTCAGAATTTCCACT | kk-d8-eeeekk | 64 | 1902 |
| 969244 | N/A | N/A | 8828 | 8843 | CTTTAAACTCAGGTGA | kk-d8-kekekk | 70 | 151 |
| 969254 | N/A | N/A | 6816 | 6831 | GCAATGCTGACTTGGC | kk-d8-kekekk | 91 | 1903 |
| 969274 | N/A | N/A | 6701 | 6716 | TATTTCTTGATGTGGT | kk-d8-kekekk | 71 | 1904 |
| 969294 | N/A | N/A | 5854 | 5869 | TTTGTAAGTGCAACCA | kk-d8-kekekk | 87 | 1095 |
| 969304 | N/A | N/A | 8366 | 8381 | CTTTATACCAGTGTCT | kk-d8-kekekk | 87 | 1890 |
| 969314 | N/A | N/A | 5449 | 5464 | GTTATATTTGATCCTC | kk-d9-eeekk | 93 | 1900 |
| 969324 | N/A | N/A | 8332 | 8347 | CACATCATTGGGTTAT | kk-d9-eeekk | 86 | 356 |
| 969334 | 1033 | 1048 | 13124 | 13139 | GAAGATTGGCTCTGGC | kk-d9-eeekk | 81 | 1480 |
| 969344 | N/A | N/A | 6818 | 6833 | ACGCAATGCTGACTTG | kk-d9-eeekk | 87 | 1905 |
| 969354 | N/A | N/A | 8831 | 8846 | AAGCTTTAAACTCAGG | kk-d9-eeekk | 95 | 1327 |
| 969364 | N/A | N/A | 6549 | 6564 | TATCAGATGGGTACTT | kk-d9-eeekk | 70 | 550 |
| 969384 | N/A | N/A | 5452 | 5467 | CGTGTTATATTTGATC | kk-d9-eeekk | 74 | 1906 |
| 969394 | N/A | N/A | 8335 | 8350 | CAACACATCATTGGGT | kk-d9-eeekk | 80 | 1907 |

TABLE 29-continued

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 969404 | N/A | N/A | 5449 | 5464 | GTTATATTTGATCCTC | kk-d9-ekeke | 96 | 1900 |
| 969414 | N/A | N/A | 8332 | 8347 | CACATCATTGGGTTAT | kk-d9-ekeke | 81 | 356 |
| 969424 | 1033 | 1048 | 13124 | 13139 | GAAGATTGGCTCTGGC | kk-d9-ekeke | 64 | 1480 |
| 969434 | N/A | N/A | 6818 | 6833 | ACGCAATGCTGACTTG | kk-d9-ekeke | 92 | 1919 |
| 969444 | N/A | N/A | 8832 | 8847 | GAAGCTTTAAACTCAG | kk-d9-ekeke | 62 | 1397 |
| 969454 | N/A | N/A | 5856 | 5871 | GTTTTGTAAGTGCAAC | kk-d9-ekeke | 86 | 1230 |
| 969464 | N/A | N/A | 8368 | 8383 | CACTTTATACCAGTGT | kk-d9-ekeke | 0 | 1908 |
| 969474 | N/A | N/A | 5448 | 5463 | TTATATTTGATCCTCA | kk-d9-kdkdk | 96 | 1909 |
| 969484 | N/A | N/A | 8320 | 8335 | TTATGAAATTATTGGT | kk-d9-kdkdk | 47 | 1910 |
| 969494 | 970 | 985 | 13061 | 13076 | AAGTATTGCCAGCTAA | kk-d9-kdkdk | 70 | 1911 |
| 969504 | N/A | N/A | 6702 | 6717 | GTATTTCTTGATGTGG | kk-d9-kdkdk | 87 | 413 |
| 971924 | N/A | N/A | 6547 | 6562 | TCAGATGGGTACTTCT | kk-d9-kekek | 82 | 411 |
| 971934 | N/A | N/A | 8743 | 8758 | TTCTATTAGAGGGCTA | kk-d9-kekek | 53 | 80 |
| 971944 | 2738 | 2753 | 14829 | 14844 | ATGCTAATTTTCTGAC | kk-d9-kekek | 97 | 1912 |
| 971954 | N/A | N/A | 8166 | 8181 | GGCATTCAGAATTTCC | kk-d9-kekek | 46 | 1913 |
| 971964 | N/A | N/A | 8306 | 8321 | GTTCAAAAGCAGCATT | kk-d9-kekek | 60 | 13 |
| 971974 | N/A | N/A | 6548 | 6563 | ATCAGATGGGTACTTC | kk-d9-kekek | 66 | 481 |
| 971994 | 1033 | 1048 | 13124 | 13139 | GAAGATTGGCTCTGGC | kkk-d8-kdkdk | 51 | 1480 |
| 972004 | N/A | N/A | 6702 | 6717 | GTATTTCTTGATGTGG | kkk-d8-kdkdk | 92 | 413 |
| 972014 | N/A | N/A | 8829 | 8844 | GCTTTAAACTCAGGTG | kkk-d8-kdkdk | 93 | 81 |
| 972024 | N/A | N/A | 5853 | 5868 | TTGTAAGTGCAACCAA | kkk-d8-kekek | 35 | 1025 |
| 972034 | N/A | N/A | 8365 | 8380 | TTTATACCAGTGTCTT | kkk-d8-kekek | 76 | 1914 |
| 972044 | 2253 | 2268 | 14344 | 14359 | TCCGTCAATATATTCT | kkk-d8-kekek | 95 | 1897 |
| 972054 | N/A | N/A | 6820 | 6835 | GAACGCAATGCTGACT | kkk-d8-kekek | 48 | 1888 |
| 972074 | N/A | N/A | 5854 | 5869 | TTTGTAAGTGCAACCA | kkk-d8-kekek | 63 | 1095 |
| 972084 | N/A | N/A | 8366 | 8381 | CTTTATACCAGTGTCT | kkk-d8-kekek | 76 | 1890 |
| 972094 | N/A | N/A | 5413 | 5428 | TATTCTCATGGTACAG | kkk-d9-keke | 68 | 1915 |
| 972104 | N/A | N/A | 8238 | 8253 | TGAGTATTGTTTTTGT | kkk-d9-keke | 92 | 1916 |
| 972114 | 970 | 985 | 13061 | 13076 | AAGTATTGCCAGCTAA | kkk-d9-keke | 63 | 1911 |
| 972124 | N/A | N/A | 6702 | 6717 | GTATTTCTTGATGTGG | kkk-d9-keke | 98 | 413 |
| 972144 | N/A | N/A | 5857 | 5872 | AGTTTTGTAAGTGCAA | kkk-d9-kkke | 96 | 1917 |
| 972154 | N/A | N/A | 8742 | 8757 | TCTATTAGAGGGCTAG | kkk-d9-kkke | 51 | 150 |
| 972164 | 2340 | 2355 | 14431 | 14446 | GTTCTAACTCTTGGGC | kkk-d9-kkke | 58 | 243 |
| 972174 | N/A | N/A | 8164 | 8179 | CATTCAGAATTTCCAC | kkk-d9-kkke | 92 | 1730 |
| 972184 | 971 | 986 | 13062 | 13077 | TAAGTATTGCCAGCTA | kkk-d9-kkke | 65 | 1918 |
| 972194 | N/A | N/A | 6819 | 6834 | AACGCAATGCTGACTT | kkk-d9-kkke | 91 | 1919 |

TABLE 30

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 793444 | N/A | N/A | 8830 | 8845 | AGCTTTAAACTCAGGT | kkk-d10-kkk | 68 | 1920 |
| 905095 | N/A | N/A | 6702 | 6717 | GTATTTCTTGATGTGG | kkk-d10-kkk | 99 | 413 |
| 905491 | N/A | N/A | 8237 | 8252 | GAGTATTGTTTTTGTG | kkk-d10-kkk | 94 | 1899 |
| 969055 | N/A | N/A | 8828 | 8843 | CTTTAAACTCAGGTGA | k-d10-kekek | 77 | 151 |
| 969065 | N/A | N/A | 6816 | 6831 | GCAATGCTGACTTGGC | k-d10-kekek | 85 | 1903 |
| 969085 | N/A | N/A | 5450 | 5465 | TGTTATATTTGATCCT | k-d10-kekek | 79 | 1887 |
| 969095 | N/A | N/A | 8333 | 8348 | ACACATCATTGGGTTA | k-d10-kekek | 47 | 426 |
| 969105 | N/A | N/A | 5410 | 5425 | TCTCATGGTACAGGAG | k-d9-kekeke | 55 | 537 |
| 969115 | N/A | N/A | 8235 | 8250 | GTATTGTTTTTGTGGG | k-d9-kekeke | 70 | 1921 |
| 969125 | 970 | 985 | 13061 | 13076 | AAGTATTGCCAGCTAA | k-d9-kekeke | 25 | 1911 |
| 969135 | N/A | N/A | 6548 | 6563 | ATCAGATGGGTACTTC | k-d9-kekeke | 43 | 481 |
| 969145 | N/A | N/A | 8744 | 8759 | ATTCTATTAGAGGGCT | k-d9-kekeke | 34 | 1326 |
| 969155 | 2736 | 2751 | 14827 | 14842 | GCTAATTTTCTGACTG | kek-d9-eekk | 94 | 1283 |
| 969165 | N/A | N/A | 8164 | 8179 | CATTCAGAATTTCCAC | kek-d9-eekk | 89 | 1730 |
| 969175 | N/A | N/A | 8829 | 8844 | GCTTTAAACTCAGGTG | kk-d10-keke | 91 | 81 |
| 969185 | N/A | N/A | 6701 | 6716 | TATTTCTTGATGTGGT | kk-d10-keke | 99 | 1904 |
| 969195 | N/A | N/A | 8828 | 8843 | CTTTAAACTCAGGTGA | kk-d10-keke | 87 | 151 |
| 969205 | N/A | N/A | 5412 | 5427 | ATTCTCATGGTACAGG | kk-d10-keke | 95 | 677 |
| 969215 | N/A | N/A | 8321 | 8336 | GTTATGAAATTATTGG | kk-d10-keke | 68 | 76 |
| 969225 | N/A | N/A | 5411 | 5426 | TTCTCATGGTACAGGA | kk-d8-eeeekk | 80 | 607 |
| 969235 | N/A | N/A | 8236 | 8251 | AGTATTGTTTTTGTGG | kk-d8-eeeekk | 85 | 1922 |
| 969245 | 968 | 983 | 13059 | 13074 | GTATTGCCAGCTAAGG | kk-d8-kekekk | 74 | 1410 |
| 969255 | N/A | N/A | 7920 | 7935 | AATTATGGAATTGCAG | kk-d8-kekekk | 35 | 1923 |
| 969265 | N/A | N/A | 8829 | 8844 | GCTTTAAACTCAGGTG | kk-d8-kekekk | 50 | 81 |
| 969275 | N/A | N/A | 6817 | 6832 | CGCAATGCTGACTTGG | kk-d8-kekekk | 60 | 1924 |
| 969285 | N/A | N/A | 8830 | 8845 | AGCTTTAAACTCAGGT | kk-d8-kekekk | 16 | 1920 |
| 969295 | N/A | N/A | 5858 | 5873 | CAGTTTTGTAAGTGCA | kk-d8-kekekk | 18 | 1577 |
| 969305 | N/A | N/A | 8744 | 8759 | ATTCTATTAGAGGGCT | kk-d8-kekekk | 34 | 1326 |
| 969315 | N/A | N/A | 5853 | 5868 | TTGTAAGTGCAACCAA | kk-d9-eeekk | 83 | 1025 |
| 969325 | N/A | N/A | 8365 | 8380 | TTTATACCAGTGTCTT | kk-d9-eeekk | 88 | 1914 |
| 969335 | 2251 | 2266 | 14342 | 14357 | CGTCAATATATTCTTT | kk-d9-eeekk | 81 | 1925 |
| 969345 | N/A | N/A | 7922 | 7937 | GGAATTATGGAATTGC | kk-d9-eeekk | 99 | 1249 |
| 969355 | N/A | N/A | 8307 | 8322 | GGTTCAAAAGCAGCAT | kk-d9-eeekk | 95 | 978 |
| 969365 | N/A | N/A | 6703 | 6718 | TGTATTTCTTGATGTG | kk-d9-eeekk | 87 | 1926 |
| 969385 | N/A | N/A | 5856 | 5871 | GTTTTGTAAGTGCAAC | kk-d9-eeekk | 83 | 1230 |
| 969395 | N/A | N/A | 8368 | 8383 | CACTTTATACCAGTGT | kk-d9-eeekk | 0 | 1908 |
| 969405 | N/A | N/A | 5853 | 5868 | TTGTAAGTGCAACCAA | kk-d9-ekeke | 87 | 1025 |

TABLE 30-continued

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 969415 | N/A | N/A | 8365 | 8380 | TTTATACCAGTGTCTT | kk-d9-ekeke | 90 | 1914 |
| 969425 | 2251 | 2266 | 14342 | 14357 | CGTCAATATATTCTTT | kk-d9-ekeke | 90 | 1925 |
| 969435 | N/A | N/A | 7922 | 7937 | GGAATTATGGAATTGC | kk-d9-ekeke | 97 | 1249 |
| 969445 | N/A | N/A | 8308 | 8323 | TGGTTCAAAAGCAGCA | kk-d9-ekeke | 82 | 1048 |
| 969455 | N/A | N/A | 5860 | 5875 | GGCAGTTTTGTAAGTG | kk-d9-ekeke | 75 | 123 |
| 969465 | N/A | N/A | 8745 | 8760 | AATTCTATTAGAGGGC | kk-d9-ekeke | 79 | 1396 |
| 969475 | N/A | N/A | 5449 | 5464 | GTTATATTTGATCCTC | kk-d9-kdkdk | 93 | 1900 |
| 969485 | N/A | N/A | 8332 | 8347 | CACATCATTGGGTTAT | kk-d9-kdkdk | 79 | 356 |
| 969495 | 1033 | 1048 | 13124 | 13139 | GAAGATTGGCTCTGGC | kk-d9-kdkdk | 79 | 1480 |
| 969505 | N/A | N/A | 6818 | 6833 | ACGCAATGCTGACTTG | kk-d9-kdkdk | 85 | 1905 |
| 971915 | N/A | N/A | 8829 | 8844 | GCTTTAAACTCAGGTG | kk-d9-kekek | 86 | 81 |
| 971925 | N/A | N/A | 6701 | 6716 | TATTTCTTGATGTGGT | kk-d9-kekek | 97 | 1904 |
| 971935 | N/A | N/A | 8828 | 8843 | CTTTAAACTCAGGTGA | kk-d9-kekek | 82 | 151 |
| 971945 | N/A | N/A | 5414 | 5429 | TTATTCTCATGGTACA | kk-d9-kekek | 47 | 1927 |
| 971955 | N/A | N/A | 8239 | 8254 | GTGAGTATTGTTTTTG | kk-d9-kekek | 88 | 1928 |
| 971965 | 970 | 985 | 13061 | 13076 | AAGTATTGCCAGCTAA | kk-d9-kekek | 62 | 1911 |
| 971975 | N/A | N/A | 6702 | 6717 | GTATTTCTTGATGTGG | kk-d9-kekek | 75 | 413 |
| 971995 | 2251 | 2266 | 14342 | 14357 | CGTCAATATATTCTTT | kkk-d8-kdkdk | 95 | 1925 |
| 972005 | N/A | N/A | 6818 | 6833 | ACGCAATGCTGACTTG | kkk-d8-kdkdk | 70 | 1905 |
| 972025 | N/A | N/A | 5857 | 5872 | AGTTTTGTAAGTGCAA | kkk-d8-kekek | 77 | 1917 |
| 972035 | N/A | N/A | 8742 | 8757 | TCTATTAGAGGGCTAG | kkk-d8-kekek | 23 | 150 |
| 972045 | 2342 | 2357 | 14433 | 14448 | CTGTTCTAACTCTTGG | kkk-d8-kekek | 88 | 383 |
| 972055 | N/A | N/A | 7924 | 7939 | TGGGAATTATGGAATT | kkk-d8-kekek | 56 | 1929 |
| 972065 | N/A | N/A | 8830 | 8845 | AGCTTTAAACTCAGGT | kkk-d8-kekek | 64 | 1920 |
| 972075 | N/A | N/A | 5858 | 5873 | CAGTTTTGTAAGTGCA | kkk-d8-kekek | 87 | 1577 |
| 972085 | N/A | N/A | 8744 | 8759 | ATTCTATTAGAGGGCT | kkk-d8-kekek | 37 | 1326 |
| 972095 | N/A | N/A | 5450 | 5465 | TGTTATATTTGATCCT | kkk-d9-keke | 71 | 1887 |
| 972105 | N/A | N/A | 8322 | 8337 | GGTTATGAAATTATTG | kkk-d9-keke | 88 | 1930 |
| 972115 | 1033 | 1048 | 13124 | 13139 | GAAGATTGGCTCTGGC | kkk-d9-keke | 75 | 1480 |
| 972125 | N/A | N/A | 6818 | 6833 | ACGCAATGCTGACTTG | kkk-d9-keke | 87 | 1905 |
| 972145 | N/A | N/A | 6547 | 6562 | TCAGATGGGTACTTCT | kkk-d9-kkke | 82 | 411 |
| 972155 | N/A | N/A | 8743 | 8758 | TTCTATTAGAGGGCTA | kkk-d9-kkke | 85 | 80 |
| 972165 | 2736 | 2751 | 14827 | 14842 | GCTAATTTTCTGACTG | kkk-d9-kkke | 92 | 1283 |
| 972175 | N/A | N/A | 8237 | 8252 | GAGTATTGTTTTTGTG | kkk-d9-kkke | 88 | 1899 |
| 972185 | 1034 | 1049 | 13125 | 13140 | TGAAGATTGGCTCTGG | kkk-d9-kkke | 61 | 1931 |
| 972195 | N/A | N/A | 7923 | 7938 | GGGAATTATGGAATTG | kkk-d9-kkke | 77 | 1596 |

TABLE 31

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 903822 | 970 | 985 | 13061 | 13076 | AAGTATTGCCAGCTAA | kkk-d10-kkk | 90 | 1911 |
| 905095 | N/A | N/A | 6702 | 6717 | GTATTTCTTGATGTGG | kkk-d10-kkk | 100 | 413 |
| 905491 | N/A | N/A | 8237 | 8252 | GAGTATTGTTTTTGTG | kkk-d10-kkk | 94 | 1899 |
| 969056 | 968 | 983 | 13059 | 13074 | GTATTGCCAGCTAAGG | k-d10-kekek | 93 | 1410 |
| 969066 | N/A | N/A | 7920 | 7935 | AATTATGGAATTGCAG | k-d10-kekek | 52 | 1923 |
| 969076 | N/A | N/A | 8830 | 8845 | AGCTTTAAACTCAGGT | k-d10-kekek | 95 | 1920 |
| 969086 | N/A | N/A | 5854 | 5869 | TTTGTAAGTGCAACCA | k-d10-kekek | 99 | 1095 |
| 969096 | N/A | N/A | 8366 | 8381 | CTTTATACCAGTGTCT | k-d10-kekek | 89 | 1890 |
| 969106 | N/A | N/A | 5447 | 5462 | TATATTTGATCCTCAA | k-d9-kekeke | 75 | 1932 |
| 969116 | N/A | N/A | 8331 | 8346 | ACATCATTGGGTTATG | k-d9-kekeke | 76 | 286 |
| 969126 | 1033 | 1048 | 13124 | 13139 | GAAGATTGGCTCTGGC | k-d9-kekeke | 21 | 1480 |
| 969136 | N/A | N/A | 6702 | 6717 | GTATTTCTTGATGTGG | k-d9-kekeke | 87 | 413 |
| 969146 | N/A | N/A | 8829 | 8844 | GCTTTAAACTCAGGTG | k-d9-kekeke | 67 | 81 |
| 969156 | N/A | N/A | 5412 | 5427 | ATTCTCATGGTACAGG | kek-d9-eekk | 96 | 677 |
| 969166 | N/A | N/A | 8237 | 8252 | GAGTATTGTTTTTGTG | kek-d9-eekk | 90 | 1899 |
| 969176 | 969 | 984 | 13060 | 13075 | AGTATTGCCAGCTAAG | kk-d10-keke | 86 | 1479 |
| 969186 | N/A | N/A | 6817 | 6832 | CGCAATGCTGACTTGG | kk-d10-keke | 96 | 1924 |
| 969206 | N/A | N/A | 5450 | 5465 | TGTTATATTTGATCCT | kk-d10-keke | 92 | 1887 |
| 969216 | N/A | N/A | 8333 | 8348 | ACACATCATTGGGTTA | kk-d10-keke | 72 | 426 |
| 969226 | N/A | N/A | 5448 | 5463 | TTATATTTGATCCTCA | kk-d8-eeeekk | 91 | 1909 |
| 969236 | N/A | N/A | 8320 | 8335 | TTATGAAATTATTGGT | kk-d8-eeeekk | 35 | 1910 |
| 969246 | 1031 | 1046 | 13122 | 13137 | AGATTGGCTCTGGCTC | kk-d8-kekekk | 18 | 654 |
| 969256 | N/A | N/A | 8162 | 8177 | TTCAGAATTTCCACTA | kk-d8-kekekk | 58 | 1186 |
| 969266 | 969 | 984 | 13060 | 13075 | AGTATTGCCAGCTAAG | kk-d8-kekekk | 34 | 1479 |
| 969276 | N/A | N/A | 7921 | 7936 | GAATTATGGAATTGCA | kk-d8-kekekk | 61 | 1183 |
| 969286 | N/A | N/A | 8306 | 8321 | GTTCAAAAGCAGCATT | kk-d8-kekekk | 34 | 13 |
| 969296 | N/A | N/A | 6548 | 6563 | ATCAGATGGGTACTTC | kk-d8-kekekk | 45 | 481 |
| 969316 | N/A | N/A | 5857 | 5872 | AGTTTTGTAAGTGCAA | kk-d9-eeekk | 94 | 1917 |
| 969326 | N/A | N/A | 8742 | 8757 | TCTATTAGAGGGCTAG | kk-d9-eeekk | 67 | 150 |
| 969336 | 2340 | 2355 | 14431 | 14446 | GTTCTAACTCTTGGGC | kk-d9-eeekk | 91 | 243 |
| 969346 | N/A | N/A | 8164 | 8179 | CATTCAGAATTTCCAC | kk-d9-eeekk | 78 | 1730 |
| 969356 | 971 | 986 | 13062 | 13077 | TAAGTATTGCCAGCTA | kk-d9-eeekk | 79 | 1918 |
| 969366 | N/A | N/A | 6819 | 6834 | AACGCAATGCTGACTT | kk-d9-eeekk | 82 | 1919 |
| 969376 | N/A | N/A | 8832 | 8847 | GAAGCTTTAAACTCAG | kk-d9-eeekk | 72 | 1397 |
| 969386 | N/A | N/A | 5860 | 5875 | GGCAGTTTTGTAAGTG | kk-d9-eeekk | 80 | 123 |
| 969396 | N/A | N/A | 8746 | 8761 | TAATTCTATTAGAGGG | kk-d9-eeekk | 59 | 220 |
| 969406 | N/A | N/A | 5857 | 5872 | AGTTTTGTAAGTGCAA | kk-d9-ekeke | 91 | 1917 |

TABLE 31-continued

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 969416 | N/A | N/A | 8742 | 8757 | TCTATTAGAGGGCTAG | kk-d9-ekeke | 67 | 150 |
| 969426 | 2340 | 2355 | 14431 | 14446 | GTTCTAACTCTTGGGC | kk-d9-ekeke | 78 | 243 |
| 969436 | N/A | N/A | 8164 | 8179 | CATTCAGAATTTCCAC | kk-d9-ekeke | 87 | 1730 |
| 969446 | 972 | 987 | 13063 | 13078 | GTAAGTATTGCCAGCT | kk-d9-ekeke | 69 | 1933 |
| 969456 | N/A | N/A | 6550 | 6565 | ATATCAGATGGGTACT | kk-d9-ekeke | 27 | 620 |
| 969466 | N/A | N/A | 8746 | 8761 | TAATTCTATTAGAGGG | kk-d9-ekeke | 46 | 220 |
| 969476 | N/A | N/A | 5853 | 5868 | TTGTAAGTGCAACCAA | kk-d9-kdkdk | 74 | 1025 |
| 969486 | N/A | N/A | 8365 | 8380 | TTTATACCAGTGTCTT | kk-d9-kdkdk | 81 | 1914 |
| 969496 | 2251 | 2266 | 14342 | 14357 | CGTCAATATATTCTTT | kk-d9-kdkdk | 91 | 1925 |
| 969506 | N/A | N/A | 7922 | 7937 | GGAATTATGGAATTGC | kk-d9-kdkdk | 89 | 1249 |
| 971916 | 969 | 984 | 13060 | 13075 | AGTATTGCCAGCTAAG | kk-d9-kekek | 65 | 1479 |
| 971926 | N/A | N/A | 6817 | 6832 | CGCAATGCTGACTTGG | kk-d9-kekek | 83 | 1924 |
| 971946 | N/A | N/A | 5451 | 5466 | GTGTTATATTTGATCC | kk-d9-kekek | 78 | 1934 |
| 971956 | N/A | N/A | 8323 | 8338 | GGGTTATGAAATTATT | kk-d9-kekek | 84 | 1935 |
| 971966 | 1033 | 1048 | 13124 | 13139 | GAAGATTGGCTCTGGC | kk-d9-kekek | 48 | 1480 |
| 971976 | N/A | N/A | 6818 | 6833 | ACGCAATGCTGACTTG | kk-d9-kekek | 79 | 1905 |
| 971996 | 2340 | 2355 | 14431 | 14446 | GTTCTAACTCTTGGGC | kkk-d8-kdkdk | 73 | 243 |
| 972006 | N/A | N/A | 7922 | 7937 | GGAATTATGGAATTGC | kkk-d8-kdkdk | 76 | 1249 |
| 972026 | N/A | N/A | 6547 | 6562 | TCAGATGGGTACTTCT | kkk-d8-kekek | 50 | 411 |
| 972036 | N/A | N/A | 8743 | 8758 | TTCTATTAGAGGGCTA | kkk-d8-kekek | 42 | 80 |
| 972046 | 2738 | 2753 | 14829 | 14844 | ATGCTAATTTTCTGAC | kkk-d8-kekek | 95 | 1912 |
| 972056 | N/A | N/A | 8166 | 8181 | GGCATTCAGAATTTCC | kkk-d8-kekek | 20 | 1913 |
| 972066 | N/A | N/A | 8306 | 8321 | GTTCAAAAGCAGCATT | kkk-d8-kekek | 24 | 13 |
| 972076 | N/A | N/A | 6548 | 6563 | ATCAGATGGGTACTTC | kkk-d8-kekek | 54 | 481 |
| 972096 | N/A | N/A | 5451 | 5466 | GTGTTATATTTGATCC | kkk-d9-keke | 96 | 1981 |
| 972106 | N/A | N/A | 8334 | 8349 | AACACATCATTGGGTT | kkk-d9-keke | 21 | 496 |
| 972116 | 2251 | 2266 | 14342 | 14357 | CGTCAATATATTCTTT | kkk-d9-keke | 94 | 1925 |
| 972126 | N/A | N/A | 7922 | 7937 | GGAATTATGGAATTGC | kkk-d9-keke | 55 | 1249 |
| 972136 | N/A | N/A | 8829 | 8844 | GCTTTAAACTCAGGTG | kkk-d9-kkke | 74 | 81 |
| 972146 | N/A | N/A | 6701 | 6716 | TATTTCTTGATGTGGT | kkk-d9-kkke | 99 | 1904 |
| 972156 | N/A | N/A | 8828 | 8843 | CTTTAAACTCAGGTGA | kkk-d9-kkke | 59 | 151 |
| 972166 | N/A | N/A | 5412 | 5427 | ATTCTCATGGTACAGG | kkk-d9-kkke | 93 | 677 |
| 972176 | N/A | N/A | 8321 | 8336 | GTTATGAAATTATTGG | kkk-d9-kkke | 96 | 76 |
| 972186 | 2252 | 2267 | 14343 | 14358 | CCGTCAATATATTCTT | kkk-d9-kkke | 98 | 1936 |
| 972196 | N/A | N/A | 8165 | 8180 | GCATTCAGAATTTCCA | kkk-d9-kkke | 95 | 1937 |

TABLE 32

Inhibition of APOL1 mRNA by deoxy MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 904082 | 2251 | 2266 | 14342 | 14357 | CGTCAATATATTCTTT | kkk-d10-kkk | 94 | 1925 |
| 905095 | N/A | N/A | 6702 | 6717 | GTATTTCTTGATGTGG | kkk-d10-kkk | 100 | 413 |
| 905491 | N/A | N/A | 8237 | 8252 | GAGTATTGTTTTTGTG | kkk-d10-kkk | 94 | 1899 |
| 969057 | 1031 | 1046 | 13122 | 13137 | AGATTGGCTCTGGCTC | k-d10-kekek | 40 | 654 |
| 969067 | N/A | N/A | 8162 | 8177 | TTCAGAATTTCCACTA | k-d10-kekek | 87 | 1186 |
| 969077 | N/A | N/A | 8306 | 8321 | GTTCAAAAGCAGCATT | k-d10-kekek | 79 | 13 |
| 969087 | N/A | N/A | 5858 | 5873 | CAGTTTTGTAAGTGCA | k-d10-kekek | 92 | 1577 |
| 969097 | N/A | N/A | 8743 | 8758 | TTCTATTAGAGGGCTA | k-d10-kekek | 45 | 80 |
| 969107 | N/A | N/A | 5448 | 5463 | TTATATTTGATCCTCA | k-d9-kekeke | 39 | 1909 |
| 969117 | N/A | N/A | 8364 | 8379 | TTATACCAGTGTCTTC | k-d9-kekeke | 82 | 1938 |
| 969127 | 2251 | 2266 | 14342 | 14357 | CGTCAATATATTCTTT | k-d9-kekeke | 96 | 1925 |
| 969137 | N/A | N/A | 6818 | 6833 | ACGCAATGCTGACTTG | k-d9-kekeke | 72 | 1905 |
| 969157 | N/A | N/A | 5449 | 5464 | GTTATATTTGATCCTC | kek-d9-eekk | 99 | 1900 |
| 969167 | N/A | N/A | 8321 | 8336 | GTTATGAAATTATTGG | kek-d9-eekk | 90 | 76 |
| 969177 | 1032 | 1047 | 13123 | 13138 | AAGATTGGCTCTGGCT | kk-d10-keke | 65 | 1411 |
| 969187 | N/A | N/A | 7921 | 7936 | GAATTATGGAATTGCA | kk-d10-keke | 92 | 1183 |
| 969207 | N/A | N/A | 5854 | 5869 | TTTGTAAGTGCAACCA | kk-d10-keke | 92 | 1095 |
| 969217 | N/A | N/A | 8366 | 8381 | CTTTATACCAGTGTCT | kk-d10-keke | 97 | 1890 |
| 969227 | N/A | N/A | 5449 | 5464 | GTTATATTTGATCCTC | kk-d8-eeeekk | 69 | 1900 |
| 969237 | N/A | N/A | 8332 | 8347 | CACATCATTGGGTTAT | kk-d8-eeeekk | 54 | 356 |
| 969247 | N/A | N/A | 5410 | 5425 | TCTCATGGTACAGGAG | kk-d8-kekekk | 26 | 537 |
| 969257 | N/A | N/A | 8235 | 8250 | GTATTGTTTTTGTGGG | kk-d8-kekekk | 39 | 1921 |
| 969267 | 1032 | 1047 | 13123 | 13138 | AAGATTGGCTCTGGCT | kk-d8-kekekk | 2 | 1411 |
| 969277 | N/A | N/A | 8163 | 8178 | ATTCAGAATTTCCACT | kk-d8-kekekk | 57 | 1902 |
| 969287 | 970 | 985 | 13061 | 13076 | AAGTATTGCCAGCTAA | kk-d8-kekekk | 27 | 1911 |
| 969297 | N/A | N/A | 6702 | 6717 | GTATTTCTTGATGTGG | kk-d8-kekekk | 52 | 413 |
| 969317 | N/A | N/A | 6547 | 6562 | TCAGATGGGTACTTCT | kk-d9-eeekk | 88 | 411 |
| 969327 | N/A | N/A | 8743 | 8758 | TTCTATTAGAGGGCTA | kk-d9-eeekk | 87 | 80 |
| 969337 | 2736 | 2751 | 14827 | 14842 | GCTAATTTTCTGACTG | kk-d9-eeekk | 94 | 1283 |
| 969347 | N/A | N/A | 8237 | 8252 | GAGTATTGTTTTTGTG | kk-d9-eeekk | 97 | 1899 |
| 969357 | 1034 | 1049 | 13125 | 13140 | TGAAGATTGGCTCTGG | kk-d9-eeekk | 82 | 1931 |
| 969367 | N/A | N/A | 7923 | 7938 | GGGAATTATGGAATTG | kk-d9-eeekk | 86 | 1596 |
| 969377 | N/A | N/A | 8308 | 8323 | TGGTTCAAAAGCAGCA | kk-d9-eeekk | 93 | 1048 |
| 969387 | N/A | N/A | 6550 | 6565 | ATATCAGATGGGTACT | kk-d9-eeekk | 52 | 620 |
| 969407 | N/A | N/A | 6547 | 6562 | TCAGATGGGTACTTCT | kk-d9-ekeke | 91 | 411 |
| 969417 | N/A | N/A | 8743 | 8758 | TTCTATTAGAGGGCTA | kk-d9-ekeke | 85 | 80 |
| 969427 | 2736 | 2751 | 14827 | 14842 | GCTAATTTTCTGACTG | kk-d9-ekeke | 88 | 1283 |

TABLE 32-continued

Inhibition of APOL1 mRNA by deoxy MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 969437 | N/A | N/A | 8237 | 8252 | GAGTATTGTTTTTGTG | kk-d9-ekeke | 98 | 1899 |
| 969447 | 1035 | 1050 | 13126 | 13141 | CTGAAGATTGGCTCTG | kk-d9-ekeke | 53 | 1939 |
| 969457 | N/A | N/A | 6704 | 6719 | GTGTATTTCTTGATGT | kk-d9-ekeke | 94 | 1940 |
| 969467 | N/A | N/A | 8831 | 8846 | AAGCTTTAAACTCAGG | kk-d9-ekeke | 95 | 1327 |
| 969477 | N/A | N/A | 5857 | 5872 | AGTTTTGTAAGTGCAA | kk-d9-kdkdk | 91 | 1917 |
| 969487 | N/A | N/A | 8742 | 8757 | TCTATTAGAGGGCTAG | kk-d9-kdkdk | 68 | 150 |
| 969497 | 2340 | 2355 | 14431 | 14446 | GTTCTAACTCTTGGGC | kk-d9-kdkdk | 90 | 243 |
| 969507 | N/A | N/A | 8164 | 8179 | CATTCAGAATTTCCAC | kk-d9-kdkdk | 84 | 1730 |
| 971917 | 1032 | 1047 | 13123 | 13138 | AAGATTGGCTCTGGCT | kk-d9-kekek | 37 | 1411 |
| 971927 | N/A | N/A | 7921 | 7936 | GAATTATGGAATTGCA | kk-d9-kekek | 51 | 1183 |
| 971947 | N/A | N/A | 5452 | 5467 | CGTGTTATATTTGATC | kk-d9-kekek | 88 | 1906 |
| 971957 | N/A | N/A | 8335 | 8350 | CAACACATCATTGGGT | kk-d9-kekek | 43 | 1907 |
| 971967 | 2251 | 2266 | 14342 | 14357 | CGTCAATATATTCTTT | kk-d9-kekek | 94 | 1925 |
| 971977 | N/A | N/A | 7922 | 7937 | GGAATTATGGAATTGC | kk-d9-kekek | 82 | 1249 |
| 971997 | 2736 | 2751 | 14827 | 14842 | GCTAATTTTCTGACTG | kkk-d8-kdkdk | 93 | 1283 |
| 972007 | N/A | N/A | 8164 | 8179 | CATTCAGAATTTCCAC | kkk-d8-kdkdk | 88 | 1730 |
| 972017 | N/A | N/A | 8829 | 8844 | GCTTTAAACTCAGGTG | kkk-d8-kekek | 68 | 81 |
| 972027 | N/A | N/A | 6701 | 6716 | TATTTCTTGATGTGGT | kkk-d8-kekek | 95 | 1904 |
| 972037 | N/A | N/A | 8828 | 8843 | CTTTAAACTCAGGTGA | kkk-d8-kekek | 40 | 151 |
| 972047 | N/A | N/A | 5414 | 5429 | TTATTCTCATGGTACA | kkk-d8-kekek | 53 | 1927 |
| 972057 | N/A | N/A | 8239 | 8254 | GTGAGTATTGTTTTTG | kkk-d8-kekek | 85 | 1928 |
| 972067 | 970 | 985 | 13061 | 13076 | AAGTATTGCCAGCTAA | kkk-d8-kekek | 47 | 1911 |
| 972077 | N/A | N/A | 6702 | 6717 | GTATTTCTTGATGTGG | kkk-d8-kekek | 73 | 413 |
| 972097 | N/A | N/A | 5855 | 5870 | TTTTGTAAGTGCAACC | kkk-d9-keke | 98 | 1164 |
| 972107 | N/A | N/A | 8367 | 8382 | ACTTTATACCAGTGTC | kkk-d9-keke | 65 | 1941 |
| 972117 | 2340 | 2355 | 14431 | 14446 | GTTCTAACTCTTGGGC | kkk-d9-keke | 66 | 243 |
| 972127 | N/A | N/A | 8164 | 8179 | CATTCAGAATTTCCAC | kkk-d9-keke | 86 | 1730 |
| 972137 | 969 | 984 | 13060 | 13075 | AGTATTGCCAGCTAAG | kkk-d9-kkke | 89 | 1479 |
| 972147 | N/A | N/A | 6817 | 6832 | CGCAATGCTGACTTGG | kkk-d9-kkke | 94 | 1924 |
| 972167 | N/A | N/A | 5450 | 5465 | TGTTATATTTGATCCT | kkk-d9-kkke | 89 | 1887 |
| 972177 | N/A | N/A | 8333 | 8348 | ACACATCATTGGGTTA | kkk-d9-kkke | 59 | 426 |
| 972187 | 2341 | 2356 | 14432 | 14447 | TGTTCTAACTCTTGGG | kkk-d9-kkke | 89 | 313 |
| 972197 | N/A | N/A | 8238 | 8253 | TGAGTATTGTTTTTGT | kkk-d9-kkke | 95 | 1916 |

TABLE 33

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 904619 | N/A | N/A | 5412 | 5427 | ATTCTCATGGTACAGG | kkk-d10-kkk | 97 | 677 |
| 905095 | N/A | N/A | 6702 | 6717 | GTATTTCTTGATGTGG | kkk-d10-kkk | 100 | 413 |
| 905491 | N/A | N/A | 8237 | 8252 | GAGTATTGTTTTTGTG | kkk-d10-kkk | 94 | 1899 |
| 969058 | N/A | N/A | 5410 | 5425 | TCTCATGGTACAGGAG | k-d10-kekek | 61 | 537 |
| 969068 | N/A | N/A | 8235 | 8250 | GTATTGTTTTTGTGGG | k-d10-kekek | 77 | 1921 |
| 969078 | 970 | 985 | 13061 | 13076 | AAGTATTGCCAGCTAA | k-d10-kekek | 54 | 1911 |
| 969088 | N/A | N/A | 6548 | 6563 | ATCAGATGGGTACTTC | k-d10-kekek | 73 | 481 |
| 969098 | N/A | N/A | 8744 | 8759 | ATTCTATTAGAGGGCT | k-d10-kekek | 45 | 1326 |
| 969108 | N/A | N/A | 5852 | 5867 | TGTAAGTGCAACCAAT | k-d9-kekeke | 67 | 955 |
| 969118 | N/A | N/A | 8741 | 8756 | CTATTAGAGGGCTAGT | k-d9-kekeke | 34 | 1674 |
| 969128 | 2340 | 2355 | 14431 | 14446 | GTTCTAACTCTTGGGC | k-d9-kekeke | 77 | 243 |
| 969138 | N/A | N/A | 7922 | 7937 | GGAATTATGGAATTGC | k-d9-kekeke | 88 | 1249 |
| 969158 | N/A | N/A | 5450 | 5465 | TGTTATATTTGATCCT | kek-d9-eekk | 94 | 1887 |
| 969168 | N/A | N/A | 8333 | 8348 | ACACATCATTGGGTTA | kek-d9-eekk | 87 | 426 |
| 969178 | 2735 | 2750 | 14826 | 14841 | CTAATTTTCTGACTGT | kk-d10-keke | 98 | 1901 |
| 969188 | N/A | N/A | 8163 | 8178 | ATTCAGAATTTCCACT | kk-d10-keke | 88 | 1902 |
| 969198 | N/A | N/A | 8830 | 8845 | AGCTTTAAACTCAGGT | kk-d10-keke | 94 | 1920 |
| 969208 | N/A | N/A | 5858 | 5873 | CAGTTTTGTAAGTGCA | kk-d10-keke | 94 | 1577 |
| 969218 | N/A | N/A | 8744 | 8759 | ATTCTATTAGAGGGCT | kk-d10-keke | 78 | 1326 |
| 969228 | N/A | N/A | 5853 | 5868 | TTGTAAGTGCAACCAA | kk-d8-eeeekk | 70 | 1025 |
| 969238 | N/A | N/A | 8365 | 8380 | TTTATACCAGTGTCTT | kk-d8-eeeekk | 89 | 1914 |
| 969248 | N/A | N/A | 5447 | 5462 | TATATTTGATCCTCAA | kk-d8-kekekk | 77 | 1932 |
| 969258 | N/A | N/A | 8331 | 8346 | ACATCATTGGGTTATG | kk-d8-kekekk | 70 | 286 |
| 969268 | 2735 | 2750 | 14826 | 14841 | CTAATTTTCTGACTGT | kk-d8-kekekk | 71 | 1901 |
| 969278 | N/A | N/A | 8236 | 8251 | AGTATTGTTTTTGTGG | kk-d8-kekekk | 66 | 1922 |
| 969288 | 1033 | 1048 | 13124 | 13139 | GAAGATTGGCTCTGGC | kk-d8-kekekk | 10 | 1480 |
| 969298 | N/A | N/A | 6818 | 6833 | ACGCAATGCTGACTTG | kk-d8-kekekk | 72 | 1905 |
| 969308 | N/A | N/A | 8829 | 8844 | GCTTTAAACTCAGGTG | kk-d9-eeekk | 91 | 81 |
| 969318 | N/A | N/A | 6701 | 6716 | TATTTCTTGATGTGGT | kk-d9-eeekk | 99 | 1904 |
| 969328 | N/A | N/A | 8828 | 8843 | CTTTAAACTCAGGTGA | kk-d9-eeekk | 92 | 151 |
| 969338 | N/A | N/A | 5412 | 5427 | ATTCTCATGGTACAGG | kk-d9-eeekk | 92 | 677 |
| 969348 | N/A | N/A | 8321 | 8336 | GTTATGAAATTATTGG | kk-d9-eeekk | 54 | 76 |
| 969358 | 2252 | 2267 | 14343 | 14358 | CCGTCAATATATTCTT | kk-d9-eeekk | 98 | 1936 |
| 969368 | N/A | N/A | 8165 | 8180 | GCATTCAGAATTTCCA | kk-d9-eeekk | 98 | 1937 |
| 969378 | 972 | 987 | 13063 | 13078 | GTAAGTATTGCCAGCT | kk-d9-eeekk | 89 | 1933 |
| 969388 | N/A | N/A | 6704 | 6719 | GTGTATTTCTTGATGT | kk-d9-eeekk | 96 | 1940 |
| 969398 | N/A | N/A | 8829 | 8844 | GCTTTAAACTCAGGTG | kk-d9-ekeke | 92 | 81 |

TABLE 33-continued

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 969408 | N/A | N/A | 6701 | 6716 | TATTTCTTGATGTGGT | kk-d9-ekeke | 99 | 1904 |
| 969418 | N/A | N/A | 8828 | 8843 | CTTTAAACTCAGGTGA | kk-d9-ekeke | 91 | 151 |
| 969428 | N/A | N/A | 5412 | 5427 | ATTCTCATGGTACAGG | kk-d9-ekeke | 95 | 677 |
| 969438 | N/A | N/A | 8321 | 8336 | GTTATGAAATTATTGG | kk-d9-ekeke | 68 | 76 |
| 969448 | 2253 | 2268 | 14344 | 14359 | TCCGTCAATATATTCT | kk-d9-ekeke | 97 | 1897 |
| 969458 | N/A | N/A | 6820 | 6835 | GAACGCAATGCTGACT | kk-d9-ekeke | 95 | 1888 |
| 969478 | N/A | N/A | 6547 | 6562 | TCAGATGGGTACTTCT | kk-d9-kdkdk | 88 | 411 |
| 969488 | N/A | N/A | 8743 | 8758 | TTCTATTAGAGGGCTA | kk-d9-kdkdk | 87 | 80 |
| 969498 | 2736 | 2751 | 14827 | 14842 | GCTAATTTTCTGACTG | kk-d9-kdkdk | 93 | 1283 |
| 969508 | N/A | N/A | 8237 | 8252 | GAGTATTGTTTTTGTG | kk-d9-kdkdk | 92 | 1899 |
| 971918 | 2735 | 2750 | 14826 | 14841 | CTAATTTTCTGACTGT | kk-d9-kekek | 83 | 1901 |
| 971928 | N/A | N/A | 8163 | 8178 | ATTCAGAATTTCCACT | kk-d9-kekek | 76 | 1902 |
| 971938 | N/A | N/A | 8832 | 8847 | GAAGCTTTAAACTCAG | kk-d9-kekek | 84 | 1397 |
| 971948 | N/A | N/A | 5856 | 5871 | GTTTTGTAAGTGCAAC | kk-d9-kekek | 88 | 1230 |
| 971958 | N/A | N/A | 8368 | 8383 | CACTTTATACCAGTGT | kk-d9-kekek | 14 | 1908 |
| 971968 | 2340 | 2355 | 14431 | 14446 | GTTCTAACTCTTGGGC | kk-d9-kekek | 61 | 243 |
| 971978 | N/A | N/A | 8164 | 8179 | CATTCAGAATTTCCAC | kk-d9-kekek | 76 | 1730 |
| 971998 | N/A | N/A | 5412 | 5427 | ATTCTCATGGTACAGG | kkk-d8-kdkdk | 81 | 677 |
| 972008 | N/A | N/A | 8237 | 8252 | GAGTATTGTTTTTGTG | kkk-d8-kdkdk | 54 | 1899 |
| 972018 | 969 | 984 | 13060 | 13075 | AGTATTGCCAGCTAAG | kkk-d8-kekek | 66 | 1479 |
| 972028 | N/A | N/A | 6817 | 6832 | CGCAATGCTGACTTGG | kkk-d8-kekek | 68 | 1924 |
| 972048 | N/A | N/A | 5451 | 5466 | GTGTTATATTTGATCC | kkk-d8-kekek | 75 | 1934 |
| 972058 | N/A | N/A | 8323 | 8338 | GGGTTATGAAATTATT | kkk-d8-kekek | 73 | 1935 |
| 972068 | 1033 | 1048 | 13124 | 13139 | GAAGATTGGCTCTGGC | kkk-d8-kekek | 16 | 1480 |
| 972078 | N/A | N/A | 6818 | 6833 | ACGCAATGCTGACTTG | kkk-d8-kekek | 71 | 1905 |
| 972088 | N/A | N/A | 8831 | 8846 | AAGCTTTAAACTCAGG | kkk-d9-keke | 84 | 1327 |
| 972098 | N/A | N/A | 5859 | 5874 | GCAGTTTTGTAAGTGC | kkk-d9-keke | 60 | 1647 |
| 972108 | N/A | N/A | 8744 | 8759 | ATTCTATTAGAGGGCT | kkk-d9-keke | 73 | 1326 |
| 972118 | 2736 | 2751 | 14827 | 14842 | GCTAATTTTCTGACTG | kkk-d9-keke | 93 | 1283 |
| 972128 | N/A | N/A | 8237 | 8252 | GAGTATTGTTTTTGTG | kkk-d9-keke | 81 | 1899 |
| 972138 | 1032 | 1047 | 13123 | 13138 | AAGATTGGCTCTGGCT | kkk-d9-kkke | 35 | 1411 |
| 972148 | N/A | N/A | 7921 | 7936 | GAATTATGGAATTGCA | kkk-d9-kkke | 90 | 1183 |
| 972168 | N/A | N/A | 5854 | 5869 | TTTGTAAGTGCAACCA | kkk-d9-kkke | 56 | 1095 |
| 972178 | N/A | N/A | 8366 | 8381 | CTTTATACCAGTGTCT | kkk-d9-kkke | 95 | 1890 |
| 972188 | N/A | N/A | 5413 | 5428 | TATTCTCATGGTACAG | kkk-d9-kkke | 79 | 1915 |
| 972198 | N/A | N/A | 8322 | 8337 | GGTTATGAAATTATTG | kkk-d9-kkke | 91 | 1930 |

TABLE 34

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 904627 | N/A | N/A | 5449 | 5464 | GTTATATTTGATCCTC | kkk-d10-kkk | 100 | 1900 |
| 905095 | N/A | N/A | 6702 | 6717 | GTATTTCTTGATGTGG | kkk-d10-kkk | 100 | 413 |
| 905491 | N/A | N/A | 8237 | 8252 | GAGTATTGTTTTTGTG | kkk-d10-kkk | 94 | 1899 |
| 969059 | N/A | N/A | 5447 | 5462 | TATATTTGATCCTCAA | k-d10-kekek | 89 | 1932 |
| 969069 | N/A | N/A | 8331 | 8346 | ACATCATTGGGTTATG | k-d10-kekek | 89 | 286 |
| 969079 | 1033 | 1048 | 13124 | 13139 | GAAGATTGGCTCTGGC | k-d10-kekek | 44 | 1480 |
| 969089 | N/A | N/A | 6702 | 6717 | GTATTTCTTGATGTGG | k-d10-kekek | 92 | 413 |
| 969099 | N/A | N/A | 8829 | 8844 | GCTTTAAACTCAGGTG | k-d10-kekek | 92 | 81 |
| 969109 | N/A | N/A | 5856 | 5871 | GTTTTGTAAGTGCAAC | k-d9-kekeke | 73 | 1230 |
| 969119 | N/A | N/A | 8742 | 8757 | TCTATTAGAGGGCTAG | k-d9-kekeke | 37 | 150 |
| 969129 | 2736 | 2751 | 14827 | 14842 | GCTAATTTTCTGACTG | k-d9-kekeke | 88 | 1283 |
| 969139 | N/A | N/A | 8164 | 8179 | CATTCAGAATTTCCAC | k-d9-kekeke | 58 | 1730 |
| 969149 | N/A | N/A | 8830 | 8845 | AGCTTTAAACTCAGGT | kek-d9-eekk | 82 | 1920 |
| 969159 | N/A | N/A | 5854 | 5869 | TTTGTAAGTGCAACCA | kek-d9-eekk | 99 | 1095 |
| 969169 | N/A | N/A | 8366 | 8381 | CTTTATACCAGTGTCT | kek-d9-eekk | 95 | 1890 |
| 969179 | N/A | N/A | 5411 | 5426 | TTCTCATGGTACAGGA | kk-d10-keke | 78 | 607 |
| 969189 | N/A | N/A | 8236 | 8251 | AGTATTGTTTTTGTGG | kk-d10-keke | 91 | 1922 |
| 969199 | N/A | N/A | 8306 | 8321 | GTTCAAAAGCAGCATT | kk-d10-keke | 89 | 13 |
| 969209 | N/A | N/A | 6548 | 6563 | ATCAGATGGGTACTTC | kk-d10-keke | 83 | 481 |
| 969229 | N/A | N/A | 5857 | 5872 | AGTTTTGTAAGTGCAA | kk-d8-eeeekk | 94 | 1917 |
| 969239 | N/A | N/A | 8742 | 8757 | TCTATTAGAGGGCTAG | kk-d8-eeeekk | 44 | 150 |
| 969249 | N/A | N/A | 5448 | 5463 | TTATATTTGATCCTCA | kk-d8-kekekk | 69 | 1909 |
| 969259 | N/A | N/A | 8364 | 8379 | TTATACCAGTGTCTTC | kk-d8-kekekk | 68 | 1938 |
| 969269 | N/A | N/A | 5411 | 5426 | TTCTCATGGTACAGGA | kk-d8-kekekk | 20 | 607 |
| 969279 | N/A | N/A | 8320 | 8335 | TTATGAAATTATTGGT | kk-d8-kekekk | 63 | 1910 |
| 969289 | 2251 | 2266 | 14342 | 14357 | CGTCAATATATTCTTT | kk-d8-kekekk | 95 | 1925 |
| 969299 | N/A | N/A | 7922 | 7937 | GGAATTATGGAATTGC | kk-d8-kekekk | 74 | 1249 |
| 969309 | 969 | 984 | 13060 | 13075 | AGTATTGCCAGCTAAG | kk-d9-eeekk | 86 | 1479 |
| 969319 | N/A | N/A | 6817 | 6832 | CGCAATGCTGACTTGG | kk-d9-eeekk | 88 | 1924 |
| 969339 | N/A | N/A | 5450 | 5465 | TGTTATATTTGATCCT | kk-d9-eeekk | 87 | 1887 |
| 969349 | N/A | N/A | 8333 | 8348 | ACACATCATTGGGTTA | kk-d9-eeekk | 51 | 426 |
| 969359 | 2341 | 2356 | 14432 | 14447 | TGTTCTAACTCTTGGG | kk-d9-eeekk | 97 | 313 |
| 969369 | N/A | N/A | 8238 | 8253 | TGAGTATTGTTTTTGT | kk-d9-eeekk | 87 | 1916 |
| 969379 | 1035 | 1050 | 13126 | 13141 | CTGAAGATTGGCTCTG | kk-d9-eeekk | 54 | 1939 |
| 969389 | N/A | N/A | 6820 | 6835 | GAACGCAATGCTGACT | kk-d9-eeekk | 95 | 1888 |
| 969399 | 969 | 984 | 13060 | 13075 | AGTATTGCCAGCTAAG | kk-d9-ekeke | 78 | 1479 |
| 969409 | N/A | N/A | 6817 | 6832 | CGCAATGCTGACTTGG | kk-d9-ekeke | 94 | 1924 |

TABLE 34-continued

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 969429 | N/A | N/A | 5450 | 5465 | TGTTATATTTGATCCT | kk-d9-ekeke | 94 | 1887 |
| 969439 | N/A | N/A | 8333 | 8348 | ACACATCATTGGGTTA | kk-d9-ekeke | 64 | 426 |
| 969449 | 2342 | 2357 | 14433 | 14448 | CTGTTCTAACTCTTGG | kk-d9-ekeke | 97 | 383 |
| 969459 | N/A | N/A | 7924 | 7939 | TGGGAATTATGGAATT | kk-d9-ekeke | 78 | 1929 |
| 969469 | N/A | N/A | 8829 | 8844 | GCTTTAAACTCAGGTG | kk-d9-kdkdk | 96 | 81 |
| 969479 | N/A | N/A | 6701 | 6716 | TATTTCTTGATGTGGT | kk-d9-kdkdk | 97 | 1904 |
| 969489 | N/A | N/A | 8828 | 8843 | CTTTAAACTCAGGTGA | kk-d9-kdkdk | 89 | 151 |
| 969499 | N/A | N/A | 5412 | 5427 | ATTCTCATGGTACAGG | kk-d9-kdkdk | 84 | 677 |
| 969509 | N/A | N/A | 8321 | 8336 | GTTATGAAATTATTGG | kk-d9-kdkdk | 71 | 76 |
| 971919 | N/A | N/A | 5411 | 5426 | TTCTCATGGTACAGGA | kk-d9-kekek | 76 | 607 |
| 971929 | N/A | N/A | 8236 | 8251 | AGTATTGTTTTTGTGG | kk-d9-kekek | 75 | 1922 |
| 971939 | N/A | N/A | 8308 | 8323 | TGGTTCAAAAGCAGCA | kk-d9-kekek | 68 | 1048 |
| 971949 | N/A | N/A | 5860 | 5875 | GGCAGTTTTGTAAGTG | kk-d9-kekek | 65 | 123 |
| 971959 | N/A | N/A | 8745 | 8760 | AATTCTATTAGAGGGC | kk-d9-kekek | 56 | 1396 |
| 971969 | 2736 | 2751 | 14827 | 14842 | GCTAATTTTCTGACTG | kk-d9-kekek | 96 | 1283 |
| 971979 | N/A | N/A | 8237 | 8252 | GAGTATTGTTTTTGTG | kk-d9-kekek | 90 | 1899 |
| 971999 | N/A | N/A | 5449 | 5464 | GTTATATTTGATCCTC | kkk-d8-kdkdk | 92 | 1900 |
| 972009 | N/A | N/A | 8321 | 8336 | GTTATGAAATTATTGG | kkk-d8-kdkdk | 91 | 76 |
| 972019 | 1032 | 1047 | 13123 | 13138 | AAGATTGGCTCTGGCT | kkk-d8-kekek | 23 | 1411 |
| 972029 | N/A | N/A | 7921 | 7936 | GAATTATGGAATTGCA | kkk-d8-kekek | 61 | 1183 |
| 972049 | N/A | N/A | 5452 | 5467 | CGTGTTATATTTGATC | kkk-d8-kekek | 82 | 1906 |
| 972059 | N/A | N/A | 8335 | 8350 | CAACACATCATTGGGT | kkk-d8-kekek | 30 | 1907 |
| 972069 | 2251 | 2266 | 14342 | 14357 | CGTCAATATATTCTTT | kkk-d8-kekek | 94 | 1925 |
| 972079 | N/A | N/A | 7922 | 7937 | GGAATTATGGAATTGC | kkk-d8-kekek | 66 | 1249 |
| 972089 | N/A | N/A | 8307 | 8322 | GGTTCAAAAGCAGCAT | kkk-d9-keke | 70 | 978 |
| 972099 | N/A | N/A | 6549 | 6564 | TATCAGATGGGTACTT | kkk-d9-keke | 37 | 550 |
| 972109 | N/A | N/A | 8745 | 8760 | AATTCTATTAGAGGGC | kkk-d9-keke | 82 | 1396 |
| 972119 | N/A | N/A | 5412 | 5427 | ATTCTCATGGTACAGG | kkk-d9-keke | 94 | 677 |
| 972129 | N/A | N/A | 8321 | 8336 | GTTATGAAATTATTGG | kkk-d9-keke | 93 | 76 |
| 972139 | 2735 | 2750 | 14826 | 14841 | CTAATTTTCTGACTGT | kkk-d9-kkke | 99 | 1901 |
| 972149 | N/A | N/A | 8163 | 8178 | ATTCAGAATTTCCACT | kkk-d9-kkke | 89 | 1902 |
| 972159 | N/A | N/A | 8830 | 8845 | AGCTTTAAACTCAGGT | kkk-d9-kkke | 82 | 1920 |
| 972169 | N/A | N/A | 5858 | 5873 | CAGTTTTGTAAGTGCA | kkk-d9-kkke | 92 | 1577 |
| 972179 | N/A | N/A | 8744 | 8759 | ATTCTATTAGAGGGCT | kkk-d9-kkke | 85 | 1326 |
| 972189 | N/A | N/A | 5451 | 5466 | GTGTTATATTTGATCC | kkk-d9-kkke | 94 | 1934 |
| 972199 | N/A | N/A | 8334 | 8349 | AACACATCATTGGGTT | kkk-d9-kkke | 58 | 496 |

TABLE 35

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 904763 | N/A | N/A | 5854 | 5869 | TTTGTAAGTGCAACCA | kkk-d10-kkk | 98 | 1095 |
| 905095 | N/A | N/A | 6702 | 6717 | GTATTTCTTGATGTGG | kkk-d10-kkk | 100 | 413 |
| 905491 | N/A | N/A | 8237 | 8252 | GAGTATTGTTTTTGTG | kkk-d10-kkk | 94 | 1899 |
| 969060 | N/A | N/A | 5448 | 5463 | TTATATTTGATCCTCA | k-d10-kekek | 82 | 1909 |
| 969070 | N/A | N/A | 8364 | 8379 | TTATACCAGTGTCTTC | k-d10-kekek | 82 | 1938 |
| 969080 | 2251 | 2266 | 14342 | 14357 | CGTCAATATATTCTTT | k-d10-kekek | 90 | 1925 |
| 969090 | N/A | N/A | 6818 | 6833 | ACGCAATGCTGACTTG | k-d10-kekek | 71 | 1905 |
| 969110 | N/A | N/A | 6546 | 6561 | CAGATGGGTACTTCTG | k-d9-kekeke | 23 | 341 |
| 969120 | N/A | N/A | 8827 | 8842 | TTTAAACTCAGGTGAC | k-d9-kekeke | 43 | 1675 |
| 969130 | N/A | N/A | 5412 | 5427 | ATTCTCATGGTACAGG | k-d9-kekeke | 51 | 677 |
| 969140 | N/A | N/A | 8237 | 8252 | GAGTATTGTTTTTGTG | k-d9-kekeke | 94 | 1899 |
| 969150 | N/A | N/A | 8306 | 8321 | GTTCAAAAGCAGCATT | kek-d9-eekk | 89 | 13 |
| 969160 | N/A | N/A | 5858 | 5873 | CAGTTTTGTAAGTGCA | kek-d9-eekk | 96 | 1577 |
| 969170 | N/A | N/A | 8743 | 8758 | TTCTATTAGAGGGCTA | kek-d9-eekk | 94 | 80 |
| 969180 | N/A | N/A | 5448 | 5463 | TTATATTTGATCCTCA | kk-d10-keke | 96 | 1909 |
| 969190 | N/A | N/A | 8320 | 8335 | TTATGAAATTATTGGT | kk-d10-keke | 63 | 1910 |
| 969200 | 970 | 985 | 13061 | 13076 | AAGTATTGCCAGCTAA | kk-d10-keke | 73 | 1911 |
| 969210 | N/A | N/A | 6702 | 6717 | GTATTTCTTGATGTGG | kk-d10-keke | 98 | 413 |
| 969230 | N/A | N/A | 6547 | 6562 | TCAGATGGGTACTTCT | kk-d8-eeeekk | 78 | 411 |
| 969240 | N/A | N/A | 8743 | 8758 | TTCTATTAGAGGGCTA | kk-d8-eeeekk | 76 | 80 |
| 969250 | N/A | N/A | 5852 | 5867 | TGTAAGTGCAACCAAT | kk-d8-kekekk | 43 | 955 |
| 969260 | N/A | N/A | 8741 | 8756 | CTATTAGAGGGCTAGT | kk-d8-kekekk | 25 | 1674 |
| 969270 | N/A | N/A | 5449 | 5464 | GTTATATTTGATCCTC | kk-d8-kekekk | 43 | 1900 |
| 969280 | N/A | N/A | 8332 | 8347 | CACATCATTGGGTTAT | kk-d8-kekekk | 34 | 356 |
| 969290 | 2340 | 2355 | 14431 | 14446 | GTTCTAACTCTTGGGC | kk-d8-kekekk | 52 | 243 |
| 969300 | N/A | N/A | 8164 | 8179 | CATTCAGAATTTCCAC | kk-d8-kekekk | 57 | 1730 |
| 969310 | 1032 | 1047 | 13123 | 13138 | AAGATTGGCTCTGGCT | kk-d9-eeekk | 63 | 1411 |
| 969320 | N/A | N/A | 7921 | 7936 | GAATTATGGAATTGCA | kk-d9-eeekk | 94 | 1183 |
| 969340 | N/A | N/A | 5854 | 5869 | TTTGTAAGTGCAACCA | kk-d9-eeekk | 99 | 1095 |
| 969350 | N/A | N/A | 8366 | 8381 | CTTTATACCAGTGTCT | kk-d9-eeekk | 96 | 1890 |
| 969360 | N/A | N/A | 5413 | 5428 | TATTCTCATGGTACAG | kk-d9-eeekk | 71 | 1915 |
| 969370 | N/A | N/A | 8322 | 8337 | GGTTATGAAATTATTG | kk-d9-eeekk | 61 | 1930 |
| 969380 | 2253 | 2268 | 14344 | 14359 | TCCGTCAATATATTCT | kk-d9-eeekk | 96 | 1897 |
| 969390 | N/A | N/A | 7924 | 7939 | TGGGAATTATGGAATT | kk-d9-eeekk | 63 | 1929 |
| 969400 | 1032 | 1047 | 13123 | 13138 | AAGATTGGCTCTGGCT | kk-d9-ekeke | 66 | 1411 |
| 969410 | N/A | N/A | 7921 | 7936 | GAATTATGGAATTGCA | kk-d9-ekeke | 95 | 1183 |
| 969430 | N/A | N/A | 5854 | 5869 | TTTGTAAGTGCAACCA | kk-d9-ekeke | 97 | 1095 |

TABLE 35-continued

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 969440 | N/A | N/A | 8366 | 8381 | CTTTATACCAGTGTCT | kk-d9-ekeke | 98 | 1890 |
| 969450 | 2738 | 2753 | 14829 | 14844 | ATGCTAATTTTCTGAC | kk-d9-ekeke | 95 | 1912 |
| 969460 | N/A | N/A | 8166 | 8181 | GGCATTCAGAATTTCC | kk-d9-ekeke | 93 | 1913 |
| 969470 | 969 | 984 | 13060 | 13075 | AGTATTGCCAGCTAAG | kk-d9-kdkdk | 69 | 1479 |
| 969480 | N/A | N/A | 6817 | 6832 | CGCAATGCTGACTTGG | kk-d9-kdkdk | 94 | 1924 |
| 969500 | N/A | N/A | 5450 | 5465 | TGTTATATTTGATCCT | kk-d9-kdkdk | 86 | 1887 |
| 969510 | N/A | N/A | 8333 | 8348 | ACACATCATTGGGTTA | kk-d9-kdkdk | 57 | 426 |
| 971920 | N/A | N/A | 5448 | 5463 | TTATATTTGATCCTCA | kk-d9-kekek | 91 | 1909 |
| 971930 | N/A | N/A | 8320 | 8335 | TTATGAAATTATTGGT | kk-d9-kekek | 82 | 1910 |
| 971940 | 972 | 987 | 13063 | 13078 | GTAAGTATTGCCAGCT | kk-d9-kekek | 53 | 1933 |
| 971950 | N/A | N/A | 6550 | 6565 | ATATCAGATGGGTACT | kk-d9-kekek | 21 | 620 |
| 971960 | N/A | N/A | 8746 | 8761 | TAATTCTATTAGAGGG | kk-d9-kekek | 34 | 220 |
| 971970 | N/A | N/A | 5412 | 5427 | ATTCTCATGGTACAGG | kk-d9-kekek | 76 | 677 |
| 971980 | N/A | N/A | 8321 | 8336 | GTTATGAAATTATTGG | kk-d9-kekek | 83 | 76 |
| 972000 | N/A | N/A | 5450 | 5465 | TGTTATATTTGATCCT | kkk-d8-kdkdk | 66 | 1887 |
| 972010 | N/A | N/A | 8333 | 8348 | ACACATCATTGGGTTA | kkk-d8-kdkdk | 48 | 426 |
| 972020 | 2735 | 2750 | 14826 | 14841 | CTAATTTTCTGACTGT | kkk-d8-kekek | 90 | 1901 |
| 972030 | N/A | N/A | 8163 | 8178 | ATTCAGAATTTCCACT | kkk-d8-kekek | 56 | 1902 |
| 972040 | N/A | N/A | 8832 | 8847 | GAAGCTTTAAACTCAG | kkk-d8-kekek | 47 | 1397 |
| 972050 | N/A | N/A | 5856 | 5871 | GTTTTGTAAGTGCAAC | kkk-d8-kekek | 59 | 1230 |
| 972060 | N/A | N/A | 8368 | 8383 | CACTTTATACCAGTGT | kkk-d8-kekek | 11 | 1908 |
| 972070 | 2340 | 2355 | 14431 | 14446 | GTTCTAACTCTTGGGC | kkk-d8-kekek | 37 | 243 |
| 972080 | N/A | N/A | 8164 | 8179 | CATTCAGAATTTCCAC | kkk-d8-kekek | 65 | 1730 |
| 972090 | 971 | 986 | 13062 | 13077 | TAAGTATTGCCAGCTA | kkk-d9-keke | 78 | 1918 |
| 972100 | N/A | N/A | 6703 | 6718 | TGTATTTCTTGATGTG | kkk-d9-keke | 71 | 1926 |
| 972110 | N/A | N/A | 8830 | 8845 | AGCTTTAAACTCAGGT | kkk-d9-keke | 85 | 1920 |
| 972120 | N/A | N/A | 5449 | 5464 | GTTATATTTGATCCTC | kkk-d9-keke | 98 | 1900 |
| 972130 | N/A | N/A | 8333 | 8348 | ACACATCATTGGGTTA | kkk-d9-keke | 58 | 426 |
| 972140 | N/A | N/A | 5411 | 5426 | TTCTCATGGTACAGGA | kkk-d9-kkke | 44 | 607 |
| 972150 | N/A | N/A | 8236 | 8251 | AGTATTGTTTTTGTGG | kkk-d9-kkke | 89 | 1922 |
| 972160 | N/A | N/A | 8306 | 8321 | GTTCAAAAGCAGCATT | kkk-d9-kkke | 80 | 13 |
| 972170 | N/A | N/A | 6548 | 6563 | ATCAGATGGGTACTTC | kkk-d9-kkke | 88 | 481 |
| 972190 | N/A | N/A | 5855 | 5870 | TTTTGTAAGTGCAACC | kkk-d9-kkke | 98 | 1164 |
| 972200 | N/A | N/A | 8367 | 8382 | ACTTTATACCAGTGTC | kkk-d9-kkke | 58 | 1941 |

TABLE 36

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 904766 | N/A | N/A | 5858 | 5873 | CAGTTTTGTAAGTGCA | kkk-d10-kkk | 97 | 1577 |
| 905095 | N/A | N/A | 6702 | 6717 | GTATTTCTTGATGTGG | kkk-d10-kkk | 99 | 413 |
| 905491 | N/A | N/A | 8237 | 8252 | GAGTATTGTTTTTGTG | kkk-d10-kkk | 93 | 1899 |
| 969061 | N/A | N/A | 5852 | 5867 | TGTAAGTGCAACCAAT | k-d10-kekek | 81 | 955 |
| 969071 | N/A | N/A | 8741 | 8756 | CTATTAGAGGGCTAGT | k-d10-kekek | 28 | 1674 |
| 969081 | 2340 | 2355 | 14431 | 14446 | GTTCTAACTCTTGGGC | k-d10-kekek | 28 | 243 |
| 969091 | N/A | N/A | 7922 | 7937 | GGAATTATGGAATTGC | k-d10-kekek | 92 | 1249 |
| 969111 | N/A | N/A | 6700 | 6715 | ATTTCTTGATGTGGTG | k-d9-kekeke | 81 | 343 |
| 969131 | N/A | N/A | 5449 | 5464 | GTTATATTTGATCCTC | k-d9-kekeke | 60 | 1900 |
| 969141 | N/A | N/A | 8321 | 8336 | GTTATGAAATTATTGG | k-d9-kekeke | 77 | 76 |
| 969151 | 970 | 985 | 13061 | 13076 | AAGTATTGCCAGCTAA | kek-d9-eekk | 88 | 1911 |
| 969161 | N/A | N/A | 6548 | 6563 | ATCAGATGGGTACTTC | kek-d9-eekk | 91 | 481 |
| 969171 | N/A | N/A | 8744 | 8759 | ATTCTATTAGAGGGCT | kek-d9-eekk | 77 | 1326 |
| 969181 | N/A | N/A | 5449 | 5464 | GTTATATTTGATCCTC | kk-d10-keke | 97 | 1900 |
| 969191 | N/A | N/A | 8332 | 8347 | CACATCATTGGGTTAT | kk-d10-keke | 77 | 356 |
| 969201 | 1033 | 1048 | 13124 | 13139 | GAAGATTGGCTCTGGC | kk-d10-keke | 70 | 1480 |
| 969211 | N/A | N/A | 6818 | 6833 | ACGCAATGCTGACTTG | kk-d10-keke | 89 | 1905 |
| 969221 | N/A | N/A | 8829 | 8844 | GCTTTAAACTCAGGTG | kk-d8-eeeekk | 95 | 81 |
| 969231 | N/A | N/A | 6701 | 6716 | TATTTCTTGATGTGGT | kk-d8-eeeekk | 96 | 1904 |
| 969241 | N/A | N/A | 8828 | 8843 | CTTTAAACTCAGGTGA | kk-d8-eeeekk | 88 | 151 |
| 969251 | N/A | N/A | 5856 | 5871 | GTTTTGTAAGTGCAAC | kk-d8-kekekk | 62 | 1230 |
| 969261 | N/A | N/A | 8742 | 8757 | TCTATTAGAGGGCTAG | kk-d8-kekekk | 25 | 150 |
| 969271 | N/A | N/A | 5853 | 5868 | TTGTAAGTGCAACCAA | kk-d8-kekekk | 54 | 1025 |
| 969281 | N/A | N/A | 8365 | 8380 | TTTATACCAGTGTCTT | kk-d8-kekekk | 51 | 1914 |
| 969291 | 2736 | 2751 | 14827 | 14842 | GCTAATTTTCTGACTG | kk-d8-kekekk | 71 | 1283 |
| 969301 | N/A | N/A | 8237 | 8252 | GAGTATTGTTTTTGTG | kk-d8-kekekk | 85 | 1899 |
| 969311 | 2735 | 2750 | 14826 | 14841 | CTAATTTTCTGACTGT | kk-d9-eeekk | 83 | 1901 |
| 969321 | N/A | N/A | 8163 | 8178 | ATTCAGAATTTCCACT | kk-d9-eeekk | 77 | 1902 |
| 969331 | N/A | N/A | 8830 | 8845 | AGCTTTAAACTCAGGT | kk-d9-eeekk | 93 | 1920 |
| 969341 | N/A | N/A | 5858 | 5873 | CAGTTTTGTAAGTGCA | kk-d9-eeekk | 92 | 1577 |
| 969351 | N/A | N/A | 8744 | 8759 | ATTCTATTAGAGGGCT | kk-d9-eeekk | 70 | 1326 |
| 969361 | N/A | N/A | 5451 | 5466 | GTGTTATATTTGATCC | kk-d9-eeekk | 98 | 1934 |
| 969371 | N/A | N/A | 8334 | 8349 | AACACATCATTGGGTT | kk-d9-eeekk | 43 | 496 |
| 969381 | 2342 | 2357 | 14433 | 14448 | CTGTTCTAACTCTTGG | kk-d9-eeekk | 93 | 383 |
| 969391 | N/A | N/A | 8166 | 8181 | GGCATTCAGAATTTCC | kk-d9-eeekk | 97 | 1913 |
| 969401 | 2735 | 2750 | 14826 | 14841 | CTAATTTTCTGACTGT | kk-d9-ekeke | 90 | 1901 |
| 969411 | N/A | N/A | 8163 | 8178 | ATTCAGAATTTCCACT | kk-d9-ekeke | 87 | 1902 |

TABLE 36-continued

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 969421 | N/A | N/A | 8830 | 8845 | AGCTTTAAACTCAGGT | kk-d9-ekeke | 92 | 1920 |
| 969431 | N/A | N/A | 5858 | 5873 | CAGTTTTGTAAGTGCA | kk-d9-ekeke | 91 | 1577 |
| 969441 | N/A | N/A | 8744 | 8759 | ATTCTATTAGAGGGCT | kk-d9-ekeke | 25 | 1326 |
| 969451 | N/A | N/A | 5414 | 5429 | TTATTCTCATGGTACA | kk-d9-ekeke | 51 | 1927 |
| 969461 | N/A | N/A | 8239 | 8254 | GTGAGTATTGTTTTTG | kk-d9-ekeke | 93 | 1928 |
| 969471 | 1032 | 1047 | 13123 | 13138 | AAGATTGGCTCTGGCT | kk-d9-kdkdk | 65 | 1411 |
| 969481 | N/A | N/A | 7921 | 7936 | GAATTATGGAATTGCA | kk-d9-kdkdk | 82 | 1183 |
| 969501 | N/A | N/A | 5854 | 5869 | TTTGTAAGTGCAACCA | kk-d9-kdkdk | 99 | 1095 |
| 969511 | N/A | N/A | 8366 | 8381 | CTTTATACCAGTGTCT | kk-d9-kdkdk | 92 | 1890 |
| 971921 | N/A | N/A | 5449 | 5464 | GTTATATTTGATCCTC | kk-d9-kekek | 80 | 1900 |
| 971931 | N/A | N/A | 8332 | 8347 | CACATCATTGGGTTAT | kk-d9-kekek | 74 | 356 |
| 971941 | 1035 | 1050 | 13126 | 13141 | CTGAAGATTGGCTCTG | kk-d9-kekek | 45 | 1939 |
| 971951 | N/A | N/A | 6704 | 6719 | GTGTATTTCTTGATGT | kk-d9-kekek | 95 | 1940 |
| 971961 | N/A | N/A | 8831 | 8846 | AAGCTTTAAACTCAGG | kk-d9-kekek | 48 | 1327 |
| 971971 | N/A | N/A | 5450 | 5465 | TGTTATATTTGATCCT | kk-d9-kekek | 81 | 1887 |
| 971981 | N/A | N/A | 8333 | 8348 | ACACATCATTGGGTTA | kk-d9-kekek | 50 | 426 |
| 971991 | N/A | N/A | 8830 | 8845 | AGCTTTAAACTCAGGT | kkk-d8-kdkdk | 74 | 1920 |
| 972001 | N/A | N/A | 5854 | 5869 | TTTGTAAGTGCAACCA | kkk-d8-kdkdk | 71 | 1095 |
| 972011 | N/A | N/A | 8366 | 8381 | CTTTATACCAGTGTCT | kkk-d8-kdkdk | 87 | 1890 |
| 972021 | N/A | N/A | 5411 | 5426 | TTCTCATGGTACAGGA | kkk-d8-kekek | 54 | 607 |
| 972031 | N/A | N/A | 8236 | 8251 | AGTATTGTTTTTGTGG | kkk-d8-kekek | 55 | 1922 |
| 972041 | N/A | N/A | 8308 | 8323 | TGGTTCAAAAGCAGCA | kkk-d8-kekek | 57 | 1048 |
| 972051 | N/A | N/A | 5860 | 5875 | GGCAGTTTTGTAAGTG | kkk-d8-kekek | 32 | 123 |
| 972061 | N/A | N/A | 8745 | 8760 | AATTCTATTAGAGGGC | kkk-d8-kekek | 41 | 1396 |
| 972071 | 2736 | 2751 | 14827 | 14842 | GCTAATTTTCTGACTG | kkk-d8-kekek | 88 | 1283 |
| 972081 | N/A | N/A | 8237 | 8252 | GAGTATTGTTTTTGTG | kkk-d8-kekek | 56 | 1899 |
| 972091 | 1034 | 1049 | 13125 | 13140 | TGAAGATTGGCTCTGG | kkk-d9-keke | 54 | 1931 |
| 972101 | N/A | N/A | 6819 | 6834 | AACGCAATGCTGACTT | kkk-d9-keke | 83 | 1919 |
| 972121 | N/A | N/A | 5854 | 5869 | TTTGTAAGTGCAACCA | kkk-d9-keke | 49 | 1095 |
| 972131 | N/A | N/A | 8366 | 8381 | CTTTATACCAGTGTCT | kkk-d9-keke | 94 | 1890 |
| 972141 | N/A | N/A | 5448 | 5463 | TTATATTTGATCCTCA | kkk-d9-kkke | 96 | 1909 |
| 972151 | N/A | N/A | 8320 | 8335 | TTATGAAATTATTGGT | kkk-d9-kkke | 85 | 1910 |
| 972161 | 970 | 985 | 13061 | 13076 | AAGTATTGCCAGCTAA | kkk-d9-kkke | 49 | 1911 |
| 972171 | N/A | N/A | 6702 | 6717 | GTATTTCTTGATGTGG | kkk-d9-kkke | 98 | 413 |
| 972191 | N/A | N/A | 5859 | 5874 | GCAGTTTTGTAAGTGC | kkk-d9-kkke | 76 | 1647 |
| 972201 | N/A | N/A | 8745 | 8760 | AATTCTATTAGAGGGC | kkk-d9-kkke | 70 | 1396 |

TABLE 37

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 905095 | N/A | N/A | 6702 | 6717 | GTATTTCTTGATGTGG | kkk-d10-kkk | 100 | 413 |
| 905139 | N/A | N/A | 6818 | 6833 | ACGCAATGCTGACTTG | kkk-d10-kkk | 94 | 1905 |
| 905491 | N/A | N/A | 8237 | 8252 | GAGTATTGTTTTTGTG | kkk-d10-kkk | 94 | 1899 |
| 969062 | N/A | N/A | 5856 | 5871 | GTTTTGTAAGTGCAAC | k-d10-kekek | 92 | 1230 |
| 969072 | N/A | N/A | 8742 | 8757 | TCTATTAGAGGGCTAG | k-d10-kekek | 42 | 150 |
| 969082 | 2736 | 2751 | 14827 | 14842 | GCTAATTTTCTGACTG | k-d10-kekek | 98 | 1283 |
| 969092 | N/A | N/A | 8164 | 8179 | CATTCAGAATTTCCAC | k-d10-kekek | 67 | 1730 |
| 969102 | N/A | N/A | 8828 | 8843 | CTTTAAACTCAGGTGA | k-d9-kekeke | 70 | 151 |
| 969112 | N/A | N/A | 6816 | 6831 | GCAATGCTGACTTGGC | k-d9-kekeke | 45 | 1903 |
| 969132 | N/A | N/A | 5450 | 5465 | TGTTATATTTGATCCT | k-d9-kekeke | 51 | 1887 |
| 969142 | N/A | N/A | 8333 | 8348 | ACACATCATTGGGTTA | k-d9-kekeke | 36 | 426 |
| 969152 | 1033 | 1048 | 13124 | 13139 | GAAGATTGGCTCTGGC | kek-d9-eekk | 87 | 1480 |
| 969162 | N/A | N/A | 6702 | 6717 | GTATTTCTTGATGTGG | kek-d9-eekk | 99 | 413 |
| 969172 | N/A | N/A | 8829 | 8844 | GCTTTAAACTCAGGTG | kek-d9-eekk | 93 | 81 |
| 969182 | N/A | N/A | 5853 | 5868 | TTGTAAGTGCAACCAA | kk-d10-keke | 81 | 1025 |
| 969192 | N/A | N/A | 8365 | 8380 | TTTATACCAGTGTCTT | kk-d10-keke | 84 | 1914 |
| 969202 | 2251 | 2266 | 14342 | 14357 | CGTCAATATATTCTTT | kk-d10-keke | 87 | 1925 |
| 969212 | N/A | N/A | 7922 | 7937 | GGAATTATGGAATTGC | kk-d10-keke | 40 | 1249 |
| 969222 | 969 | 984 | 13060 | 13075 | AGTATTGCCAGCTAAG | kk-d8-eeeekk | 59 | 1479 |
| 969232 | N/A | N/A | 6817 | 6832 | CGCAATGCTGACTTGG | kk-d8-eeeekk | 68 | 1924 |
| 969252 | N/A | N/A | 6546 | 6561 | CAGATGGGTACTTCTG | kk-d8-kekekk | 10 | 341 |
| 969262 | N/A | N/A | 8827 | 8842 | TTTAAACTCAGGTGAC | kk-d8-kekekk | 16 | 1675 |
| 969272 | N/A | N/A | 5857 | 5872 | AGTTTTGTAAGTGCAA | kk-d8-kekekk | 84 | 1917 |
| 969282 | N/A | N/A | 8743 | 8758 | TTCTATTAGAGGGCTA | kk-d8-kekekk | 26 | 80 |
| 969292 | N/A | N/A | 5412 | 5427 | ATTCTCATGGTACAGG | kk-d8-kekekk | 34 | 677 |
| 969302 | N/A | N/A | 8321 | 8336 | GTTATGAAATTATTGG | kk-d8-kekekk | 86 | 76 |
| 969312 | N/A | N/A | 5411 | 5426 | TTCTCATGGTACAGGA | kk-d9-eeekk | 86 | 607 |
| 969322 | N/A | N/A | 8236 | 8251 | AGTATTGTTTTTGTGG | kk-d9-eeekk | 90 | 1922 |
| 969332 | N/A | N/A | 8306 | 8321 | GTTCAAAAGCAGCATT | kk-d9-eeekk | 86 | 13 |
| 969342 | N/A | N/A | 6548 | 6563 | ATCAGATGGGTACTTC | kk-d9-eeekk | 67 | 481 |
| 969362 | N/A | N/A | 5855 | 5870 | TTTTGTAAGTGCAACC | kk-d9-eeekk | 99 | 1164 |
| 969372 | N/A | N/A | 8367 | 8382 | ACTTTATACCAGTGTC | kk-d9-eeekk | 91 | 1941 |
| 969382 | 2738 | 2753 | 14829 | 14844 | ATGCTAATTTTCTGAC | kk-d9-eeekk | 88 | 1912 |
| 969392 | N/A | N/A | 8239 | 8254 | GTGAGTATTGTTTTTG | kk-d9-eeekk | 92 | 1928 |
| 969402 | N/A | N/A | 5411 | 5426 | TTCTCATGGTACAGGA | kk-d9-ekeke | 79 | 607 |
| 969412 | N/A | N/A | 8236 | 8251 | AGTATTGTTTTTGTGG | kk-d9-ekeke | 89 | 1922 |
| 969422 | N/A | N/A | 8306 | 8321 | GTTCAAAAGCAGCATT | kk-d9-ekeke | 82 | 13 |

TABLE 37-continued

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 969432 | N/A | N/A | 6548 | 6563 | ATCAGATGGGTACTTC | kk-d9-ekeke | 73 | 481 |
| 969452 | N/A | N/A | 5451 | 5466 | GTGTTATATTTGATCC | kk-d9-ekeke | 96 | 1934 |
| 969462 | N/A | N/A | 8323 | 8338 | GGGTTATGAAATTATT | kk-d9-ekeke | 88 | 1935 |
| 969472 | 2735 | 2750 | 14826 | 14841 | CTAATTTTCTGACTGT | kk-d9-kdkdk | 84 | 1901 |
| 969482 | N/A | N/A | 8163 | 8178 | ATTCAGAATTTCCACT | kk-d9-kdkdk | 79 | 1902 |
| 969492 | N/A | N/A | 8830 | 8845 | AGCTTTAAACTCAGGT | kk-d9-kdkdk | 86 | 1920 |
| 969502 | N/A | N/A | 5858 | 5873 | CAGTTTTGTAAGTGCA | kk-d9-kdkdk | 95 | 1577 |
| 969512 | N/A | N/A | 8744 | 8759 | ATTCTATTAGAGGGCT | kk-d9-kdkdk | 74 | 1326 |
| 971922 | N/A | N/A | 5853 | 5868 | TTGTAAGTGCAACCAA | kk-d9-kekek | 69 | 1025 |
| 971932 | N/A | N/A | 8365 | 8380 | TTTATACCAGTGTCTT | kk-d9-kekek | 89 | 1914 |
| 971942 | 2253 | 2268 | 14344 | 14359 | TCCGTCAATATATTCT | kk-d9-kekek | 94 | 1897 |
| 971952 | N/A | N/A | 6820 | 6835 | GAACGCAATGCTGACT | kk-d9-kekek | 78 | 1888 |
| 971972 | N/A | N/A | 5854 | 5869 | TTTGTAAGTGCAACCA | kk-d9-kekek | 98 | 1095 |
| 971982 | N/A | N/A | 8366 | 8381 | CTTTATACCAGTGTCT | kk-d9-kekek | 86 | 1890 |
| 971992 | N/A | N/A | 8306 | 8321 | GTTCAAAAGCAGCATT | kkk-d8-kdkdk | 23 | 13 |
| 972002 | N/A | N/A | 5858 | 5873 | CAGTTTTGTAAGTGCA | kkk-d8-kdkdk | 93 | 1577 |
| 972012 | N/A | N/A | 8743 | 8758 | TTCTATTAGAGGGCTA | kkk-d8-kdkdk | 78 | 80 |
| 972022 | N/A | N/A | 5448 | 5463 | TTATATTTGATCCTCA | kkk-d8-kekek | 92 | 1909 |
| 972032 | N/A | N/A | 8320 | 8335 | TTATGAAATTATTGGT | kkk-d8-kekek | 86 | 1910 |
| 972042 | 972 | 987 | 13063 | 13078 | GTAAGTATTGCCAGCT | kkk-d8-kekek | 73 | 1933 |
| 972052 | N/A | N/A | 6550 | 6565 | ATATCAGATGGGTACT | kkk-d8-kekek | 28 | 620 |
| 972062 | N/A | N/A | 8746 | 8761 | TAATTCTATTAGAGGG | kkk-d8-kekek | 41 | 220 |
| 972072 | N/A | N/A | 5412 | 5427 | ATTCTCATGGTACAGG | kkk-d8-kekek | 70 | 677 |
| 972082 | N/A | N/A | 8321 | 8336 | GTTATGAAATTATTGG | kkk-d8-kekek | 79 | 76 |
| 972092 | 2252 | 2267 | 14343 | 14358 | CCGTCAATATATTCTT | kkk-d9-keke | 97 | 1936 |
| 972102 | N/A | N/A | 7923 | 7938 | GGGAATTATGGAATTG | kkk-d9-keke | 63 | 1596 |
| 972122 | N/A | N/A | 5858 | 5873 | CAGTTTTGTAAGTGCA | kkk-d9-keke | 92 | 1577 |
| 972132 | N/A | N/A | 8743 | 8758 | TTCTATTAGAGGGCTA | kkk-d9-keke | 91 | 80 |
| 972142 | N/A | N/A | 5449 | 5464 | GTTATATTTGATCCTC | kkk-d9-kkke | 98 | 1900 |
| 972152 | N/A | N/A | 8332 | 8347 | CACATCATTGGGTTAT | kkk-d9-kkke | 78 | 356 |
| 972162 | 1033 | 1048 | 13124 | 13139 | GAAGATTGGCTCTGGC | kkk-d9-kkke | 70 | 1480 |
| 972172 | N/A | N/A | 6818 | 6833 | ACGCAATGCTGACTTG | kkk-d9-kkke | 88 | 1905 |
| 972182 | N/A | N/A | 8831 | 8846 | AAGCTTTAAACTCAGG | kkk-d9-kkke | 72 | 1327 |
| 972192 | N/A | N/A | 6549 | 6564 | TATCAGATGGGTACTT | kkk-d9-kkke | 69 | 550 |

TABLE 38

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 905095 | N/A | N/A | 6702 | 6717 | GTATTTCTTGATGTGG | kkk-d10-kkk | 99 | 413 |
| 905469 | N/A | N/A | 8164 | 8179 | CATTCAGAATTTCCAC | kkk-d10-kkk | 94 | 1730 |
| 905491 | N/A | N/A | 8237 | 8252 | GAGTATTGTTTTTGTG | kkk-d10-kkk | 93 | 1899 |
| 969063 | N/A | N/A | 6546 | 6561 | CAGATGGGTACTTCTG | k-d10-kekek | 44 | 341 |
| 969073 | N/A | N/A | 8827 | 8842 | TTTAAACTCAGGTGAC | k-d10-kekek | 45 | 1675 |
| 969083 | N/A | N/A | 5412 | 5427 | ATTCTCATGGTACAGG | k-d10-kekek | 83 | 677 |
| 969093 | N/A | N/A | 8237 | 8252 | GAGTATTGTTTTTGTG | k-d10-kekek | 90 | 1899 |
| 969103 | 968 | 983 | 13059 | 13074 | GTATTGCCAGCTAAGG | k-d9-kekeke | 70 | 1410 |
| 969113 | N/A | N/A | 7920 | 7935 | AATTATGGAATTGCAG | k-d9-kekeke | 55 | 1923 |
| 969123 | N/A | N/A | 8830 | 8845 | AGCTTTAAACTCAGGT | k-d9-kekeke | 52 | 1920 |
| 969133 | N/A | N/A | 5854 | 5869 | TTTGTAAGTGCAACCA | k-d9-kekeke | 95 | 1095 |
| 969143 | N/A | N/A | 8366 | 8381 | CTTTATACCAGTGTCT | k-d9-kekeke | 92 | 1890 |
| 969153 | 2251 | 2266 | 14342 | 14357 | CGTCAATATATTCTTT | kek-d9-eekk | 93 | 1925 |
| 969163 | N/A | N/A | 6818 | 6833 | ACGCAATGCTGACTTG | kek-d9-eekk | 91 | 1905 |
| 969183 | N/A | N/A | 5857 | 5872 | AGTTTTGTAAGTGCAA | kk-d10-keke | 92 | 1917 |
| 969193 | N/A | N/A | 8742 | 8757 | TCTATTAGAGGGCTAG | kk-d10-keke | 72 | 150 |
| 969203 | 2340 | 2355 | 14431 | 14446 | GTTCTAACTCTTGGGC | kk-d10-keke | 84 | 243 |
| 969213 | N/A | N/A | 8164 | 8179 | CATTCAGAATTTCCAC | kk-d10-keke | 84 | 1730 |
| 969223 | 1032 | 1047 | 13123 | 13138 | AAGATTGGCTCTGGCT | kk-d8-eeeekk | 55 | 1411 |
| 969233 | N/A | N/A | 7921 | 7936 | GAATTATGGAATTGCA | kk-d8-eeeekk | 95 | 1183 |
| 969253 | N/A | N/A | 6700 | 6715 | ATTTCTTGATGTGGTG | kk-d8-kekekk | 69 | 343 |
| 969273 | N/A | N/A | 6547 | 6562 | TCAGATGGGTACTTCT | kk-d8-kekekk | 62 | 411 |
| 969293 | N/A | N/A | 5450 | 5465 | TGTTATATTTGATCCT | kk-d8-kekekk | 46 | 1887 |
| 969303 | N/A | N/A | 8333 | 8348 | ACACATCATTGGGTTA | kk-d8-kekekk | 20 | 426 |
| 969313 | N/A | N/A | 5448 | 5463 | TTATATTTGATCCTCA | kk-d9-eeekk | 96 | 1909 |
| 969323 | N/A | N/A | 8320 | 8335 | TTATGAAATTATTGGT | kk-d9-eeekk | 39 | 1910 |
| 969333 | 970 | 985 | 13061 | 13076 | AAGTATTGCCAGCTAA | kk-d9-eeekk | 63 | 1911 |
| 969343 | N/A | N/A | 6702 | 6717 | GTATTTCTTGATGTGG | kk-d9-eeekk | 97 | 413 |
| 969363 | N/A | N/A | 5859 | 5874 | GCAGTTTTGTAAGTGC | kk-d9-eeekk | 79 | 1647 |
| 969373 | N/A | N/A | 8745 | 8760 | AATTCTATTAGAGGGC | kk-d9-eeekk | 73 | 1396 |
| 969383 | N/A | N/A | 5414 | 5429 | TTATTCTCATGGTACA | kk-d9-eeekk | 48 | 1927 |
| 969393 | N/A | N/A | 8323 | 8338 | GGGTTATGAAATTATT | kk-d9-eeekk | 77 | 1935 |
| 969403 | N/A | N/A | 5448 | 5463 | TTATATTTGATCCTCA | kk-d9-ekeke | 96 | 1909 |
| 969413 | N/A | N/A | 8320 | 8335 | TTATGAAATTATTGGT | kk-d9-ekeke | 74 | 1910 |
| 969423 | 970 | 985 | 13061 | 13076 | AAGTATTGCCAGCTAA | kk-d9-ekeke | 49 | 1911 |
| 969433 | N/A | N/A | 6702 | 6717 | GTATTTCTTGATGTGG | kk-d9-ekeke | 96 | 413 |
| 969453 | N/A | N/A | 5452 | 5467 | CGTGTTATATTTGATC | kk-d9-ekeke | 76 | 1906 |

TABLE 38-continued

Inhibition of APOL1 mRNA by deoxy, MOE, and cEt gapmers targeting SEQ ID NO: 1 and 2

| Compound Number | SEQ ID: 1 Start Site | SEQ ID: 1 Stop Site | SEQ ID: 2 Start Site | SEQ ID: 2 Stop Site | Sequence | Chemistry | % inhibition | SEQ ID NO |
|---|---|---|---|---|---|---|---|---|
| 969463 | N/A | N/A | 8335 | 8350 | CAACACATCATTGGGT | kk-d9-ekeke | 80 | 1907 |
| 969473 | N/A | N/A | 5411 | 5426 | TTCTCATGGTACAGGA | kk-d9-kdkdk | 89 | 607 |
| 969483 | N/A | N/A | 8236 | 8251 | AGTATTGTTTTTGTGG | kk-d9-kdkdk | 72 | 1922 |
| 969493 | N/A | N/A | 8306 | 8321 | GTTCAAAAGCAGCATT | kk-d9-kdkdk | 73 | 13 |
| 969503 | N/A | N/A | 6548 | 6563 | ATCAGATGGGTACTTC | kk-d9-kdkdk | 78 | 481 |
| 971923 | N/A | N/A | 5857 | 5872 | AGTTTTGTAAGTGCAA | kk-d9-kekek | 81 | 1917 |
| 971933 | N/A | N/A | 8742 | 8757 | TCTATTAGAGGGCTAG | kk-d9-kekek | 52 | 150 |
| 971943 | 2342 | 2357 | 14433 | 14448 | CTGTTCTAACTCTTGG | kk-d9-kekek | 88 | 383 |
| 971953 | N/A | N/A | 7924 | 7939 | TGGGAATTATGGAATT | kk-d9-kekek | 87 | 1929 |
| 971963 | N/A | N/A | 8830 | 8845 | AGCTTTAAACTCAGGT | kk-d9-kekek | 87 | 1920 |
| 971973 | N/A | N/A | 5858 | 5873 | CAGTTTTGTAAGTGCA | kk-d9-kekek | 91 | 1577 |
| 971983 | N/A | N/A | 8744 | 8759 | ATTCTATTAGAGGGCT | kk-d9-kekek | 46 | 1326 |
| 971993 | 970 | 985 | 13061 | 13076 | AAGTATTGCCAGCTAA | kkk-d8-kdkdk | 54 | 1911 |
| 972003 | N/A | N/A | 6548 | 6563 | ATCAGATGGGTACTTC | kkk-d8-kdkdk | 79 | 481 |
| 972013 | N/A | N/A | 8744 | 8759 | ATTCTATTAGAGGGCT | kkk-d8-kdkdk | 78 | 1326 |
| 972023 | N/A | N/A | 5449 | 5464 | GTTATATTTGATCCTC | kkk-d8-kekek | 66 | 1900 |
| 972033 | N/A | N/A | 8332 | 8347 | CACATCATTGGGTTAT | kkk-d8-kekek | 58 | 356 |
| 972043 | 1035 | 1050 | 13126 | 13141 | CTGAAGATTGGCTCTG | kkk-d8-kekek | 36 | 1939 |
| 972053 | N/A | N/A | 6704 | 6719 | GTGTATTTCTTGATGT | kkk-d8-kekek | 84 | 1940 |
| 972063 | N/A | N/A | 8831 | 8846 | AAGCTTTAAACTCAGG | kkk-d8-kekek | 16 | 1327 |
| 972073 | N/A | N/A | 5450 | 5465 | TGTTATATTTGATCCT | kkk-d8-kekek | 59 | 1887 |
| 972083 | N/A | N/A | 8333 | 8348 | ACACATCATTGGGTTA | kkk-d8-kekek | 32 | 426 |
| 972093 | 2341 | 2356 | 14432 | 14447 | TGTTCTAACTCTTGGG | kkk-d9-keke | 88 | 313 |
| 972103 | N/A | N/A | 8165 | 8180 | GCATTCAGAATTTCCA | kkk-d9-keke | 84 | 1937 |
| 972113 | N/A | N/A | 8306 | 8321 | GTTCAAAAGCAGCATT | kkk-d9-keke | 85 | 13 |
| 972123 | N/A | N/A | 6548 | 6563 | ATCAGATGGGTACTTC | kkk-d9-keke | 85 | 481 |
| 972133 | N/A | N/A | 8829 | 8844 | GCTTTAAACTCAGGTG | kkk-d9-keke | 82 | 81 |
| 972143 | N/A | N/A | 5853 | 5868 | TTGTAAGTGCAACCAA | kkk-d9-kkke | 78 | 1025 |
| 972153 | N/A | N/A | 8365 | 8380 | TTTATACCAGTGTCTT | kkk-d9-kkke | 80 | 1914 |
| 972163 | 2251 | 2266 | 14342 | 14357 | CGTCAATATATTCTTT | kkk-d9-kkke | 95 | 1925 |
| 972173 | N/A | N/A | 7922 | 7937 | GGAATTATGGAATTGC | kkk-d9-kkke | 65 | 1249 |
| 972183 | N/A | N/A | 8307 | 8322 | GGTTCAAAAGCAGCAT | kkk-d9-kkke | 74 | 978 |
| 972193 | N/A | N/A | 6703 | 6718 | TGTATTTCTTGATGTG | kkk-d9-kkke | 87 | 1926 |

Example 2: Dose-Dependent Antisense Inhibition of Human APOL1 in A431 Cells

Gapmers from Example 1 exhibiting significant in vitro inhibition of APOL1 mRNA were selected and tested at various doses in A431 cells. The antisense oligonucleotides were tested in a series of experiments that had similar culture conditions. The results for each experiment are presented in separate tables shown below.

Cells were plated at a density of 10,000 cells per well and transfected free uptake with various concentrations of 3-10-3 cEt gapmers, as specified in the Tables below. After a treatment period of approximately 16 hours, RNA was isolated from the cells and APOL1 mRNA levels were measured by quantitative real-time PCR. Human primer probe set RTS35962 was used to measure mRNA levels. APOL1 mRNA levels were adjusted according to total RNA content, as measured by RIBOGREEN®. Results are presented as percent inhibition of APOL1, relative to untreated control cells.

The half maximal inhibitory concentration ($IC_{50}$) of each oligonucleotide is also presented. APOL1 mRNA levels were significantly reduced in a dose-dependent manner in antisense oligonucleotide treated cells.

TABLE 39

Multi-dose assay with 3-10-3 cEt gapmers

| Compound Number | % inhibition 62.5 nM | 250 nM | 1,000 nM | 4,000 nM | $IC_{50}$ (μm) |
|---|---|---|---|---|---|
| 793406 | 19 | 60 | 83 | 93 | 0.2 |
| 903830 | 54 | 85 | 95 | 97 | <0.1 |
| 903862 | 49 | 69 | 88 | 93 | <0.1 |
| 903894 | 41 | 67 | 87 | 94 | 0.1 |
| 904119 | 49 | 70 | 82 | 85 | <0.1 |
| 904758 | 36 | 63 | 83 | 92 | 0.1 |
| 904760 | 75 | 93 | 99 | 99 | <0.1 |
| 904823 | 50 | 74 | 85 | 91 | <0.1 |
| 905142 | 32 | 74 | 90 | 95 | 0.1 |
| 905143 | 52 | 76 | 92 | 97 | <0.1 |
| 905270 | 44 | 78 | 90 | 94 | <0.1 |
| 905271 | 44 | 66 | 86 | 91 | 0.1 |
| 905398 | 59 | 82 | 94 | 96 | <0.1 |
| 905462 | 42 | 73 | 90 | 95 | 0.1 |
| 905463 | 42 | 67 | 85 | 94 | 0.1 |
| 905494 | 51 | 73 | 84 | 91 | <0.1 |
| 905654 | 57 | 74 | 92 | 94 | <0.1 |
| 905655 | 61 | 80 | 90 | 94 | <0.1 |

TABLE 40

Multi-dose assay with 3-10-3 cEt gapmers

| Compound Number | % inhibition 62.5 nM | 250 nM | 1,000 nM | 4,000 nM | $IC_{50}$ (μm) |
|---|---|---|---|---|---|
| 793406 | 15 | 58 | 82 | 88 | 0.3 |
| 903544 | 46 | 72 | 87 | 92 | <0.1 |
| 904026 | 62 | 88 | 96 | 98 | <0.1 |
| 904058 | 62 | 83 | 94 | 98 | <0.1 |
| 904121 | 50 | 78 | 86 | 90 | <0.1 |
| 904216 | 32 | 64 | 78 | 82 | 0.2 |
| 904761 | 19 | 46 | 78 | 92 | 0.3 |
| 905114 | 36 | 73 | 88 | 91 | 0.1 |
| 905144 | 35 | 50 | 75 | 82 | 0.2 |
| 905146 | 42 | 71 | 87 | 97 | 0.1 |
| 905401 | 52 | 79 | 89 | 94 | <0.1 |

TABLE 40-continued

Multi-dose assay with 3-10-3 cEt gapmers

| Compound Number | % inhibition 62.5 nM | 250 nM | 1,000 nM | 4,000 nM | $IC_{50}$ (μm) |
|---|---|---|---|---|---|
| 905402 | 57 | 82 | 94 | 96 | <0.1 |
| 905496 | 29 | 68 | 90 | 93 | 0.1 |
| 905497 | 78 | 91 | 95 | 96 | <0.1 |
| 905498 | 60 | 84 | 94 | 94 | <0.1 |
| 905657 | 47 | 67 | 84 | 93 | 0.1 |
| 905688 | 25 | 71 | 86 | 92 | 0.2 |
| 905689 | 68 | 87 | 93 | 94 | <0.1 |
| 905690 | 57 | 78 | 88 | 92 | <0.1 |

TABLE 41

Multi-dose assay with 3-10-3 cEt gapmers

| Compound Number | % inhibition 62.5 nM | 250 nM | 1,000 nM | 4,000 nM | $IC_{50}$ (μm) |
|---|---|---|---|---|---|
| 793406 | 10 | 57 | 83 | 92 | 0.3 |
| 903644 | 35 | 72 | 85 | 92 | 0.1 |
| 903996 | 50 | 79 | 88 | 97 | <0.1 |
| 904027 | 28 | 61 | 81 | 88 | 0.2 |
| 904443 | 54 | 84 | 96 | 98 | <0.1 |
| 904444 | 74 | 91 | 96 | 98 | <0.1 |
| 904763 | 70 | 91 | 97 | 98 | <0.1 |
| 904764 | 47 | 84 | 95 | 99 | <0.1 |
| 904828 | 79 | 92 | 97 | 97 | <0.1 |
| 905020 | 46 | 73 | 90 | 95 | <0.1 |
| 905147 | 37 | 71 | 87 | 93 | 0.1 |
| 905148 | 22 | 60 | 83 | 94 | 0.2 |
| 905276 | 29 | 63 | 83 | 92 | 0.2 |
| 905370 | 8 | 46 | 74 | 84 | 0.4 |
| 905371 | 38 | 67 | 86 | 94 | 0.1 |
| 905372 | 59 | 82 | 92 | 95 | <0.1 |
| 905468 | 40 | 67 | 87 | 94 | 0.1 |
| 905499 | 72 | 87 | 92 | 93 | <0.1 |
| 905691 | 53 | 77 | 85 | 92 | <0.1 |

TABLE 42

Multi-dose assay with 3-10-3 cEt gapmers

| Compound Number | % inhibition 62.5 nM | 250 nM | 1,000 nM | 4,000 nM | $IC_{50}$ (μm) |
|---|---|---|---|---|---|
| 793406 | 12 | 56 | 81 | 92 | 0.3 |
| 903613 | 47 | 68 | 81 | 88 | <0.1 |
| 903805 | 28 | 58 | 75 | 82 | 0.2 |
| 903998 | 56 | 86 | 93 | 96 | <0.1 |
| 904029 | 34 | 58 | 79 | 88 | 0.2 |
| 904030 | 45 | 78 | 92 | 96 | <0.1 |
| 904253 | 46 | 74 | 85 | 92 | <0.1 |
| 904766 | 96 | 98 | 99 | 99 | <0.1 |
| 904829 | 41 | 75 | 84 | 89 | 0.1 |
| 905021 | 38 | 73 | 90 | 95 | 0.1 |
| 905022 | 47 | 76 | 92 | 97 | <0.1 |
| 905149 | 38 | 65 | 85 | 93 | 0.1 |
| 905277 | 24 | 50 | 80 | 92 | 0.3 |
| 905373 | 74 | 93 | 98 | 99 | <0.1 |
| 905404 | 27 | 58 | 77 | 88 | 0.2 |
| 905501 | 29 | 67 | 86 | 92 | 0.1 |
| 905565 | 20 | 49 | 73 | 89 | 0.3 |
| 905757 | 18 | 56 | 78 | 86 | 0.3 |
| 905758 | 26 | 65 | 85 | 92 | 0.2 |

TABLE 43

Multi-dose assay with 3-10-3 cEt gapmers

| Compound Number | % inhibition 62.5 nM | 250 nM | 1,000 nM | 4,000 nM | $IC_{50}$ (μm) |
|---|---|---|---|---|---|
| 793406 | 36 | 64 | 85 | 94 | 0.1 |
| 903807 | 46 | 78 | 90 | 95 | <0.1 |
| 903872 | 38 | 72 | 88 | 94 | 0.1 |
| 903999 | 32 | 66 | 83 | 91 | 0.1 |
| 904000 | 90 | 98 | 99 | 100 | <0.1 |
| 904001 | 95 | 99 | 100 | 100 | <0.1 |
| 904063 | 24 | 65 | 81 | 89 | 0.2 |
| 904223 | 47 | 75 | 84 | 89 | <0.1 |
| 904224 | 60 | 86 | 91 | 94 | <0.1 |
| 904254 | 35 | 62 | 82 | 86 | 0.1 |
| 904862 | 9 | 49 | 64 | 89 | 0.4 |
| 905086 | 28 | 55 | 80 | 89 | 0.2 |
| 905120 | 70 | 90 | 97 | 98 | <0.1 |
| 905374 | 48 | 70 | 80 | 88 | <0.1 |
| 905407 | 38 | 67 | 86 | 93 | 0.1 |
| 905408 | 23 | 61 | 83 | 92 | 0.2 |
| 905471 | 59 | 82 | 86 | 86 | <0.1 |
| 905600 | 52 | 81 | 94 | 98 | <0.1 |
| 905631 | 32 | 52 | 71 | 83 | 0.2 |

TABLE 44

Multi-dose assay with 3-10-3 cEt gapmers

| Compound Number | % inhibition 62.5 nM | 250 nM | 1,000 nM | 4,000 nM | $IC_{50}$ (μm) |
|---|---|---|---|---|---|
| 793406 | 17 | 59 | 83 | 91 | 0.2 |
| 903874 | 44 | 70 | 87 | 95 | 0.1 |
| 903939 | 64 | 87 | 94 | 97 | <0.1 |
| 904002 | 53 | 82 | 92 | 97 | <0.1 |
| 904003 | 47 | 76 | 90 | 96 | <0.1 |
| 904034 | 41 | 70 | 88 | 94 | 0.1 |
| 904226 | 77 | 95 | 98 | 99 | <0.1 |
| 904675 | 80 | 95 | 99 | 99 | <0.1 |
| 905121 | 64 | 87 | 93 | 95 | <0.1 |
| 905123 | 62 | 85 | 92 | 95 | <0.1 |
| 905473 | 47 | 61 | 65 | 61 | <0.1 |
| 905475 | 43 | 71 | 90 | 96 | 0.1 |
| 905505 | 58 | 87 | 95 | 97 | <0.1 |
| 905601 | 49 | 79 | 92 | 96 | <0.1 |
| 905633 | 51 | 81 | 92 | 94 | <0.1 |
| 905634 | 54 | 82 | 91 | 96 | <0.1 |
| 905665 | 30 | 76 | 91 | 94 | 0.1 |
| 905697 | 51 | 78 | 92 | 96 | <0.1 |
| 905698 | 85 | 97 | 99 | 99 | <0.1 |

TABLE 45

Multi-dose assay with 3-10-3 cEt gapmers

| Compound Number | % inhibition 62.5 nM | 250 nM | 1,000 nM | 4,000 nM | $IC_{50}$ (μm) |
|---|---|---|---|---|---|
| 793406 | 73 | 85 | 92 | 95 | <0.1 |
| 903940 | 64 | 83 | 92 | 96 | <0.1 |
| 904101 | 74 | 85 | 92 | 94 | <0.1 |
| 904102 | 75 | 88 | 94 | 96 | <0.1 |
| 904420 | 22 | 40 | 58 | 62 | 0.8 |
| 904452 | 78 | 88 | 93 | 96 | <0.1 |
| 904484 | 76 | 87 | 92 | 96 | <0.1 |
| 904515 | 43 | 72 | 85 | 91 | 0.1 |
| 904517 | 78 | 89 | 92 | 93 | <0.1 |
| 905028 | 63 | 82 | 90 | 93 | <0.1 |

TABLE 45-continued

Multi-dose assay with 3-10-3 cEt gapmers

| Compound Number | % inhibition 62.5 nM | 250 nM | 1,000 nM | 4,000 nM | $IC_{50}$ (μm) |
|---|---|---|---|---|---|
| 905029 | 85 | 88 | 93 | 96 | <0.1 |
| 905093 | 58 | 82 | 91 | 95 | <0.1 |
| 905094 | 95 | 99 | 99 | 99 | <0.1 |
| 905476 | 54 | 85 | 95 | 97 | <0.1 |
| 905477 | 78 | 93 | 96 | 98 | <0.1 |
| 905510 | 65 | 84 | 90 | 94 | <0.1 |
| 905636 | 17 | 45 | 69 | 78 | 0.4 |
| 905667 | 41 | 65 | 82 | 89 | 0.1 |
| 905700 | 75 | 88 | 92 | 95 | <0.1 |

TABLE 46

Multi-dose assay with 3-10-3 cEt gapmers

| Compound Number | % inhibition 62.5 nM | 250 nM | 1,000 nM | 4,000 nM | $IC_{50}$ (μm) |
|---|---|---|---|---|---|
| 793406 | 68 | 81 | 90 | 95 | <0.1 |
| 903976 | 80 | 90 | 95 | 97 | <0.1 |
| 904103 | 61 | 79 | 87 | 91 | <0.1 |
| 904104 | 85 | 92 | 95 | 97 | <0.1 |
| 904264 | 72 | 81 | 85 | 85 | <0.1 |
| 904424 | 41 | 75 | 91 | 95 | 0.1 |
| 904680 | 74 | 87 | 94 | 96 | <0.1 |
| 904743 | 46 | 68 | 86 | 93 | 0.1 |
| 904744 | 82 | 92 | 97 | 98 | <0.1 |
| 904840 | 66 | 81 | 89 | 93 | <0.1 |
| 904871 | 64 | 75 | 90 | 95 | <0.1 |
| 904872 | 68 | 82 | 93 | 96 | <0.1 |
| 904968 | 53 | 78 | 89 | 94 | <0.1 |
| 905031 | 38 | 66 | 83 | 89 | 0.1 |
| 905032 | 53 | 78 | 89 | 93 | <0.1 |
| 905095 | 83 | 95 | 97 | 98 | <0.1 |
| 905479 | 82 | 89 | 94 | 95 | <0.1 |
| 905511 | 54 | 75 | 87 | 90 | <0.1 |
| 905704 | 61 | 84 | 93 | 96 | <0.1 |

TABLE 47

Multi-dose assay with 3-10-3 cEt gapmers

| Compound Number | % inhibition 62.5 nM | 250 nM | 1,000 nM | 4,000 nM | $IC_{50}$ (μm) |
|---|---|---|---|---|---|
| 793406 | 21 | 63 | 83 | 93 | 0.2 |
| 904009 | 35 | 68 | 88 | 95 | 0.1 |
| 904041 | 67 | 88 | 95 | 97 | <0.1 |
| 904202 | 24 | 62 | 77 | 88 | 0.2 |
| 904425 | 84 | 97 | 99 | 99 | <0.1 |
| 904426 | 37 | 72 | 90 | 95 | 0.1 |
| 904522 | 37 | 73 | 86 | 94 | 0.1 |
| 904619 | 49 | 83 | 94 | 98 | <0.1 |
| 904681 | 28 | 62 | 86 | 94 | 0.2 |
| 904713 | 23 | 53 | 72 | 82 | 0.3 |
| 904745 | 58 | 83 | 94 | 97 | <0.1 |
| 904746 | 75 | 92 | 98 | 99 | <0.1 |
| 904778 | 54 | 80 | 92 | 96 | <0.1 |
| 904873 | 50 | 80 | 93 | 97 | <0.1 |
| 904969 | 35 | 71 | 88 | 95 | 0.1 |
| 905128 | 42 | 70 | 83 | 88 | 0.1 |
| 905418 | 42 | 78 | 90 | 95 | <0.1 |
| 905513 | 38 | 73 | 90 | 95 | 0.1 |
| 905706 | 32 | 70 | 84 | 89 | 0.1 |

TABLE 48

| Multi-dose assay with 3-10-3 cEt gapmers | | | | | |
|---|---|---|---|---|---|
| | % inhibition | | | | |
| Compound Number | 62.5 nM | 250 nM | 1,000 nM | 4,000 nM | $IC_{50}$ (μm) |
| 793406 | 12 | 55 | 80 | 90 | 0.3 |
| 903820 | 56 | 85 | 94 | 98 | <0.1 |
| 903821 | 63 | 89 | 97 | 98 | <0.1 |
| 904523 | 40 | 72 | 90 | 95 | 0.1 |
| 904716 | 33 | 63 | 85 | 92 | 0.1 |
| 904717 | 53 | 82 | 93 | 97 | <0.1 |
| 904718 | 39 | 73 | 88 | 95 | 0.1 |
| 904747 | 47 | 79 | 91 | 94 | <0.1 |
| 904748 | 60 | 83 | 93 | 95 | <0.1 |
| 905036 | 52 | 77 | 91 | 95 | <0.1 |
| 905292 | 46 | 75 | 91 | 95 | <0.1 |
| 905419 | 41 | 71 | 84 | 88 | 0.1 |
| 905422 | 19 | 59 | 88 | 97 | 0.2 |
| 905485 | 32 | 61 | 80 | 92 | 0.2 |
| 905580 | 35 | 71 | 89 | 96 | 0.1 |
| 905581 | 39 | 70 | 89 | 95 | 0.1 |
| 905582 | 19 | 65 | 86 | 94 | 0.2 |
| 905707 | 50 | 76 | 89 | 91 | <0.1 |
| 905867 | 33 | 67 | 84 | 92 | 0.1 |

TABLE 49

| Multi-dose assay with 3-10-3 cEt gapmers | | | | | |
|---|---|---|---|---|---|
| | % inhibition | | | | |
| Compound Number | 62.5 nM | 250 nM | 1,000 nM | 4,000 nM | $IC_{50}$ (μm) |
| 793406 | 15 | 56 | 79 | 91 | 0.3 |
| 903825 | 72 | 89 | 94 | 95 | <0.1 |
| 903856 | 68 | 75 | 89 | N/A | <0.1 |
| 904209 | 61 | 89 | 96 | 96 | <0.1 |
| 904210 | 65 | 90 | 97 | 98 | <0.1 |
| 904720 | 31 | 70 | 92 | 95 | 0.1 |
| 905456 | 48 | 85 | 91 | 94 | <0.1 |
| 905457 | 45 | 70 | 84 | 89 | <0.1 |
| 905520 | 36 | 68 | 96 | 97 | 0.1 |
| 905521 | 30 | 65 | 88 | 97 | 0.1 |
| 905712 | 25 | 60 | 86 | 94 | 0.2 |
| 905808 | 37 | 74 | 90 | 92 | 0.1 |

TABLE 50

| Multi-dose assay with 3-10-3 cEt gapmers | | | | | |
|---|---|---|---|---|---|
| | % inhibition | | | | |
| Compound Number | 62.5 nM | 250 nM | 1,000 nM | 4,000 nM | $IC_{50}$ (μm) |
| 793406 | 9 | 59 | 85 | 94 | 0.3 |
| 903826 | 47 | 81 | 93 | 97 | <0.1 |
| 903956 | 48 | 74 | 88 | 94 | <0.1 |
| 904082 | 56 | 84 | 93 | 95 | <0.1 |
| 904083 | 82 | 95 | 97 | 98 | <0.1 |
| 904084 | 83 | 96 | 98 | 98 | <0.1 |
| 904114 | 48 | 71 | 86 | 89 | <0.1 |
| 904211 | 62 | 88 | 96 | 98 | <0.1 |
| 904212 | 79 | 93 | 97 | 98 | <0.1 |
| 904242 | 33 | 61 | 81 | 89 | 0.2 |
| 904626 | 25 | 55 | 82 | 93 | 0.2 |
| 904627 | 86 | 93 | 99 | 99 | <0.1 |
| 904628 | 67 | 90 | 98 | 99 | <0.1 |
| 905139 | 54 | 83 | 94 | 97 | <0.1 |
| 905140 | 35 | 71 | 88 | 95 | 0.1 |
| 905490 | 66 | 85 | 91 | 92 | <0.1 |
| 905491 | 74 | 91 | 95 | 96 | <0.1 |

TABLE 50-continued

| Multi-dose assay with 3-10-3 cEt gapmers | | | | | |
|---|---|---|---|---|---|
| | % inhibition | | | | |
| Compound Number | 62.5 nM | 250 nM | 1,000 nM | 4,000 nM | $IC_{50}$ (μm) |
| 905586 | 35 | 63 | 81 | 88 | 0.1 |
| 905684 | 57 | 86 | 95 | 97 | <0.1 |

Cells were also plated at a density of 10,000 cells per well and transfected free uptake with various concentrations of antisense oligonucleotide, as specified in the Tables below. After a treatment period of approximately 16 hours, RNA was isolated from the cells and APOL1 mRNA levels were measured by quantitative real-time PCR. Human primer probe set HTS7376 (forward sequence GGCAGCCTTGTACTCTTGGAA, designated herein as SEQ ID NO: 1942; reverse sequence GCTGGTAATCCCGGTCAAAG, designated herein as SEQ ID NO: 1943; probe sequence CTGGGATG-GAGTTGGGAATCACAGCCX, designated herein as SEQ ID NO: 1944) was used to measure mRNA levels. APOL1 mRNA levels were adjusted according to total RNA content, as measured by RIBOGREEN®. Results are presented as percent inhibition of APOL1, relative to untreated control cells.

The half maximal inhibitory concentration ($IC_{50}$) of each oligonucleotide is also presented. APOL1 mRNA levels were significantly reduced in a dose-dependent manner in antisense oligonucleotide treated cells.

TABLE 51

| Multi-dose assay with 3-10-3 cEt gapmers | | | | | |
|---|---|---|---|---|---|
| | % inhibition | | | | |
| Compound Number | 62.5 nM | 250 nM | 1,000 nM | 4,000 nM | $IC_{50}$ (μm) |
| 793406 | 73 | 84 | 90 | 95 | <0.1 |
| 903807 | 59 | 83 | 91 | 95 | <0.1 |
| 903872 | 69 | 76 | 86 | 90 | <0.1 |
| 903999 | 76 | 85 | 93 | 94 | <0.1 |
| 904000 | 83 | 94 | 96 | 97 | <0.1 |
| 904001 | 95 | 97 | 98 | 98 | <0.1 |
| 904063 | 71 | 83 | 89 | 92 | <0.1 |
| 904223 | 38 | 48 | 63 | 74 | 0.3 |
| 904224 | 83 | 91 | 93 | 95 | <0.1 |
| 904254 | 28 | 50 | 72 | 72 | 0.3 |
| 904862 | 0 | 30 | 55 | 74 | 1.0 |
| 905086 | 8 | 32 | 65 | 72 | 0.7 |
| 905120 | 79 | 88 | 94 | 96 | <0.1 |
| 905374 | 59 | 67 | 77 | 82 | <0.1 |
| 905407 | 62 | 83 | 88 | 93 | <0.1 |
| 905408 | 68 | 82 | 90 | 94 | <0.1 |
| 905471 | 37 | 55 | 64 | 47 | 0.4 |
| 905600 | 73 | 88 | 93 | 97 | <0.1 |
| 905631 | 19 | 39 | 51 | 69 | 0.8 |

TABLE 52

| Multi-dose assay with 3-10-3 cEt gapmers | | | | | |
|---|---|---|---|---|---|
| | % inhibition | | | | |
| Compound Number | 62.5 nM | 250 nM | 1,000 nM | 4,000 nM | $IC_{50}$ (μm) |
| 793406 | 71 | 83 | 91 | 95 | <0.1 |
| 903874 | 27 | 52 | 76 | 87 | 0.2 |

TABLE 52-continued

| Multi-dose assay with 3-10-3 cEt gapmers | | | | | |
|---|---|---|---|---|---|
| | % inhibition | | | | |
| Compound Number | 62.5 nM | 250 nM | 1,000 nM | 4,000 nM | $IC_{50}$ (μm) |
| 903939 | 82 | 92 | 96 | 97 | <0.1 |
| 904002 | 39 | 65 | 81 | 91 | 0.1 |
| 904003 | 62 | 82 | 90 | 94 | <0.1 |
| 904034 | 55 | 74 | 87 | 90 | <0.1 |
| 904226 | 60 | 85 | 91 | 93 | <0.1 |
| 904675 | 81 | 94 | 98 | 99 | <0.1 |
| 905121 | 78 | 89 | 93 | 95 | <0.1 |
| 905123 | 83 | 92 | 95 | 96 | <0.1 |
| 905473 | 82 | 86 | 86 | 88 | <0.1 |
| 905475 | 72 | 83 | 91 | 95 | <0.1 |
| 905505 | 42 | 73 | 87 | 91 | 0.1 |
| 905601 | 49 | 76 | 89 | 95 | <0.1 |
| 905633 | 40 | 72 | 84 | 86 | 0.1 |
| 905634 | 53 | 76 | 88 | 91 | <0.1 |
| 905665 | 61 | 79 | 89 | 93 | <0.1 |
| 905697 | 34 | 70 | 84 | 88 | 0.1 |
| 905698 | 91 | 97 | 99 | 99 | <0.1 |

TABLE 53

| Multi-dose assay with 3-10-3 cEt gapmers | | | | | |
|---|---|---|---|---|---|
| | % inhibition | | | | |
| Compound Number | 62.5 nM | 250 nM | 1,000 nM | 4,000 nM | $IC_{50}$ (μm) |
| 793406 | 64 | 83 | 91 | 94 | <0.1 |
| 903501 | 65 | 82 | 95 | 95 | <0.1 |
| 903543 | 65 | 80 | 92 | 95 | <0.1 |
| 903596 | 100 | 84 | 91 | 95 | <0.1 |
| 903639 | 37 | 35 | 62 | 61 | 0.6 |
| 903991 | 22 | 42 | 44 | 44 | >4.0 |
| 903997 | 25 | 54 | 77 | 85 | 0.2 |
| 904055 | 39 | 47 | 76 | 89 | 0.2 |
| 904509 | 51 | 45 | 52 | 43 | 0.1 |
| 904629 | 30 | 58 | 83 | 86 | 0.2 |
| 905005 | 32 | 48 | 63 | 63 | 0.4 |
| 905015 | 39 | 58 | 72 | 81 | 0.1 |
| 905019 | 34 | 63 | 78 | 86 | 0.1 |
| 905037 | 42 | 63 | 69 | 75 | 0.1 |
| 905111 | 3 | 44 | 36 | 70 | 1.2 |
| 905141 | 14 | 50 | 76 | 92 | 0.3 |
| 905269 | 38 | 58 | 84 | 92 | 0.1 |
| 905469 | 56 | 81 | 90 | 95 | <0.1 |
| 905685 | 54 | 76 | 95 | 95 | <0.1 |

TABLE 54

| Multi-dose assay with 3-10-3 cEt gapmers | | | | | |
|---|---|---|---|---|---|
| | % inhibition | | | | |
| Compound Number | 62.5 nM | 250 nM | 1,000 nM | 4,000 nM | $IC_{50}$ (μm) |
| 793406 | 18 | 54 | 78 | 84 | 0.3 |
| 903545 | 51 | 68 | 75 | 86 | <0.1 |
| 903557 | 30 | 54 | 65 | 72 | 0.3 |
| 903558 | 55 | 69 | 70 | 83 | <0.1 |
| 903564 | 57 | 65 | 64 | 79 | <0.1 |
| 903572 | 40 | 60 | 82 | 90 | 0.1 |
| 903573 | 48 | 66 | 65 | 80 | <0.1 |
| 903574 | 29 | 44 | 58 | 56 | 0.8 |
| 903585 | 40 | 66 | 63 | 70 | 0.1 |
| 903587 | 37 | 43 | 58 | 81 | 0.3 |
| 903595 | 56 | 72 | 79 | 88 | <0.1 |
| 903597 | 51 | 60 | 69 | 66 | <0.1 |

TABLE 54-continued

| Multi-dose assay with 3-10-3 cEt gapmers | | | | | |
|---|---|---|---|---|---|
| | % inhibition | | | | |
| Compound Number | 62.5 nM | 250 nM | 1,000 nM | 4,000 nM | $IC_{50}$ (μm) |
| 903598 | 28 | 27 | 65 | 62 | 0.8 |
| 903599 | 31 | 58 | 64 | 79 | 0.2 |
| 903600 | 43 | 61 | 61 | 79 | 0.1 |
| 903606 | 57 | 73 | 84 | 91 | <0.1 |
| 903607 | 55 | 69 | 85 | 82 | <0.1 |
| 903639 | 17 | 0 | 23 | 39 | >4.0 |
| 905037 | 0 | 21 | 3 | 37 | >4.0 |

In another assay, cells were plated at a density of 10,000 cells per well and transfected free uptake with various concentrations of antisense oligonucleotide, as specified in the Tables below. After a treatment period of approximately 16 hours, RNA was isolated from the cells and APOL1 mRNA levels were measured by quantitative real-time PCR. Human primer probe set RTS35962 was used to measure mRNA levels. APOL1 mRNA levels were adjusted according to total RNA content, as measured by RIBOGREEN®. Results are presented as percent inhibition of APOL1, relative to untreated control cells.

The half maximal inhibitory concentration ($IC_{50}$) of each oligonucleotide is also presented. APOL1 mRNA levels were significantly reduced in a dose-dependent manner in antisense oligonucleotide treated cells.

TABLE 55

| Multi-dose assay with 3-10-3 cEt gapmers | | | | | | | |
|---|---|---|---|---|---|---|---|
| | % inhibition | | | | | | |
| Compound Number | 4.8 nM | 19.5 nM | 78.1 nM | 312.5 nM | 1,250 nM | 5,000 nM | $IC_{50}$ (μM) |
| 793406 | 0 | 0 | 24 | 53 | 75 | 87 | 0.2 |
| 793444 | 0 | 0 | 4 | 21 | 31 | 53 | 0.9 |
| 903822 | 49 | 0 | 27 | 53 | 74 | 88 | 0.2 |
| 904082 | 1 | 14 | 57 | 87 | 91 | 90 | 0.1 |
| 904101 | 5 | 15 | 28 | 67 | 80 | 86 | 0.2 |
| 904226 | 11 | 22 | 71 | 94 | 98 | 99 | 0.1 |
| 904628 | 8 | 21 | 59 | 87 | 96 | 98 | 0.1 |
| 904763 | 13 | 17 | 46 | 85 | 95 | 98 | 0.1 |
| 905032 | 17 | 16 | 60 | 87 | 95 | 97 | 0.1 |

TABLE 56

| Multi-dose assay with 3-10-3 cEt gapmers | | | | | | | |
|---|---|---|---|---|---|---|---|
| | % inhibition | | | | | | |
| Compound Number | 4.8 nM | 19.5 nM | 78.1 nM | 312.5 nM | 1,250 nM | 5,000 nM | $IC_{50}$ (μM) |
| 905139 | 0 | 0 | 48 | 82 | 91 | 96 | 0.2 |
| 905373 | 10 | 20 | 74 | 93 | 98 | 99 | 0.1 |
| 905469 | 11 | 0 | 38 | 73 | 88 | 96 | 0.2 |
| 905505 | 18 | 27 | 74 | 94 | 96 | 98 | 0.1 |
| 905521 | 13 | 2 | 35 | 75 | 88 | 95 | 0.2 |
| 905633 | 20 | 38 | 79 | 96 | 98 | 99 | 0.1 |
| 905634 | 14 | 22 | 60 | 90 | 96 | 98 | 0.1 |
| 905665 | 0 | 15 | 40 | 74 | 88 | 94 | 0.1 |
| 905758 | 31 | 0 | 30 | 61 | 85 | 89 | 0.2 |

In another assay, cells were plated at a density of 11,000 cells per well and transfected free uptake with various concentrations of antisense oligonucleotide, as specified in the Tables below. After a treatment period of approximately 16 hours, RNA was isolated from the cells and APOL1 mRNA levels were measured by quantitative real-time PCR. Human primer probe set RTS35962 was used to measure mRNA levels. APOL1 mRNA levels were adjusted according to total RNA content, as measured by RIBOGREEN®. Results are presented as percent inhibition of APOL1, relative to untreated control cells.

The half maximal inhibitory concentration ($IC_{50}$) of each oligonucleotide is also presented. APOL1 mRNA levels were significantly reduced in a dose-dependent manner in antisense oligonucleotide treated cells.

TABLE 57

Multi-dose assay with deoxy, MOE, and cEt gapmers

| Compound Number | Chemistry | % inhibition 8 nM | 40 nM | 200 nM | 1000 nM | 5000 nM | $IC_{50}$ (μM) |
|---|---|---|---|---|---|---|---|
| 969157 | kek-d9-eekk | 0 | 31 | 83 | 98 | 99 | 0.07 |
| 969162 | kek-d9-eekk | 20 | 70 | 98 | 99 | 99 | 0.02 |
| 969210 | kk-d10-keke | 12 | 64 | 96 | 98 | 99 | 0.03 |
| 969361 | kk-d9-eeekk | 13 | 52 | 94 | 98 | 99 | 0.04 |
| 969408 | kk-d9-ekeke | 10 | 53 | 91 | 98 | 99 | 0.04 |
| 969433 | kk-d9-ekeke | 8 | 58 | 92 | 96 | 96 | 0.03 |
| 969437 | kk-d9-ekeke | 14 | 47 | 91 | 97 | 98 | 0.04 |
| 969502 | kk-d9-kdkdk | 5 | 41 | 87 | 95 | 95 | 0.05 |
| 971997 | kkk-d8-kdkdk | 1 | 34 | 79 | 93 | 94 | 0.07 |
| 972002 | kkk-d8-kdkdk | 12 | 57 | 86 | 92 | 92 | 0.04 |
| 972116 | kkk-d9-keke | 14 | 53 | 90 | 96 | 96 | 0.04 |
| 972139 | kkk-d9-kkke | 20 | 59 | 94 | 99 | 99 | 0.03 |
| 972163 | kkk-d9-kkke | 20 | 65 | 94 | 96 | 96 | 0.02 |
| 972190 | kkk-d9-kkke | 19 | 38 | 84 | 97 | 99 | 0.05 |
| 972268 | kkk-d10-kkk | 15 | 42 | 81 | 91 | 93 | 0.05 |

In another assay, cells were plated at a density of 10,000 cells per well and transfected free uptake with various concentrations of antisense oligonucleotide, as specified in the Tables below. After a treatment period of approximately 16 hours, RNA was isolated from the cells and APOL1 mRNA levels were measured by quantitative real-time PCR. Human primer probe set RTS35962 was used to measure mRNA levels. APOL1 mRNA levels were adjusted according to total RNA content, as measured by RIBOGREEN®. Results are presented as percent inhibition of APOL1, relative to untreated control cells.

The half maximal inhibitory concentration ($IC_{50}$) of each oligonucleotide is also presented. APOL1 mRNA levels were significantly reduced in a dose-dependent manner in antisense oligonucleotide treated cells.

TABLE 58

Multi-dose assay with deoxy, MOE, and cEt gapmers

| Compound Number | Chemistry | % inhibition 15.6 nM | 62.5 nM | 250 nM | 1,000 nM | $IC_{50}$ (μM) |
|---|---|---|---|---|---|---|
| 905095 | kkk-d10-kkk | 39 | 87 | 98 | 99 | <0.01 |
| 905491 | kkk-d10-kkk | 37 | 66 | 88 | 94 | 0.03 |
| 905634 | kkk-d10-kkk | 31 | 55 | 86 | 94 | 0.04 |
| 969064 | k-d10-kekek | 22 | 50 | 80 | 91 | 0.1 |
| 969084 | k-d10-kekek | 26 | 56 | 78 | 92 | 0.1 |
| 969164 | kek-d9-eekk | 23 | 63 | 90 | 97 | 0.05 |
| 969194 | kk-d10-keke | 26 | 56 | 81 | 92 | 0.1 |
| 969204 | kk-d10-keke | 11 | 47 | 82 | 94 | 0.1 |
| 969214 | kk-d10-keke | 33 | 75 | 91 | 96 | 0.02 |
| 969314 | kk-d9-eeekk | 2 | 31 | 67 | 89 | 0.1 |
| 969354 | kk-d9-eeekk | 15 | 48 | 76 | 92 | 0.1 |

TABLE 58-continued

Multi-dose assay with deoxy, MOE, and cEt gapmers

| Compound Number | Chemistry | % inhibition 15.6 nM | 62.5 nM | 250 nM | 1,000 nM | $IC_{50}$ (μM) |
|---|---|---|---|---|---|---|
| 969404 | kk-d9-ekeke | 8 | 37 | 69 | 64 | 0.2 |
| 969474 | kk-d9-kdkdk | 15 | 44 | 76 | 93 | 0.1 |
| 971944 | kk-d9-kekek | 25 | 59 | 84 | 93 | 0.05 |
| 971984 | kk-d9-kekek | 21 | 38 | 69 | 89 | 0.1 |
| 972014 | kkk-d8-kdkdk | 18 | 54 | 81 | 93 | 0.1 |
| 972044 | kkk-d8-kekek | 30 | 57 | 84 | 94 | 0.04 |
| 972124 | kkk-d9-keke | 50 | 80 | 96 | 97 | <0.01 |
| 972144 | kkk-d9-kkke | 15 | 60 | 87 | 94 | 0.1 |

TABLE 59

Multi-dose assay with deoxy, MOE, and cEt gapmers

| Compound Number | Chemistry | % inhibition 15.6 nM | 62.5 nM | 250 nM | 1,000 nM | $IC_{50}$ (μM) |
|---|---|---|---|---|---|---|
| 905095 | kkk-d10-kkk | 38 | 88 | 98 | 99 | <0.01 |
| 969155 | kek-d9-eekk | 13 | 42 | 69 | 87 | 0.1 |
| 969175 | kk-d10-keke | 6 | 35 | 67 | 85 | 0.1 |
| 969185 | kk-d10-keke | 10 | 59 | 87 | 96 | 0.1 |
| 969205 | kk-d10-keke | 18 | 46 | 74 | 90 | 0.1 |
| 969254 | kk-d8-kekekk | 5 | 12 | 44 | 80 | 0.3 |
| 969345 | kk-d9-eeekk | 8 | 38 | 84 | 96 | 0.1 |
| 969355 | kk-d9-eeekk | 21 | 60 | 86 | 94 | 0.1 |
| 969434 | kk-d9-ekeke | 6 | 23 | 59 | 80 | 0.2 |
| 969435 | kk-d9-ekeke | 23 | 62 | 89 | 97 | 0.05 |
| 969475 | kk-d9-kdkdk | 9 | 38 | 68 | 89 | 0.1 |
| 971925 | kk-d9-kekek | 44 | 77 | 92 | 96 | <0.01 |
| 971995 | kkk-d8-kdkdk | 23 | 61 | 84 | 93 | 0.1 |
| 972004 | kkk-d8-kdkdk | 24 | 59 | 82 | 86 | 0.1 |
| 972104 | kkk-d9-keke | 16 | 47 | 74 | 90 | 0.1 |
| 972146 | kkk-d9-kkke | 45 | 78 | 95 | 98 | <0.01 |
| 972165 | kkk-d9-kkke | 2 | 46 | 76 | 87 | 0.1 |
| 972174 | kkk-d9-kkke | 5 | 25 | 64 | 82 | 0.2 |
| 972194 | kkk-d9-kkke | 3 | 24 | 54 | 80 | 0.2 |

TABLE 60

Multi-dose assay with deoxy, MOE, and cEt gapmers

| Compound Number | Chemistry | % inhibition 15.6 nM | 62.5 nM | 250 nM | 1,000 nM | $IC_{50}$ (μM) |
|---|---|---|---|---|---|---|
| 905095 | kkk-d10-kkk | 63 | 94 | 99 | 99 | <0.01 |
| 969056 | k-d10-kekek | 29 | 50 | 70 | 87 | 0.1 |
| 969076 | k-d10-kekek | 14 | 46 | 80 | 92 | 0.1 |
| 969086 | k-d10-kekek | 24 | 58 | 86 | 96 | 0.1 |
| 969156 | kek-d9-eekk | 0 | 37 | 76 | 90 | 0.1 |
| 969157 | kek-d9-eekk | 37 | 71 | 91 | 98 | 0.02 |
| 969186 | kk-d10-keke | 11 | 44 | 80 | 93 | 0.1 |
| 969206 | kk-d10-keke | 33 | 59 | 81 | 92 | 0.04 |
| 969226 | kk-d8-eeeekk | 0 | 30 | 61 | 87 | 0.2 |
| 969316 | kk-d9-eeekk | 10 | 49 | 79 | 93 | 0.1 |
| 969336 | kk-d9-eeekk | 20 | 35 | 65 | 85 | 0.1 |
| 969406 | kk-d9-ekeke | 25 | 53 | 79 | 91 | 0.1 |
| 972046 | kkk-d8-kekek | 26 | 46 | 68 | 88 | 0.1 |
| 972096 | kkk-d9-keke | 24 | 66 | 89 | 95 | 0.04 |
| 972116 | kkk-d9-keke | 35 | 72 | 90 | 95 | 0.03 |
| 972166 | kkk-d9-kkke | 17 | 48 | 72 | 88 | 0.1 |
| 972176 | kkk-d9-kkke | 21 | 56 | 85 | 93 | 0.1 |
| 972186 | kkk-d9-kkke | 36 | 70 | 92 | 96 | 0.02 |
| 972196 | kkk-d9-kkke | 33 | 73 | 90 | 92 | 0.03 |

TABLE 61

Multi-dose assay with deoxy, MOE, and cEt gapmers

| Compound Number | Chemistry | % inhibition 15.6 nM | 62.5 nM | 250 nM | 1,000 nM | $IC_{50}$ (μM) |
|---|---|---|---|---|---|---|
| 904082 | kkk-d10-kkk | 38 | 62 | 87 | 93 | 0.03 |
| 905095 | kkk-d10-kkk | 63 | 93 | 98 | 99 | <0.01 |
| 969087 | k-d10-kekek | 0 | 52 | 79 | 91 | 0.1 |
| 969127 | k-d9-kekeke | 0 | 46 | 78 | 90 | 0.1 |
| 969187 | kk-d10-keke | 17 | 38 | 75 | 86 | 0.1 |
| 969207 | kk-d10-keke | 36 | 46 | 78 | 91 | 0.1 |
| 969217 | kk-d10-keke | 14 | 41 | 74 | 92 | 0.1 |
| 969337 | kk-d9-eeekk | 35 | 62 | 81 | 92 | 0.03 |
| 969347 | kk-d9-eeekk | 38 | 72 | 91 | 96 | 0.02 |
| 969377 | kk-d9-eeekk | 41 | 68 | 85 | 91 | 0.02 |
| 969437 | kk-d9-ekeke | 40 | 78 | 92 | 97 | 0.02 |
| 969457 | kk-d9-ekeke | 36 | 65 | 83 | 92 | 0.03 |
| 969467 | kk-d9-ekeke | 20 | 58 | 84 | 92 | 0.1 |
| 971967 | kk-d9-kekek | 20 | 41 | 75 | 90 | 0.1 |
| 971997 | kkk-d8-kdkdk | 40 | 66 | 85 | 93 | 0.02 |
| 972027 | kkk-d8-kekek | 17 | 61 | 80 | 89 | 0.1 |
| 972097 | kkk-d9-keke | 21 | 67 | 89 | 97 | 0.05 |
| 972147 | kkk-d9-kkke | 34 | 61 | 83 | 92 | 0.04 |
| 972197 | kkk-d9-kkke | 43 | 69 | 88 | 94 | 0.02 |

TABLE 62

Multi-dose assay with deoxy, MOE, and cEt gapmers

| Compound Number | Chemistry | % inhibition 15.6 nM | 62.5 nM | 250 nM | 1,000 nM | $IC_{50}$ (μM) |
|---|---|---|---|---|---|---|
| 904619 | kkk-d10-kkk | 24 | 50 | 84 | 93 | 0.1 |
| 905095 | kkk-d10-kkk | 74 | 94 | 99 | 100 | <0.01 |
| 969158 | kek-d9-eekk | 31 | 40 | 70 | 89 | 0.1 |
| 969167 | kek-d9-eekk | 14 | 43 | 64 | 84 | 0.1 |
| 969178 | kk-d10-keke | 27 | 56 | 80 | 93 | 0.1 |
| 969198 | kk-d10-keke | 31 | 53 | 79 | 92 | 0.1 |
| 969318 | kk-d9-eeekk | 37 | 78 | 94 | 98 | 0.02 |
| 969358 | kk-d9-eeekk | 28 | 61 | 86 | 96 | 0.04 |
| 969368 | kk-d9-eeekk | 39 | 72 | 91 | 97 | 0.02 |
| 969388 | kk-d9-eeekk | 18 | 51 | 79 | 91 | 0.1 |
| 969407 | kk-d9-ekeke | 8 | 30 | 61 | 86 | 0.2 |
| 969408 | kk-d9-ekeke | 36 | 66 | 90 | 96 | 0.03 |
| 969428 | kk-d9-ekeke | 40 | 41 | 71 | 90 | 0.1 |
| 969448 | kk-d9-ekeke | 33 | 61 | 86 | 96 | 0.04 |
| 969458 | kk-d9-ekeke | 19 | 40 | 74 | 92 | 0.1 |
| 969477 | kk-d9-kdkdk | 16 | 34 | 72 | 85 | 0.1 |
| 969497 | kk-d9-kdkdk | 3 | 28 | 59 | 75 | 0.2 |
| 971987 | kkk-d10-kkk | 8 | 17 | 51 | 80 | 0.2 |
| 972178 | kkk-d9-kkke | 19 | 54 | 78 | 91 | 0.1 |

TABLE 63

Multi-dose assay with deoxy, MOE, and cEt gapmers

| Compound Number | Chemistry | % inhibition 15.6 nM | 62.5 nM | 250 nM | 1,000 nM | $IC_{50}$ (μM) |
|---|---|---|---|---|---|---|
| 905095 | kkk-d10-kkk | 65 | 94 | 99 | 99 | <0.01 |
| 969159 | kek-d9-eekk | 21 | 46 | 84 | 96 | 0.1 |
| 969169 | kek-d9-eekk | 22 | 41 | 69 | 89 | 0.1 |
| 969208 | kk-d10-keke | 25 | 53 | 84 | 89 | 0.1 |
| 969219 | kk-d10-keke | 16 | 35 | 66 | 87 | 0.1 |
| 969289 | kk-d8-kekekk | 3 | 36 | 70 | 88 | 0.1 |
| 969328 | kk-d9-eeekk | 19 | 40 | 61 | 85 | 0.1 |
| 969338 | kk-d9-eeekk | 13 | 34 | 72 | 90 | 0.1 |
| 969359 | kk-d9-eeekk | 24 | 61 | 84 | 93 | 0.05 |
| 969389 | kk-d9-eeekk | 20 | 42 | 77 | 92 | 0.1 |

TABLE 63-continued

Multi-dose assay with deoxy, MOE, and cEt gapmers

| Compound Number | Chemistry | % inhibition 15.6 nM | 62.5 nM | 250 nM | 1,000 nM | $IC_{50}$ (μM) |
|---|---|---|---|---|---|---|
| 969398 | kk-d9-ekeke | 14 | 41 | 62 | 86 | 0.1 |
| 969449 | kk-d9-ekeke | 43 | 64 | 83 | 92 | 0.02 |
| 969469 | kk-d9-kdkdk | 25 | 63 | 83 | 94 | 0.05 |
| 969479 | kk-d9-kdkdk | 40 | 71 | 91 | 96 | 0.02 |
| 969498 | kk-d9-kdkdk | 10 | 40 | 71 | 87 | 0.1 |
| 969508 | kk-d9-kdkdk | 17 | 34 | 70 | 88 | 0.1 |
| 971969 | kk-d9-kekek | 28 | 63 | 86 | 92 | 0.04 |
| 972118 | kkk-d9-keke | 10 | 42 | 70 | 87 | 0.1 |
| 972139 | kkk-d9-kkke | 35 | 69 | 88 | 96 | 0.03 |

TABLE 64

Multi-dose assay with deoxy, MOE, and cEt gapmers

| Compound Number | Chemistry | % inhibition 15.6 nM | 62.5 nM | 250 nM | 1,000 nM | $IC_{50}$ (μM) |
|---|---|---|---|---|---|---|
| 905095 | kkk-d10-kkk | 68 | 93 | 99 | 99 | <0.01 |
| 969160 | kek-d9-eekk | 39 | 73 | 92 | 96 | 0.02 |
| 969180 | kk-d10-keke | 7 | 38 | 74 | 92 | 0.10 |
| 969210 | kk-d10-keke | 59 | 89 | 97 | 99 | <0.01 |
| 969229 | kk-d8-eeeekk | 4 | 23 | 80 | 91 | 0.10 |
| 969340 | kk-d9-eeekk | 23 | 60 | 87 | 98 | 0.05 |
| 969350 | kk-d9-eeekk | 12 | 46 | 74 | 92 | 0.10 |
| 969380 | kk-d9-eeekk | 27 | 59 | 84 | 93 | 0.05 |
| 969409 | kk-d9-ekeke | 22 | 48 | 80 | 93 | 0.10 |
| 969419 | kk-d9-ekeke | 8 | 25 | 58 | 84 | 0.20 |
| 969429 | kk-d9-ekeke | 17 | 41 | 71 | 85 | 0.10 |
| 969430 | kk-d9-ekeke | 29 | 59 | 83 | 96 | 0.05 |
| 969440 | kk-d9-ekeke | 29 | 60 | 82 | 95 | 0.04 |
| 972069 | kkk-d8-kekek | 25 | 55 | 84 | 93 | 0.10 |
| 972119 | kkk-d9-keke | 15 | 41 | 73 | 83 | 0.10 |
| 972120 | kkk-d9-keke | 32 | 65 | 88 | 96 | 0.03 |
| 972129 | kkk-d9-keke | 9 | 42 | 75 | 85 | 0.10 |
| 972189 | kkk-d9-kkke | 32 | 63 | 84 | 91 | 0.04 |
| 972190 | kkk-d9-kkke | 38 | 71 | 93 | 98 | 0.02 |

Example 3: Tolerability of Modified Oligonucleotides Targeting Human APOL1 in BALB/c Mice BALB/c mice are a multipurpose mouse model frequently utilized for safety and efficacy testing. The mice were treated with antisense oligonucleotides selected from studies described above and evaluated for changes in the levels of various plasma chemistry markers.

Treatment

Groups of 6- to 7-week-old male mice were injected subcutaneously once with 200 mg/kg of modified oligonucleotides. One group of male BALB/c mice was injected with PBS. Mice were euthanized 72-96 hours after the single dose and plasma was harvested for further analysis.

Study 1

To evaluate the effect of modified oligonucleotides on liver function, plasma levels of transaminases were measured using an automated clinical chemistry analyzer (Beckman Coulter AU480, Brea, Calif.). Modified oligonucleotides that caused changes in the levels of transaminases outside the expected range for antisense oligonucleotides were excluded in further studies. Compound IDs 793406, 903807, 903822, 903853, 904016, 904063, 904082, 904084, 904101, 904212, 904223, 904224, 904226, 904424, 904426, 904443, 904444, 904619, 904627, 904628, 904763, 904766, 905031, 905032, 905036, 905095, 905121, 905123, 905139, 905141, 905143, 905146, 905147, 905269, 905373, 905408, 905418, 905469, 905471, 905491, 905496, 905505, 905510, 905511, 905521, 905581, 905582, 905633, 905634, 905636, 905654, 905655, 905665, 905684, 905688, 905690, 905697, 905700, 905758 and 905867 were considered tolerable in this study and were selected for further evaluation.

Study 2

In a second study to evaluate the effect of modified oligonucleotides on liver function, plasma levels of transaminases were measured using an automated clinical chemistry analyzer (Beckman Coulter AU480, Brea, Calif.). Modified oligonucleotides that caused changes in the levels of transaminases outside the expected range for antisense oligonucleotides were excluded in further studies. Compound IDs 969157, 969160, 969162, 969210, 969214, 969231, 969318, 969347, 969361, 969362, 969408, 969433, 969437, 969479, 969501, 969502, 971925, 971973, 971997, 972002, 972116, 972139, 972163, 972190, 972268, and 972288 were considered tolerable in this study and were selected for further evaluation.

Example 4: Effect of Antisense Inhibition of hAPOL1 in a Transgenic Mouse Model A transgenic mouse model was developed using the Fosmid ABC12-49114000M18, digested to produce a 31.6 Kb fragment containing only the APOL1 gene with 5 Kb upstream and 12 Kb downstream of the gene. The gene fragment was inserted into eggs from C57BL/6NTAc mice by pronuclear injection to produce two founder lines. Line 1 was used for the experiments described herein. Human APOL1 transcript is predominantly detectable in the liver, with hAPOL1 protein robustly detectable in the plasma of these mice. The efficacy of modified oligonucleotides was evaluated in this model.

Transgenic mice were maintained on a 12-hour light/dark cycle and were fed ad libitum normal Purina mouse chow. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in PBS for injection.

Study 1

The hAPOL1 transgenic mice were divided into groups of 2-4 mice each. Groups received subcutaneous injections of modified oligonucleotide at a dose of 25 mg/kg three times a week for one week, 3 total doses. One group of mice received subcutaneous injections of control oligonucleotide 549148 (GGCTACTACGCCGTCA, designated SEQ ID NO: 1948; a 3-10-3 cEt gapmer with no known target) at a dose of 25 mg/kg three times a week for one week, 3 total doses. One group of mice received subcutaneous injections of PBS three times per week for one week. The saline-injected group served as the control group to which oligonucleotide-treated groups were compared.

On day 7, animals were sacrificed and RNA was extracted from kidney and liver for real-time PCR analysis of hAPOL1 mRNA expression. Results are presented as percent change of mRNA, relative to PBS control, normalized with RIBOGREEN®. Two separate experiments were conducted with similar conditions and are presented in separate tables. As shown in the tables below, treatment with antisense oligonucleotides resulted in significant reduction of hAPO1 mRNA in comparison to the PBS control.

TABLE 65

Percent inhibition of APOL1 by 3-10-3 cEt gapmers in transgenic mice relative to the PBS control

| Compound ID | % Inhibition (liver) | % inhibition (kidney) |
|---|---|---|
| 549148 | 15 | 5 |
| 793406 | 83 | 29 |
| 903853 | 82 | 37 |
| 904016 | 64 | 21 |
| 904063 | 49 | 0 |
| 904082 | 93 | 46 |
| 904212 | 69 | 24 |
| 904223 | 66 | 10 |
| 904224 | 65 | 15 |
| 904226 | 89 | 28 |
| 904424 | 59 | 13 |
| 904426 | 43 | 27 |
| 904443 | 75 | 16 |
| 904444 | 65 | 26 |
| 904627 | 96 | 50 |
| 904628 | 77 | 43 |
| 905031 | 86 | 15 |
| 905032 | 92 | 38 |
| 905036 | 80 | 23 |
| 905141 | 90 | 1 |
| 905143 | 75 | 0 |
| 905146 | 76 | 20 |
| 905147 | 79 | 0 |
| 905269 | 54 | 8 |
| 905373 | 86 | 46 |
| 905408 | 78 | 10 |
| 905418 | 67 | 20 |
| 905471 | 87 | 32 |
| 905496 | 71 | 21 |
| 905505 | 95 | 16 |
| 905511 | 92 | 40 |
| 905521 | 86 | 31 |
| 905581 | 55 | 6 |
| 905582 | 51 | 0 |
| 905633 | 79 | 32 |
| 905636 | 22 | 0 |
| 905655 | 63 | 18 |
| 905688 | 81 | 3 |
| 905690 | 74 | 21 |
| 905697 | 81 | 7 |
| 905758 | 85 | 44 |
| 905867 | 83 | 31 |

TABLE 66

Percent inhibition of APOL1 by 3-10-3 cEt gapmers in transgenic mice relative to the PBS control

| Compound ID | % Inhibition (liver) | % inhibition (kidney) |
|---|---|---|
| 549148 | 10 | 7 |
| 793406 | 73 | 37 |
| 903807 | 51 | 32 |
| 903822 | 93 | 50 |
| 904084 | 87 | 43 |
| 904619 | 86 | 48 |
| 904763 | 88 | 56 |
| 904766 | 82 | 65 |
| 905095 | 92 | 69 |
| 904101 | 58 | 47 |
| 905121 | 93 | 66 |
| 905123 | 74 | 49 |
| 905139 | 87 | 51 |
| 905469 | 83 | 56 |
| 905491 | 95 | 69 |
| 905510 | 95 | 61 |
| 905634 | 60 | 46 |
| 905654 | 53 | 40 |
| 905665 | 85 | 47 |

TABLE 66-continued

| Percent inhibition of APOL1 by 3-10-3 cEt gapmers in transgenic mice relative to the PBS control | | |
|---|---|---|
| Compound ID | % Inhibition (liver) | % inhibition (kidney) |
| 905684 | 52 | 33 |
| 905700 | 79 | 45 |

Study 2

The hAPOL1 transgenic mice were divided into groups of 4 mice each. Groups received subcutaneous injections of modified oligonucleotide at a dose of 25 mg/kg twice a week for 1 weeks for 3 total doses. One group of mice received subcutaneous injections of control oligonucleotide 549148 at a dose of 25 mg/kg three times a week for one week, 3 total doses. One group of mice received subcutaneous injections of PBS three times a week for 1 week. The saline-injected group served as the control group to which oligonucleotide-treated groups were compared.

On day 7, animals were sacrificed and RNA was extracted from kidney and liver for real-time PCR analysis of measurement of hAPOL1 mRNA expression. Results are presented as percent change of mRNA, relative to PBS control, normalized with RIBOGREEN®. As shown in the tables below, treatment with antisense oligonucleotides resulted in significant reduction of hAPO1 mRNA in comparison to the PBS control.

TABLE 67

| Percent inhibition of APOL1 by gapmers in transgenic mice relative to the PBS control | | | |
|---|---|---|---|
| Compound ID | Chemistry | Inhibition % (liver) | inhibition % (kidney) |
| 549148 | kkk-d10-kkk | 2 | 0 |
| 793406 | kkk-d10-kkk | 88 | 32 |
| 969157 | kek-d9-eekk | 85 | 41 |
| 969160 | kek-d9-eekk | 78 | 41 |
| 969162 | kek-d9-eekk | 92 | 56 |
| 969210 | kk-10-keke | 88 | 35 |
| 969214 | kk-d10-keke | 89 | 45 |
| 969231 | kk-d8-eeeekk | 57 | 29 |
| 969318 | kk-d9-eeekk | 64 | 17 |
| 969347 | kk-d9-eeekk | 75 | 22 |
| 969361 | kk-9-eeekk | 61 | 38 |
| 969362 | kk-d9-eeekk | 74 | 21 |
| 969408 | kk-d9-ekeke | 84 | 40 |
| 969433 | kk-d9-ekeke | 84 | 37 |
| 969437 | kk-d9-ekeke | 94 | 44 |
| 969479 | kk-d9-kdkdk | 74 | 23 |
| 969501 | kk-d9-kdkdk | 80 | 30 |
| 969502 | kk-9-kdkdk | 83 | 43 |
| 971925 | kk-d9-kekek | 78 | 39 |
| 971973 | kk-d9-kekek | 82 | 26 |
| 971997 | kkk-d8-kdkdk | 76 | 36 |
| 972002 | kkk-d8-kdkdk | 81 | 54 |
| 972116 | kkk-d9-keke | 80 | 46 |
| 972139 | kkk-d9-kkke | 88 | 56 |
| 972163 | kkk-d9-kkke | 91 | 52 |
| 972190 | kkk-d9-kkke | 90 | 46 |
| 972268 | kkk-d10-kkk | 50 | 46 |
| 972288 | kkk-d10-kkk | 64 | 28 |

Study 3: Effect of Antisense Inhibition of APOL1 on Mice with Proteinuria hAPOL1 transgenic mice were divided into groups of 3-4 mice each. Groups received subcutaneous injections of modified oligonucleotide 972190 at a dose of 50 mg/kg once a week for 4 weeks. One group of mice received subcutaneous injections of control oligonucleotide 549148 at a dose of 50 mg/kg once a week for 4 weeks. One group of mice received subcutaneous injections of PBS once a week for 4 weeks. A single dose of IFNγ was administered at 1.125×10' U/kg one day after the last oligonucleotide dose in order to induce proteinuria in the mice. The saline-injected group served as the control group to which oligonucleotide-treated groups were compared.

Urine was collected and the animals were sacrificed 48 hours after the IFNγ administration. RNA was extracted from kidney and liver for real-time PCR analysis of measurement of hAPOL1 mRNA expression. Results are presented as percent change of mRNA, relative to PBS control, normalized with RIBOGREEN®. As shown in the tables below, treatment with antisense oligonucleotides resulted in significant reduction of hAPO1 mRNA in comparison to the PBS control. As also shown in the tables below, treatment with 972190 resulted in significant reduction of urinary albumin and plasma ALT levels in comparison to control animals dosed with IFNγ. The results indicate that treatment with modified oligonucleotides targeting APOL1 protected APOL1 transgenic mice from proteinuria and reduced elevations in plasma ALT levels.

TABLE 68

| Percent expression of APOL1 by gapmers in transgenic mice relative to PBS control | | | |
|---|---|---|---|
| Treatment | IFNγ treatment | Kidney | Liver |
| PBS | Yes | 179 | 120 |
| 549148 | No | 76 | 133 |
| | Yes | 140 | 142 |
| 972190 | No | 41 | 7 |
| | Yes | 47 | 3 |

TABLE 68

| Effect of inhibition of APOL1 by gapmers in transgenic mice relative to the control | | | |
|---|---|---|---|
| Treatment | IFNγ treatment | Urinary albumin (μg/mg creatinine) | Plasma ALT (IU/L) |
| PBS | No | 41 | 163 |
| | Yes | 727 | 211 |
| 549148 | No | 77 | 207 |
| | Yes | 980 | 225 |
| 972190 | No | 56 | 63 |
| | Yes | 50 | 61 |

Example 5: Tolerability of Modified Oligonucleotides Targeted to hAPOL1 in CD1 Mice CD1® mice (Charles River, Mass.) are a multipurpose mouse model, frequently utilized for safety and efficacy testing. The mice were treated with 3-10-3 cEt gapmer oligonucleotides selected from the studies described above and evaluated for changes in the levels of various plasma chemistry markers.

Treatment

Groups of 7-8-week-old male CD1 mice were injected subcutaneously twice a week for six weeks with 25 mg/kg of ISIS oligonucleotides (50 mg/kg/week dose). One group of male CD1 mice was injected subcutaneously twice a week for 6 weeks with PBS. Mice were euthanized 48 hours after the last dose, and organs and plasma were harvested for further analysis. Two separate studies were conducted with similar conditions and are presented in separate tables for each end-point analysis.

Study 1

Plasma Chemistry Markers

To evaluate the effect of ISIS oligonucleotides on liver and kidney function, plasma levels of transaminases, albumin, bilirubin, creatinine, and BUN were measured using an automated clinical chemistry analyzer (Beckman Coulter AU480, Brea, Calif.). The results are presented in the Table below. ISIS oligonucleotides that caused changes in the levels of any of the liver or kidney function markers outside the expected range for antisense oligonucleotides were excluded in further studies.

TABLE 68

Plasma chemistry markers in CD1 mice plasma at week 6

| Compound ID | ALT (IU/L) | AST (IU/L) | Albumin (g/dL) | BUN (mg/dL) | Creatinine (mg/dL) | T. Bil (mg/dL) |
|---|---|---|---|---|---|---|
| PBS | 26 | 43 | 2.7 | 21.3 | 0.05 | 0.3 |
| 793406 | 42 | 75 | 2.6 | 21.7 | 0.04 | 0.3 |
| 903853 | 413 | 470 | 2.5 | 22.8 | 0.06 | 0.3 |
| 904082 | 33 | 54 | 2.6 | 21.4 | 0.07 | 0.2 |
| 904226 | 40 | 74 | 2.4 | 21.1 | 0.05 | 0.2 |
| 904627 | 1122 | 1245 | 2.4 | 19.6 | 0.06 | 0.2 |
| 904628 | 41 | 75 | 2.5 | 22.5 | 0.02 | 0.2 |
| 905032 | 106 | 84 | 2.5 | 23.6 | 0.04 | 0.2 |
| 905373 | 81 | 88 | 2.4 | 22.4 | 0.05 | 0.1 |
| 905505 | 62 | 88 | 2.2 | 21.1 | 0.05 | 0.1 |
| 905511 | 303 | 159 | 2.2 | 20.3 | 0.05 | 0.1 |
| 905521 | 120 | 117 | 2.5 | 22.0 | 0.06 | 0.1 |
| 905633 | 31 | 40 | 2.5 | 23.1 | 0.06 | 0.1 |
| 905758 | 68 | 92 | 2.3 | 19.0 | 0.04 | 0.1 |
| 905867 | 168 | 199 | 2.3 | 24.0 | 0.03 | 0.1 |

Hematology Assays

Blood obtained from all mouse groups were sent to IDEXX BioResearch for hematocrit (HCT) measurements and analysis, as well as measurements of the various blood cells, such as WBC, RBC, lymphocytes, monocytes, and platelets. The results are presented in the tables below. ISIS oligonucleotides that caused changes in the levels of any of the hematology markers outside the expected range for antisense oligonucleotides were excluded in further studies.

TABLE 69

Hematology markers in CD1 mice

| Compound ID | HCT (%) | LYM ($10^3$/μL) | MON ($10^3$/μL) | PLT ($10^3$/μL) | RBC ($10^6$/μL) | WBC ($10^3$/μL) |
|---|---|---|---|---|---|---|
| PBS | 43 | 4.4 | 0.2 | 1225 | 9.3 | 5.5 |
| 793406 | 44 | 5.7 | 0.4 | 892 | 9.6 | 7.5 |
| 903853 | 44 | 5.9 | 0.4 | 673 | 9.1 | 7.4 |
| 904082 | 41 | 5.4 | 0.3 | 1009 | 9.0 | 6.5 |
| 904226 | 41 | 4.3 | 0.3 | 624 | 9.2 | 5.2 |
| 904627 | 44 | 3.8 | 0.5 | 764 | 9.3 | 6.1 |
| 904628 | 42 | 2.7 | 0.1 | 765 | 9.2 | 4.0 |
| 905032 | 38 | 2.3 | 0.2 | 861 | 8.1 | 3.1 |
| 905373 | 42 | 4.7 | 0.4 | 922 | 8.8 | 6.1 |
| 905505 | 39 | 4.4 | 0.3 | 1252 | 8.3 | 6.1 |
| 905511 | 44 | 7.0 | 0.7 | 858 | 9.2 | 9.9 |
| 905521 | 42 | 3.1 | 0.3 | 734 | 8.8 | 4.1 |
| 905633 | 44 | 3.6 | 0.3 | 853 | 9.4 | 4.6 |
| 905758 | 40 | 3.2 | 0.3 | 628 | 8.5 | 4.0 |
| 905867 | 40 | 5.0 | 0.5 | 833 | 8.6 | 7.3 |

Study 2

Plasma Chemistry Markers

To evaluate the effect of ISIS oligonucleotides on liver and kidney function, plasma levels of transaminases, bilirubin, creatinine, and BUN were measured using an automated clinical chemistry analyzer (Hitachi Olympus AU400e, Melville, N.Y.). The results are presented in the Table below. ISIS oligonucleotides that caused changes in the levels of any of the liver or kidney function markers outside the expected range for antisense oligonucleotides were excluded in further studies.

TABLE 70

Plasma chemistry markers in CD1 mice plasma at week 6

| Compound ID | ALT (IU/L) | AST (IU/L) | Albumin (g/dL) | BUN (mg/dL) | Creatinine (mg/dL) | T. Bil (mg/dL) |
|---|---|---|---|---|---|---|
| PBS | 248 | 213 | 2.7 | 21.3 | 0.11 | 0.19 |
| 793444 | 51 | 73 | 2.4 | 23.4 | 0.11 | 0.14 |
| 903822 | 68 | 171 | 2.6 | 23.8 | 0.13 | 0.15 |
| 904101 | 39 | 62 | 2.5 | 19.5 | 0.10 | 0.15 |
| 904619 | 590 | 466 | 2.1 | 17.2 | 0.06 | 0.14 |
| 904763 | 90 | 87 | 2.5 | 24.0 | 0.08 | 0.16 |
| 904766 | 297 | 262 | 2.3 | 19.3 | 0.07 | 0.16 |
| 905095 | 246 | 294 | 2.2 | 18.5 | 0.07 | 0.19 |
| 905139 | 92 | 95 | 2.4 | 18.3 | 0.09 | 0.16 |
| 905469 | 60 | 72 | 2.5 | 19.1 | 0.10 | 0.17 |
| 905491 | 972 | 989 | 1.9 | 22.4 | 0.06 | 0.20 |
| 905634 | 42 | 71 | 2.3 | 17.1 | 0.08 | 0.13 |
| 905665 | 182 | 118 | 2.1 | 20.8 | 0.07 | 0.13 |

Hematology Assays

Blood obtained from all mouse groups were sent to IDEXX BioResearch for hematocrit (HCT) measurements and analysis, as well as measurements of the various blood cells, such as WBC, RBC, lymphocytes, monocytes, and platelets. The results are presented in the tables below. ISIS oligonucleotides that caused changes in the levels of any of the hematology markers outside the expected range for antisense oligonucleotides were excluded in further studies.

TABLE 71

Hematology markers in CD1 mice

| Compound ID | HCT (%) | LYM ($10^3$/μL) | MON ($10^3$/μL) | PLT ($10^3$/μL) | RBC ($10^6$/μL) | WBC ($10^3$/μL) |
|---|---|---|---|---|---|---|
| PBS | 50 | 2.8 | 0.3 | 824 | 10.7 | 6.2 |
| 793444 | 46 | 3.0 | 0.2 | 831 | 10.5 | 4.0 |
| 903822 | 44 | 4.0 | 0.2 | 525 | 10.1 | 5.4 |
| 904101 | 47 | 7.7 | 0.9 | 733 | 10.3 | 10.9 |
| 904619 | 42 | 21.0 | 1.2 | 686 | 9.5 | 26.5 |
| 904763 | 49 | 3.5 | 0.2 | 950 | 11.2 | 4.3 |
| 904766 | 51 | 7.9 | 0.9 | 603 | 11.5 | 10.3 |
| 905095 | 46 | 8.2 | 0.7 | 645 | 10.2 | 11.2 |
| 905139 | 49 | 4.2 | 0.4 | 997 | 10.7 | 6.2 |
| 905469 | 52 | 4.2 | 0.2 | 614 | 11.8 | 5.4 |
| 905491 | 43 | 7.8 | 2.4 | 495 | 9.6 | 23.1 |
| 905634 | 43 | 3.2 | 0.3 | 716 | 9.6 | 4.2 |
| 905665 | 41 | 4.7 | 0.3 | 686 | 8.6 | 6.6 |

Study 3

Body and Organ Weights

To evaluate the effect of ISIS oligonucleotides on animal health, body and organ weights measured at the end of the study. The results are presented in the Table below. ISIS oligonucleotides that caused changes in the levels of any of the weights outside the expected range for antisense oligonucleotides were excluded in further studies.

TABLE 72

| Body and organ weights of CD1 mice plasma at week 6 | | | | |
|---|---|---|---|---|
| | Liver | Kidney | Spleen | Body weight |
| PBS | 2.1 | 0.6 | 0.1 | 41.6 |
| 969157 | 2.4 | 0.6 | 0.2 | 39.0 |
| 969160 | 2.2 | 0.5 | 0.2 | 36.7 |
| 969162 | 2.2 | 0.6 | 0.2 | 40.8 |
| 969210 | 2.2 | 0.6 | 0.2 | 41.0 |
| 969214 | 2.1 | 0.6 | 0.2 | 41.0 |
| 969361 | 2.2 | 0.5 | 0.2 | 40.3 |
| 969408 | 2.4 | 0.6 | 0.2 | 42.4 |
| 969433 | 2.6 | 0.6 | 0.2 | 43.3 |
| 969437 | 2.5 | 0.6 | 0.2 | 41.3 |
| 969502 | 2.4 | 0.6 | 0.2 | 37.9 |
| 971925 | 2.5 | 0.7 | 0.2 | 41.5 |
| 971997 | 2.2 | 0.5 | 0.1 | 40.1 |
| 972002 | 2.7 | 0.5 | 0.2 | 40.4 |
| 972116 | 2.1 | 0.5 | 0.2 | 38.8 |
| 972139 | 2.4 | 0.5 | 0.2 | 40.3 |
| 972163 | 2.1 | 0.5 | 0.2 | 41.1 |
| 972190 | 2.3 | 0.6 | 0.1 | 41.0 |
| 972268 | 3.1 | 0.6 | 0.3 | 46.0 |

Plasma Chemistry Markers

To evaluate the effect of ISIS oligonucleotides on liver and kidney function, plasma levels of transaminases, albumin, bilirubin, creatinine, and BUN were measured using an automated clinical chemistry analyzer (Beckman Coulter AU480, Brea, Calif.). The results are presented in the Table below. ISIS oligonucleotides that caused changes in the levels of any of the liver or kidney function markers outside the expected range for antisense oligonucleotides were excluded in further studies.

TABLE 73

| Plasma chemistry markers in CD1 mice plasma at week 6 | | | | | | |
|---|---|---|---|---|---|---|
| | ALT (IU/L) | AST (IU/L) | Albumin (g/dL) | BUN (mg/dL) | Creatinine (mg/dL) | T. Bil (mg/dL) |
| PBS | 31 | 77 | 3.1 | 26.4 | 0.2 | 0.2 |
| 969157 | 818 | 1083 | 2.9 | 23.2 | 0.2 | 0.3 |

TABLE 73-continued

| Plasma chemistry markers in CD1 mice plasma at week 6 | | | | | | |
|---|---|---|---|---|---|---|
| | ALT (IU/L) | AST (IU/L) | Albumin (g/dL) | BUN (mg/dL) | Creatinine (mg/dL) | T. Bil (mg/dL) |
| 969160 | 482 | 715 | 2.8 | 22.4 | 0.2 | 0.2 |
| 969162 | 68 | 141 | 2.6 | 21.5 | 0.1 | 0.2 |
| 969210 | 87 | 166 | 2.6 | 25.5 | 0.2 | 0.2 |
| 969214 | 456 | 502 | 2.6 | 23.9 | 0.1 | 0.2 |
| 969361 | 70 | 147 | 2.8 | 23.0 | 0.1 | 0.2 |
| 969408 | 76 | 138 | 2.6 | 23.3 | 0.1 | 0.1 |
| 969433 | 84 | 136 | 2.6 | 20.0 | 0.1 | 0.2 |
| 969437 | 240 | 281 | 2.4 | 21.5 | 0.1 | 0.1 |
| 969502 | 184 | 217 | 2.7 | 23.1 | 0.1 | 0.1 |
| 971925 | 114 | 168 | 2.8 | 23.6 | 0.1 | 0.2 |
| 971997 | 52 | 101 | 2.9 | 22.1 | 0.1 | 0.1 |
| 972002 | 147 | 192 | 2.5 | 21.2 | 0.1 | 0.1 |
| 972116 | 75 | 107 | 3.0 | 21.1 | 0.1 | 0.1 |
| 972139 | 61 | 115 | 2.7 | 22.2 | 0.1 | 0.1 |
| 972163 | 86 | 124 | 3.0 | 20.4 | 0.1 | 0.2 |
| 972190 | 70 | 93 | 2.8 | 20.5 | 0.1 | 0.2 |
| 972268 | 41 | 79 | 2.6 | 19.1 | 0.1 | 0.1 |

Hematology Assays

Blood obtained from all mouse groups were sent to IDEXX BioResearch for hematocrit (HCT) measurements and analysis, as well as measurements of the various blood cells, such as WBC, RBC, lymphocytes, monocytes, and platelets. The results are presented in the tables below. ISIS oligonucleotides that caused changes in the levels of any of the hematology markers outside the expected range for antisense oligonucleotides were excluded in further studies.

TABLE 74

| Hematology markers in CD1 mice | | | | | | | | |
|---|---|---|---|---|---|---|---|---|
| | Neutrophil (%) | WBC (K/μL) | RBC (M/μL) | Lymphocytes (%) | HCT (%) | Platelet Count (K/μL) | Lymphocytes (/μL) | Monocytes (/μL) |
| PBS | 16 | 4 | 10 | 54 | 47 | 1152 | 2185 | 144 |
| 969157 | 23 | 6 | 10 | 65 | 48 | 1338 | 4078 | 543 |
| 969160 | 20 | 13 | 10 | 69 | 46 | 974 | 7953 | 1425 |
| 696162 | 16 | 8 | 10 | 74 | 46 | 1002 | 6067 | 641 |
| 969210 | 20 | 7 | 10 | 70 | 48 | 920 | 5322 | 524 |
| 969214 | 17 | 5 | 10 | 69 | 44 | 1076 | 3781 | 687 |
| 969361 | 16 | 9 | 9 | 75 | 43 | 931 | 6617 | 599 |
| 969408 | 35 | 7 | 9 | 58 | 42 | 1069 | 4416 | 506 |
| 969433 | 25 | 6 | 10 | 70 | 46 | 1054 | 3900 | 182 |
| 969437 | 23 | 7 | 11 | 69 | 47 | 1316 | 4780 | 526 |
| 969502 | 14 | 8 | 10 | 75 | 44 | 1075 | 5845 | 651 |
| 971925 | 18 | 5 | 10 | 74 | 44 | 961 | 3529 | 312 |
| 971997 | 18 | 4 | 9 | 73 | 43 | 1216 | 2646 | 239 |
| 972002 | 27 | 7 | 9 | 67 | 41 | 1069 | 4781 | 286 |
| 972116 | 23 | 6 | 10 | 69 | 44 | 1141 | 4415 | 336 |
| 972139 | 19 | 5 | 9 | 77 | 37 | 877 | 3947 | 224 |
| 972163 | 10 | 6 | 10 | 81 | 43 | 925 | 5197 | 437 |
| 972190 | 15 | 7 | 10 | 77 | 47 | 1453 | 5281 | 400 |
| 972268 | 39 | 7 | 10 | 54 | 46 | 1468 | 3891 | 406 |

Example 6: Tolerability of Modified Oligonucleotides Targeted to hAPOL1 in Sprague-Dawley Rats Sprague-Dawley rats are a multipurpose model used for safety and efficacy evaluations. The rats were treated with 3-10-3 cEt gapmer oligonucleotides from the studies described in the Examples above and evaluated for changes in the levels of various plasma chemistry markers.

Treatment

Male Sprague-Dawley rats were maintained on a 12-hour light/dark cycle and fed ad libitum with Purina normal rat chow, diet 5001. Groups of 4 Sprague-Dawley rats each were injected subcutaneously once a week for 6 weeks with 50 mg/kg of ISIS oligonucleotide. Forty-eight hours after the last dose, rats were euthanized and organs and plasma were harvested for further analysis. Two separate studies were conducted with similar conditions.

Study 1

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured and the results are presented in the Table below expressed in IU/L. ISIS oligonucleotides that caused changes in the levels of any markers of liver function outside the expected range for antisense oligonucleotides were excluded in further studies.

TABLE 75

Liver function markers in Sprague-Dawley rats

| Compound ID | ALT (IU/L) | AST (IU/L) |
|---|---|---|
| PBS | 45 | 66 |
| 793406 | 31 | 56 |
| 904082 | 67 | 114 |
| 904226 | 125 | 251 |
| 904628 | 42 | 87 |
| 905032 | 195 | 293 |
| 905373 | 54 | 90 |
| 905505 | 66 | 94 |
| 905521 | 41 | 67 |
| 905633 | 83 | 114 |
| 905758 | 85 | 144 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in the Table below, expressed in mg/dL. ISIS oligonucleotides that caused changes in the levels of any of the kidney function markers outside the expected range for antisense oligonucleotides were excluded in further studies.

TABLE 76

Kidney function markers in Sprague-Dawley rats

| Compound ID | Albumin (g/dL) | BUN (mg/dL) | Creatinine (mg/dL) | T.Bil (mg/dL) |
|---|---|---|---|---|
| PBS | 3.7 | 16.0 | 0.3 | 0.2 |
| 793406 | 2.9 | 23.1 | 0.4 | 0.2 |
| 904082 | 4.0 | 27.0 | 0.4 | 0.2 |
| 904226 | 2.8 | 26.6 | 0.4 | 0.2 |
| 904628 | 3.2 | 18.9 | 0.4 | 0.1 |
| 905032 | 3.5 | 21.0 | 0.5 | 0.2 |
| 905373 | 3.1 | 19.9 | 0.4 | 0.1 |
| 905505 | 3.4 | 18.2 | 0.4 | 0.2 |
| 905521 | 1.9 | 78.0 | 1.1 | 0.1 |
| 905633 | 3.3 | 20.6 | 0.4 | 0.1 |
| 905758 | 3.1 | 37.5 | 0.4 | 0.2 |

Hematology Assays

Blood obtained from all rat groups were sent to Antech Diagnostics for hematocrit (HCT) measurements and analysis, as well as measurements of the various blood cells, such as WBC, RBC, and total hemoglobin content. The results are presented in the Table below. ISIS oligonucleotides that caused changes in the levels of any of the hematology markers outside the expected range for antisense oligonucleotides were excluded in further studies.

TABLE 77

Hematology markers in Sprague-Dawley rats

| Compound ID | HCT (%) | LYM ($10^3$/μL) | MON ($10^3$/μL) | EOS ($10^3$/μL) | BAS ($10^{3/L}$) | NEU ($10^{3/L}$) | RET ($10^3$/L) |
|---|---|---|---|---|---|---|---|
| PBS | 51 | 9 | 0.5 | 88 | 15 | 1.2 | 263 |
| 793406 | 47 | 14 | 2.1 | 101 | 53 | 3.3 | 156 |
| 904226 | 33 | 11 | 1.4 | 0 | 54 | 0.6 | 99 |
| 904628 | 42 | 21 | 3.0 | 18 | 167 | 1.3 | 176 |
| 905032 | 48 | 19 | 1.7 | 54 | 56 | 1.2 | 112 |
| 905373 | 43 | 19 | 1.4 | 18 | 49 | 0.9 | 216 |
| 905505 | 46 | 13 | 1.3 | 15 | 58 | 0.6 | 119 |
| 905521 | 44 | 11 | 1.3 | 17 | 24 | 2.5 | 37 |
| 905633 | 47 | 8 | 0.8 | 55 | 17 | 0.8 | 149 |
| 905758 | 50 | 24 | 3.7 | 37 | 74 | 2.1 | 128 |

TABLE 78

Hematology markers in Sprague-Dawley rats

| Compound ID | MCH (pg) | MCHC (g/dL) | MCV (fL) | PLT ($10^3$/μL) | HGB | RBC ($10^6$/μL) | WBC ($10^3$/μL) |
|---|---|---|---|---|---|---|---|
| PBS | 19 | 32 | 59 | 747 | 16 | 9 | 11 |
| 793406 | 18 | 33 | 55 | 625 | 15 | 9 | 20 |
| 904226 | 18 | 33 | 55 | 145 | 11 | 6 | 13 |
| 904628 | 18 | 32 | 55 | 220 | 13 | 8 | 26 |
| 905032 | 18 | 33 | 54 | 684 | 16 | 9 | 22 |
| 905373 | 17 | 32 | 55 | 619 | 14 | 8 | 21 |
| 905505 | 18 | 33 | 55 | 590 | 15 | 9 | 15 |
| 905521 | 17 | 34 | 52 | 799 | 15 | 9 | 15 |
| 905633 | 19 | 34 | 54 | 658 | 16 | 9 | 10 |
| 905758 | 18 | 33 | 53 | 559 | 17 | 10 | 30 |

Organ Weights

Liver, spleen and kidney weights were measured at the end of the study, and are presented in the Table below. ISIS oligonucleotides that caused any changes in organ weights outside the expected range for antisense oligonucleotides were excluded from further studies.

TABLE 79

Organ weights (g)

| Compound ID | Liver (g) | Kidney (g) | Spleen (g) |
|---|---|---|---|
| PBS | 14.8 | 2.7 | 0.8 |
| 793406 | 13.5 | 2.5 | 1.0 |
| 904082 | 13.8 | 3.6 | 1.7 |
| 904226 | 13.4 | 3.2 | 2.2 |
| 904628 | 15.6 | 2.7 | 3.2 |
| 905032 | 10.6 | 2.6 | 1.2 |
| 905373 | 14.7 | 2.4 | 1.9 |
| 905505 | 14.0 | 2.6 | 1.5 |
| 905521 | 11.7 | 3.4 | 0.8 |
| 905633 | 13.3 | 2.3 | 1.2 |
| 905758 | 12.9 | 2.7 | 2.1 |

Study 2

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured and the results are presented in the Table below expressed in IU/L. ISIS oligonucleotides that caused changes in the levels of any markers of liver function outside the expected range for antisense oligonucleotides were excluded in further studies.

TABLE 80

Liver function markers in Sprague-Dawley rats

| Compound ID | ALT (IU/L) | AST (IU/L) |
|---|---|---|
| PBS | 44 | 65 |
| 793444 | 59 | 89 |
| 903822 | 46 | 148 |
| 904101 | 55 | 89 |
| 904763 | 66 | 96 |
| 905139 | 212 | 447 |
| 905469 | 41 | 78 |
| 905634 | 135 | 112 |
| 905665 | 82 | 105 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in the Table below, expressed in mg/dL. ISIS oligonucleotides that caused changes in the levels of any of the kidney function markers outside the expected range for antisense oligonucleotides were excluded in further studies.

TABLE 81

Kidney function markers in Sprague-Dawley rats

| Compound ID | Albumin (g/dL) | BUN (mg/dL) | Creatinine (mg/dL) | T.Bil (mg/dL) |
|---|---|---|---|---|
| PBS | 3.5 | 17.5 | 0.3 | 0.2 |
| 793444 | 3.3 | 18.7 | 0.3 | 0.2 |
| 903822 | 3.0 | 16.7 | 0.3 | 0.3 |
| 904101 | 3.5 | 21.4 | 0.4 | 0.2 |
| 904763 | 3.4 | 19.1 | 0.4 | 0.2 |
| 905139 | 4.0 | 21.0 | 0.4 | 2.5 |
| 905469 | 3.4 | 16.7 | 0.3 | 0.1 |
| 905634 | 3.5 | 19.3 | 0.4 | 0.2 |
| 905665 | 2.9 | 20.0 | 0.4 | 0.2 |

Hematology Assays

Blood obtained from all rat groups were sent to Antech Diagnostics for hematocrit (HCT) measurements and analysis, as well as measurements of the various blood cells, such as WBC, RBC, and total hemoglobin content. The results are presented in the Table below. ISIS oligonucleotides that caused changes in the levels of any of the hematology markers outside the expected range for antisense oligonucleotides were excluded in further studies. N.d. indicates that the parameter was not measured for that particular oligonucleotide.

TABLE 82

Hematology markers in Sprague-Dawley rats

| Compound ID | WBC (K/μL) | RBC (M/μL) | Lymphocyte (/μL) | HCT (%) | Monocyte (/μL) | Platelet Count (K/μL) |
|---|---|---|---|---|---|---|
| PBS | 11 | 8.4 | 7781 | 53 | 30 | 687 |
| 793444 | 16 | 9.5 | n.d. | 55 | n.d. | 559 |
| 903822 | 13 | 6.5 | 12446 | 40 | 462 | 670 |
| 904101 | 13 | 8.7 | 11510 | 51 | 35 | 680 |
| 904763 | 10 | 8.3 | 8612 | 49 | n.d. | 785 |
| 905139 | 20 | 7.9 | 14922 | 46 | 274 | 769 |
| 905469 | 12 | 7.8 | n.d. | 49 | n.d. | 592 |
| 905634 | 12 | 8.6 | 10853 | 51 | 0 | 668 |
| 905665 | 13 | 9.1 | 6794 | 56 | 79 | 814 |

Organ Weights

Liver, spleen and kidney weights were measured at the end of the study, and are presented in the Table below. ISIS oligonucleotides that caused any changes in organ weights outside the expected range for antisense oligonucleotides were excluded from further studies.

TABLE 83

Organ weights (g)

| Compound ID | Liver (g) | Kidney (g) | Spleen (g) |
|---|---|---|---|
| PBS | 18.7 | 3.0 | 0.9 |
| 793444 | 13.4 | 2.7 | 1.0 |
| 903822 | 16.0 | 3.2 | 2.9 |
| 904101 | 16.6 | 2.9 | 1.4 |
| 904763 | 18.0 | 2.6 | 1.2 |
| 905139 | 16.9 | 3.4 | 1.9 |
| 905469 | 18.4 | 2.9 | 1.9 |
| 905634 | 20.3 | 2.8 | 1.4 |
| 905665 | 16.5 | 3.0 | 1.4 |

Study 3

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured and the results are presented in the Table below expressed in IU/L. ISIS oligonucleotides that caused changes in the levels of any markers of liver function outside the expected range for antisense oligonucleotides were excluded in further studies.

TABLE 84

Liver function markers in Sprague-Dawley rats

| | ALT (IU/L) | AST (IU/L) | Bilirubin (mg/dL) |
|---|---|---|---|
| PBS | 34 | 58 | 0.2 |
| 969162 | 41 | 119 | 0.2 |
| 972139 | 35 | 94 | 0.2 |
| 972002 | 41 | 83 | 0.2 |
| 972163 | 37 | 81 | 0.2 |
| 972116 | 31 | 59 | 0.1 |
| 972190 | 62 | 93 | 0.1 |
| 972268 | 336 | 286 | 0.8 |
| 969408 | 104 | 132 | 0.2 |
| 969361 | 240 | 386 | 0.4 |
| 969433 | 31 | 99 | 0.1 |
| 971997 | 50 | 84 | 0.2 |
| 969210 | 32 | 87 | 0.2 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in the Table below, expressed in mg/dL. ISIS oligonucleotides that caused changes in the levels of any of the kidney function markers outside the expected range for antisense oligonucleotides were excluded in further studies.

TABLE 85

Plasma levels for kidney markers in Sprague-Dawley rats

| | BUN (mg/dL) | Creatinine (mg/dL) | Albumin (g/dL) |
|---|---|---|---|
| PBS | 17 | 0.2 | 3.3 |
| 969162 | 21 | 0.3 | 2.8 |
| 972139 | 67 | 0.8 | 2.8 |
| 972002 | 23 | 0.3 | 2.7 |
| 972163 | 19 | 0.3 | 2.9 |
| 972116 | 19 | 0.3 | 2.9 |
| 972190 | 19 | 0.3 | 3.0 |
| 972268 | 16 | 0.3 | 3.0 |
| 969408 | 19 | 0.3 | 3.2 |
| 969361 | 24 | 0.4 | 2.8 |
| 969433 | 21 | 0.3 | 2.7 |
| 971997 | 21 | 0.3 | 2.9 |
| 969210 | 19 | 0.3 | 3.1 |

TABLE 86

Urine levels for kidney markers in Sprague-Dawley rats

| | Creatinine (mg/dL) | Protein (mg/dL) | Protein/Creatinine ratio |
|---|---|---|---|
| PBS | 121 | 113 | 1.0 |
| 969162 | 101 | 452 | 4.2 |
| 972139 | 61 | 283 | 4.0 |
| 972002 | 110 | 895 | 7.4 |
| 972163 | 96 | 394 | 4.0 |
| 972116 | 105 | 405 | 3.8 |
| 972190 | 109 | 261 | 2.4 |
| 972268 | 52 | 214 | 4.1 |
| 969408 | 51 | 147 | 3.0 |
| 969361 | 48 | 255 | 5.2 |
| 969433 | 51 | 224 | 4.3 |
| 971997 | 67 | 268 | 4.3 |
| 969210 | 86 | 338 | 3.9 |

Hematology Assays

Blood obtained from all rat groups were sent to Antech Diagnostics for hematocrit (HCT) measurements and analysis, as well as measurements of the various blood cells, such as WBC, RBC, and total hemoglobin content. The results are presented in the Table below. ISIS oligonucleotides that caused changes in the levels of any of the hematology markers outside the expected range for antisense oligonucleotides were excluded in further studies. N.d. indicates that the parameter was not measured for that particular oligonucleotide.

TABLE 87

Hematology markers in Sprague-Dawley rats

| Compound ID | WBC (K/μL) | RBC (M/μL) | Lymphocyte (/μL) | HCT (%) | Monocyte (/μL) | Platelet Count (K/μL) |
|---|---|---|---|---|---|---|
| PBS | 8 | 9 | 7035 | 51 | 252 | 725 |
| 969162 | 23 | 6 | 20273 | 36 | 2219 | 144 |
| 972139 | 20 | 6 | 16184 | 34 | 2500 | 427 |
| 972002 | 18 | 7 | 13972 | 43 | 1946 | 547 |
| 972163 | 25 | 8 | 22377 | 43 | 2302 | 556 |
| 972116 | 26 | 7 | 22581 | 42 | 1973 | 325 |
| 972190 | 9 | 8 | 8171 | 48 | 791 | 703 |
| 972268 | 20 | 8 | 16780 | 48 | 2237 | 737 |
| 969408 | 15 | 8 | 11733 | 46 | 1840 | 685 |
| 969361 | 32 | 7 | 25970 | 43 | 4802 | 230 |
| 969433 | 22 | 5 | 17649 | 31 | 2434 | 112 |
| 971997 | 24 | 7 | 20272 | 38 | 2077 | 458 |
| 969210 | 34 | 6 | 27724 | 37 | 3880 | 294 |

Organ Weights

Liver, spleen and kidney weights, as well as body weights, were measured at the end of the study, and are presented in the Table below. ISIS oligonucleotides that caused any changes in weights outside the expected range for antisense oligonucleotides were excluded from further studies.

TABLE 88

Weights (g)

| | Liver | Kidney | Spleen | BW |
|---|---|---|---|---|
| PBS | 17 | 3.1 | 0.8 | 412 |
| 969162 | 17 | 3.3 | 3.3 | 358 |
| 972139 | 16 | 4.5 | 2.8 | 322 |
| 972002 | 24 | 3.8 | 2.5 | 365 |
| 972163 | 16 | 3.1 | 2.2 | 351 |
| 972116 | 17 | 3.5 | 2.8 | 357 |
| 972190 | 16 | 3.0 | 1.4 | 342 |
| 972268 | 17 | 2.9 | 1.4 | 355 |
| 969408 | 15 | 2.6 | 1.4 | 359 |
| 969361 | 17 | 2.6 | 2.9 | 344 |
| 969433 | 20 | 4.0 | 4.1 | 365 |
| 971997 | 16 | 2.6 | 2.3 | 355 |
| 969210 | 16 | 3.5 | 2.7 | 378 |

Example 7: Dose-Dependent Inhibition of hAPOL1 in Transgenic Mouse Model

Transgenic mice hAPOL1 mice, described above, were maintained on a 12-hour light/dark cycle and were fed ad libitum normal Purina mouse chow. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Study 1

The hAPOL1 transgenic mice were divided into groups of 4 mice each. Groups received subcutaneous injections of 3-10-3 cEt gapmers at a dose of 5, 15, or 50 mg/kg once a week for four weeks, 4 total doses, as indicated in the tables below. One group of mice received subcutaneous injections of PBS once a week for 4 weeks. The saline-injected group served as the control group to which oligonucleotide-treated groups were compared.

RNA Analysis

Mice were sacrificed 48 hours after the last dose and RNA was extracted from kidney and liver for real-time PCR analysis of measurement of mRNA expression of hAPOL1.

Results are presented as percent change of mRNA, relative to PBS control, normalized with RIBOGREEN®. Two separate experiments were conducted with similar conditions and are presented in separate tables. As shown in the tables below, treatment with antisense oligonucleotides resulted in significant reduction of hAPO1 mRNA in comparison to the PBS control.

TABLE 89

Percent inhibition hAPOL1 mRNA in the transgenic mouse kidney relative to the PBS control (experiment 1)

| Weekly Dose Compound ID | 5 mg/kg | 15 mg/kg | 50 mg/kg | $ED_{50}$ (mg/kg/week) |
|---|---|---|---|---|
| | % Inhibition hAPOL1 | | | |
| 793406 | 0 | 20 | 35 | >50 |
| 793444 | 6 | 17 | 38 | >50 |
| 903822 | 1 | 21 | 32 | >50 |
| 904101 | 0 | 0 | 17 | >50 |
| 904763 | 7 | 20 | 49 | >50 |
| 905139 | 0 | 21 | 35 | >50 |
| 905469 | 11 | 25 | 50 | >50 |
| 905634 | 0 | 0 | 39 | >50 |
| 905665 | 0 | 23 | 39 | >50 |

TABLE 90

Percent inhibition hAPOL1 mRNA in the transgenic mouse liver relative to the PBS control (experiment 2)

| Weekly Dose Compound ID | 5 mg/kg | 15 mg/kg | 50 mg/kg | $ED_{50}$ (mg/kg/week) |
|---|---|---|---|---|
| | % Inhibition hAPOL | | | |
| 793406 | 6 | 68 | 92 | 11.8 |
| 793444 | 9 | 29 | 73 | 26.5 |
| 903822 | 24 | 78 | 95 | 8.5 |
| 904101 | 0 | 19 | 70 | 32.8 |
| 904763 | 36 | 83 | 92 | 6.8 |
| 905139 | 39 | 73 | 93 | 7.0 |
| 905469 | 39 | 75 | 96 | 9.3 |
| 905634 | 13 | 72 | 93 | 9.3 |
| 905665 | 2 | 71 | 92 | 10.5 |

Study 2

The hAPOL1 transgenic mice were divided into groups of 4 mice each. Groups received subcutaneous injections of 3-10-3 cEt gapmers at a dose of 5, 15, or 50 mg/kg once a week for four weeks, 4 total doses, as indicated in the tables below. One group of mice received subcutaneous injections of PBS once a week for 4 weeks. The saline-injected group served as the control group to which oligonucleotide-treated groups were compared.

RNA Analysis

Mice were sacrificed 48 hours after the last dose and RNA was extracted from kidney and liver for real-time PCR analysis of measurement of mRNA expression of hAPOL1. Results are presented as percent change of mRNA, relative to PBS control, normalized with RIBOGREEN®. Two separate experiments were conducted with similar conditions and are presented in separate tables. As shown in the tables below, treatment with antisense oligonucleotides resulted in significant reduction of hAPO1 mRNA in comparison to the PBS control.

TABLE 91

Percent inhibition hAPOL1 mRNA in the transgenic mouse kidney relative to the PBS control (experiment 1)

| Weekly Dose Compound ID | 5 mg/kg | 15 mg/kg | 50 mg/kg | ED50 (mg/kg/week) |
|---|---|---|---|---|
| | % Inhibition hAPOL1 | | | |
| 793406 | 22 | 42 | 51 | 40.6 |
| 904082 | 33 | 50 | 61 | 18.1 |
| 904226 | 17 | 36 | 59 | 31.7 |
| 904628 | 33 | 41 | 50 | >50 |
| 905032 | 22 | 15 | 45 | >50 |
| 905373 | 26 | 50 | 35 | >50 |
| 905505 | 22 | 52 | 57 | 23.6 |
| 905521 | 25 | 46 | 53 | 21.4 |
| 905633 | 18 | 16 | 48 | >50 |
| 905758 | 27 | 27 | 49 | >50 |

TABLE 92

Percent inhibition hAPOL1 mRNA in the transgenic mouse liver relative to the PBS control (experiment 2)

| Weekly Dose Compound ID | 5 mg/kg | 15 mg/kg | 50 mg/kg | $ED_{50}$ (mg/kg/week) |
|---|---|---|---|---|
| | % Inhibition hAPOL1 | | | |
| 793406 | 19 | 60 | 94 | 11.7 |
| 904082 | 54 | 81 | 94 | 4.4 |
| 904226 | 32 | 73 | 96 | 8.0 |
| 904628 | 57 | 70 | 91 | 3.7 |
| 905032 | 65 | 92 | 96 | 3.3 |
| 905373 | 39 | 84 | 35 | >50 |
| 905505 | 28 | 83 | 92 | 7.6 |
| 905521 | 0 | 68 | 95 | 12.3 |
| 905633 | 0 | 18 | 79 | 21.9 |
| 905758 | 0 | 60 | 81 | 11.8 |

Study 3

The hAPOL1 transgenic mice were divided into groups of 4 mice each. Groups received subcutaneous injections of modified oligonucleotide at a dose of 1.5, 5, 15, or 50 mg/kg once a week for four weeks, 4 total doses, as indicated in the tables below. One group of mice received subcutaneous injections of PBS once a week for 4 weeks. The saline-injected group served as the control group to which oligonucleotide-treated groups were compared.

RNA Analysis

Mice were sacrificed 48 hours after the last dose and RNA was extracted from kidney and liver for real-time PCR analysis of measurement of mRNA expression of hAPOL1. Results are presented as percent change of mRNA, relative to PBS control, normalized with RIBOGREEN®. As shown in the tables below, treatment with antisense oligonucleotides resulted in significant reduction of hAPO1 mRNA in comparison to the PBS control.

TABLE 93

Percent inhibition hAPOL1 mRNA in the transgenic mouse kidney relative to the PBS control

| Weekly Dose Compound ID | 1.5 mg/kg | 5 mg/kg | 15 mg/kg | 50 mg/kg | $ED_{40}$ (mg/kg/week) |
|---|---|---|---|---|---|
| | | % Inhibition hAPOL1 | | | |
| 793406 | 0 | 33 | 43 | 60 | 13.7 |
| 904763 | 19 | 29 | 52 | 62 | 9.3 |
| 905469 | 20 | 26 | 34 | 59 | 15.9 |

TABLE 93-continued

| Percent inhibition hAPOL1 mRNA in the transgenic mouse kidney relative to the PBS control | | | | | |
|---|---|---|---|---|---|
| Weekly Dose Compound ID | 1.5 mg/kg | 5 mg/kg | 15 mg/kg | 50 mg/kg | $ED_{40}$ (mg/kg/week) |
| | | % Inhibition hAPOL1 | | | |
| 905505 | 28 | 23 | 45 | 47 | >50 |
| 905634 | 9 | 16 | 27 | 45 | >50 |
| 905665 | 12 | 30 | 45 | 56 | 13.2 |
| 972163 | 0 | 32 | 45 | 60 | 13.5 |
| 972190 | 13 | 27 | 46 | 57 | 13.1 |

TABLE 94

| Percent inhibition hAPOL1 mRNA in the transgenic mouse liver relative to the PBS control | | | | | |
|---|---|---|---|---|---|
| Weekly Dose Compound ID | 1.5 mg/kg | 5 mg/kg | 15 mg/kg | 50 mg/kg | $ED_{50}$ (mg/kg/week) |
| | | % Inhibition hAPOL1 | | | |
| 793406 | 4 | 58 | 61 | 96 | 6.4 |
| 904763 | 17 | 42 | 72 | 93 | 5.4 |
| 905469 | 31 | 37 | 61 | 96 | 7.0 |
| 905505 | 15 | 45 | 78 | 95 | 5.7 |
| 905634 | 2 | 32 | 48 | 72 | 15.8 |
| 905665 | 3 | 43 | 79 | 91 | 5.4 |
| 972163 | 14 | 60 | 85 | 93 | 4.2 |
| 972190 | 18 | 48 | 83 | 92 | 5.1 |

Example 8: Confirmation of Dose-Dependent Antisense Inhibition of Human Lead Compounds Targeting APOL1 in A431 Cells Gapmers selected from the studies described above were tested at various doses in A431 cells.

Study 1

Cells were plated at a density of 10,000 cells per well and transfected free uptake with various concentrations of antisense oligonucleotides, as specified in the Table below. After a treatment period of approximately 16 hours, RNA was isolated from the cells and APOL1 mRNA levels were measured by quantitative real-time PCR. Human primer probe set RTS35962 was used to measure mRNA levels. APOL1 mRNA levels were adjusted according to total RNA content, as measured by RIBOGREEN®. Results are presented as percent inhibition of APOL1, relative to untreated control cells.

The half maximal inhibitory concentration ($IC_{50}$) of each oligonucleotide is also presented. APOL1 mRNA levels were significantly reduced in a dose-dependent manner in antisense oligonucleotide treated cells.

TABLE 95

| Multi-dose assay with 3-10-3 cEt gapmers | | | | | | |
|---|---|---|---|---|---|---|
| | % inhibition | | | | | |
| Compound Number | 8 nM | 40 nM | 200 nM | 1000 nM | 5000 nM | $IC_{50}$ (μM) |
| 905505 | 22 | 69 | 92 | 97 | 97 | 0.02 |
| 905373 | 13 | 55 | 92 | 98 | 98 | 0.03 |
| 905634 | 10 | 41 | 86 | 97 | 98 | 0.05 |
| 793406 | 6 | 15 | 53 | 84 | 93 | 0.19 |
| 905633 | 21 | 68 | 94 | 98 | 98 | 0.02 |
| 904763 | 11 | 37 | 81 | 96 | 97 | 0.06 |

Study 2

Cells were plated at a density of 10,000 cells per well and transfected free uptake with various concentrations of antisense oligonucleotides, as specified in the Table below. After a treatment period of approximately 16 hours, RNA was isolated from the cells and APOL1 mRNA levels were measured by quantitative real-time PCR. Human primer probe set RTS35962 was used to measure mRNA levels. APOL1 mRNA levels were adjusted according to total RNA content, as measured by RIBOGREEN®. Results are presented as percent inhibition of APOL1, relative to untreated control cells.

The half maximal inhibitory concentration ($IC_{50}$) of each oligonucleotide is also presented. APOL1 mRNA levels were significantly reduced in a dose-dependent manner in antisense oligonucleotide treated cells.

TABLE 96

| Multi-dose assay to confirm lead compounds | | | | | | | |
|---|---|---|---|---|---|---|---|
| | | % inhibition | | | | | |
| Compound Number | Chemistry | 8 nM | 40 nM | 200 nM | 1000 nM | 5000 nM | $IC_{50}$ (μM) |
| 793406 | kkk-10-kkk | 4 | 11 | 41 | 72 | 88 | 0.34 |
| 904763 | kkk-10-kkk | 6 | 23 | 63 | 93 | 98 | 0.12 |
| 905469 | kkk-10-kkk | 9 | 15 | 48 | 81 | 94 | 0.22 |
| 905505 | kkk-10-kkk | 0 | 35 | 81 | 95 | 98 | 0.07 |
| 905634 | kkk-10-kkk | 7 | 18 | 59 | 86 | 93 | 0.15 |
| 905665 | kkk-10-kkk | 7 | 11 | 56 | 82 | 93 | 0.19 |
| 972163 | kkk-9-kkke | 2 | 36 | 85 | 95 | 95 | 0.06 |
| 972190 | kkk-9-kkke | 2 | 24 | 69 | 94 | 99 | 0.10 |

Example 9: Effect of ISIS Antisense Oligonucleotides Targeting Human APOL1 in Cynomolgus Monkeys Cynomolgus monkeys were treated with ISIS antisense oligonucleotides selected from studies described in the Examples above. Antisense oligonucleotide efficacy and tolerability, as well as their pharmacokinetic profile in the liver and kidney, were evaluated. Cynomolgus monkeys are reported to have an APOL1 pseudogene.

The human antisense oligonucleotides tested are cross-reactive with the cynomolgus genomic sequence (the complement of GENBANK Accession No. NC_022281.1 truncated from nucleotides 15021761 to Ser. No. 15/036,414, designated herein as SEQ ID NO: 1949). The greater the complementarity between the human oligonucleotide and the cynomolgus monkey sequence, the more likely the human oligonucleotide can cross-react with the cynomolgus monkey sequence. The start and stop sites of each oligonucleotide to SEQ ID NO: 1949 is presented in the Table below. "Start site" indicates the 5'-most nucleoside to which the gapmer is targeted in the cynomolgus monkey gene sequence. 'Mismatches' indicates the number of nucleobases of the human oligonucleotide that are mismatched with the cynomolgus gene sequence along its length.

TABLE 97

| Antisense oligonucleotides complementary to the cynomolgus APOL1 genomic sequence (SEQ ID NO: 1949) | | | | |
|---|---|---|---|---|
| Compound ID | Target Start Site | Mismatches | Chemistry | SEQ ID NO |
| 793406 | 9979 | 1 | kkk-d10-kkk | 13 |
| 904763 | 8065 | 0 | kkk-d10-kkk | 1095 |
| 905469 | 9836 | 2 | kkk-d10-kkk | 1730 |
| 905505 | 9999 | 3 | kkk-d10-kkk | 76 |
| 905634 | 10424 | 2 | kkk-d10-kkk | 1326 |
| 905665 | 10821 | 3 | kkk-d10-kkk | 81 |
| 972190 | 8066 | 0 | kkk-d9-kkke | 1164 |
| 972163 | 15761, 16086 | 2 | kkk-d9-kkke | 1925 |

Treatment

Prior to the study, the monkeys were kept in quarantine during which the animals were observed daily for general health. The monkeys were 2-4 years old and weighed 2-4 kg each. Eight groups of 4 randomly assigned male cynomolgus monkeys each were administered 30 mg/kg of modified oligonucleotide or PBS. once a week for 12 weeks. One group of monkeys received a dose of saline once a week for 12 weeks. The saline-injected group served as the control group to which oligonucleotide-treated groups were compared. Approximately 48 hours after the last dose, monkeys were sacrificed and tissues were collected for analysis.

Assessment of tolerability was based on clinical observations, body weights, food consumption, and clinical pathology. Complete necropsies were performed with a recording of any macroscopic abnormality. Terminal necropsy was performed on Day 85. Organ weights were taken. In addition, blood, CSF, and tissues (at necropsy) were collected for toxicokinetic evaluations. The protocols described in the Example were approved by the Institutional Animal Care and Use Committee (IACUC).

Target Reduction

RNA Analysis

RNA was extracted from liver for real-time PCR analysis of mRNA expression of cynoAPOL1. RTS35787 (Forward sequence: CTCCTGCTGAGTGACCATAAAG (SEQ ID NO: 1945); Reverse sequence: GGACTTCTTCGAGCCAGTTT (SEQ ID NO: 1946); Probe sequence: AGAGTGGTGGCTACTGCTGAACTG (SEQ ID NO: 1947)) was used to detect cynomolgus APOL1. Results are presented as percent change of mRNA, relative to saline control, normalized with monkey Cyclophylin A. As shown in the table below, treatment with modified oligonucleotides resulted in reduction of the cynomolgus APOL1 mRNA in comparison to the PBS control for some oligonucleotides.

TABLE 98

| Inhibition of Cynomolgus APOL1 compared to the PBS control | | |
|---|---|---|
| Compound ID | mismatch to cynomolgus sequence | % Inhibition |
| 793406 | 1 | 40 |
| 904763 | 0 | 74 |
| 905469 | 2 | 0 |
| 905505 | 3 | 0 |
| 905634 | 2 | 91 |
| 905665 | 3 | 0 |
| 972163 | 2 | 0 |
| 972190 | 0 | 93 |

Tolerability Studies

Body and Organ Weight Measurements

To evaluate the effect of ISIS oligonucleotides on the overall health of the animals, body and organ weights were measured. Body weights were measured on day 84 and are presented in the Table below. Organ weights were measured after euthanasia and the data is also presented in the Table below. The results indicate that effect of treatment with antisense oligonucleotides on body and organ weights was within the expected range for antisense oligonucleotides. Specifically, treatment with ISIS 972190 was well tolerated in terms of the body and organ weights of the monkeys.

TABLE 99

| Body and organ weights in Cynomolgus Monkeys after 12 weeks of treatment with modified oligonucleotide | | | | | | |
|---|---|---|---|---|---|---|
| | Body Weight (g) | Heart (g) | Kidney (g) | Spleen (g) | Thymus (g) | Liver with gall bladder (g) |
| PBS | 2473 | 9.7 | 12.6 | 2.3 | 3.5 | 50 |
| 793406 | 2419 | 9.1 | 11.9 | 3.5 | 3.0 | 53 |
| 904763 | 2511 | 9.5 | 14.3 | 2.9 | 4.0 | 56 |
| 905469 | 2395 | 9.3 | 16.0 | 3.5 | 2.5 | 59 |
| 905505 | 2550 | 9.4 | 12.9 | 4.7 | 4.5 | 65 |
| 905634 | 2488 | 9.8 | 14.7 | 3.6 | 3.2 | 61 |
| 905665 | 2462 | 9.8 | 14.2 | 3.9 | 4.1 | 56 |
| 972163 | 2606 | 10.8 | 14.8 | 3.3 | 4.2 | 68 |
| 972190 | 2666 | 11.0 | 14.6 | 3.0 | 3.6 | 64 |

Liver Function

To evaluate the effect of ISIS oligonucleotides on hepatic function, blood samples were collected from all the study groups. The blood samples were collected via femoral venipuncture, 48 hrs post-dosing. The monkeys were fasted overnight prior to blood collection. Blood was collected in tubes containing $K_2$-EDTA anticoagulant, which were centrifuged to obtain plasma. Levels of various liver function markers were measured using a Toshiba 200FR NEO chemistry analyzer (Toshiba Co., Japan). Plasma levels of ALT and AST were measured and the results are presented in the Table below, expressed in IU/L. Bilirubin, a liver function marker, was similarly measured and is presented in the Table below, expressed in mg/dL. The results indicate that antisense oligonucleotides had no effect on liver function outside the expected range for antisense oligonucleotides. Specifically, treatment with ISIS 972190 was well tolerated in terms of the liver function in monkeys.

TABLE 100

| Liver function markers in cynomolgus monkey plasma | | | | |
|---|---|---|---|---|
| | ALT (IU/L) | AST (IU/L) | Bilirubin (mg/dL) | Albumin (g/dL) |
| PBS | 37 | 57 | 0.3 | 4.3 |
| 793406 | 59 | 55 | 0.3 | 4.3 |
| 904763 | 50 | 48 | 0.3 | 4.4 |
| 905469 | 54 | 68 | 0.2 | 3.9 |
| 905505 | 46 | 54 | 0.2 | 4.1 |
| 905634 | 566 | 417 | 0.5 | 4.1 |

TABLE 100-continued

| Liver function markers in cynomolgus monkey plasma | | | | |
|---|---|---|---|---|
| | ALT (IU/L) | AST (IU/L) | Bilirubin (mg/dL) | Albumin (g/dL) |
| 905665 | 57 | 80 | 0.3 | 4.3 |
| 972163 | 58 | 81 | 0.2 | 4.1 |
| 972190 | 47 | 46 | 0.2 | 4.2 |

Kidney Function

To evaluate the effect of ISIS oligonucleotides on kidney function, blood samples were collected from all the study groups. The blood samples were collected via femoral venipuncture, 48 hrs post-dosing. The monkeys were fasted overnight prior to blood collection. Blood was collected in tubes containing $K_2$-EDTA anticoagulant, which were centrifuged to obtain plasma. Levels of BUN and creatinine were measured using a Toshiba 200FR NEO chemistry analyzer (Toshiba Co., Japan). Results are presented in the Table below, expressed in mg/dL.

A urinalysis was also conducted prior to sacrifice using a COBAS U 411 analyzer, Combur 10 Test M urine sticks (Roche, Germany), and a Toshiba 120 FR automated chemistry analyzer (Toshiba Co., Japan). Urine was tested for potassium (U-K), microprotein (UTP), creatinine (UCRE), albumin (UALB), chlorine (Ca), sodium (Na), and the protein/creatinine ratio was calculated (P/C). The results are presented in the tables below.

The plasma and urine chemistry data indicate that most of the ISIS oligonucleotides did not have any effect on the kidney function outside the expected range for antisense oligonucleotides. Specifically, treatment with ISIS 972190 was well tolerated in terms of the kidney function of the monkeys.

TABLE 101

| Plasma BUN and creatinine levels (mg/dL) in cynomolgus monkeys | | |
|---|---|---|
| | BUN | Creatinine |
| Saline | 25 | 0.7 |
| 793406 | 24 | 1.0 |
| 904763 | 25 | 0.7 |
| 905469 | 28 | 0.8 |
| 905505 | 27 | 0.9 |
| 905634 | 27 | 1.0 |
| 905665 | 24 | 0.8 |
| 972163 | 30 | 0.8 |
| 972190 | 20 | 0.8 |

TABLE 102

| Urine levels in cynomolgus monkeys | | | |
|---|---|---|---|
| | P/C (ratio) | Creatinine (mg/dL) | Albumin (mg/dL) |
| Saline | 0.08 | 84 | 0.3 |
| 793406 | 0.14 | 71 | 1.7 |
| 904763 | 0.04 | 44 | 0.03 |
| 905469 | 0.10 | 52 | 0.2 |
| 905505 | 0.02 | 77 | 0.1 |
| 905634 | 0.06 | 106 | 0.5 |
| 905665 | 0.04 | 124 | 0.4 |
| 972163 | 0.01 | 69 | 0.2 |
| 972190 | 0.03 | 34 | 0.01 |

Hematology

To evaluate any effect of ISIS oligonucleotides in cynomolgus monkeys on hematologic parameters, blood samples of approximately 1.3 mL of blood was collected from each of the available study animals in tubes containing $K_2$-EDTA. Samples were analyzed for red blood cell (RBC) count, white blood cells (WBC) count, individual white blood cell counts, such as that of monocytes, neutrophils, lymphocytes, as well as for platelet count, hemoglobin content and hematocrit, using an ADVIA120 hematology analyzer (Bayer, USA). The data is presented in the Tables below.

The data indicate the oligonucleotides did not cause any changes in hematologic parameters outside the expected range for antisense oligonucleotides at this dose. Specifically, treatment with ISIS 972190 was well tolerated in terms of the hematologic parameters of the monkeys.

TABLE 103

| Blood cell counts in cynomolgus monkeys | | | | | | |
|---|---|---|---|---|---|---|
| | RBC ($\times 10^6$/μL) | Platelets ($\times 10^3$/μL) | WBC ($\times 10^3$/μL) | Neutrophils ($\times 10^3$/μL) | Lymphocytes ($\times 10^3$/μL) | Monocytes ($\times 10^3$/μL) |
| Saline | 5.9 | 380 | 8.7 | 2.5 | 5.8 | 0.2 |
| 793406 | 6.8 | 437 | 11.1 | 4.4 | 6.2 | 0.3 |
| 904763 | 6.1 | 412 | 10.6 | 5.2 | 5.0 | 0.2 |
| 905469 | 5.6 | 483 | 9.8 | 6.1 | 3.4 | 0.2 |
| 905505 | 5.8 | 400 | 13.2 | 5.5 | 7.0 | 0.4 |
| 905634 | 6.3 | 340 | 9.9 | 4.0 | 5.2 | 0.3 |
| 905665 | 6.0 | 440 | 8.3 | 2.8 | 5.0 | 0.2 |
| 972163 | 5.9 | 377 | 11.5 | 5.4 | 5.5 | 0.3 |
| 972190 | 6.0 | 392 | 10.5 | 4.5 | 5.6 | 0.3 |

TABLE 104

| Hematologic parameters in cynomolgus monkeys | | |
|---|---|---|
| | Hemoglobin (g/dL) | HCT (%) |
| Saline | 14 | 44 |
| 793406 | 15 | 47 |
| 904763 | 14 | 45 |
| 905469 | 12 | 41 |
| 905505 | 13 | 42 |
| 905634 | 14 | 46 |
| 905665 | 13 | 43 |
| 972163 | 13 | 44 |
| 972190 | 13 | 43 |

C-Reactive Protein and C3 Activation

To evaluate any inflammatory effect of ISIS oligonucleotides in cynomolgus monkeys, blood samples were taken for analysis. The monkeys were fasted overnight prior to blood collection. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C3 levels were measured to evaluate any complement activation due to oligonucleotide treatment. C-reactive protein (CRP), which is synthesized in the liver and which serves as a marker of inflammation, was measured using a Toshiba 200FR NEO chemistry analyzer (Toshiba Co., Japan). The results indicate that treatment with ISIS 972190 did not cause any inflammation in monkeys.

TABLE 105

| C-reactive protein levels (mg/L) in cynomolgus monkey plasma | |
|---|---|
| | CRP |
| Saline | 1.7 |
| 793406 | 1.4 |
| 904763 | 2.4 |
| 905469 | 8.4 |
| 905505 | 4.1 |
| 905634 | 6.7 |
| 905665 | 10.7 |
| 972163 | 4.7 |
| 972190 | 9.5 |

Oligonucleotide Concentration Analysis

Quantification analysis of the concentration of each antisense oligonucleotide in different organs was performed. Most of the oligonucleotides had an acceptable pharmacokinetic profile in the liver and kidney.

TABLE 106

| Antisense oligonucleotide concentration (μg/g tissue) | | |
|---|---|---|
| ISIS No | Liver | Kidney |
| 793406 | 349 | 1253 |
| 904763 | 296 | 982 |
| 905469 | 288 | 2636 |
| 905505 | 547 | 1712 |
| 905634 | 516 | 2307 |
| 905665 | 392 | 942 |
| 972163 | 553 | 2054 |
| 972190 | 978 | 2654 |

Overall, the results of the study indicate that ISIS 972190 is the most potent and well tolerated compound of those tested for inhibiting APOL1 and is an important candidate for the treatment of APOL1-associated diseases.

What is claimed:

1. A compound comprising a modified oligonucleotide, wherein the modified oligonucleotide consists of 12 to 30 linked nucleosides and has a nucleobase sequence comprising the nucleobase sequence SEQ ID NO: 1164, or a pharmaceutically acceptable salt thereof.

2. The compound of claim 1, wherein the modified oligonucleotide consists of 16 to 30 linked nucleosides.

3. The compound of claim 2, wherein the modified oligonucleotide consists of 16 linked nucleosides.

4. The compound of claim 1, wherein the modified oligonucleotide comprises at least one modified internucleoside linkage, and/or at least one modified sugar, and/or at least one modified nucleobase.

5. The compound of claim 4, wherein the at least one modified internucleoside linkage is a phosphorothioate internucleoside linkage.

6. The compound of claim 4, wherein the at least one modified sugar is a bicyclic sugar.

7. The compound of claim 6, wherein the bicyclic sugar comprises a a 4'-$CH_2$-O-2' group or a 4'-$CH(CH_3)$-O-2' group or a 4'-$(CH_2)_2$-O-2' group.

8. The compound of claim 4, wherein the at least one modified sugar comprises a 2'-$O(CH)_2$-$OCH_3$ group or a 2'-O-$CH_3$ group.

9. The compound of claim 4, wherein the at least one modified nucleobase is a 5-methylcytosine.

10. The compound of claim 1, wherein the modified oligonucleotide comprises:

a gap segment consisting of nine linked deoxynucleosides;

a 5' wing segment consisting of three linked nucleosides; and a 3' wing segment consisting of four linked nucleosides;

wherein the gap segment is positioned between the 5' wing segment and the 3' wing segment, wherein each nucleoside of each wing segment comprises a cEt sugar; wherein each internucleoside linkage is a phosphorothioate linkage; wherein each cytosine is a 5-methylcytosine.

11. The compound of claim 1, wherein the pharmaceutically acceptable salt is a sodium salt.

12. The compound of claim 1, wherein the pharmaceutically acceptable salt is a potassium salt.

13. A composition comprising the compound of claims 1-12 and a pharmaceutically acceptable carrier.

14. A method of inhibiting expression of APOL1 in a cell comprising contacting the cell with a compound according to claims 1-12, thereby inhibiting expression of APOL1 in the cell.

15. The method of claim 14, wherein the cell is in the kidney of an individual.

* * * * *